(12) United States Patent
D'amico et al.

(10) Patent No.: US 9,187,486 B2
(45) Date of Patent: Nov. 17, 2015

(54) BICYCLIC PYRIDAZINE COMPOUNDS AS PIM INHIBITORS

(75) Inventors: Derin C. D'amico, Newbury Park, CA (US); Bradley J. Herberich, Newbury Park, CA (US); Claire L. M. Jackson, Thousand Oaks, CA (US); Liping H. Pettus, Thousand Oaks, CA (US); Andrew Tasker, Simi Valley, CA (US); Hui-Ling Wang, Thousand Oaks, CA (US); Bin Wu, Thousand Oaks, CA (US); Ryan Wurz, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 28 days.

(21) Appl. No.: 14/114,481

(22) PCT Filed: Apr. 19, 2012

(86) PCT No.: PCT/US2012/034272
§ 371 (c)(1),
(2), (4) Date: Apr. 4, 2014

(87) PCT Pub. No.: WO2012/148775
PCT Pub. Date: Nov. 1, 2012

(65) Prior Publication Data
US 2014/0221344 A1 Aug. 7, 2014

Related U.S. Application Data

(60) Provisional application No. 61/480,703, filed on Apr. 29, 2011.

(51) Int. Cl.
*C07D 487/04* (2006.01)
(52) U.S. Cl.
CPC .................... *C07D 487/04* (2013.01)

(58) Field of Classification Search
CPC ...................................... C07D 487/04
USPC .............................. 514/210.21; 544/236, 248
See application file for complete search history.

(56) References Cited

U.S. PATENT DOCUMENTS

2004/0192696 A1 9/2004 Green et al.

FOREIGN PATENT DOCUMENTS

CA 1246568 A1 12/1988

OTHER PUBLICATIONS

Pinedo et al. (2000).*
McMahon et al. (2000).*
Zugravescu et al: "Synthesis of 1 pyridazine and benzopyridazine derivatives. III" , REVUE ROUMAINE DE CHIMIE—ROMANIAN JOURNAL OF CHEMISTRY, ED ITU RA ACADEMIEI ROMANE, RO, vol. 10, Jan. 1, 1965, pp. 641-647.
Youssef et al: "Synthesis of some Heterocyclic Systems of Anticipated Biological Activities Via 6-Aryl-4-pyrazol 1-ylpyridazin-3-one", AFINIDAD, BARCELONA, ES, vol. 61. Jan. 1, 2004, pp. 500-509.
Gafitanu E et al: "New pyridazine derivatives with physiological properties", REVISTA MEDICO-CHIRURGICALA, XX, XX, vol. 81, Jan. 1, 1977, pp. 469-474.

* cited by examiner

*Primary Examiner* — Paul V Ward
(74) *Attorney, Agent, or Firm* — Bernard P. Friedrichsen

(57) ABSTRACT

The invention relates to bicyclic compounds of formulas I and I', and salts thereof. In some embodiments, the invention relates to inhibitors or modulators of Pim-1 and/or Pim-2, and/or Pim-3 protein kinase activity or enzyme function. In still further embodiments, the invention relates to pharmaceutical compositions comprising compounds disclosed herein, and their use in the prevention and treatment of Pim kinase related conditions and diseases, preferably cancer.

16 Claims, No Drawings

BICYCLIC PYRIDAZINE COMPOUNDS AS PIM INHIBITORS

RELATED APPLICATIONS

This application is a US national stage application under 35 U.S.C. §371 of International Application No. PCT/US2012/034272, having an international filing date of Apr. 19, 2012, which claims the benefit of, and priority to, United States Provisional Application No. 61/480,703, filed on Apr. 29, 2011, each specification of which is hereby incorporated herein by reference in its entirety.

FIELD OF THE INVENTION

The present invention relates to certain bicyclic pyridazines, e.g. triazole-pyridazine and imidazo-pyridazine compounds that are Pim inhibitors, pharmaceutical compositions containing such compounds, and processes for preparing such compounds. Provided herein also are methods of treating disorders or diseases treatable by inhibition of Pims, such as cancer, and the like.

BACKGROUND

The role of Pim serine/threonine kinases in the pathogenesis and therapy of hematological malignancies and solid cancers is of interest to the medical community. Pim proteins are constitutively active and are over-expressed in a subset of human cancers, many of hematological origin. Pim kinases also regulate aspects of transformation and drug resistance in hematological malignancies such as DLBCL, MM, and AML where they are overexpressed or mutated. Aberrant expression of Pim-1 or Pim-2 promotes tumor development in mouse models of lymphoma and prostate cancer. Elevated Pim-1 levels correlate with poor prognosis in DLBCL and mantle cell lymphoma. Pims play a role in some solid tumors (prostate cancer, and head and neck cancer). Whereas elevated levels of Pim-1 and Pim-2 were mostly found in hematological malignancies and prostate cancer, increased Pim-3 expression was observed in different solid tumors. Pim kinases are constitutively active and their activity supports in vitro and in vivo tumour cell growth and survival through modification of an increasing number of common as well as isoform-specific substrates including several cell cycle regulators and apoptosis mediators. Pim-1 but not Pim-2 mediates homing and migration of normal and malignant hematopoietic cells by regulating chemokine receptor surface expression. Knockdown experiments by RNA interference or dominant-negative acting mutants suggested that Pim kinases are important for maintenance of a transformed phenotype and therefore potential therapeutic targets.

There exists a need for compounds that inhibit the growth of tumors, treat cancer, modulate cell cycle arrest, and/or inhibit molecules such as Pim-1, Pim-2, or Pim-3 and pharmaceutical formulations and medicaments that contain such compounds.

SUMMARY OF THE INVENTION

The present invention comprises a new class of bicyclic pyridazines, e.g. triazole-pyridazine and imidazo-pyridazine compounds useful in the treatment of diseases, such as Pim-mediated diseases, for example cancer. Accordingly, the invention also comprises pharmaceutical compositions comprising the compounds, methods for the treatment of Pim-mediated diseases and other maladies, such as treatment of hematological malignancies and of solid tumors, for example prostate cancer, and head and neck cancer, using the compounds and compositions of the invention, and intermediates and processes useful for the preparation of the compounds of the invention.

The compounds of the invention are represented by the following general structure:

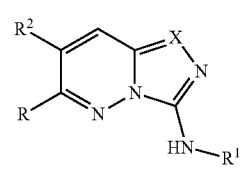

wherein X, R; $R^1$ and $R^2$ are defined below; and a pharmaceutically acceptable salt thereof.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula 1:

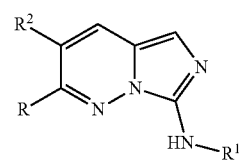

wherein
R is halo, alkyl, cycloalkyl, optionally substituted aryl, optionally substituted 5-membered heterocyclyl, or optionally substituted 6-membered heterocyclyl;
$R^1$ is optionally substituted 5-membered nitrogen containing heteroaryl, or optionally substituted 6-membered nitrogen containing heteroaryl; and
$R^2$ is H, fluoro, $C_{1-2}$ alkyl, or $C_{1-2}$ alkoxy;
and a pharmaceutically acceptable salt thereof;
provided $R^1$ is not unsubstituted 3-pyridyl when $R^2$ is H and R is 2,6-difluorophenyl;
further provided $R^1$ is not 5-methyl-3-phenyl-4-isoxazolyl when $R^2$ is H and R is 2,6-difluorophenyl; and further provided $R^1$ is not 4-chloro-3-pyridyl when $R^2$ is H and R is 2,6-difluorophenyl.

In another embodiment, $R^2$ is H.

In another embodiment, $R^1$ is optionally substituted pyridyl, optionally substituted pyrimidinyl, optionally substituted pyridazinyl, optionally substituted pyrrolyl, optionally substituted isoxazolyl or optionally substituted isothiazolyl.

In another embodiment, $R^1$ is substituted 3-pyridyl, substituted 5-pyrimidinyl, substituted 3-pyridazinyl, substituted 3-pyrrolyl, substituted 4-isoxazolyl or substituted isothiazol-4-yl.

In another embodiment, $R^1$ is substituted with optionally substituted 4-6-membered heterocyclyl, optionally substituted 4-6-membered heterocyclyloxy, optionally substituted cycloalkyl, optionally substituted aryl, amino, alkylamino or dialkylamino.

In another embodiment, R is $C_{1-6}$ alkyl, $C_{3-6}$ cycloalkyl, optionally substituted 5-membered saturated or partially unsaturated heterocyclyl, or optionally substituted saturated or partially unsaturated 6-membered heterocyclyl.

In another embodiment, R is methyl, ethyl, propyl, tert-butyl, cyclopropyl, cyclopentyl, pyran, 5,6-dihydro-2H-pyranyl, 3,6-dihydro-2H-pyranyl, tetrahydropyran, pyrrolidinyl, piperidinyl, morpholinyl, or imidazolidinyl; wherein any ring is optionally substituted with one or more substituents selected from methyl, or oxo.

In another embodiment, R is optionally substituted phenyl, optionally substituted 5-membered heteroaryl or optionally substituted 6-membered heteroaryl.

In another embodiment, R is optionally substituted phenyl, optionally substituted thiazolyl, optionally substituted pyrazolyl, optionally substituted pyrazinyl, optionally substituted pyridazinyl, optionally substituted pyrimidinyl, or optionally substituted pyridyl.

In another embodiment, R is thiazol-2-yl, 2-fluorophenyl, 2,6-difluorophenyl, 2,4-difluorophenyl, 2-chlorophenyl, 2,4-dichlorophenyl, 2-fluoro-3-pyridyl, 2-chloro-3-pyridyl, 2-fluoro-4-methylsulphonylphenyl, or chloro.

In another embodiment, $R^1$ is pyrid-3-yl, pyrimidin-3-yl or isothiazol-4-yl, wherein $R^1$ is substituted with amino, dialkylamino, substituted or unsubstituted 5-membered nitrogen-containing heterocyclyl, substituted or unsubstituted 6-membered nitrogen-containing heterocyclyl, 6-membered nitrogen-containing heterocyclyloxy, 6-membered nitrogen-containing heterocyclylamino, 5-membered nitrogen-containing heterocyclylamino, or 6-membered nitrogen-containing heterocyclylamino, wherein the substituted 5-membered nitrogen-containing heterocyclyl, or substituted 6-membered nitrogen-containing heterocyclyl are substituted with one or more substituents selected from amino, oxo, methyl, and fluoro.

Another aspect of the current invention relates to compounds having the general structure of formula 2

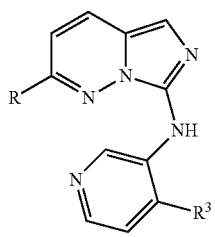

2 wherein
R is halo, optionally substituted phenyl, optionally substituted 5-membered heteroaryl, or optionally substituted 6-membered heteroaryl;
$R^3$ is optionally substituted 4-6-membered heterocyclyl, optionally substituted 4-6-membered heterocyclyloxy, optionally substituted cycloalkyl, optionally substituted aryl, amino, alkylamino or dialkylamino;
and a pharmaceutically acceptable salt thereof.

In another embodiment, R is substituted with halo, nitro, alkylaminocarbonyl, cycloalkylaminocarbonyl, phenylaminocarbonyl, dialkylaminocarbonyl, benzylaminocarbonyl, heterocyclylcarbonyl, alkoxy, hydroxyl, haloalkoxy, cyano, amino, alkyl, alkylsulfonyl, alkylamino, cycloalkyl, haloalkyl, oxo, cycloalkylamino, or heterocyclyl.

In another embodiment, R is phenyl, 2,6-difluorophenyl, 2,3-difluorophenyl, 2-fluorophenyl, 3-fluorophenyl, 2-fluoro-5-nitrophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-cyanophenyl, 3-aminophenyl, 3-amino-2-methylphenyl, 2-cyanophenyl, 3-cyanophenyl, 2-chlorophenyl, 2-chloro-6-fluorophenyl, 3-methylsulfonylphenyl, 4-methylsulfonylphenyl, 3-dimethylaminophenyl, 3-amino-4-morpholinophenyl, 3-amino-6-trifluoromethoxyphenyl,
2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl,
1H-pyrazol-5-yl, 1-methyl-1H-pyrazol-4-yl, thiazol-2-yl, 2-(2-methylpiperidin-1-yl)thiazol-4-yl, or 2-(pyrrolidin-1-yl)thiazol-4-yl.

In another embodiment, R is 2,6-difluorophenyl, 2-chloro-6-fluorophenyl, or 2-(isopropoxy)-pyrazin-6-yl.

In another embodiment, $R^3$ is optionally substituted 5-6-membered nitrogen containing heterocyclyl, optionally substituted 4-6-membered nitrogen containing heterocyclyloxy, optionally substituted cycloalkyl, optionally substituted aryl, amino, alkylamino or dialkylamino.

In another embodiment, $R^3$ is dimethylamino, 3-aminophenyl, 2-oxo-(1,2-dihydropyrid-5-yl), 2-amino-5-pyridyl, 3-amino-5-pyridyl, 3-aminocyclohexyl, 3-hydroxypiperidin-1-yl, 3-amino-piperidin-1-yl, piperazinyl, 3-aminopyrrolidinyl, 3-azetidinyloxy, 3-piperidinyloxy, 3,4-dihydroxy-piperidin-1-yl or 3-amino -4-hydroxy-5-methylpiperidin-1-yl.

A family of specific compounds of particular interest within Formula 1 consists of compounds and pharmaceutically-acceptable salts thereof as follows:

N-(4-((3S)-3-amino-1-piperidinyl)-3-pyridinyl)-2-(2,6-difluorophenyl)imidazo[1,5-b]pyridazin-7-amine;
2-(2,6-difluorophenyl)-N-(4-(1-piperazinyl)-3-pyridinyl)imidazo[1,5-b]pyridazin-7-amine;
N-(4-(1-piperazinyl)-3-pyridinyl)-2-(1,3-thiazol-2-yl) imidazo[1,5-b]pyridazin-7-amine;
N-(4-((3S)-3-amino-1-piperidinyl)-3-pyridinyl)-2-(2-chlorophenyl)imidazo[1,5-b]pyridazin-7-amine;
2-(2-chlorophenyl)-N-(4-(1-piperazinyl)-3-pyridinyl)imidazo[1,5-b]pyridazin-7-amine;
N-(4-((3S)-3-amino-1-piperidinyl)-3-pyridinyl)-2-(2-chloro-3-pyridinyl)imidazo[1,5-b]pyridazin-7-amine;
N-(4-((3S)-3-amino-1-piperidinyl)-3-pyridinyl)-2-(2-fluoro-3-pyridinyl)imidazo[1,5-b]pyridazin-7-amine;
N-(4-((3S)-3-amino-1-piperidinyl)-3-pyridinyl)-2-(1,3-thiazol-2-yl)imidazo[1,5-b]pyridazin-7-amine;
N-(4-(3-azetidinyloxy)-3-pyridinyl)-2-(2,6-difluorophenyl)imidazo[1,5-b]pyridazin-7-amine;
2-(2-chlorophenyl)-N-(4-((3R)-3-piperidinyloxy)-3-pyridinyl)imidazo[1,5-b]pyridazin-7-amine;
N-(4-((3S)-3-amino-1-piperidinyl)-3-pyridinyl)-2-(2,4-dichlorophenyl)imidazo[1,5-b]pyridazin-7-amine;
N-(4-((3S)-3-amino-1-piperidinyl)-3-pyridinyl)-2-(2,4-difluorophenyl)imidazo[1,5-b]pyridazin-7-amine;
N-(4-((3S)-3-amino-1-pyrrolidinyl)-3-pyridinyl)-2-(2,6-difluorophenyl)imidazo[1,5-b]pyridazin-7-amine;
(S)-N-(4-(3-aminopiperidin-1-yl)pyrimidin-5-yl)-2-(2-fluorophenyl) imidazo[1,5-b]pyridazin-7-amine;
N-(4-((3S)-3-amino-1-piperidinyl)-3-pyridinyl)-2-(2-fluorophenyl)imidazo[1,5-b]pyridazin-7-amine;
2-(2-chlorophenyl)-N-(4-((3S)-3-piperidinyloxy)-3-pyridinyl)imidazo[1,5-b]pyridazin-7-amine;
(3R)-1-(3-((2-(2-chlorophenyl)imidazo[1,5-b]pyridazin-7-yl)amino)-4-pyridinyl)-3-piperidinol;
(3R)-1-(3-((2-(1,3-thiazol-2-yl)imidazo[1,5-b]pyridazin-7-yl)amino)-4-pyridinyl)-3-piperidinol;
(3S)-1-(3-((2-(2,6-difluorophenyl)imidazo[1,5-b]pyridazin-7-yl)amino)-4-pyridinyl)-3-piperidinol;
(3R,4R,5S)-3-amino-1-(3-((2-(2,6-difluorophenyl)imidazo[1,5-b]pyridazin-7-yl)amino)-4-pyridinyl)-5-methyl-4-piperidinol;
(3R,4R,5S)-3-amino-5-methyl-1-(3-((2-(1,3-thiazol-2-yl)imidazo[1,5-b]pyridazin-7-yl)amino)-4-pyridinyl)-4-piperidinol;
N-(4-((3S)-3-amino-1-piperidinyl)-3-pyridinyl)-2-(2-fluoro-4-(methylsulfonyl)phenyl)imidazo[1,5-b]pyridazin-7-amine;
(3R,4R,5S)-3-amino-1-(3-((2-(2-fluoro-4-(methylsulfonyl)phenyl)imidazo[1,5-b]pyridazin-7-yl)amino)-4-pyridinyl)-5-methyl-4-piperidinol;
N-(4-((3S)-3-amino-1-piperidinyl)-3-pyridinyl)-2-chloroimidazo[1,5-b]pyridazin-7-amine;
(3S,4S)-1-(3-((2-(2,6-difluorophenyl)imidazo[1,5-b]pyridazin-7-yl)amino)-4-pyridinyl)-3,4-piperidinediol;
(3R,4R)-1-(3-((2-(2,6-difluorophenyl)imidazo[1,5-b]pyridazin-7-yl)amino)-4-pyridinyl)-3,4-piperidinediol;
$N^3$-(2-(2,6-difluorophenyl)imidazo[1,5-b]pyridazin-7-yl)-$N^4,N^4$-dimethyl-3,4-pyridinediamine;
N-(4-(3-aminophenyl)-3-pyridinyl)-2-(2,6-difluorophenyl)imidazo[1,5-b]pyridazin-7-amine;
3'-((2-(2,6-difluorophenyl)imidazo[1,5-b]pyridazin-7-yl)amino)-3,4'-bipyridin-6(1H)-one;
N3'-(2-(2,6-difluorophenyl)imidazo[1,5-b]pyridazin-7-yl)-3,4'-bipyridine-3',5-diamine;
N3'-(2-(2,6-difluorophenyl)imidazo[1,5-b]pyridazin-7-yl)-4,4'-bipyridine-2,3'-diamine;
N-(5-((3S)-3-amino-1-piperidinyl)-4-isothiazolyl)-2-(2,6-difluorophenyl)imidazo[1,5-b]pyridazin-7-amine;
N-(4-((1R,3S)-3-aminocyclohexyl)-3-pyridinyl)-2-(2,6-difluorophenyl)imidazo[1,5-b]pyridazin-7-amine; and
N-(4-((1S,3R)-3-aminocyclohexyl)-3-pyridinyl)-2-(2,6-difluorophenyl)imidazo[1,5-b]pyridazin-7-amine Another aspect of the current invention relates to compounds having the general structure of formula 1'

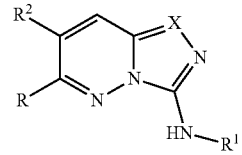

wherein
X is N or CH;
R is H, halo, alkyl, cycloalkyl, optionally substituted aryl, optionally substituted 5-membered heterocyclyl, or optionally substituted 6-membered heterocyclyl;
$R^1$ is optionally substituted phenyl, optionally substituted 5-membered nitrogen containing heteroaryl, or optionally substituted 6-membered nitrogen containing heteroaryl; and
$R^2$ is H;
and a pharmaceutically acceptable salt thereof;
provided $R^1$ is not unsubstituted 3-pyridyl when, X is CH and R is 2,6-difluorophenyl; further provided $R^1$ is not 5-methyl-3-phenyl-4-isoxazolyl when, X is CH and R is 2,6-difluorophenyl; further provided R is not H if X is CH; further provided $R^1$ is not 4-(5-methyl-4-isoxazolyl)-3-pyridinyl when X is N and R is 2,6-difluorophenyl; further provided $R^1$ is not substituted 4-pyridinyl; and further provided $R^1$ is not 4-chloro-3-pyridyl when, X is CH and R is 2,6-difluorophenyl.

In another embodiment, $R^1$ is optionally substituted phenyl.

In another embodiment, $R^1$ is optionally substituted pyridyl, optionally substituted pyrimidinyl, optionally substituted pyridazinyl, optionally substituted pyrrolyl, optionally substituted isoxazolyl or optionally substituted isothiazolyl.

In another embodiment, $R^1$ is substituted 3-pyridyl, substituted 5-pyrimidinyl, substituted 3-pyridazinyl, substituted 3-pyrrolyl, substituted 4-isoxazolyl or substituted isothiazol-4-yl.

In another embodiment, $R^1$ is substituted with optionally substituted 4-6-membered heterocyclyl, optionally substituted 4-6-membered heterocyclyloxy, 5-6 membered nitrogen-containing heterocyclylamino, optionally substituted cycloalkyl, optionally substituted cycloalkenyl, optionally substituted aryl, N-alkoxyalkyl-N-alkylamino, N-alkoxyalkylamino, amino, alkylamino or dialkylamino.

In another embodiment, R is $C_{1-6}$ alkyl, $C_{3-6}$ cycloalkyl, optionally substituted 5-membered saturated or partially unsaturated heterocyclyl, or optionally substituted saturated or partially unsaturated 6-membered heterocyclyl.

In another embodiment, R is methyl, ethyl, propyl, tert-butyl, cyclopropyl, cyclopentyl, pyran, 5,6-dihydro-2H-pyranyl, 3,6-dihydro-2H-pyranyl, tetrahydropyran, pyrrolidinyl, piperidinyl, morpholinyl, or imidazolidinyl; wherein any ring is optionally substituted with one or more substituents selected from methyl, or oxo.

In another embodiment, R is optionally substituted phenyl, optionally substituted 5-membered heteroaryl or optionally substituted 6-membered heteroaryl.

In another embodiment, R is optionally substituted phenyl, optionally substituted thiazolyl, optionally substituted pyrazolyl, optionally substituted pyrazinyl, optionally substituted pyridazinyl, optionally substituted pyrimidinyl, or optionally substituted pyridyl.

In another embodiment, R is thiazol-2-yl, 2-fluorophenyl, 2,6-difluorophenyl, 2,4-difluorophenyl, 2-chlorophenyl, 2,4-dichlorophenyl, 2-fluoro-3-pyridyl, 2-chloro-3-pyridyl, 2-fluoro-4-methylsulphonylphenyl, or chloro.

In another embodiment, $R^1$ is pyrid-3-yl, pyrimidin-3-yl or isothiazol-4-yl, wherein $R^1$ is substituted with amino, $C_{1-4}$ alkylamino, di($C_{1-4}$) alkylamino, N—$C_{1-4}$ alkoxy-$C_{1-4}$ alkyl-N—$C_{1-4}$ alkylamino, N—$C_{1-4}$ alkoxy-$C_{1-4}$ alkylamino, optionally substituted cycloalkyl, optionally substituted cycloalkenyl, optionally substituted aryl, substituted or unsubstituted 5-membered nitrogen-containing heterocyclyl, substituted or unsubstituted 6-membered nitrogen-containing heterocyclyl, 4-6-membered nitrogen-containing heterocyclyloxy, 5-membered nitrogen-containing heterocyclylamino, or 6-membered nitrogen-containing heterocyclylamino, wherein the substituted 5-membered nitrogen-containing heterocyclyl, or substituted 6-membered nitrogen-containing heterocyclyl are substituted with one or more substituents selected from amino, oxo, methyl, and fluoro.

In another embodiment, X is CH.

In another embodiment, X is N.

Another aspect of the current invention relates to compounds having the general structure of formula 2'

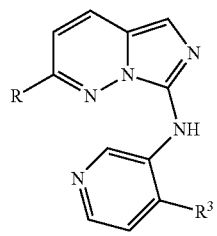

2' wherein
R is halo, optionally substituted phenyl, optionally substituted 5-membered heteroaryl, or optionally substituted 6-membered heteroaryl;
$R^3$ is optionally substituted 4-6-membered heterocyclyl, optionally substituted 4-6-membered heterocyclyloxy, optionally substituted cycloalkyl, optionally substituted aryl, amino, alkylamino or dialkylamino;
and a pharmaceutically acceptable salt thereof.

In another embodiment, R is phenyl, 2,6-difluorophenyl, 2,3-difluorophenyl, 2-fluorophenyl, 3-fluorophenyl, 2-fluoro-5-nitrophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-cyanophenyl, 3-aminophenyl, 3-amino-2-methylphenyl, 2-cyanophenyl, 3-cyanophenyl, 2-chlorophenyl, 2-chloro-6-fluorophenyl, 3-methylsulfonylphenyl, 4-methylsulfonylphenyl, 3-dimethylaminophenyl, 3-amino-4-morpholinophenyl, 3-amino-6-trifluoromethoxyphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 1H-pyrazol-5-yl, 1-methyl-1H-pyrazol-4-yl, thiazol-2-yl, 2-(2-methylpiperidin-1-yl)thiazol-4-yl, or 2-(pyrrolidin-1-yl)thiazol-4-yl.

In another embodiment, R is 2,6-difluorophenyl, 2-chloro-6-fluorophenyl, 3-fluoropyridin-2-yl, or 2-(isopropoxy)-pyrazin-6-yl.

In another embodiment, $R^3$ is optionally substituted 5-6-membered nitrogen containing heterocyclyl, optionally substituted 4-6-membered nitrogen containing heterocyclyloxy, optionally substituted cycloalkyl, optionally substituted cycloalkenyl, optionally substituted aryl, amino, N-alkoxy-alkyl-N-alkylamino, alkylamino or dialkylamino.

In another embodiment, $R^3$ is dimethylamino, N-(2-methoxypropyl)-N-methylamino, N-(2-methylpropyl)-N-methylamino, 3,5-dimethylisoxazol-4-yl, 3-aminophenyl, 2-oxo-(1,2-dihydropyrid-5-yl), 1,2,3,6-tetrahydropyridin-4-yl, 2-amino-5-pyridyl, 3-amino-5-pyridyl, 3-aminocyclohexen-1-yl, 3-aminocyclohexyl, 3-azetidinyloxy, 3-piperidinyloxy, 3-amino-pyrrolidinyl, 1-piperidinyl, 3-hydroxypiperidin-1-yl, 3-amino-piperidin-1-yl, 3-methylamino-piperidin-1-yl, 3,4-dihydroxy-piperidin-1-yl, 3-amino-2-methylpiperidin-1-yl, 3-amino-3-methylpiperidin-1-yl, 3-amino-5-methylpiperidin-1-yl, 3-amino-5-trifluoromethylpiperidin-1-yl, 3-amino-6-methylpiperidin-1-yl, 3-amino-4-fluoropiperidin-1-yl, 3-amino-5-fluoropiperidin-1-yl, 3-amino-4-hydroxy-5-methylpiperidin-1-yl, piperazinyl, 3-methylpiperazin-1-yl or 2,5-dimethylpiperazin-1-yl.

Another aspect of the current invention relates to compounds having the general structure of formula 3'

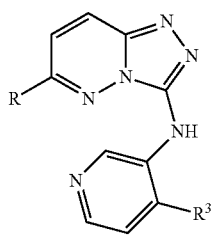

wherein
R is H, optionally substituted phenyl, optionally substituted 5-membered heteroaryl, or optionally substituted 6-membered heteroaryl;
$R^3$ is optionally substituted 4-6-membered heterocyclyl, optionally substituted 4-6-membered heterocyclyloxy, optionally substituted cycloalkyl, optionally substituted aryl, amino, alkylamino or dialkylamino;
and a pharmaceutically acceptable salt thereof.

In another embodiment, R is phenyl, 2,6-difluorophenyl, 2,3-difluorophenyl, 2-fluorophenyl, 3-fluorophenyl, 2-fluoro-5-nitrophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-cyanophenyl, 3-aminophenyl, 3-amino-2-methylphenyl, 2-cyanophenyl, 3-cyanophenyl, 2-chlorophenyl, 2-chloro-6-fluorophenyl, 3-methylsulfonylphenyl, 4-methylsulfonylphenyl, 3-dimethylaminophenyl, 3-amino-4-morpholinophenyl, 3-amino-6-trifluoromethoxyphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 1H-pyrazol-5-yl, 1-methyl-1H-pyrazol-4-yl, thiazol-2-yl, 2-(2-methylpiperidin-1-yl)thiazol-4-yl, or 2-(pyrrolidin-1-yl)thiazol-4-yl.

In another embodiment, wherein R is 2,6-difluorophenyl, 2-chloro-6-fluorophenyl, 3-fluoropyridin-2-yl, or 2-(isopropoxy)-pyrazin-6-yl.

In another embodiment, $R^3$ is optionally substituted 5-6-membered nitrogen containing heterocyclyl, optionally substituted 4-6-membered nitrogen containing heterocyclyloxy, optionally substituted cycloalkyl, optionally substituted cycloalkenyl, optionally substituted aryl, amino, N-alkoxyalkyl-N-alkylamino, alkylamino or dialkylamino.

In another embodiment, $R^3$ is dimethylamino, N-(2-methoxypropyl)-N-methylamino, N-(2-methylpropyl)-N-methylamino, 5-methylisoxazol-4-yl, 3,5-dimethylisoxazol-4-yl, 3-aminophenyl, 2-oxo-(1,2-dihydropyrid-5-yl), 1,2,3,6-tetrahydropyridin-4-yl, 2-amino-5-pyridyl, 3-amino-5-pyridyl, 3-aminocyclohexen-1-yl, 3-aminocyclohexyl, 3-azetidinyloxy, 3-piperidinyloxy, 3-amino-pyrrolidinyl, 1-piperidinyl, 3-hydroxypiperidin-1-yl, 3-amino-piperidin-1-yl, 3-methylamino-piperidin-1-yl, 3,4-dihydroxy-piperidin-1-yl, 3-amino-2-methylpiperidin-1-yl, 3-amino-3-methylpiperidin-1-yl, 3-amino-5-methylpiperidin-1-yl, 3-amino-5-trifluoromethylpiperidin-1-yl, 3-amino-6-methylpiperidin-1-yl, 3-amino-4-fluoropiperidin-1-yl, 3-amino-5-fluoropiperidin-1-yl, 3-amino-4-hydroxy-5-methylpiperidin-1-yl, piperazinyl, 3-methylpiperazin-1-yl or 2,5-dimethylpiperazin-1-yl.

A family of specific compounds of particular interest within Formula 1' consists of compounds and pharmaceutically-acceptable salts thereof as follows:

(3R,4R,5S)-3-amino-1-(3-((2-(2,6-difluorophenyl)imidazo[1,5-b]pyridazin-7-yl)amino)pyridin-4-yl)-5-methylpiperidin-4-ol;

(3R,4R,5S)-3-amino-5-methyl-1-(3-((2-(1,3-thiazol-2-yl)imidazo[1,5-b]pyridazin-7-yl)amino)-4-pyridinyl)-4-piperidinol;

(3R,4S,5R)-3-amino-1-(3-((2-(2,6-difluorophenyl)imidazo[1,5-b]pyridazin-7-yl)amino)-4-pyridinyl)-5-methyl-4-piperidinol;

N-(4-((trans)-3-amino-2-methyl-1-piperidinyl)-3-pyridinyl)-2-(3-fluoro-2-pyridinyl)imidazo[1,5-b]pyridazin-7-amine (enantiomer 1);

rac-N-(4-((cis)-3-amino-5-(trifluoromethyl)piperidin-1-yl)pyridin-3-yl)-2-(2,6-difluorophenyl)imidazo[1,5-b]pyridazin-7-amine;

N-(4-((cis)-3-amino-5-methylpiperidin-1-yl)pyridin-3-yl)-2-(pyridin-2-yl)imidazo[1,5-b]pyridazin-7-amine;

N-(4-((cis)-3-amino-5-methylpiperidin-1-yl)pyridin-3-yl)-2-(3-fluoropyridin-2-yl)imidazo[1,5-b]pyridazin-7-amine;

(3R,4R,5S)-3-amino-1-(3-((2-(3-fluoropyridin-2-yl)imidazo[1,5-b]pyridazin-7-yl)amino)pyridin-4-yl)-5-methylpiperidin-4-ol;

3-(7-((4-((3S,5R)-3-amino-5-methyl-1-piperidinyl)-3-pyridinyl)amino)imidazo[1,5-b]pyridazin-2-yl)-N-cyclopropyl-4-fluorobenzamide;

3-(7-((4-((3S)-3-amino-1-piperidinyl)-3-pyridinyl)amino)imidazo[1,5-b]pyridazin-2-yl)-N-cyclopropyl-4-fluorobenzamide;

N-(4-(5-amino-2-methylpiperidin-1-yl)pyridin-3-yl)-2-(2,6-difluorophenyl)imidazo[1,5-b]pyridazin-7-amine (diastereomer 2);

N-(4-(5-amino-2-methylpiperidin-1-yl)pyridin-3-yl)-2-(2,6-difluorophenyl)imidazo[1,5-b]pyridazin-7-amine (diastereomer 3);

N-(4-((trans)-3-amino-4-methylpiperidin-1-yl)pyridin-3-yl)-2-(2,6-difluorophenyl)imidazo[1,5-b]pyridazin-7-amine (enantiomer 1);

N-(4-((cis)-5-amino-2-methylpiperidin-1-yl)pyridin-3-yl)-2-(3-fluoropyridin-2-yl)imidazo[1,5-b]pyridazin-7-amine (enantiomer 2);

N-(4-((cis)-3-amino-5-methylpiperidin-1-yl)pyridin-3-yl)-2-(2,6-difluorophenyl)imidazo[1,5-b]pyridazin-7-amine (enantiomer 1);

N-(4-((cis)-3-amino-5-methylpiperidin-1-yl)pyridin-3-yl)-2-(2-fluorophenyl)imidazo[1,5-b]pyridazin-7-amine (enantiomer 1);

(S)-N-(4-(3-aminopiperidin-1-yl)pyridin-3-yl)-2-(3-chloropyridin-2-yl)imidazo[1,5-b]pyridazin-7-amine;

N-(4-((3S,5R)-3-amino-5-methylpiperidin-1-yl)pyridin-3-yl)-2-(thiazol-2-yl)imidazo[1,5-b]pyridazin-7-;

N-(4-((3S)-3-amino-1-piperidinyl)-3-pyridinyl)-2-(3-fluoro-2-pyridinyl)imidazo[1,5-b]pyridazin-7-amine;

N-(4-((trans)-5-amino-2-methylpiperidin-1-yl)pyridin-3-yl)-2-(3-fluoropyridin-2-yl)imidazo[1,5-b]pyridazin-7-amine (enantiomer 2);

N-(4-((2R,3S)-3-amino-2-methyl-1-piperidinyl)-3-pyridinyl)-2-(3-fluoro-2-pyridinyl)imidazo[1,5-b]pyridazin-7-amine;

N-(4-((3S)-3-amino-1-piperidinyl)-3-pyridinyl)-2-(2,6-difluorophenyl)imidazo[1,5-b]pyridazin-7-amine;

N-(4-((3S,5S)-3-amino-5-methylpiperidin-1-yl)pyridin-3-yl)-2-(2,6-difluorophenyl)imidazo[1,5-b]pyridazin-7-amine;

N-(4-((3S)-3-amino-1-piperidinyl)-3-pyridinyl)-2-(1,3-thiazol-2-yl)imidazo[1,5-b]pyridazin-7-amine; and N-(4-((cis)-3-amino-5-methylpiperidin-1-yl)pyridin-3-yl)-6-(2,6-difluorophenyl)-[1,2,4]triazolo[4,3-b]pyridazin-3-amine Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of cancer.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5-to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5-to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

"Heterocycle" means a ring comprising at least one carbon atom and at least one other atom selected from N, O and S. Examples of heterocycles that may be found in the claims include, but are not limited to, the following:

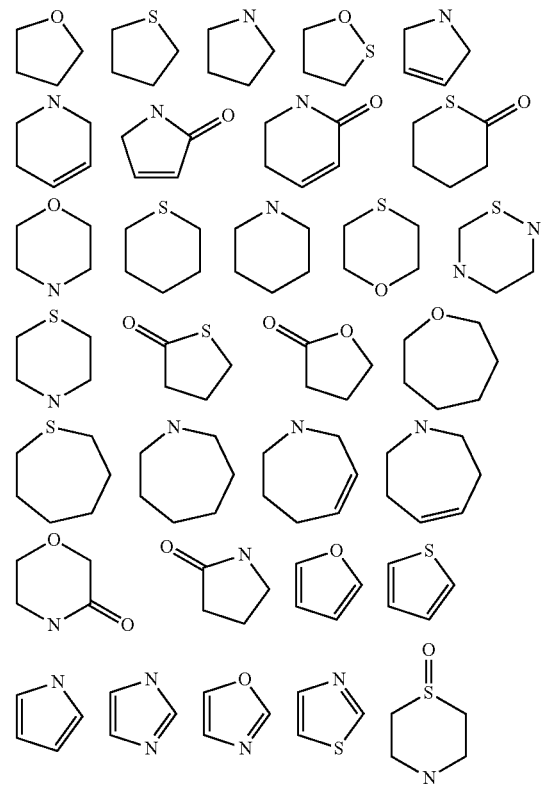

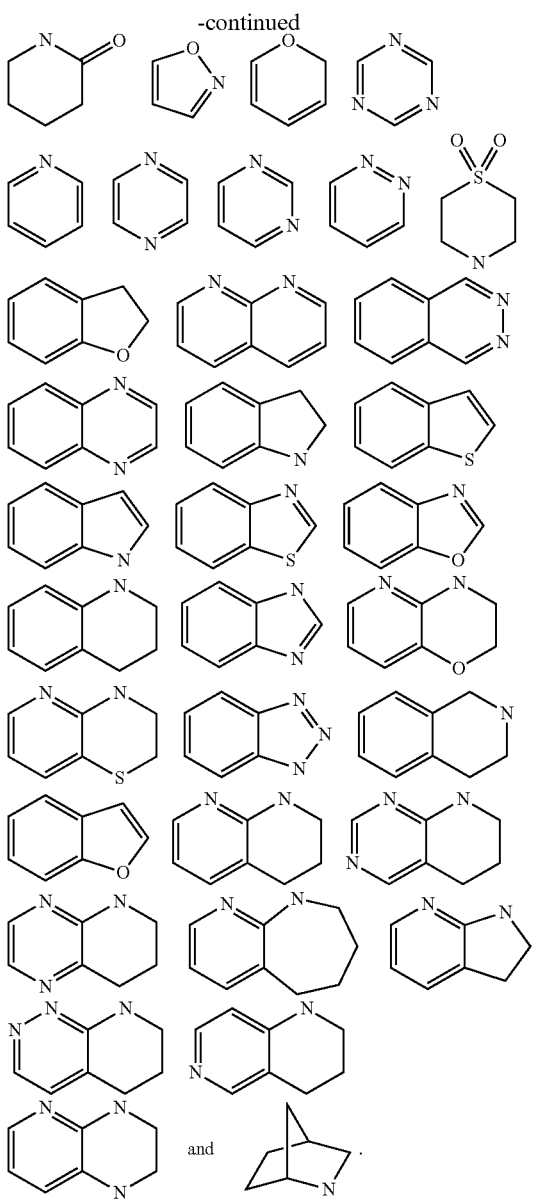

The terms "carboxy" or "carboxyl", whether used alone or with other terms, such as "carboxyalkyl", denotes —CO₂H.

The term "carbonyl", whether used alone or with other terms, such as "aminocarbonyl", denotes —(C=O)—.

The term "alkoxycarbonyl" denotes an ester group, containing an alkoxy substituted carbonyl.

The term "aminocarbonyl" denotes an amide group of the formula —C(=O)NH₂.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical. More preferred are phenylaminocarbonyl and substituted phenylaminocarbonyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "N-alkoxyalkylamino" and "N-alkoxyalkyl-N-alkylamino" denotes amino groups are substituted with one alkoxyalkyl radical and one alkyl radical and one alkoxyalkyls, respectively. More preferred alkoxyalkylamino radicals are "lower alkoxyalkylamino" radicals having an alkyl radical and alkoxy portions of one to six carbon atoms, attached to a nitrogen atom. Even more preferred are lower alkylamino radicals having one to three carbon atoms.

The term "arylamino" denotes amino groups which have been substituted with one or two aryl radicals, such as N-phenylamino. The arylamino radicals may be further substituted on the aryl ring portion of the radical.

The term "heterocyclylamino" denotes amino groups which have been substituted with one or two heterocyclyl radicals, such as N-thienylamino. The "heterocyclylamino" radicals may be further substituted on the heterocyclyl ring portion of the radical. The term heterocyclylamino includes heteroarylamino.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "heteroaryloxy" embraces optionally substituted heteroaryl radicals, as defined above, attached to an oxygen atom.

The term "cycloalkyl" includes saturated carbocyclic groups. Preferred cycloalkyl groups include C₃-C₆ rings. More preferred compounds include, cyclopentyl, cyclopropyl, and cyclohexyl.

The term "cycloalkenyl" includes partially saturated carbocyclic groups. Preferred cycloalkenyl groups include C₅-C₆ rings. More preferred compounds include, cyclopentenyl, cyclohexadienyl and cyclohexenyl.

"Benzo group", alone or in combination, means the divalent radical C₄H₄=, one representation of which is —CH=CH—CH=CH—, that when vicinally attached to another ring forms a benzene-like ring—for example tetrahydronaphthylene, indole and the like.

The term "oxo" represents the groups =O (as in carbonyl).

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups, and the like, for example as illustrated in the following examples:

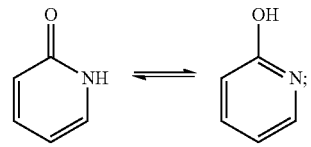 [SMILES: O=c1cccc[nH]1 ; Oc1ccccn1]

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)).

Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

An aspect of the present invention is a method for inhibiting Pim kinase activity in a cell, comprising contacting the cell with an effective amount of a compound of Formulas 1-2 and 1'-3'.

Another aspect of the present invention provides a method for treating a condition by modulation of Pim kinase activity comprising administering to a patient in need of such treatment an effective amount of a compound of Formulas 1-2 and 1'-3'.

Another embodiment of the present invention provides a method for treating a cancer disorder in a patient, comprising administering to the patient a composition comprising an amount of a compound of Formulas 1-2 and 1'-3' effective to inhibit Pim kinase activity in the patient.

Another embodiment of the present invention provides a method for treating a cancer disorder in a patient, wherein the cancer is protate, head and neck or lymphoma, comprising administering to the patient a composition comprising an amount of a compound of Formulas 1-2 and 1'-3' effective to inhibit Pim kinase activity in the patient.

Another aspect of the present invention provides the use of any one of the compounds of Formulas 1-2 and 1'-3' in the manufacture of a medicament for the treatment of cancer.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of Formulas 1-2 and 1'-3' may range from approximately 0.1-1000 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %, Combinations While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurrin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including CDK inhibitors, mTor inhibitors, Pi3k inhibitors, and Aurora kinase inhibitors.

Synthetic Methods

The compounds of the invention can be prepared according to the following procedures of Schemes 1-8, wherein the substituents are as defined for Formulas 1-2 and 1'-3', above, except where noted.

The following abbreviations may be used herein:
Ar argon
ACN, MeCN acetonitrile
Anh. anhydrous
A-Phos bis[di-tert-butyl-(4-dimethylaminophenyl)phosphine)]palladium (II) dichloride
Amphos (2-diphenylphosphinoethyl)trimethylammonium nitrate aq aqueous
ATP adenosine 5'-triphosphate
$Boc_2O$ Di-tert-butyl dicarbonate
Calcd or Calc'd calculated
$CDCl_3$ chloroform-deuterated
$CHCl_3$ chloroform
$CO_2$ carbon dioxide
$CS_2$ carbon disulfide
Conc. concentrated
$Cs_2CO_3$ cesium carbonate
CuI copper iodide
DCC N,N-dicyclohexylcarbodiimide
DCE 1,2-dichloroethane
DCM, $CH_2Cl_2$ dichloromethane
DEA diethylamine
DIPEA diisopropylethyl amine
DMAP dimethylaminopyridine
DMF N,N-dimethylformamide
DMF-d6 deuterated N,N-dimethylformamide
DMSO dimethyl sulfoxide
DMSO-d6 deuterated dimethyl sulfoxide
$D_2O$ deuterium oxide
EDTA ethyldiamine tetraacetic acid
EDC, EDC-HCl $N^1$-((ethylimino)methylene)-$N^3,N^3$-dimethylpropane-1,3-diamine hydrochloride
ESI electrospray ionization
$Et_2O$ diethyl ether
$Et_3N$ triethylamine
EtOAc ethyl acetate
EtOH ethyl alcohol
FBS fetal bovine serum
g grams
h hour
$H_2$ hydrogen
HCl hydrochloric acid
HI hydroiodic acid
$H_2SO_4$ sulfuric acid
$HNO_3$ nitric acid
$HCO_2H$ formic acid
$H_2NNH_2$ hydrazine
$H_2O$ water
$H_2O_2$ hydrogen peroxide
Hex hexanes
HOAc acetic acid
HOBt 1-hydroxybenzotriazole
HPLC high pressure liquid chromatography
HDPE hugh density polyethylene
HEPES 4-(2-hydroxyethyl)-piperazineethane sulfonic acid
IPA or iPrOH or iPr isopropyl alcohol
KOH potassium hydroxide
KOAc potassium acetate
$K_2CO_3$ potassium carbonate
L liter
LCMS, LC-MS or LC/MS liquid chromatography mass spectroscopy
LiHMDS lithium bis(trimethylsilyl)amide
LiOH lithium hydroxide
m/z mass divided by charge
MeOH methyl alcohol
MeOH-d4 deuterated methanol
mg milligrams
min minutes
mL milliliters
$MgSO_4$ magnesium sulfate
MS mass spectra
MTBE methyl tert-butyl ether
$N_2$ nitrogen
$NH_3$ ammonia
$NHEt_2$ diethylamine
$NEt_3$ triethylamine
$NH_4Cl$ ammonium chloride
$NH_4OH$ ammonium hydroxide
$NaBH_4$ sodium borohydride
NaCl sodium chloride
NaH sodium hydride
NaOAc sodium acetate
NaOH sodium hydroxide
$Na_2CO_3$ sodium carbonate
$NaHCO_3$ sodium bicarbonate
$NaN_3$ sodium azide
$NaNO_2$ sodium nitrite
$Na_2SO_4$ sodium sulfate
NBS N-bromosuccinimide
NMP N-methylpyrrolidone
NMR nuclear magnetic resonance
$PMe_3$ trimethylphosphine
$Pd(PPh_3)_4$ tetrakistriphenylphosphinepalladium (0)
$Pd_2(dba)_3$ tris(dibenzylideneacetone)dipalladium (0)
$Pd(dppf)Cl_2$ [(1,1-bis(diphenylphosphino)ferrocene]dichloropalladium(II)
$PdCl_2$ palladium chloride
Pd/C palladium on carbon
P protecting group
Pos. ion positive ion
PTFE polytetrafluoroethylene
rt or RT room temperature
Sat. saturated
SFC supercritical fluid chromatography
TBSOTf tert-butyldimethylsilyl trifluoromethanesulfonate
TFA trifluoroacetic acid
THF tetrahydrofuran
THF d8 deuterated tetrahydro furan
wt weight
TFE 2,2,2-trifluoroethanol
ZnBr zinc bromide

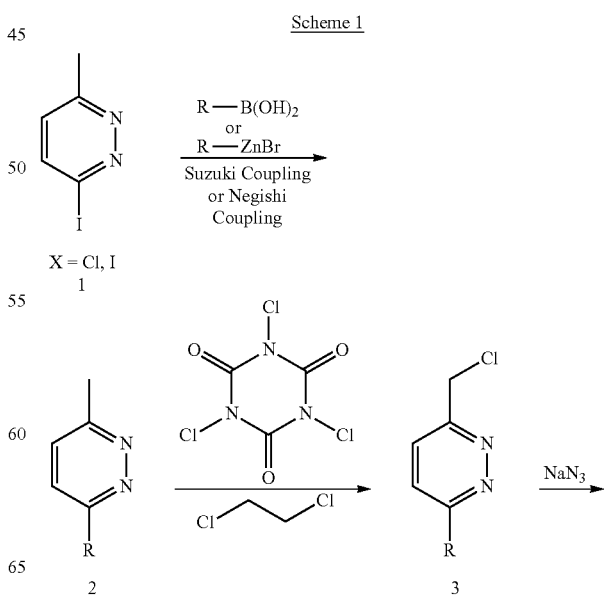

Scheme 1

Heteroaryl and aryl substituted azidomethyl-pyridazines 4 can be prepared according to the general method set out in Scheme 1. Via Suzuki coupling, treatment of the methyl halo pyridazines 1 with a boronic acid or ester ($R^1$—$B(OR^a)_2$), (where $R^a$ is H or alkyl) a base such as $Na_2CO_3$, a palladium compound such as $Pd(PPh_3)_4$ and a solvent such as dioxane provides the heteroaryl or aryl pyridazine intermediates 2. The reaction is maintained at a temperature about 105-115° C. Alternatively, via Negishi Coupling, treatment of the methyl halo pyridazines 1 with an aryl zinc bromide ($R^1$—ZnBr) and a palladium compound such as and A-Phos in a solvent such as THF provides the heteroaryl or aryl pyridazine intermediates 2. The reaction was maintained at a temperature about 60° C. Chlorination provides the chloro intermediates 3. Treatment of 3 with $NaN_3$ provides heteroaryl and aryl substituted azidomethyl-pyridazines 4.

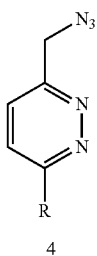

4 pyridine intermediates 5. The nitro and alkenyl groups can be reduced using conditions such as 10% Pd/C with $H_2$ gas to yield 6. Treatment of 6 with thiophosgene and a base such as $NEt_3$ yields isothiocyanates 8. Alternatively, pyridyl or phenyl amines 6 can be treated with 1,1'-thiocarbonyldiimidazole in a solvent such as THF to give isothiocyanates 8. The reaction was maintained at a temperature about 60° C. Alternatively, treatment of 6 with $NaNO_2$ in the presence of acids such as $H_2SO_4$ followed by the addition of $NaN_3$ provided 7. Isothiocyanates 8 can be prepared by the treatment of azides 7 with a phosphine such as $PMe_3$ followed by the addition of $CS_2$.

Scheme 3

Scheme 2

Alkylamino, alkoxy, alkyl, and halogen substituted pyridyl and alkylamino substituted phenyl isothiocyanates 8 (where $R^b$ is H or alkyl, $R^c$ is H or alkyl, or where $R^b$ and $R^c$ together form a heterocyclic ring; and $R^d$ is alkyl, cycloalkyl or 5-6-membered heterocyclyl) can be prepared according to the general method set out in Scheme 2. 4-Chloro-3-nitropyridine, 3-fluoro-4-nitropyridine or 1-fluoro-2-nitrobenzene is treated with an amine and a base such as DIPEA or with an alcohol and a base such as NaH to provide alkyl amino or alkoxy substituted nitro pyridine or alkylamino phenyl intermediates 5. Alternatively, a Suzuki coupling with alkenyl and phenyl boronic esters with a base such as $Na_2CO_3$, a palladium compound such as $Pd(PPh_3)_4$ and a solvent such as dioxane provides the alkenyl and phenyl substituted nitro -continued -continued

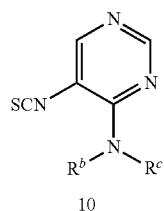

10

Alkylamino substituted pyrimidyl isothiocyanates 10 can be prepared according to the general method set out in Scheme 3. Treatment of 5-amino-4-chloropyrimidine with an alkyl amine and a base such as $Cs_2CO_3$ and a solvent such as DMF provides alkyl amino pyrimidyl amines 9. The reaction was maintained at a temperature about 150° C. Alkyl amino pyrimidyl amines 9 can be treated with 1,1'-thiocarbonyldiimidazole in a solvent such as THF to give isothiocyanates 10. The reaction is maintained at a temperature about 60° C.

Scheme 4

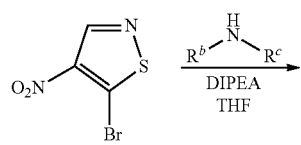

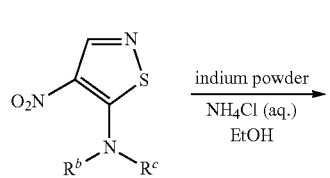

11

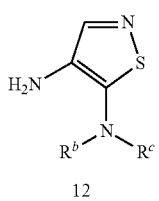

12

| 1. $NaNO_2$, $H_2SO_4$
| 2. $NaN_3$

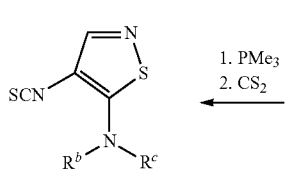

14  13

Alkylamino substituted thiazolyl isothiocyanates 14 can be prepared according to the general method set out in Scheme 4.

5-Bromo-4-isothiazole can be treated with alkylamines and a base such as DIPEA in a solvent such as THF to provide 11. The nitro group of 11 can be reduced with indium powder to give 4-amino thiazoles 12. Treatment of 12 with $NaNO_2$ in the presence of acids such as $H_2SO_4$ followed by the addition of $NaN_3$ provides 13. Thiazolyl isothiocyanates 14 can be prepared by the treatment of azides 13 with a phosphine such as $PMe_3$ followed by the addition of $CS_2$.

Scheme 5

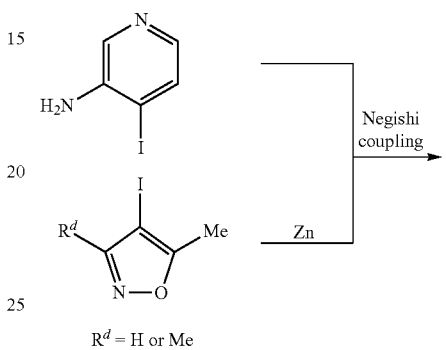

$R^d$ = H or Me

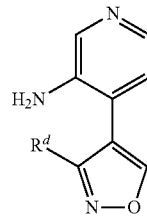

15

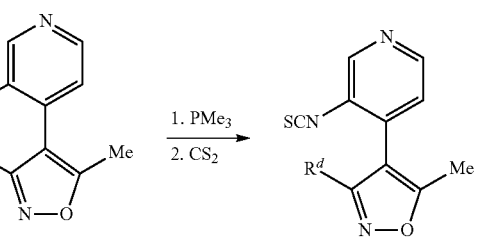

16  17

Isoxazole substituted pyridyl isothiocyanates 17 can be prepared according to the general method set out in Scheme 5. A Negishi coupling between 3-amino-4-iodo pyridine and 4-iodo-5-methylisoxazole or 3,5-dimethyl-4-iodoisoxazole with a palladium compound such as A-Phos and a solvent such as THF provides isoxazole substituted pyridyl amines 15. Treatment of 15 with $NaNO_2$ in the presence of acids such as $H_2SO_4$ acid followed by the addition of $NaN_3$ provided 16. Isoxazole substituted pyridyl isothiocyanates 17 can be prepared by the treatment of azides 16 with a phosphine such as $PMe_3$ followed by the addition of $CS_2$.

Scheme 6

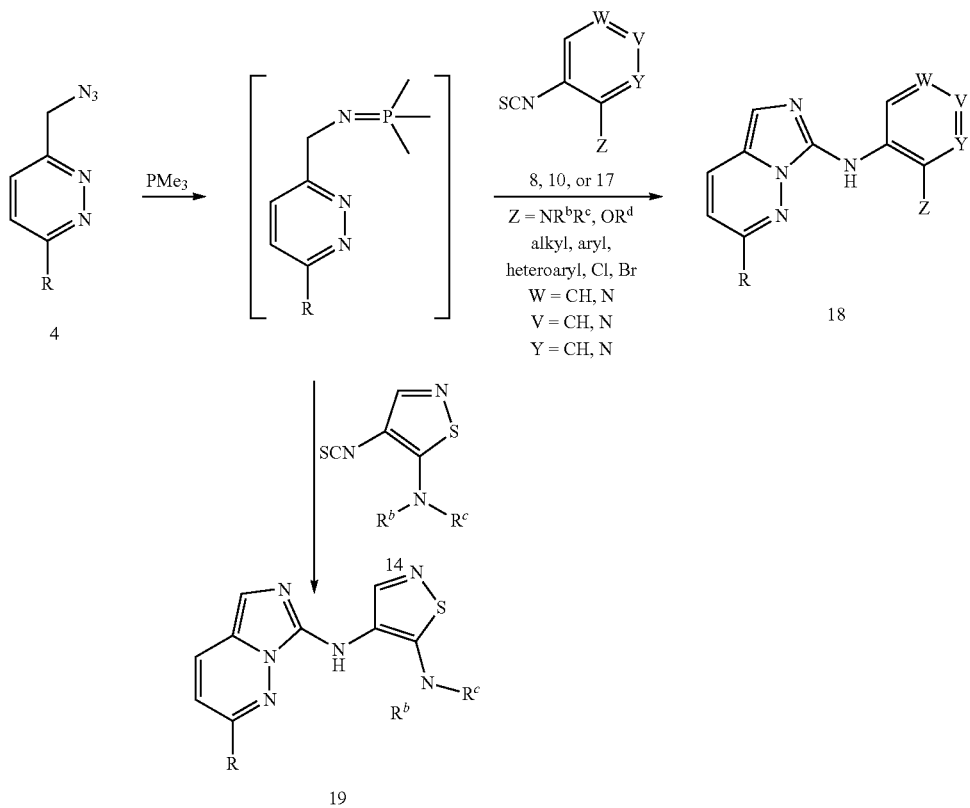

The pyridylamino, pyrimidylamino and phenylamino substituted imidazo pyridazines 18 can be prepared according to the general method set out in Scheme 6. Treatment of azidomethyl-pyridazines 4 with a phosphine such as PMe₃ followed by the addition of heteroaryl or phenyl isothiocyanates 8, 10 or 17 yields the imidazo pyridazines 18. In a similar fashion, thiazolylamino substituted imidazo pyridazines 19 PMe₃ followed by the addition of thiazolyl isothiocyanates 14.

Aryl and heteroaryl substituted pyridyl imidazo pyridazines 21 can be prepared according to the general method set out in Scheme 7. A Suzuki coupling reaction of 20 with a boronic acid or ester ($R^3$—$B(OR^a)_2$), a base such as $Na_2CO_3$, a palladium compound such as $Pd(PPh_3)_4$ and a solvent such as dioxane provides the aryl and heteroaryl substituted pyridines 21. The reaction is maintained at a temperature about 120° C. or 130° C.

Scheme 7

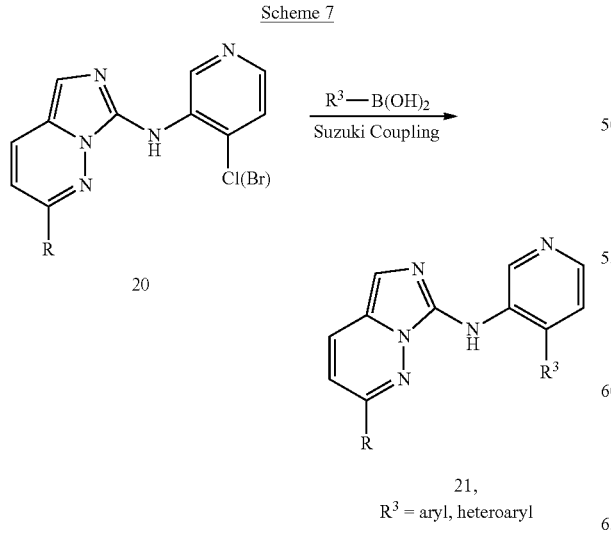

Scheme 8

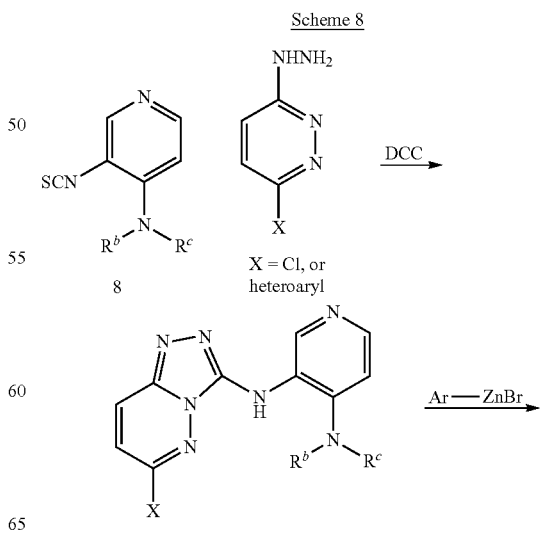

-continued

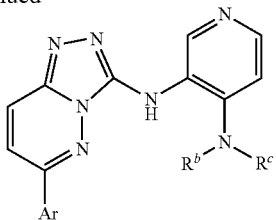

23

Aryl and heteroaryl substituted pyridyl triazolo pyridazines 23 can be prepared according to the general method set out in Scheme 8. Treatment of isothiocyanate 8 with 3-choro-6-hydrazinylpyridazine or 3-choro-6-phenylpyridazine followed by the addition of DCC provides 22. A Negishi coupling reaction of chloro substituted pyridyl triazolo pyridazine 22 with an aryl zinc bromide, a palladium compound such as A-Phos and a solvent such as THF provides the aryl substituted pyridyl triazolo pyridazines 23. The reaction is maintained at a temperature about 90° C.

The starting compounds defined in Schemes 1-8 may also be present with functional groups in protected form if necessary and/or in the form of salts, provided a salt-forming group is present and the reaction in salt form is possible. If so desired, one compound of formulas 1-2 and 1'-3' can be converted into another compound of formulas 1-2 and 1'-3' or a N-oxide thereof; a compound of formulas 1-2 and 1'-3' can be converted into a salt; a salt of a compound of formulas 1-2 and 1'-3' can be converted into the free compound or another salt; and/or a mixture of isomeric compounds of formulas 1-2 and 1'-3' can be separated into the individual isomers.

N-Oxides can be obtained in a known manner by reacting a compound of formulas 1-2 and 1'-3' with $H_2O_2$ or a peracid, e.g. 3-chloroperoxy-benzoic acid, in an inert solvent, e.g. dichloromethane, at a temperature between about −10-35° C., such as about 0° C.-RT.

If one or more other functional groups, for example carboxy, hydroxy, amino, or mercapto, are or need to be protected in a compound of formulas 1-2 and 1'-3' or in the synthesis of a compound of formulas 1-2 and 1'-3', because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas 1-2 and 1'-3' with a salt-forming group may be prepared in a manner known per se. Acid addition salts of compounds of formulas 1-2 may thus be obtained by treatment with an acid or with a suitable anion exchange reagent. A salt with two acid molecules (for example a dihalogenide of a compound of formulas 1-2 and 1'-3') may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas 1-2 and 1'-3'.

Salts can usually be converted to free compounds, e.g. by treating with suitable basic agents, for example with alkali metal carbonates, alkali metal hydrogen carbonates, or alkali metal hydroxides, typically potassium carbonate or NaOH.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, 2-propanol, nitriles, typically MeCN, halogenated hydrocarbons, typically DCM, acid amides, typically DMF, bases, typically heterocyclic nitrogen bases, e.g. pyridine, carboxylic acids, typically lower alkanecarboxylic acids, e.g., HOAc, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas 1-2 and 1'-3', including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction. As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ Ed. (2001); M. Bodansky, A. Bodanszky: The practice of Peptide Synthesis Springer-Verlag, Berlin Heidelberg 1984; J. Seyden-Penne: Reductions by the Alumino- and Borohydrides in Organic Synthesis, $2^{nd}$ Ed., Wiley-VCH, 1997; and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas 1-2 and 1'-3'. These detailed descriptions fall within the scope, and serve to exemplify, the above described General Synthetic Procedures which form part of the invention. These detailed descriptions are presented for illustrative purposes only and are not intended as a restriction on the scope of the invention.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. MS data was determined by electrospray ionization technique. All examples were purified to >90% purity as determined by high-performance liquid chromatography. Unless otherwise stated, reactions were run at RT.

Analytical Methods:

Unless otherwise indicated, HPLC analyses were run on an Agilent Model 1100 system with an Agilent Technologies Zorbax SB-$C_8$ (5μ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Methods:

Unless otherwise indicated, samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min. The mobile phase used a mixture of solvent A ($H_2O$/0.1% $HCO_2H$ or TFA) and solvent B (ACN/0.1% $HCO_2H$ or TFA) with a 5 to for a gradient from 10% to 90% solvent B. The gradient was followed by a 0.5 min period 9 min time period to return to 10% solvent B and a 2.5 min 10% solvent B re-equilibration (flush) of the column Preparative HPLC Methods Where indicated, compounds of the present invention were purified via reverse phase HPLC using the following conditions:

Prep HPLC Method 1 Preparative reverse-phase HPLC was performed on a 30×250 mm Phenomenex Luna PFP(2) perfluorophenyl column (OOG-4448-UO-AX, 5 μm particle, A=0.1% TFA in water; B=0.1% TFA in ACN). The column and a 60 inch, 0.020 id stainless steel segment of tubing were immersed into a 45° C. glycol bath; Flow=40 mL min$^{-1}$ Gradient: 0→5 min: isocratic at @10% B; 5→60 min:linear gradient to 55% B; 60→70 min: isocratic at @55% B; at 70.01 min. step to 100% B, hold for 10 min; at 80.1 min, step to 10% B; 80 min end.

Prep HPLC Method 2 Preparative reverse-phase HPLC was performed on a Waters Xterra Prep $C_{18}$ MS Packed by Vydac/The Separations Group, 50 mm×300 mm (PA0000-050730, 10 μm particle size, spherical shape, A=0.1% TFA in water; B=10% TFE-0.1% TFA-89.9% ACN; glycol from an external heat transfer unit set to 45° C. was flowed through the column jacket. The manual injector sample loop, and the precolumn tubing were immersed into the heat transfer bath); gradient: 0→4 min@20 mL/min, 25% B; 4→5 min, 20→100 mL/min@25% B; 5→25 min@100 mL/min, linear gradient to 55% B; 25→35 min@100 mL/min, isocratic at 55% B; 35 min, step to 100% B@100 mL/min; 35→50 min@100 mL/min, 100% B; 50 min, step to 25% B@ 100 mL/min; 60 min end.

Prep HPLC Method 3 Preparative reverse-phase HPLC was performed on a Gilson GX-281 equipped with a Phenomenex Synergi $C_{18}$ column (00F-4435-U0-AX) (150×30 mm, 5 μm) or a SiliaChrom XT $C_{18}$ column with UV detection at 254 nm eluting with 5-95% MeCN in $H_2O$ with 0.1% TFA for 11 min at 45 mL/min. The gradient is followed by a 1 min return to 5% MeCN.

Prep HPLC method 4 Preparative reverse-phase HPLC was performed on a Shimadzu SIL-10AP auto injector and Shimadzu FRC-10A fraction collector equipped with a Phenomenex Synergi $C_{18}$ column (00F-4436-U0-AX) (150×30 mm, 10 μm) with UV detection at 254 nm eluting with 5-100% MeCN in water with 0.1% TFA for 15 min at 35 mL/min. The gradient is followed by a 1 min return to 5% MeCN.

Prep HPLC method 5 Preparative reverse-phase HPLC was performed with a Phenomenex Gemini-NX C18 110A column (100×21 mm, 5 pan) with UV detection at 254 nm (Waters 2487 or Waters PD) eluting with 10-60% or 10-90% $CH_3CN$ in water with 0.1% $NH_4OH$ for 8 min at 44 mL/min. The gradient is followed by a 2 minute return to 10% $CH_3CN$.

Mass Spectra (MS)

Unless otherwise indicated, all mass spectral data for starting materials, intermediates and/or exemplary compounds are reported as mass/charge (m/z), having an (M+H$^+$) or (M−H$^-$) molecular ion, depending on the inonization mode (positive or negative). The molecular ion reported was obtained by electrospray detection method. Compounds having an isotopic atom, such as bromine and the like, are reported according to the detected isotopic pattern, as appreciated by those skilled in the art.

Preparation I.
3-(azidomethyl)-6-(2,6-difluorophenyl)pyridazine

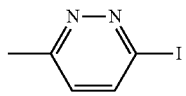

Step 1. 3-iodo-6-methylpyridazine. In a 1-L round bottomed flask, a mixture of 3-chloro-6-methylpyridazine (8.84 g, 68.8 mmol) and HI (57% wt. in $H_2O$) (144 mL, 688 mmol) was heated in an oil bath at 100° C. for 2 h. The mixture was cooled in an ice bath and stirred for 15 min. The precipitated solid was filtered through a fritted funnel and the aqueous solution was discarded. The solid was stirred in 400 mL of EtOAc and 100 mL of saturated $NaHCO_3$ (aq). The basic aqueous layer was separated and extracted with EtOAc (2×100 mL). The combined organic layers were dried over anh. $Na_2SO_4$, filtered and concentrated to give 3-iodo-6-methylpyridazine (8.15 g, 37.0 mmol, 54% yield) as a tan solid. MS (ESI, pos. ion) m/z: 220.9 (M+1). $^1$H NMR (400 MHz, $CDCl_3$) δ ppm 7.73 (d, J=8.61 Hz, 1 H), 7.01 (d, J=8.61 Hz, 1 H), 2.66 (s, 3 H).

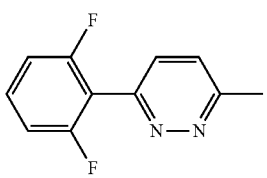

Step 2. 3-(2,6-difluorophenyl)-6-methylpyridazine. In a 1-L round bottomed flask was placed 3-iodo-6-methylpyridazine (8.15 g, 37.0 mmol) and A-phos (1.05 g, 1.48 mmol). The flask was sealed and purged with argon for 5 min. (2,6-Difluorophenyl)zinc(II) bromide (0.5 M solution in THF) (104 mL, 51.9 mmol, Rieke Metals Inc.) was added by cannula and the flask was fitted with a reflux condensor and the mixture was heated in an oil bath at 60° C. for 1 h. After cooling to RT, 120 mL of 1 M NaOH (aq.) was added. The mixture was extracted with EtOAc (3×200 mL). The combined organic layers were dried over anh. $Na_2SO_4$, filtered and concentrated to give a brown solid. The crude material was purified by silica gel chromatography (20-50% EtOAc in hexanes) to provide 3-(2,6-difluorophenyl)-6-methylpyridazine (7.12 g, 34.5 mmol, 93% yield) as a tan solid. MS (ESI, pos. ion) m/z: 207.1 (M+1). $^1$H NMR (400 MHz, $CDCl_3$) δ ppm 7.51-7.56 (m, 1 H), 7.36-7.46 (m, 2 H), 6.98-7.10 (m, 2 H), 2.80 (s, 3 H).

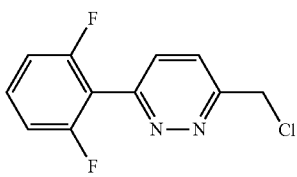 [SMILES: Fc1cccc(F)c1-c1ccc(CCl)nn1]

Step 3. 3-(chloromethyl)-6-(2,6-difluorophenyl)pyridazine. A mixture of 3-(2,6-difluorophenyl)-6-methylpyridazine (7.12 g, 34.5 mmol) and trichloroisocyanuric acid (3.21 g, 13.81 mmol) in DCE (300 mL) was stirred and heated at 90° C. The mixture was cooled and filtered through a medium glass frit. The white solid was washed with DCM. The solid was discarded and the collected filtrate was concentrated and purified by silica gel chromatography (15-60% EtOAc in hexanes) to provide 3-(chloromethyl)-6-(2,6-difluorophenyl)pyridazine (5.04 g, 20.94 mmol, 61% yield) as a tan solid. MS (ESI, pos. ion) m/z: 240.9 (M+1). $^1$H NMR (400 MHz, $CDCl_3$) δ ppm 7.83 (d, J=8.80 Hz, 2 H), 7.68-7.74 (m, 2 H), 7.40-7.50 (m, 1 H), 7.02-7.12 (m, 2 H), 4.98 (s, 2 H).

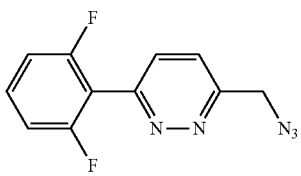 [SMILES: [N-]=[N+]=NCc1ccc(-c2c(F)cccc2F)nn1]

Step 4. 3-(azidomethyl)-6-(2,6-difluorophenyl)pyridazine. A mixture of 3-(chloromethyl)-6-(2,6-difluorophenyl)pyridazine (5.04 g, 20.94 mmol) and $NaN_3$ (1.77 g, 27.2 mmol) in DMF (20 mL) was stirred at RT for 3 h. Water was added and the mixture was extracted with EtOAc (3×). The combined organic layers were washed with brine (2×), dried over anh. $Na_2SO_4$, filtered and concentrated. The crude was purified by silica gel chromatography (25-75% EtOAc in hexanes) to provide 3-(azidomethyl)-6-(2,6-difluorophenyl)pyridazine (4.85 g, 19.62 mmol, 94% yield) as a light-yellow solid. MS (ESI, pos. ion) m/z: 248.0 (M+1). $^1$H NMR (400 MHz, $CDCl_3$) δ ppm 7.64-7.74 (m, 2 H), 7.38-7.50 (m, 1 H), 7.00-7.13 (m, 2 H), 4.85 (s, 2 H).

Preparation II.
2-(6-(azidomethyl)pyridazin-3-yl)thiazole

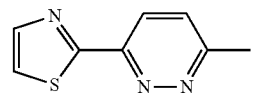

Step 1. 2-(6-methylpyridazin-3-yl)thiazole. In a 20 mL glass microwave tube, 3-chloro-6-methylpyridazine (508 mg, 3.95 mmol) and Pd(dppf)$Cl_2$ (161 mg, 0.20 mmol) were treated with thiazol-2-ylzinc(II) bromide (11.9 mL of 0.5 M solution in THF, 5.95 mmol, Aldrich) via syringe under an atmosphere of argon. The solution was heated in the microwave at 70° C. for 30 min. The reaction was treated with 0.34 M EDTA (pH=7.4 with LiOH) (3.5 mL) and stirred for 10 min. It was extracted with EtOAc (50 mL), washed with brine (2×25 mL) and dried over $MgSO_4$, filtered through a plug of Celite and concentrated. Purification by silica gel chromatography (0-20% MeOH in $CH_2Cl_2$) afforded 2-(6-methylpyridazin-3-yl)thiazole (665 mg, 95% yield) as a rust-colored solid after drying under high vacuum overnight. MS (ESI, pos. ion) m/z: 178.1 (M+1). $^1$H NMR (400 MHz, DMSO-$d_6$) δ ppm 8.25 (1 H, d, J=8.8 Hz), 8.09 (1 H, d, J=3.3 Hz), 7.93-8.02 (1 H, m), 7.76 (1 H, d, J=8.6 Hz), 2.71 (3 H, s).

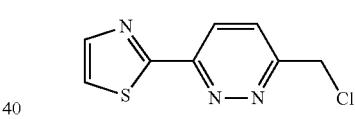

Step 2. 2-(6-(chloromethyl)pyridazin-3-yl)thiazole. 2-(6-Methylpyridazin-3-yl)thiazole (643 mg, 3.63 mmol) was treated with DCE (20 mL) and trichloroisocyanuric acid (590 mg, 2.54 mmol). The flask was fitted with a reflux condenser and heated to 90° C. in an oil bath. After 30 min, the mixture was cooled to RT filtered through a 0.45 μm acrodisc directly onto a plug of silica gel and purified by silica gel chromatography (30-100% EtOAc in hexanes) to afford 2-(6-(chloromethyl)pyridazin-3-yl)thiazole (276 mg, 36% yield) as an off-white crystalline solid. MS (ESI, pos. ion) m/z: 212.0 (M+1). $^1$H NMR (400 MHz, $CDCl_3$) δ ppm 8.38 (1H, d, J=8.8 Hz), 8.01 (1 H, d, J=3.1 Hz), 7.81 (1 H, d, J=8.8 Hz), 7.55 (1 H, d, J=3.1 Hz), 4.94 (2 H, s).

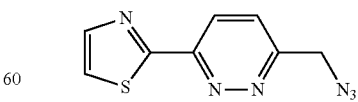

Step 3. 2-(6-(azidomethyl)pyridazin-3-yl)thiazole. 2-(6-(Chloromethyl)pyridazin-3-yl)thiazole (337 mg, 1.59 mmol) in DMF (3 mL) was treated with $NaN_3$ (135 mg, 2.07 mmol) and stirred at RT overnight (15 h). The reaction was treated with water, extracted with EtOAc (25 mL), washed with brine (2×25 mL), dried over MgSO$_4$, filtered and concentrated. The crude residue was purified by silica gel chromatography (0-50% EtOAc in hexanes) to provide 2-(6-(azidomethyl)pyridazin-3-yl)thiazole (295 mg, 85% yield) as a light yellow crystalline solid. MS (ESI, pos. ion) m/z: 219.1 (M+1). $^1$H NMR (400 MHz, CDCl$_3$) δ ppm 8.38 (1 H, d, J=8.8 Hz), 8.01 (1 H, d, J=3.1 Hz), 7.68 (1 H, d, J=8.6 Hz), 7.55 (1 H, d, J=3.1 Hz), 4.80 (2 H, s).

Preparation III.
3-(azidomethyl)-6-(2-chlorophenyl)pyridazine

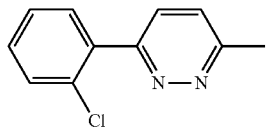

Step 1. 3-(2-chlorophenyl)-6-methylpyridazine. A mixture of 3-chloro-6-methylpyridazine (1.00 g, 7.78 mmol, Aldrich), 2-chlorophenylboronic acid (1.46 g, 9.33 mmol), and Pd(PPh$_3$)$_4$ (0.449 g, 0.389 mmol) was purged with argon and treated with dioxane (10 mL) and 1 M Na$_2$CO$_3$ (aq., 11.7 mL, 11.7 mmol) and heated in the microwave at 110° C. for 35 min. The mixture was diluted with EtOAc (50 mL), washed with 1 N NaOH (10 mL), followed by brine (25 mL). The organic extracts were concentrated under reduced pressure (rotary evaporator) and dried over MgSO$_4$ and concentrated. The residue was purified by silica gel chromatography (40-100% EtOAc in hexanes) to afford 3-(2-chlorophenyl)-6-methylpyridazine (1.51 g, 95% yield) as a light yellow crystalline solid. MS (ESI, pos. ion) m/z: 205.1 (M+1). $^1$H NMR (400 MHz, CDCl$_3$) δ ppm 7.69-7.79 (2 H, m), 7.46-7.54 (1 H, m), 7.35-7.45 (3 H, m), 2.79 (3 H, s).

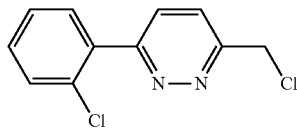 [SMILES: ClCc1ccc(-c2ccccc2Cl)nn1]

Step 2. 3-(chloromethyl)-6-(2-chlorophenyl)pyridazine. 3-(2-Chlorophenyl)-6-methylpyridazine (1.16 g, 5.67 mmol) was treated with DCE (25 mL) and trichloroisocyanuric acid (0.527 g, 2.27 mmol), the flask fitted with a reflux condenser and heated to 90° C. in an oil bath for 30 min. The mixture was filtered through a 0.45 μm acrodisc directly onto a plug of silica gel and purified by silica gel chromatography (0-50% EtOAc in hexanes) to afford 3-(chloromethyl)-6-(2-chlorophenyl)pyridazine (1.11 g, 82% yield) as an off-white crystalline solid. MS (ESI, pos. ion) m/z: 239.0 (M+1). $^1$H NMR (400 MHz, CDCl$_3$) δ ppm 7.94 (1 H, d, J=8.8 Hz), 7.71-7.82 (2 H, m), 7.49-7.57 (1 H, m), 7.38-7.48 (2 H, m), 4.97 (2 H, s).

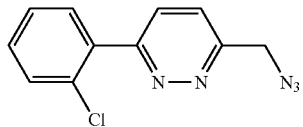 [SMILES: [N-]=[N+]=NCc1ccc(-c2ccccc2Cl)nn1]

Step 3. 3-(azidomethyl)-6-(2-chlorophenyl)pyridazine. 3-(Chloromethyl)-6-(2-chlorophenyl)pyridazine (1.20 g, 5.02 mmol) in DMF (10 mL) was treated with NaN$_3$ (0.424 g, 6.52 mmol) and stirred at RT overnight (15 h). The mixture was treated with H$_2$O, extracted with EtOAc (2×35 mL), washed with brine (2×25 mL), dried over MgSO$_4$, filtered and concentrated. Purification by silica gel chromatography (0-60% EtOAc in hexanes) afforded 3-(azidomethyl)-6-(2-chlorophenyl)pyridazine (1.12 g, 91% yield) as a viscous colorless oil which crystallized upon standing. MS (ESI, pos. ion) m/z: 245.9 (M+1). $^1$H NMR (400 MHz, CDCl$_3$) δ ppm 7.93 (1 H, d, J=8.8 Hz), 7.71-7.79 (1 H, m), 7.63 (1 H, d, J=8.8 Hz), 7.48-7.56 (1 H, m), 7.37-7.47 (2 H, m), 4.83 (2 H, s).

Preparation IV.
3-(Azidomethyl)-6-(2-chloro-3-pyridinyl)pyridazine

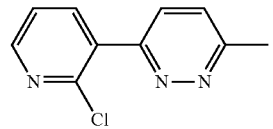

Step 1. 3-(2-Chloro-3-pyridinyl)-6-methylpyridazine. A mixture of 3-chloro-6-methylpyridazine (1.20 g, 9.33 mmol), 2-chloro-3-pyridinylboronic acid (1.62 g, 10.27 mmol, Frontier Scientific, Logan, Utah), Na$_2$CO$_3$ (1.98 g, 18.67 mmol), Pd(PPh$_3$)$_4$ (0.54 g, 0.46 mmol) in 12 mL of dioxane and 4 mL of H$_2$O was heated in a microwave at 105° C. for 45 min. The reaction was diluted with 100 mL of EtOAc, washed with 5 mL of 0.5 N NaOH (aq.), followed by 5 mL of brine. The organic extract was concentrated and the residue was purified by silica gel chromatography (50-100% EtOAc in hexanes) to give 3-(2-chloro-3-pyridinyl)-6-methylpyridazine (571 mg, 29% yield) as an off white crystalline solid. MS (ESI, pos. ion) m/z: 190.1 (M+1).

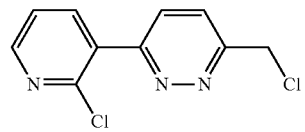 [SMILES: ClCc1ccc(-c2cccnc2Cl)nn1]

Step 2. 3-(chloromethyl)-6-(2-chloro-3-pyridinyl)pyridazine. To a solution of 3-(2-chloro-3-pyridinyl)-6-methylpyridazine (360 mg, 1.75 mmol) in DCE (5 mL) was added trichloroisocyanuric acid (163 mg, 0.70 mmol) in one portion. The reaction was heated at 90° C. in an oil bath for 1 h. After cooling to RT, the precipitated solid was filtered through a fritted funnel and rinsed with 3×25 mL of DCM. The filtrate was washed with 2×10 mL of 0.5 M NaOH (aq.) followed by 5 mL of brine. The DCM solution was concentrated and the residue was purified by silica gel chromatography (25-85% EtOAc in hexanes) to give 3-(chloromethyl)-6-(2-chloro-3-pyridinyl)pyridazine (215 mg, 51% yield) as a brown crystalline solid. MS (ESI, pos. ion) m/z: 204.1 (M+1).

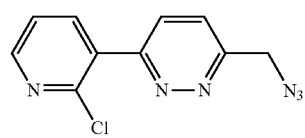

Step 3. 3-(azidomethyl)-6-(2-chloro-3-pyridinyl)pyridazine. To a solution of 3-(chloromethyl)-6-(2-chloropyridin-3-yl)pyridazine (211 mg, 0.88 mmol) in 5 mL of acetone at RT was added NaN₃ (86 mg, 1.32 mmol). The mixture was stirred at RT for 5 h. The reaction mixture was concentrated and the residue was partitioned between 5 mL of H₂O and 50 mL of EtOAc. The organic solution was concentrated and the residue was absorbed onto silical gel (5 g) and purified by silica gel chromatography (25-85% EtOAc in hexanes) to give 3-(azidomethyl)-6-(2-chloro-3-pyridinyl)pyridazine (178 mg, 82% yield) as an off white crystalline solid. MS (ESI, pos. ion) m/z: 247.0 (M+1). $^1$H NMR (400 MHz, DMSO-d₆) δ ppm 8.63 (1H, dd, J=4.7, 1.8 Hz), 8.27-8.08 (2 H, m), 7.95 (1 H, d, J=8.8 Hz), 7.69 (1 H, dd, J=7.5, 4.8 Hz), 4.92 (2 H, s).

Preparation V. 3-(azidomethyl)-6-chloropyridazine

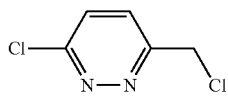

Step 1. 3-chloro-6-(chloromethyl)pyridazine. A mixture of 3-chloro-6-methylpyridazine (1.00 g, 7.78 mmol) and 1,3,5-trichloroisocyanuric acid (0.72 g, 3.11 mmol) in DCE (50 mL) was stirred and heated at 90° C. The mixture was cooled and filtered through a Whatman 0.45 μm frit. The collected white solid was washed with DCM. The solid was discarded and the collected filtrate was concentrated and purified by silica gel chromatography (0-50% EtOAc in hexanes) to provide 3-chloro-6-(chloromethyl)pyridazine (0.84 g, 5.12 mmol, 66% yield) as a slightly purple solid. MS (ESI, pos. ion) m/z: 162.9 (M+1).

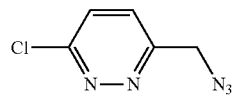

Step 2. 3-(azidomethyl)-6-chloropyridazine. A mixture of 3-chloro-6-(chloromethyl)pyridazine (835 mg, 5.12 mmol) and NaN₃ (433 mg, 6.66 mmol) in DMF (10 mL) was stirred overnight at RT. Water was added and the mixture was extracted with EtOAc (3×). The combined organic layers were washed with brine, dried over anh. Na₂SO₄, filtered and concentrated. The crude material was purified by silica gel chromatography (0-50% EtOAc in hexanes) to provide 3-(azidomethyl)-6-chloropyridazine (700 mg, 4.13 mmol, 81% yield) as an off-white solid. MS (ESI, pos. ion) m/z: 170.0 (M+1). $^1$H NMR (400 MHz, CDCl₃) δ ppm 7.57 (s, 2 H), 4.76 (s, 2 H).

The following compounds in Table 1 can be prepared via procedures similar to that described above:

TABLE 1

| Preparation | IUPAC Name | M + 1 | Preparation Method | Structure |
|---|---|---|---|---|
| VI | 3-(azidomethyl)-6-(2-fluorophenyl)pyridazine | 230.0 | III | 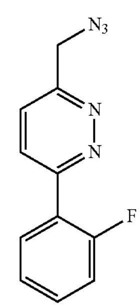 [SMILES: [N-]=[N+]=NCc1ccc(-c2ccccc2F)nn1] |
| VII | 3-(azidomethyl)-6-(2-fluoro-4-(methylsulfonyl)phenyl)pyridazine | 308.1 | III | 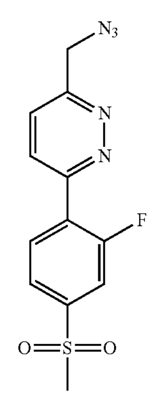 [SMILES: CS(=O)(=O)c1ccc(-c2ccc(CN=[N+]=[N-])nn2)c(F)c1] |

TABLE 1-continued

| Preparation | IUPAC Name | M + 1 | Preparation Method | Structure |
|---|---|---|---|---|
| VIII | 3-(azidomethyl)-6-(2-fluoro-3-pyridinyl)pyridazine | 231.1 | IV | 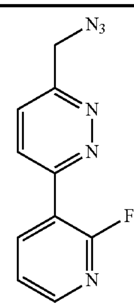 |
| IX | 3-(azidomethyl)-6-(2,4-dichlorophenyl)pyridazine | 280.1/282.1 | IV | 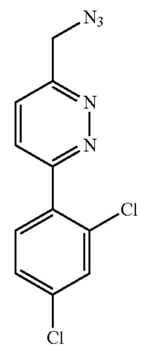 [SMILES: [N-]=[N+]=NCc1ccc(-c2ccc(Cl)cc2Cl)nn1] |
| X | 3-(azidomethyl)-6-(2,4-difluorophenyl)pyridazine | 248.0 | IV | 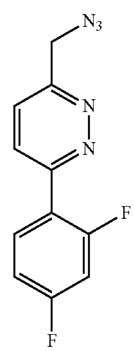 [SMILES: [N-]=[N+]=NCc1ccc(-c2ccc(F)cc2F)nn1] |

Preparation XI. tert-butyl ((3S)-1-(3-isothiocyanato-4-pyridinyl)-3-piperidinyl)carbamate.

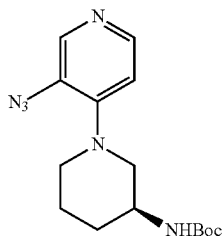 [SMILES: CC(C)(C)OC(=O)N[C@H]1CCCN(c2ccncc2N=[N+]=[N-])C1]

Step 1. tert-butyl ((3S)-1-(3-azido-4-pyridinyl)-3-piperidinyl)carbamate. A 3 neck, 100 mL Morton flask was charged with tert-butyl ((3S)-1-(3-amino-4-pyridinyl)-3-piperidinyl) carbamate (1.4 g, 4.79 mmol, prepared similar to that described in WO08/106,692), acetone (10 mL), H$_2$O (20 mL) and a stirbar. The flask was immersed into an ice-EtOH bath and stirred for 15 min. The heterogenous solution was treated with ice-cold 8 M H$_2$SO$_4$ (2.99 mL, 23.94 mmol) and stirred for 2 min. The temperature of the bath was maintained with dry ice and ranged from −15 to −5° C. The solution became homogenous over this time period. The solution was stirred an additional 3 min, and a solution of NaNO$_2$ (354 mg, 5.13 mmol) in water (2 mL) was added dropwise. The solution was stirred for 10 min. The solution was treated with NaN$_3$ (934 mg, 14.37 mmol), and stirred for 20 min. A powder addition funnel charged with anh. Na$_2$CO$_3$ (3.05 g, 28.7 mmol) was fitted to the center opening. The powder was added over a 5 min period, and the flask was removed from the cooling bath. The slurry was stirred/sonicated under a stream of N$_2$ for 1 h. The slurry was N$_2$-pressure filtered through a 28 mL Bohdan reaction vessel glass frit fitted with a 0.22 μm PTFE, 25 mm syringe filter unit (Millipore, SLFG025NK). The solids were washed with water (3×10 mL) and dried under a stream of N$_2$ overnight. The solids were further dried in a vacuum oven (45° C., <1 mm Hg) for 1 h to afford tert-butyl ((3S)-1-(3-azido-4-pyridinyl)-3-piperidinyl)carbamate (1.45 g, 4.55 mmol, 95% yield). $^1$H NMR (400 MHz, CDCl$_3$) δ ppm 1.47 (s, 9 H) 1.61-1.91 (m, 4 H) 3.12 (br. s., 3 H) 3.25 (br. d, J=11.30 Hz, 1 H) 3.89 (br. s., 1 H) 5.03 (br. s., 1 H) 6.78 (d, J=5.48 Hz, 1 H) 8.21 (d, J=5.48 Hz, 1 H) 8.28 (s, 1 H).

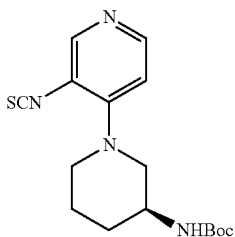

Step 2. tert-butyl ((3S)-1-(3-isothiocyanato-4-pyridinyl)-3-piperidinyl)carbamate. A dry, 3 neck, 100 mL Morton flask was configured as follows: opening 1: septa/Ar inlet; opening 2 (center): septa/PTFE addition needle; opening 3: septa. The flask was charged with tert-butyl ((3S)-1-(3-azido-4-pyridinyl)-3-piperidinyl)carbamate (3.25 g, 10.22 mmol), a stirbar, and dry THF (10 mL). The slurry was stirred for 10 min, and immersed into an ice-water bath. A syringe charged with 1.0 M PMe$_3$ in THF (10.73 mL, 10.73 mmol, Aldrich) was fitted to the PTFE addition needle and added over a 15 min period via a syringe pump. The reaction was stirred for 15 min. The solution was charged to a dry 50 mL glass syringe via the PTFE addition needle to afford (S)-tert-butyl (1-(3-((trimethylphosphoranylidene)amino)pyridin-4-yl)piperidin-3-yl)carbamate. A dry, 250 mL, one neck round bottom flask was charged with dry THF (16 mL), carbon disulfide (6.17 mL, 102 mmol) and a stirbar. The flask was fitted with a septa/Ar inlet, and immersed into an ice-water bath. The solution was stirred for 15 min. The septa was pierced with the PTFE addition needle fitted to the 50 mL glass syringe containing the solution of (S)-tert-butyl (1-(3-((trimethylphosphoranylidene)amino)pyridin-4-yl)piperidin-3-yl)carbamate and the solution (19 mL) was added via syringe pump over a 1 h period. The reaction was stirred an additional 10 min and the solvent was removed in vacuo. The residue was further dried at <1 mm Hg at RT to afford tert-butyl ((3S)-1-(3-isothiocyanato-4-pyridinyl)-3-piperidinyl)carbamate. MS (ESI, pos. ion) m/z: 335.0 [M+H].

Preparation XII. tert-butyl 4-(3-isothiocyanato-4-pyridinyl)-1-piperazinecarboxylate

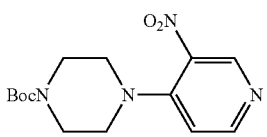 [SMILES: CC(C)(C)OC(=O)N1CCN(c2ccncc2[N+](=O)[O-])CC1]

Step 1. tert-butyl 4-(3-nitro-4-pyridinyl)-1-piperazinecarboxylate. To a solution of t-Boc-piperazine (1.41 g, 7.57 mmol, Alfa-Aesar) in 2-propanol (63 mL) was added DIPEA (2.75 mL, 15.77 mmol) and 4-chloro-3-nitropyridine (1.00 g, 6.31 mmol, Oakwood Products Inc., West Columbia, S.C.). The mixture was heated to 60° C. and stirred for 2 h. The mixture was cooled to RT and concentrated. The residue was diluted with EtOAc and washed with brine. The crude material was purified by silica gel chromatography (25-100% EtOAc in hexanes) to provide tert-butyl 4-(3-nitro-4-pyridinyl)-1-piperazinecarboxylate (1.74 g, 5.64 mmol, 89% yield) as a yellow solid. MS (ESI, pos. ion) m/z: 309.2 [M+H]. $^1$H NMR (400 MHz, CDCl$_3$) δ ppm 8.87 (s, 1 H), 8.41 (d, J=5.87 Hz, 1 H), 6.85 (d, J=6.06 Hz, 1 H), 3.62 (dd, J=6.26, 4.30 Hz, 4 H), 3.14-3.30 (m, 4 H), 1.48 (s, 9 H).

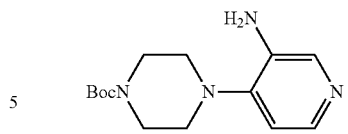

Step 2. tert-butyl 4-(3-amino-4-pyridinyl)-1- piperazinecarboxylate. A solution of tert-butyl 4-(3-nitro-4-pyridinyl)-1-piperazinecarboxylate (1.74 g, 5.64 mmol) in EtOH (56 mL) was degassed by bubbling N$_2$ through the solution for 10 min. 10% Pd/C (0.60 g, 0.56 mmol) was added as a suspension in H$_2$O (5 mL). A gas bag with a 3-way stopcock filled with H$_2$ was attached to the flask. The flask was evacuated under vacuum and back-filled with H$_2$ (3×). The mixture was stirred for 3 h at RT. The solution was degassed by bubbling N$_2$ through the solution for 10 min and was filtered through Celite. The Celite plug was washed with EtOAc. The solution was concentrated and the crude material was purified by silica gel chromatography (0-5% MeOH in CH$_2$Cl$_2$) to provide tert-butyl 4-(3-amino-4-pyridinyl)-1-piperazinecarboxylate (1.31 g, 4.72 mmol, 84% yield) as an off-white foam. MS (ESI, pos. ion) m/z: 279.2 [M+H]. $^1$H NMR (400 MHz, CDCl$_3$) δ ppm 8.03 (s, 1 H), 7.97 (d, J=5.28 Hz, 1 H), 6.76 (d, J=5.09 Hz, 1 H), 3.75 (br. s., 2 H), 3.52-3.61 (m, 4 H), 2.87-2.98 (m, 4 H), 1.48 (s, 9 H).

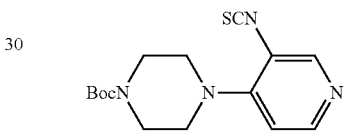

Step 3. tert-butyl 4-(3-isothiocyanato-4-pyridinyl)-1-piperazinecarboxylate. NEt$_3$ (0.12 mL, 0.90 mmol) followed by thiophosgene (1.0 M solution in THF) (0.31 mL, 0.31 mmol) was added to a solution of tert-butyl 4-(3-aminopyridin-4-yl)piperazine-1-carboxylate (83 mg, 0.30 mmol) in THF (2.7 mL) at RT. After 1 h at RT, more thiophosgene (1.0 M solution in THF) (0.16 mL, 0.16 mmol) and NEt$_3$ (0.06 mL, 0.45 mmol) were added and the reaction was stirred for an additional 30 min. The mixture was diluted with EtOAc, washed with H$_2$O (2×) and brine and the organic layer was dried over anh. Na$_2$SO$_4$, filtered and concentrated to give tert-butyl 4-(3-isothiocyanato-4-pyridinyl)-1-piperazinecarboxylate (67 mg, 0.21 mmol, 70% yield) as a brown oil. MS (ESI, pos. ion) m/z: 321.2 [M+H]. $^1$H NMR (400 MHz, CDCl$_3$) δ ppm 8.36 (s, 1 H), 8.31 (d, J=5.67 Hz, 1 H), 6.80 (d, J=5.67 Hz, 1 H), 3.62-3.69 (m, 4 H), 3.16-3.22 (m, 4 H), 1.50 (s, 9 H).

Preparation XIII. tert-butyl ((3R,4R,5S)-4-((tert-butyl(dimethyl)silyl)oxy)-1-(3-isothiocyanato-4-pyridinyl)-5-methyl-3-piperidinyl)carbamate

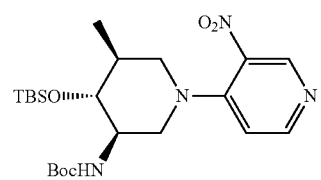 [SMILES: C[C@H]1CN(c2ccncc2[N+](=O)[O-])C[C@@H](NC(=O)OC(C)(C)C)[C@@H]1O[Si](C)(C)C(C)(C)C]

Step 1. tert-butyl ((3R,4R,5S)-1-(3-nitro-4-pyridinyl)-4-((tert-butyl(dimethyl)silyl)oxy)-5-methyl-3-piperidinyl)carbamate. To a solution of tert-butyl ((3R,4R,5S)-4-((tert-butyl(dimethyl)silyl)oxy)-5-methyl-3-piperidinyl)carbamate (1.72 g, 4.99 mmol, mixture of isomers, prepared similar to that described in US 2010/0056576 A1) in 2-propanol (50 mL) was added 4-chloro-3-nitropyridine (1.19 g, 7.49 mmol) and DIPEA (2.17 mL, 12.48 mmol). The mixture was heated to 60° C. and stirred for 2 h. The mixture was cooled to RT and concentrated. The residue was diluted with EtOAc and washed with brine, dried over anh. $Na_2SO_4$, filtered and concentrated. The crude material was purified by silica gel chromatography (0-50% EtOAc in hexanes) to provide tert-butyl ((3R,4R,5S)-1-(3-nitro-4-pyridinyl)-4-((tert-butyl(dimethyl) silyl)oxy)-5-methyl-3-piperidinyl)carbamate (1.06 g, 2.27 mmol, 46% yield). TLC (2/1 Hex/EtOAc) Rf=0.08. MS (ESI, pos. ion) m/z: 467.0 [M+H].

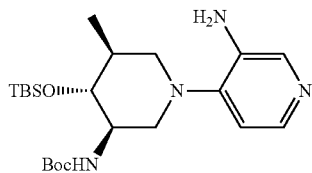

Step 2. tert-butyl ((3R,4R,5S)-1-(3-amino-4-pyridinyl)-4-((tert-butyl(dimethyl)silyl)oxy)-5-methyl-3-piperidinyl)carbamate. $N_2$ was bubbled through a solution of tert-butyl ((3R,4R,5S)-1-(3-nitro-4-pyridinyl)-4-((tert-butyl(dimethyl)silyl)oxy)-5-methyl-3-piperidinyl)carbamate (1.19 g, 2.55 mmol) in EtOH (25 mL) for 10 min. Pd/C (10%, 0.27 g, 0.26 mmol) was added as a suspension in $H_2O$ (2 mL). A gas bag with a 3-way stopcock filled with $H_2$ was attached to the flask. The flask was evacuated under vacuum and back-filled with $H_2$ (3×). The mixture was stirred for 5 h at RT. $N_2$ solution was bubbled the reaction mixture for 10 min. The mixture was filtered through Celite and the filtrate concentrated to afford tert-butyl ((3R,4R,5S)-1-(3-amino-4-pyridinyl)-4-((tert-butyl(dimethyl)-silyl)oxy)-5-methyl-3-piperidinyl)carbamate (1.04 g, 2.37 mmol, 93% yield). MS (ESI, pos. ion) m/z: 437.0 [M+H]. $^1$H NMR (400 MHz, $CDCl_3$) δ ppm 8.03 (s, 1 H), 7.95 (d, J=5.28 Hz, 1 H), 6.78 (d, J=5.28 Hz, 1 H), 3.79 (br. s., 2 H), 3.69 (br. s., 1 H), 3.59 (d, J=10.95 Hz, 1 H), 3.22-3.29 (m, 1 H), 3.18 (t, J=8.90 Hz, 1 H), 2.36-2.49 (m, 2 H), 1.84-1.94 (m, 1 H), 1.45 (s, 9 H), 1.05 (d, J=6.65 Hz, 3 H), 0.92 (s, 9 H), 0.13 (d, J=9.59 Hz, 6 H).

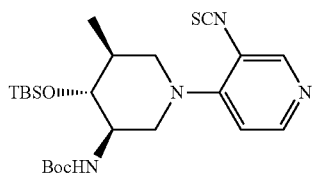

Step 3. tert-butyl ((3R,4R,5S)-4-((tert-butyl(dimethyl)silyl)oxy)-1-(3-isothiocyanato-4-pyridinyl)-5-methyl-3-piperidinyl)carbamate. 1,1'-Thiocarbonyldiimidazole (0.51 g, 2.86 mmol) was added to a solution of tert-butyl ((3R,4R,5S)-1-(3-amino-4-pyridinyl)-4-((tert-butyl(dimethyl)silyl)oxy)-5-methyl-3-piperidinyl)carbamate (625 mg, 1.43 mmol) in THF (7 mL) at RT. The reaction was heated at 60° C. for 2 h. The mixture was cooled to RT, diluted with $H_2O$ and the organic layer was dried over anh. $Na_2SO_4$, filtered and concentrated. The crude material was purified by silica gel chromatography (0-100% EtOAc in hexanes) to provide tert-butyl ((3R,4R,5S)-4-((tert-butyl(dimethyl)silyl)oxy)-1-(3-isothiocyanato-4-pyridinyl)-5-methyl-3-piperidinyl)carbamate (475 mg, 0.99 mmol, 69% yield) as a pale yellow foam. MS (ESI, pos. ion) m/z: 479.0 [M+H]. $^1$H NMR (400 MHz, $CDCl_3$) δ ppm 8.33 (s, 1 H), 8.25 (d, J=5.67 Hz, 1 H), 6.87 (d, J=5.28 Hz, 1 H), 3.79 (d, J=13.11 Hz, 1 H), 3.56-3.70 (m, 2 H), 3.30 (t, J=8.71 Hz, 1 H), 2.87 (t, J=10.66 Hz, 1 H), 2.71 (dd, J=12.91, 10.56 Hz, 1 H), 1.84-1.99 (m, 1 H), 1.46 (s, 9 H), 1.08 (s, 3 H), 0.92 (s, 9 H), 0.15 (s, 6 H).

Preparation XIV. tert-butyl 3-((3-isothiocyanato-4-pyridinyl)oxy)-1-azetidinecarboxylate

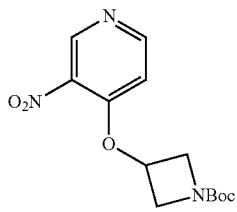 [SMILES: CC(C)(C)OC(=O)N1CC(Oc2ccncc2[N+](=O)[O-])C1]

Step 1. tert-butyl 3-((3-nitro-4-pyridinyl)oxy)-1-azetidinecarboxylate. To a solution of N-boc-3-hydroxyazetidine (2.54 g, 14.68 mmol) in 20 mL of DMF at 0° C. was added NaH (685 mg of 60% wt. in oil, 17.13 mmol). The ice bath was removed, and the mixture was stirred at RT for 15 min. A solution of 4-chloro-3-nitropyridine (1.94 g, 12.24 mmol) in THF (5 mL) was added dropwise, and the resulting brown mixture was stirred at RT for 15 min. The reaction was quenched with 50 mL of ice cold sat. $NH_4Cl$ solution and extracted with EtOAc (3×75 mL). The combined organic extracts were washed with 2×10 mL of brine, and concentrated. The brown residue was purified by silica gel chromatography (55-100% EtOAc in hexanes) to give tert-butyl 3-((3-nitro-4-pyridinyl)oxy)-1-azetidinecarboxylate (4.5 g, containing small amount of DMF) as a brown amorphous solid. MS (ESI, pos. ion) m/z: 296.0 (M+1).

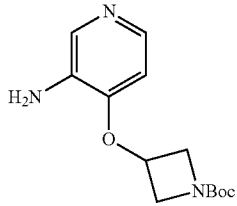

Step 2. 3-((3-amino-4-pyridinyl)oxy)-1-azetidinecarboxylate. A solution of tert-butyl 3-((3-nitro-4-pyridinyl)oxy)-1-azetidinecarboxylate (4.5 g, containing small amount of DMF) in 100 mL of EtOH and 1 mL of $H_2O$ was hydrogenated with a balloon full of $H_2$ in the presence of Pd/C (10 wt %, 1.34 g) at RT for 7 h. The mixture was filtered through a pad of Celite and rinsed with 50 mL of EtOAc. The filtrate was concentrated. The brown residue was purified by silica gel chromatography (0-5% MeOH in EtOAc) to provide 3-((3-amino-4-pyridinyl)oxy)-1-azetidinecarboxylate (2.77 g, 85% yield for 2 steps) as an off white crystalline solid. MS (ESI, pos. ion) m/z: 266.1 (M+1). $^1$H NMR (400 MHz, DMSO-$d_6$) δ ppm 8.43 (1H, s), 8.39 (1 H, d, J=5.7 Hz), 7.00 (1 H, d, J=5.7 Hz), 5.22 (1 H, dt, J=6.6, 3.0 Hz), 4.39 (2 H, m), 3.88 (2 H, m), 1.40 (9 H, s).

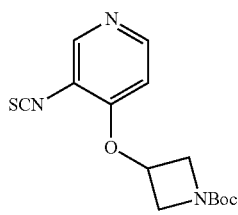

Step 3. tert-butyl 3-((3-isothiocyanato-4-pyridinyl)oxy)-1-azetidinecarboxylate. At 0° C., NEt₃ (2.07 mL, 14.93 mmol) followed by thiophosgene (0.42 mL, 5.60 mmol) were added to a solution of 3-((3-amino-4-pyridinyl)oxy)-1-azetidinecarboxylate (990 mg, 3.73 mmol) in THF (25 mL). A brown precipitate appeared. The heterogeneous mixture was stirred at RT for 1 h. The mixture was diluted with EtOAc, washed with H₂O (2×) and brine. The organic layer was dried anh. Na₂SO₄, filtered and concentrated. The brown residue was purified by silica gel chromatography (100% EtOAc) to give tert-butyl 3-((3-isothiocyanato-4-pyridinyl)oxy)-1-azetidinecarboxylate (1.06 g, 93% yield) as a brown amorphous solid. MS (ESI, pos. ion) m/z: 308.1 (M+1). ¹H NMR (400 MHz, DMSO-d₆) δ ppm 8.43 (1 H, s), 8.38 (1 H, d, J=5.7 Hz), 7.00 (1 H, d, J=5.7 Hz), 5.22 (1 H, dt, J=6.6, 3.0 Hz), 4.38 (2 H, m), 3.88 (2 H, m), 1.40 (9 H, m).

Preparation XV. tert-butyl (3R)-3-((3-isothiocyanato-4-pyridinyl)oxy)-1-piperidinecarboxylate

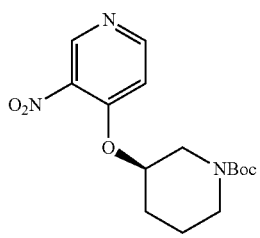 [SMILES: CC(C)(C)OC(=O)N1CCC[C@@H](Oc2ccncc2[N+](=O)[O-])C1]

Step 1. tert-butyl (3R)-3-((3-nitro-4-pyridinyl)oxy)-1-piperidinecarboxylate To a solution of (R)-tert-butyl 3-hydroxypiperidine-1-carboxylate (1.22 g, 6.06 mmol, Astatech Inc., Bristol, Pa.) in DMF (15 mL) at 0° C. was added NaH (60% wt. in oil) (283 mg, 7.06 mmol). The ice bath was removed, and the mixture was stirred at RT for 15 min. Solid 4-chloro-3-nitropyridine (800 mg, 5.05 mmol) was added and the resulting brown mixture was stirred at 0° C. for 15 min before warming to RT. The reaction was quenched with ice and extracted with EtOAc (50 mL), washed with brine (2×30 mL) and dried over MgSO₄, filtered and concentrated. Purification by silica gel chromatography (10-100% EtOAc in hexanes) afforded tert-butyl (3R)-3-((3-nitro-4-pyridinyl)oxy)-1-piperidinecarboxylate (1.14 g, 70% yield) as a bright yellow crystalline solid. MS (ESI, pos. ion) m/z: 346.1 (M+Na⁺). ¹H NMR (400 MHz, CDCl₃) δ ppm 9.00 (1 H, s), 8.61 (1 H, d, J=5.9 Hz), 7.07 (1 H, br. s.), 4.48-4.59 (1 H, m), 3.76 (1 H, br. s.), 3.49 (3 H, br. s.), 2.06 (1 H, d, J=7.8 Hz), 1.94 (2 H, dd, J=11.7, 5.5 Hz), 1.41 (9 H, br. s.), 1.25 (1 H, br. s.).

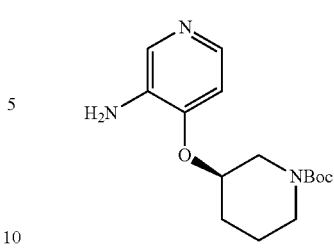

Step 2. tert-butyl (3R)-3-((3-amino-4-pyridinyl)oxy)-1-piperidinecarboxylate. tert-Butyl (3R)-3-((3-nitro-4-pyridinyl)oxy)-1-piperidinecarboxylate (1.14 g, 3.53 mmol) was treated with EtOH (20 mL) and 10 wt % Pd/C (375 mg, 3.53 mmol). The flask was purged with H₂, fitted with a balloon of H₂ and stirred at RT for 4 h. The mixture was filtered through Celite, and the pad was washed with MeOH. The filtrate was concentrated to afford tert-butyl (3R)-3-((3-amino-4-pyridinyl)oxy)-1-piperidinecarboxylate (1.09 g) as a viscous oil with traces of charcoal remaining. The crude was used in the subsequent step without further purification. MS (ESI, pos. ion) m/z: 294.2 (M+1).

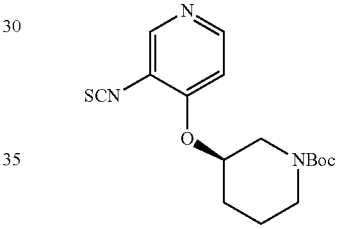

Step 3. tert-butyl (3R)-3-((3-isothiocyanato-4-pyridinyl)oxy)-1-piperidinecarboxylate. tert-Butyl (3R)-3-((3-amino-4-pyridinyl)oxy)-1-piperidinecarboxylate (1.00 g, 3.41 mmol) was treated with 1,1'-thiocarbonyldiimidazole (1.34 g, 7.50 mmol) and THF (20 mL). The flask was fitted with a reflux condenser and the reaction was heated to 60° C. for 30 min. It was cooled to RT and stirred overnight (15 h). The mixture was concentrated under reduced pressure (rotary evaporator) and the resulting residue purified by silica gel chromatography (0-100% EtOAc in hexanes) to afford tert-butyl (3R)-3-((3-isothiocyanato-4-pyridinyl)oxy)-1-piperidinecarboxylate (1.09 g, 96% yield) as a pale yellow viscous oil. MS (ESI, pos. ion) m/z: 336.2 (M+1). ¹H NMR (400 MHz, CDCl₃) δ ppm 8.34 (1 H, d, J=5.7 Hz), 8.27 (1 H, s), 6.91 (1 H, br. s.), 4.46 (1 H, d, J=2.9 Hz), 3.50 (1 H, br. s.), 2.05 (2 H, s), 1.93 (1 H, br. s.), 1.57 (2 H, s), 1.35 (9 H, br. s.), 1.26 (2 H, t, J=7.1 Hz).

Preparation XVI. tert-butyl (3S)-3-((3-isothiocyanato-4-pyridinyl)oxy)-1-piperidinecarboxylate The title compound was prepared and isolated as a pale yellow viscous oil from (S)-tert-butyl 3-hydroxypiperidine-1-carboxylate and 4-chloro-3-nitropyridine following an analogous procedure to Preparation XV. MS (ESI, pos. ion) m/z: 336.2 (M+1). ¹H NMR (400 MHz, CDCl₃) δ ppm 8.34

(1H, d, J=5.7 Hz), 8.27 (1 H, s), 6.90 (1 H, br. s.), 4.41-4.50 (1 H, m), 3.91 (1 H, br. s.), 3.49 (3 H, br. s.), 2.05 (3 H, br. m), 1.35 (9 H, br. s.).

Preparation XVII. tert-butyl ((3S)-1-(5-isothiocyanato-4-pyrimidinyl)-3-piperidinyl)carbamate

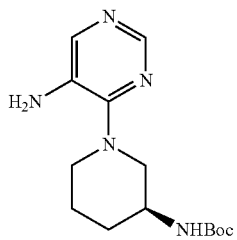

Step 1. tert-butyl ((3S)-1-(5-amino-4-pyrimidinyl)-3-piperidinyl) carbamate. A mixture of (S)-tert-butyl piperidin-3-ylcarbamate (486 mg, 2.42 mmol), 5-amino-4-chloropyrimidine (262 mg, 2.02 mmol, Magical Scientific, Atchison, Kans.) and $Cs_2CO_3$ (988 mg, 3.03 mmol) in 2 mL of DMF was heated in a microwave at 150° C. for 45 min. The mixture was diluted with 50 mL of EtOAc and filtered through a pad of Celite. The filtrate was washed with 5 mL saturated $NH_4Cl$ (aq.) followed by 5 mL of brine. The organic solution was concentrated and purified by silica gel chromatography (60-100% EtOAc in hexanes) to give tert-butyl ((3S)-1-(5-amino-4-pyrimidinyl)-3-piperidinyl)carbamate (233 mg, 39% yield, 90% purity). This material used without further purification. MS (ESI, pos. ion) m/z: 294.2 (M+1).

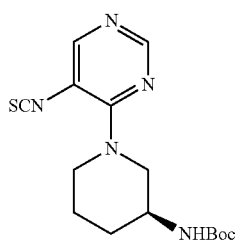

Step 2. tert-butyl ((3S)-1-(5-isothiocyanato-4-pyrimidinyl)-3-piperidinyl)carbamate.

A mixture of tert-butyl ((3S)-1-(5-amino-4-pyrimidinyl)-3-piperidinyl) arbamate (230 mg, 0.78 mmol) and 1,1'-thiocarbonyldiimidazole (279 mg, 1.56 mmol) in THF (4 mL) was heated at 60° C. in an oil bath for 2 h. After cooling to RT, $H_2O$ was added and the mixture was extracted with EtOAc (3×). The combined organic layers were dried over anh. $Na_2SO_4$, filtered and concentrated. Purification by silica gel chromatography (50-100% EtOAc in hexanes) provided tert-butyl ((3S)-1-(5-isothiocyanato-4-pyrimidinyl)-3-piperidinyl)carbamate (64 mg, 24% yield, 90% purity) as an off-white solid. MS (ESI, pos. ion) m/z: 336.2 (M+1).

Preparation XVIII. tert-butyl ((3S)-1-(4-isothiocyanato-5-isothiazolyl)-3-piperidinyl)carbamate

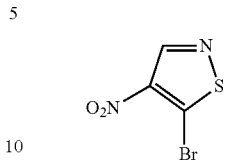

Step 1. 5-bromo-4-nitroisothiazole. The procedure was modified from the reported method (Journal of Heterocyclic Chemistry, 1980, 17, 385). A 25 mL, one neck round bottom flask was charged with $H_2SO_4$, 95% (6.0 mL, 86 mmol), $HNO_3$, 90% (2.3 mL, 54.8 mmol), and a stirbar. The flask was fitted with a reflux condenser with a PTFE addition needle spanning the length of the condenser. The flask was immersed into an ice-water bath and stirred for 15 min. A syringe was charged with 5-bromoisothiazole (1.12 g, 6.83 mmol, Focus Synthesis, San Diego, Calif.) and fitted to the PTFE addition needle. The bromide was added via syringe pump over a 20 min period and the mixture was stirred an additional 20 min. The cooling bath was removed, and the flask was placed into a 45° C. heat transfer block. The solution was stirred for 1 h, and the temperature was increased to 70° C. The reaction was stirred for 1 h, and the temperature was increased to 90° C. Heating was discontinued after 2 h and the solution was cooled overnight. The solution was carefully poured onto stirring $H_2O$ (40 mL), and stirred under a stream of $N_2$ for 2 h. The aqueous solution was extracted with $CHCl_3$ (6×20 mL). The organic phase was washed with 5% $NaHCO_3$ (2×20 mL), and treated with $MgSO_4$. The resulting slurry was $N_2$-pressure filtered through a glass frit (10 mL Bohdan) fitted with a 0.22 μm PTFE, 25 mm syringe filter unit (Millipore, SLFG025NK). The filtrate was concentrated in vacuo to afford 5-bromo-4-nitroisothiazole (823 mg, 3.94 mmol, 58% yield) as an oil. The material was used without characterization.

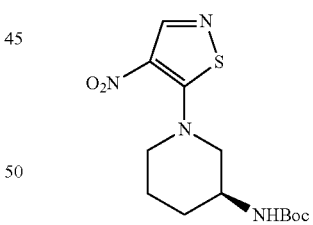

Step 2. tert-butyl ((3S)-1-(4-nitro-5-isothiazolyl)-3-piperidinyl) carbamate. A 50 mL, one neck round bottom flask was charged with 5-bromo-4-nitroisothiazole (0.8123 g, 3.89 mmol), dry THF (10 mL), and a stirbar. The flask was fitted with a septa/Ar inlet, and a solution of (S)-tert-butyl piperidin-3-ylcarbamate (1.11 g, 5.52 mmol, Aldrich) and dry DIPEA (1.01 mL, 5.83 mmol) in 10 mL dry THF was added via syringe. The solution became warm (ca. 45° C.) upon completion of the addition. The reaction was stirred for 30 min, during which time, a precipitate formed. The slurry was $N_2$-pressure filtered through a 10 mL Bohdan reaction vessel glass frit fitted with a 0.22 μm PTFE, 25 mm syringe filter unit (Millipore, SLFG025NK). The solids were washed with dry THF (3×3 mL), and discarded. The filtrate was concentrated in vacuo, and the residue was treated with EtOH (25 mL). The solution was heated until homogenous, and cooled to RT. Crystals formed over a 12 h period. The slurry was N$_2$-pressure filtered through a 10 mL Bohdan glass frit fitted with a 0.22 μm PTFE, 25 mm syringe filter unit (Millipore, SLFG025NK). The solids were washed with cold EtOH (3×3 mL), dried initially under a stream of N$_2$. The solids were further dried in a vacuum oven (80° C., <1 mm Hg) for 1 h to afford ((3S)-1-(4-nitro-5-isothiazolyl)-3-piperidinyl)carbamate (616 mg, 1.88 mmol, 48% yield). The mother liquor and EtOH washes were combined and concentrated in vacuo. The material was treated with EtOH (10 mL), and heated to reflux using a heat transfer block at 100° C. The solution was N$_2$-pressure filtered hot through a glass frit (10 mL Bohdan) fitted with a 0.22 μm PTFE, 25 mm syringe filter unit (Millipore, SLFG025NK) into a 25 mL round bottom flask. Crystals formed over a 16 h period at RT. The slury was N$_2$-pressure filtered through a glass frit (10 mL Bohdan) fitted with a 0.22 μm PTFE, 25 mm syringe filter unit (Millipore, SLFG025NK). The solids were washed with cold EtOH (2×2 mL), and dried initially under a stream of N$_2$. The material was further dried in a vacuum oven (40° C., <1 mm Hg) for 2 h to afford tert-butyl ((3S)-1-(4-nitro-5-isothiazolyl)-3-piperidinyl)-carbamate (224 mg, 0.682 mmol, 18% yield; combined yield=66%). MS (ESI, pos. ion) m/z: 329.1 (M+1). $^1$H NMR (400 MHz, CDCl$_3$) δ ppm 1.46 (s, 9 H) 1.73 (br. s., 1 H) 1.78-1.88 (m, 1 H) 1.89-2.03 (m, 2 H) 3.38 (m, J=8.60 Hz, 2 H) 3.43 (d, J=10.60 Hz, 1 H) 3.55 (d, J=10.56 Hz, 1 H) 3.90 (br. s., 1 H) 4.85 (br. s., 1 H) 8.72 (s, 1 H).

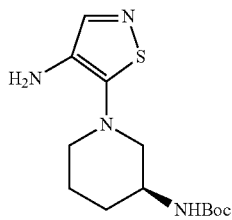

Step 3. tert-butyl ((3S)-1-(4-amino-5-isothiazolyl)-3-piperidinyl) carbamate. A 30 mL Bohdan microwave vessel was charged with tert-butyl ((3S)-1-(4-nitro-5-isothiazolyl)-3-piperidinyl)carbamate (672 mg, 2.05 mmol), EtOH (11 mL), indium powder (963 mg, 8.39 mmol, Aldrich), 4.1 M aqueous NH$_4$Cl (4.99 mL, 20.46 mmol) and a stirbar. The vessel was swept with N$_2$, and crimped with a PTFE-lined seal. The vessel was placed into a 120° C. heat transfer block for 1.5 h. The vessel was briefly cooled, and de-pressurized by inserting a 25 gauge needle through the PTFE septa. The crimp-seal was removed, and the slurry was N$_2$-pressure filtered warm through a 10 mL Bohdan glass frit fitted with a 0.22 μm PTFE, 25 mm syringe filter unit (Millipore, SLFG025NK). The solids were washed with hot EtOH (3×5 mL), and discarded. The filtrate and washes were combined and concentrated under a stream of N$_2$. The residue was suspended in H$_2$O (50 mL), and extracted with CHCl$_3$ (5×20 mL). The combined extracts were washed with H$_2$O (2×20 mL), and treated with MgSO$_4$. The resulting slurry was vacuum filtered through a fine glass frit. The filtrate was concentrated in vacuo. The residue was purified by silica gel chromatography (9/1 CHCl$_3$/THF) to afford tert-butyl ((3S)-1-(4-amino-5-isothiazolyl)-3-piperidinyl)-carbamate (536 mg, 1.80 mmol, 88% yield). MS (ESI, pos. ion) m/z: 299.0 (M+1). $^1$H NMR (400 MHz, CDCl$_3$) δ ppm 1.45 (s, 9 H) 1.48-1.56 (m, 1 H) 1.67-1.79 (m, 1 H) 1.79-1.92 (m, 2 H) 2.76 (dd, J=11.05, 7.14 Hz, 1 H) 2.85-2.95 (m, 1 H) 2.95-3.05 (m, 1 H) 3.18-3.47 (m, 3 H) 3.84 (br. s., 1 H) 4.82 (br. s., 1 H) 8.02 (s, 1 H).

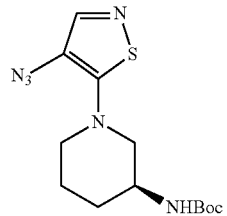 [SMILES: CC(C)(C)OC(=O)N[C@H]1CCCN(c2sncc2N=[N+]=[N-])C1]

Step 4. tert-butyl ((3S)-1-(4-azido-5-isothiazolyl)-3-piperidinyl) carbamate. A 25 mL, one neck round bottom flask was charged with tert-butyl ((3S)-1-(4-amino-5-isothiazolyl)-3-piperidinyl)carbamate (537 mg, 1.80 mmol), acetone (7 mL), water (7 mL) and a stirbar. The flask was immersed into a ice-water bath and stirred for 15 min. The solution was treated with 8 M H$_2$SO$_4$ (0.90 mL, 7.19 mmol), and stirred for 5 min. The homogenous solution was treated with NaNO$_2$ (163 mg, 2.36 mmol) and stirred for 10 min. NaN$_3$ (351 mg, 5.40 mmol) was added. The reaction was stirred cold for 30 min. The slurry was N$_2$-pressure filtered cold through a 10 mL Bohdan glass frit fitted with a 0.22 μm PTFE, 25 mm syringe filter unit (Millipore, SLFG025NK). The filtrate was slowly added to a ice-cold solution of Na$_2$CO$_3$ (1.14 g, 10.79 mmol) in H$_2$O (10 mL). The solids were washed with H$_2$O (3×5 mL), and the washes were added to the Na$_2$CO$_3$ solution. The solids were dried in a vacuum oven (45° C., <1 mm Hg) for 20 min. The solids were dissolved in CHCl$_3$, and treated with MgSO$_4$. The resulting slurry was N$_2$-pressure filtered through a 10 mL Bohdan glass frit fitted with a 0.22 μm PTFE, 25 mm syringe filter unit (Millipore, SLFG025NK). The solvent was removed in vacuo to afford tert-butyl ((3S)-1-(4-azido-5-isothiazolyl)-3-piperidinyl)carbamate (213 mg, 0.66 mmol, 37% yield). The material was used directly.

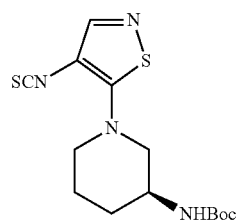

Step 5. tert-butyl ((3S)-1-(4-isothiocyanato-5-isothiazolyl)-3-piperidinyl)carbamate. A dry, 25 mL pear flask was charged with tert-butyl ((3S)-1-(4-azido-5-isothiazolyl)-3-piperidinyl)carbamate (213 mg, 0.66 mmol), a stirbar, and dry THF (4 mL). The flask was fitted with a septa/Ar inlet and immersed into a ice-water bath. The solution was stirred for 10 min and a 1.0 M solution of PMe$_3$ in THF (0.69 mL, 0.69 mmol) was added dropwise. The solution was stirred cold for 15 min. The solution was taken up into a 5 mL syringe (total volume=4.4 mL) to afford (S)-tert-butyl (1-(3-((trimethylphosphoranylidene)amino)isothiazol-5-yl)piperidin-3-yl) carbamate. A dry, 25 mL pear flask was charged with dry THF (2 mL), carbon disulfide (0.79 mL, 13.11 mmol), and a stirbar. The flask was fitted with a septa/Ar inlet/PTFE addition needle and immersed into an ice-water bath. The solution was stirred for 15 min. The syringe containing (S)-tert-butyl (1-(3-((trimethylphosphoranylidene)amino)isothiazol-5-yl)piperidin-3-yl)carbamate, as described above, was fitted to the PTFE addition needle. The solution was added via syringe pump over a 1 h period. The solution was stirred for 1 h, and concentrated in vacuo. The residue was dried in a vacuum oven (60° C., <1 mm Hg) for 1 h to afford tert-butyl ((3S)-1-(4-isothiocyanato-5-isothiazolyl) -3-piperidinyl)carbamate. The material was used without characterization.

Preparation XIX. 2-((1R,3S)-3-(3-isothiocyanato-4-pyridinyl) cyclohexyl)-1H-isoindole-1,3(2H)-dione and 2-((1S,3R)-3-(3-isothiocyanato-4-pyridinyl) cyclohexyl)-1H-isoindole-1,3(2H)-dione (1/1)

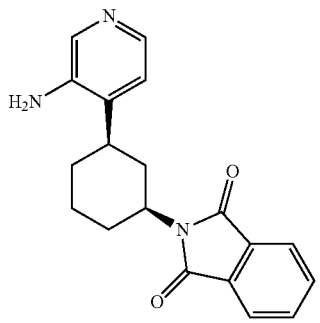

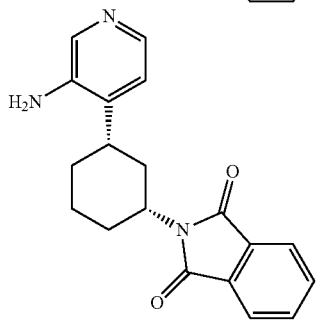

Step 1. 2-((1R,3S)-3-(3-amino-4-pyridinyl)cyclohexyl)-1H-isoindole-1,3(2H)-dione and 2-((1S,3R)-3-(3-amino-4-pyridinyl)cyclohexyl)-1H-isoindole -1,3(2H)-dione (1/1).

A 250 mL Parr vessel was charged with 2-(3-(3-nitropyridin-4-yl) cyclohex-2-en-1-yl)isoindoline-1,3-dione (328 mg, 0.94 mmol, prepared analogous to that described in WO 2009/109576 A1), and HOAc (14 mL). The vessel was fitted with a nitrogen/vacuum source, and carefully evacuated to <10 mm Hg. The vacuum was released with $N_2$ to complete 1 cycle of deoxygenation. The system was degassed an additional 2 cycles. The vessel was charged with 10% Pd/C (200 mg, 0.19 mmol). The vessel was fitted to a Parr hydrogenator with a vacuum and nitrogen source. The vessel was carefully evacuated to ~30 mm Hg vacuum. The vacuum was released with $N_2$ to complete 1 cycle of deoxygenation. The system was similarly deoxygenated two additional times and evacuated. The vacuum was released with $H_2$, and the vessel was pressurized to 60 psi. The slurry was agitated at 60 psi for 4 days. The system was evacuated, and refilled with $N_2$. The slurry was $N_2$-pressure filtered through a 10 mL Bohdan glass frit fitted with a 0.22 μm PTFE, 25 mm syringe filter unit (Millipore, SLFG025NK). The catalyst was washed with dry TFE (3×10 mL), and the combined filtrate and washes were concentrated in vacuo. The crude was purified using the prep HPLC method 1 to afford 2-((1R,3S)-3-(3-amino-4-pyridinyl) cyclohexyl)-1H-isoindole-1,3(2H)-dione and 2-((1S, 3R)-3-(3-amino-4-pyridinyl) cyclohexyl)-1H-isoindole-1,3 (2H)-dione (1/1) as a TFA salt (219 mg, 0.25 mmol, 54% yield). MS (ESI, pos. ion) m/z: 322.0 (M+1). $^1$H NMR (400 MHz, DMF-d6) δ ppm 1.49-1.61 (m, 1 H) 1.61-1.77 (m, 1 H) 1.84-2.10 (m, 4 H) 2.25 (qd, J=12.62, 3.62 Hz, 1 H) 2.41 (d, J=12.13 Hz, 1 H) 3.22 (t, J=11.84 Hz, 1 H) 4.40 (tt, J=12.13, 3.72 Hz, 1 H) 6.56 (br. s., 3 H) 7.69 (d, J=5.67 Hz, 1 H) 7.86-7.94 (m, 4 H) 8.14 (d, J=5.67 Hz, 1 H) 8.31 (s, 1 H). $^{19}$F NMR (376 MHz, DMF-d6) δ ppm −74.06 (br. s., 3F). A 25 mL round bottom flask was charged with the TFA salt of 2-((1R,3S)-3-(3-amino-4-pyridinyl)cyclohexyl)-1H-isoindole-1,3(2H)-dione and 2-((1S,3R)-3-(3-amino-4-pyridinyl) cyclohexyl)-1H-isoindole -1,3(2H)-dione (1/1) (219 mg, 0.25 mmol), EtOH (10 mL), and a stirbar. The solution was treated with Si-carbonate (1.67 g, 1.0 mmol, Silicycle, inc.), and stirred for 1 h at RT. The slurry was $N_2$-pressure filtered through a 10 mL Bohdan reaction vessel glass frit fitted with a 0.22 μm PTFE, 25 mm syringe filter unit (Millipore, SLFG025NK). The silica was washed with warm TFE (5×6 mL), and the combined filtrate and washes were concentrated in vacuo. The material was dried at RT and <1 mm Hg for 16 h to afford 2-((1R,3S)-3-(3-amino-4-pyridinyl)cyclohexyl)-1H-isoindole-1,3(2H)-dione and 2-((1S,3R)-3-(3-amino-4-pyridinyl)cyclohexyl)-1H-isoindole-1,3(2H)-dione (1/1) as a freebase (202 mg, 0.31 mmol, 67% yield). The freebase was used in the subsequent reactions

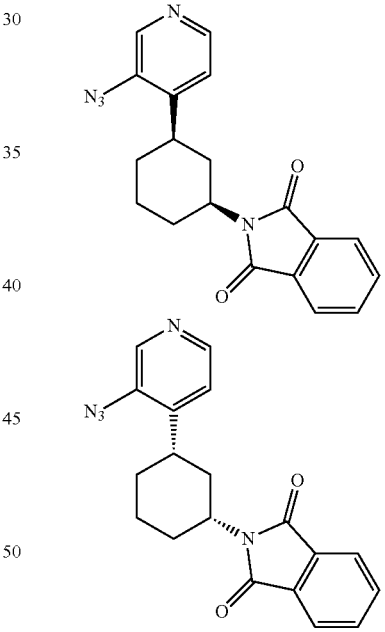

Step 2. 2-((1R,3S)-3-(3-azido-4-pyridinyl)cyclohexyl)-1H-isoindole-1,3(2H)-dione and 2-((1S,3R)-3-(3-azido-4-pyridinyl)cyclohexyl)-1H-isoindole -1,3(2H)-dione (1/1). A 25 mL, one neck round bottom flask was charged with 2-((1R,3S)-3-(3-amino -4-pyridinyl)cyclohexyl)-1H-isoindole-1,3 (2H)-dione and 2-((1S,3R)-3-(3-amino-4-pyridinyl)cyclohexyl)-1H-isoindole-1,3(2H)-dione (1/1 (202 mg, 0.31 mmol), a stirbar, and acetone (5 mL). The solution was stirred for 10 min. The flask was charged with $H_2O$ (5 mL), and was immersed into an ice-water bath. The mixture was stirred for 5 min, and 8 M $H_2SO_4$ (0.24 mL, 1.88 mmol) was added. The solution was stirred for 10 min and $NaNO_2$ (48 mg, 0.69 mmol) was cautiously added. The mixture was stirred for 15 min, and NaN₃ (82 mg, 1.26 mmol) was added in 2 roughly equal portions. The reaction was stirred for 15 min. The cold solution was cautiously added to a stirring, ice-water bath cooled solution of Na₂CO₃ (266 mg, 2.51 mmol) dissolved in 10 mL H₂O. The slurry was stirred in an ice-water bath under a stream of N₂ for 1 h. The mixture was extracted with CHCl₃ (4×30 mL), and the combined extracts were washed with H₂O (1×10 mL). The organic phase was treated with MgSO₄, and the resulting slurry was vacuum filtered through a fine glass frit. The filtrate was concentrated in vacuo. The crude material was purified by silica gel chromatography (4% THF in CHCl₃) to afford 2-((1R,3S)-3-(3-azido-4-pyridinyl)cyclohexyl)-1H-isoindole-1,3(2H)-dione and 2-((1S,3R)-3-(3-azido-4-pyridinyl)cyclohexyl)-1H-isoindole-1,3(2H)-dione (1/1) (191 mg, 0.28 mmol, 88% yield). MS (ESI, pos. ion) m/z: 347.9 (M+1). ¹H NMR (400 MHz, CDCl₃) δ ppm 1.40-1.67 (m, 2 H) 1.87-1.97 (m, 2 H) 1.98-2.12 (m, 2 H) 2.28 (qd, J=12.72, 3.52 Hz, 1 H) 2.35-2.47 (m, 1 H) 3.00 (t, J=12.13 Hz, 1 H) 4.25-4.40 (m, 1 H) 7.21 (d, J=5.09 Hz, 1 H) 7.71 (dd, J=5.09, 2.74 Hz, 2 H) 7.77-7.87 (m, 2 H) 8.32 (d, J=4.89 Hz, 1 H) 8.45 (s, 1 H).

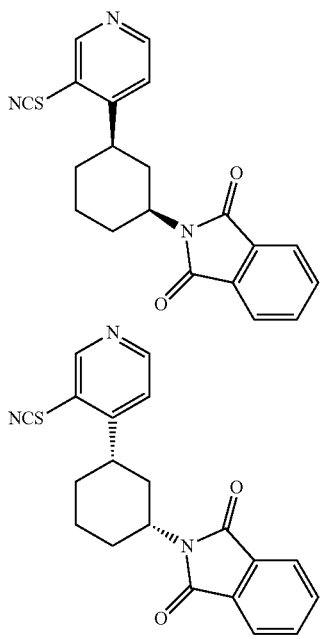

Step 3. 2-((1R,3S)-3-(3-isothiocyanato-4-pyridinyl)cyclohexyl)-1H-isoindole-1,3(2H)-dione and 2-((1S,3R)-3-(3-isothiocyanato-4-pyridinyl)cyclohexyl)-1H-isoindole-1,3(2H)-dione (1/1). The sequence was carried out in two reaction flasks. Flask 1: A dry, 15 mL one neck round bottom flask was charged with 2-((1R,3S)-3-(3-azido-4-pyridinyl)cyclohexyl)-1H-isoindole-1,3(2H)-dione and 2-((1S,3R)-3-(3-azido-4-pyridinyl)cyclohexyl)-1H-isoindole-1,3(2H)-dione (1/1) (191 mg, 0.28 mmol), dry THF (5 mL), and a stirbar. The flask was fitted with a septa/Ar inlet and immersed in a water-ice bath. The mixture was stirred for 10 min, and a 1.0 M solution of PMe₃ in THF (0.67 mL, 0.67 mmol, Aldrich) was added dropwise. The solution was stirred cold for 5 min, and the cooling bath was removed. The solution was stirred for 10 min. Flask 2: A dry, 25 mL one neck round bottom flask was charged with carbon disulfide (0.67 mL, 11.02 mmol), dry THF and a stirbar. The flask was fitted with a septa/PTFE addition needle/Ar inlet and immersed into an ice-water bath. The contents of flask 1 were charged to a syringe, and the syringe was fitted to the PTFE addition needle. The solution (total volume in THF=8 mL) was added via syringe pump over a 30 min period. The mixture was stirred an additional 15 min, and was concentrated in vacuo. The residue was dried in a vacuum oven (60° C., <1 mm Hg) for 30 min to afford 2-((1R,3S)-3-(3-isothiocyanato-4-pyridinyl)cyclohexyl)-1H-isoindole-1,3(2H)-dione and 2-((1S,3R)-3-(3-isothiocyanato-4-pyridinyl)cyclohexyl)-1H-isoindole-1,3(2H)-dione (1/1). The material was used without characterization.

Preparation XX. (3R,4R)-3,4-bis((tert-butyl(dimethyl)silyl)oxy)piperidine and (3S,4S)-3,4-bis((tert-butyl(dimethyl)silyl)oxy)piperidine (1/1)

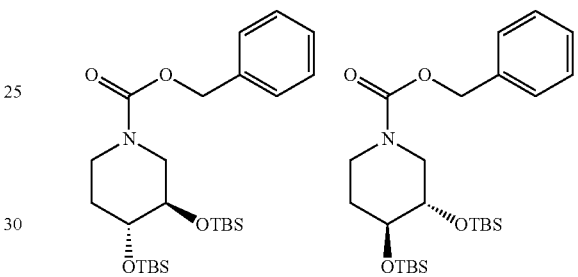

Step 1. benzyl (3R,4R)-3,4-bis((tert-butyl(dimethyl)silyl)oxy)-1-piperidinecarboxylate and benzyl (3S,4S)-3,4-bis((tert-butyl(dimethyl)silyl)oxy)-1-piperidinecarboxylate (1/1). Benzyl 7-oxa-3-azabicyclo[4.1.0]heptane-3-carboxylate (5.00 g, 21.44 mmol, Bioorg. Med. Chem. Lett. 2007, 17, 1254) in 5% K₂CO₃ in 1/1 EtOH/H₂O (214 mL) was heated at reflux for 3 h. After cooling to RT, the mixture was concentrated. EtOH (300 mL) was added to the liquid and removed in vacuo. The resulting solid was extracted with CHCl₃ (2×250 mL). The combined CHCl₃ fractions were dried over anh. Na₂SO₄, filtered and concentrated to give benzyl (3R,4R)-3,4-dihydroxy-1-piperidinecarboxylate and benzyl (3S,4S)-3,4-dihydroxy-1-piperidinecarboxylate (1/1) (5.98 g) as a light yellow syrup. MS (ESI, pos. ion) m/z: 252.1 [M+H]. A heterogenous mixture of benzyl (3R,4R)-3,4-dihydroxy-1-piperidinecarboxylate and benzyl (3S,4S)-3,4-dihydroxy-1-piperidinecarboxylate (1/1) (5.98 g, 23.80 mmol), tert-butyldimethylchlorosilane (10.76 g, 71.4 mmol) and imidazole (7.85 mL, 119 mmol) in DMF (24 mL) was stirred at RT overnight. H₂O (300 mL) was added and the mixture was extracted with Et₂O (3×100 mL). The combined organic layers were washed with H₂O (300 mL) followed by brine (200 mL) and dried over anh. Na₂SO₄, filtered and concentrated. The crude material was purified by silica gel chromatography (0-20% EtOAc in hexanes) to provide benzyl (3R,4R)-3,4-bis((tert-butyl(dimethyl)silyl)oxy)-1-piperidinecarboxylate and benzyl (3S,4S)-3,4-bis((tert-butyl(dimethyl)silyl)oxy)-1-piperidinecarboxylate (1/1) (6.37 g, 13.28 mmol, 62% yield over two steps) as a clear, colorless oil. MS (ESI, pos. ion) m/z: 480.1 [M+H].

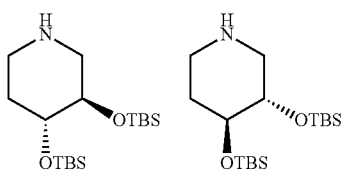 [SMILES: CC(C)(C)[Si](C)(C)O[C@@H]1CCNC[C@H]1O[Si](C)(C)C(C)(C)C ; CC(C)(C)[Si](C)(C)O[C@H]1CCNC[C@@H]1O[Si](C)(C)C(C)(C)C]

Step 2. (3R,4R)-3,4-bis((tert-butyl(dimethyl)silyl)oxy)piperidine and (3S,4S)-3,4-bis((tert-butyl(dimethyl)silyl)oxy)piperidine (1/1). A solution of benzyl (3R,4R)-3,4-bis((tert-butyl(dimethyl)silyl)oxy)-1-piperidinecarboxylate and benzyl (3S,4S)-3,4-bis((tert-butyl(dimethyl)silyl)oxy)-1-piperidinecarboxylate (1/1) (6.37 g, 13.28 mmol) in EtOH (67 mL) and EtOAc (67 mL) was degassed by bubbling $N_2$ (g) through the solution for 10 min. Pd/C (10% wt 1.41 g, 1.33 mmol) was added as a suspension in $H_2O$ (7 mL). A gas bag with a 3-way stopcock filled with $H_2$ was attached to the flask. The flask was evacuated under vacuum and back-filled with $H_2$ (3×). The mixture was stirred overnight at RT. The solution was degassed by bubbling $N_2$ (g) through the solution for 10 min and was filtered through Celite. The solution was concentrated to afford (3R,4R)-3,4-bis((tert-butyl(dimethyl)silyl)oxy)piperidine and (3S,4S)-3,4-bis((tert-butyl(dimethyl)silyl)oxy)piperidine (1/1) (4.59 g, 13.28 mmol, 100% yield) as a clear, colorless oil. MS (ESI, pos. ion) m/z: 346.1 [M+H]. $^1$H NMR (400 MHz, $CDCl_3$) δ ppm 3.59 (d, J=2.93 Hz, 1 H), 3.30 (d, J=1.96 Hz, 1 H), 3.04 (dd, J=13.30, 2.15 Hz, 1 H), 2.88 (ddd, J=13.20, 10.27, 3.13 Hz, 1 H), 2.61 (dt, J=13.16, 4.28 Hz, 1 H), 2.50 (dd, J=13.30, 4.50 Hz, 1 H), 2.22 (br. s., 1 H), 1.84 (ddt, J=13.55, 10.12, 3.62, 3.62 Hz, 1 H), 1.23-1.34 (m, 1 H), 0.79-0.91 (m, 18 H), −0.04-0.06 (m, 12 H).

| Preparation | IUPAC Name | M + 1 | Preparation Method | Structure |
|---|---|---|---|---|
| XXI | 4-((3R)-3-((tert-butyl(dimethyl)silyl)oxy)-1-piperidinyl)-3-isothiocyanatopyridine | 350.1 | XII | 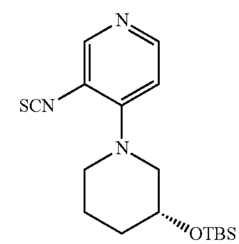 |
| XXII | 4-((3S)-3-((tert-butyl(dimethyl)silyl)oxy)-1-piperidinyl)-3-isothiocyanatopyridine | 350.0 | XII | 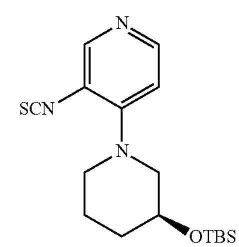 |
| XXIII | 3-isothiocyanato-N,N-dimethyl-4-pyridinamine | 180.1 | X11 | 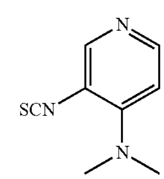 |
| XXIV | 4-chloro-3-isothiocyanatopyridine | 170.9 | XII | 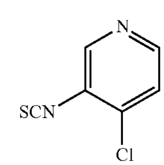 |
| XXV | 4-bromo-3-isothiocyanatopyridine and 4-chloro-3-isothiocyanatopyridine (1/1) | 171.0 and 215.0 | XII | 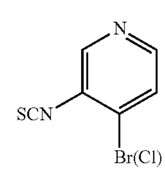 |

| Preparation | IUPAC Name | M + 1 | Preparation Method | Structure |
|---|---|---|---|---|
| XXVI | 4-((3S,4S)-3,4-bis((tert-butyl(dimethyl)silyl)oxy)-1-piperidinyl)-3-isothiocyanatopyridine and 4-((3R,4R)-3,4-bis((tert-butyl(dimethyl)silyl)oxy)-1-piperidinyl)-3-isothiocyanatopyridine (1/1) | 480.0 | XIII | 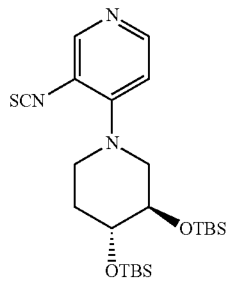 |
| XXVII | tert-butyl ((3S)-1-(3-isothiocyanato-4-pyridinyl)-3-pyrrolidinyl)carbamate | 321.2 | XIII | 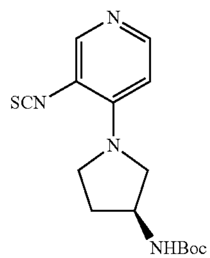 |

Preparation XXVIII.
3-(azidomethyl)-6-(3-fluoropyridin-2-yl)pyridazine

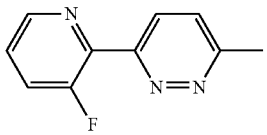

Step 1. 3-(3-fluoropyridin-2-yl)-6-methylpyridazine. A mixture of 3-fluoro-2-(tributylstannyl)pyridine (670 mg, 1.73 mmol, Indofine Chemical Company, #08-1135), 3-iodo-6-methylpyridazine (347 mg, 1.57 mmol, Preparation I, step 1), CuI (30 mg, 0.15 mmol) and Pd(PPh$_3$)$_4$ (109 mg, 0.095 mmol) in DMF (3 mL) in a sealed glass tube was heated in a microwave at 125° C. for 45 min. The resulting dark brown reaction mixture was purified by silica gel chromatography (30-75% EtOAc in hexanes) to afford 3-(3-fluoropyridin-2-yl)-6-methylpyridazine (200 mg, 67% yield) as a brown crystalline solid. MS (ESI, pos. ion) m/z: 190.0 (M+1).

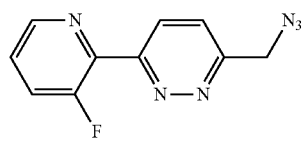 [SMILES: [N-]=[N+]=NCc1ccc(-c2ncccc2F)nn1]

Step 2. 3-(azidomethyl)-6-(3-fluoropyridin-2-yl)pyridazine. A solution of 3-(3-fluoropyridin-2-yl)-6-methylpyridazine (200 mg, 1.05 mmol) in 5 mL of DCE was treated with trichloroisocyanuric acid (98 mg, 0.42 mmol). The mixture was heated at 90° C. for 1 h. The mixture was cooled to RT and the precipitate was filtered off with a fritted funnel and rinsed with 2×20 mL of DCM. The brown solid was discarded. The filtrate was washed with 2×5 mL of 0.5 M NaOH (aq.) followed by brine (5 mL), dried over Na$_2$SO$_4$, and concentrated. The residue was purified by silica gel chromatography (55-75% EtOAc in hexanes) to give 3-(chloromethyl)-6-(3-fluoropyridin-2-yl)pyridazine as a brown crystalline solid. MS (ESI, pos. ion) m/z: 224.0 (M+1). A solution of the 3-(chloromethyl)-6-(3-fluoropyridin-2-yl)pyridazine in 1 mL of DMF at RT was treated with NaN$_3$ (69 mg, 1.05 mmol) and stirred at RT for 5 h. The mixture was filtered through a fritted funnel and the collected solid was rinsed with 2×5 mL of EtOAc. The solid was discarded and the filtrate was concentrated and the crude material was purified by silica gel chromatography (35-75% EtOAc in hexanes) to give 3-(azidomethyl)-6-(3-fluoropyridin-2-yl)pyridazine (100 mg, 41% yield) as an off white amorphous solid. MS (ESI, pos. ion) m/z: 231.1 (M+1). $^1$H NMR (400 MHz, DMSO-d$_6$) δ ppm 8.64 (1 H, m), 8.27 (1 H, d, J=8.8 Hz), 8.00 (1 H, m), 7.94 (1 H, m), 7.69 (1 H, dt, J=8.4, 4.2 Hz), 4.89 (2 H, s). $^{19}$F NMR (376 MHz, DMSO-d$_6$) δ ppm-121.47.

Preparation XXIX.
3-(azidomethyl)-6-(pyridin-2-yl)pyridazine

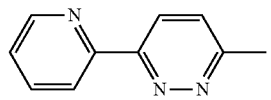

Step 1. 3-methyl-6-(pyridin-2-yl)pyridazine. 2-(Tributylstannyl)pyridine (1.15 g, 3.12 mmol, Indofine Chemical Company, Hillsborough, N.J., #: 08-1135), 3-iodo-6-methylpyridazine (624 mg, 2.84 mmol), CuI (54 mg, 0.28 mmol) and Pd(PPh$_3$)$_4$ (197 mg, 0.17 mmol, Strem Chemicals, Newburyport, Mass.) in DMF (5.0 mL) were heated at 100° C. overnight (16 h). The reaction mixture was treated with water and extracted with EtOAc (2×75 mL). The combined organic layers were washed with brine and dried over Na$_2$SO$_4$, filtered and concentrated. The crude material was purified by silica gel chromatography (0-20% MeOH in DCM) to afford 3-methyl-6-(pyridin-2-yl)pyridazine (347 mg, 2.03 mmol, 71% yield) as a light yellow semi-solid. MS (ESI, pos. ion) m/z: 172.1 (M+1).

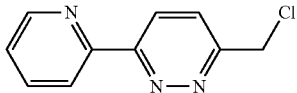

Step 2. 3-(chloromethyl)-6-(pyridin-2-yl)pyridazine. A solution of 3-methyl-6-(pyridin-2-yl)pyridazine (330 mg, 1.93 mmol) in DCE (5.0 mL) was treated with trichloroisocyanuric acid (179 mg, 0.77 mmol). The reaction was heated at 90° C. for 1 h. The mixture was then cooled to RT and the suspension filtered through a 0.45 um acrodisc and the crude material was purified by silica gel chromatography (50-100% EtOAc in hexanes) to afford 3-(chloromethyl)-6-(pyridin-2-yl)pyridazine (176 mg, 0.79 mmol, 56% yield) as a white, crystalline solid. MS (ESI, pos. ion) m/z: 206.1 (M+1). $^1$H NMR (400 MHz, CDCl$_3$) δ ppm 8.67-8.74 (2 H, m), 8.62 (1 H, d, J=8.8 Hz), 7.86-7.93 (1 H, m), 7.82 (1 H, d, J=8.8 Hz), 7.41 (1 H, ddd, J=7.5, 4.8, 1.0 Hz), 4.96 (2 H, s).

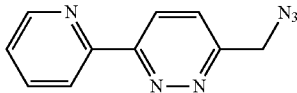 [SMILES: ClCc1ccc(-c2ccccn2)nn1]

Step 3. 3-(azidomethyl)-6-(pyridin-2-yl)pyridazine. 3-(Chloromethyl)-6-(pyridin-2-yl)pyridazine (176 mg, 0.79 mmol) in DMF (3 mL) at RT was treated with NaN$_3$ (251 mg, 3.86 mmol) and the mixture stirred at RT for 15 h. The reaction mixture was treated with water, and extracted with EtOAc (50 mL). The organic layer was washed with brine (2×25 mL) and dried over Na$_2$SO$_4$, filtered and concentrated. The crude material was purified by silica gel chromatography (25-75% EtOAc in hexanes) gave 3-(azidomethyl)-6-(pyridin-2-yl)pyridazine (116 mg, 0.55 mmol, 70% yield) as an off-white crystalline solid. MS (ESI, pos. ion) m/z: 213.1 (M+1). $^1$H NMR (400 MHz, CDCl$_3$) δ ppm 8.67-8.75 (2 H, m), 8.62 (1 H, d, J=8.6 Hz), 7.89 (1 H, td, J=7.7, 1.8 Hz), 7.68 (1 H, d, J=8.8 Hz), 7.35-7.45 (1 H, m), 4.81 (2 H, s).

Preparation XXX. 3-(6-(azidomethyl)pyridazin-3-yl)-N-cyclopropyl-4-fluorobenzamide

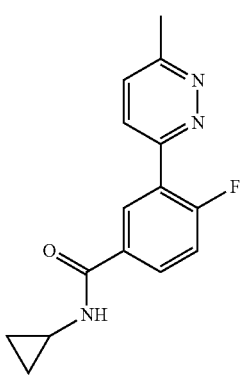 [SMILES: Cc1ccc(-c2cc(C(=O)NC3CC3)ccc2F)nn1]

Step 1. N-cyclopropyl-4-fluoro-3-(6-methylpyridazin-3-yl)benzamide. A mixture of 5-(cyclopropylcarbamoyl)-2-fluorophenylboronic acid (672 mg, 3.01 mmol, Combi-Blocks Inc, BB3348), Pd(PPh$_3$)$_4$ (139 mg, 0.12 mmol, Strem Chemicals Inc) and 3-chloro-6-methylpyridazine (310 mg, 2.41 mmol), in dioxane (6 mL) and 2 M Na$_2$CO$_3$(aq., 3.6 mL, 7.23 mmol) in a sealed glass tube was heated in a microwave at 120° C. for 30 min. It was partitioned between 5 mL of 0.5 N NaOH and 50 mL of EtOAc. The organic layer was separated, washed with brine and concentrated. The brown residue was purified by silica gel chromatography (55-100% EtOAc in hexanes) to give N-cyclopropyl-4-fluoro-3-(6-methylpyridazin-3-yl)benzamide (475 mg, 72% yield) as an off white amorphous solid. MS (ESI, pos. ion) m/z: 272 (M+1). $^1$H NMR (400 MHz, DMSO-d$_6$) δ ppm 8.63 (1 H, d, J=3.5 Hz), 8.41 (1 H, dd, J=7.3, 2.1 Hz), 7.98 (2 H, m), 7.72 (1 H, d, J=8.8 Hz), 7.49 (1 H, dd, J=10.6, 9.0 Hz), 2.88 (1 H, m), 2.70 (3 H, s), 0.72 (2 H, m), 0.59 (2 H, m). $^{19}$F NMR (376 MHz, DMSO-d$_6$) δ ppm −114.67.

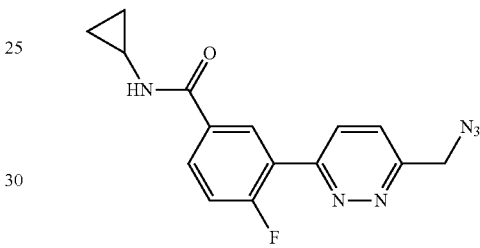

Step 2. 3-(6-(azidomethyl)pyridazin-3-yl)-N-cyclopropyl-4-fluorobenzamide. A solution of N-cyclopropyl-4-fluoro-3-(6-methylpyridazin-3-yl)benzamide (430 mg, 1.58 mmol) in 35 mL of DCE was treated with trichloroisocyanuric acid (122 mg, 0.52 mmol) and heated at 90° C. for 1.5 h. Additional trichloroisocyanuric acid (16 mg, 0.07 mmol) was added to the reaction mixture, which was heated for another 30 min at 90° C. The reaction mixture was cooled to RT and the white solid was filtered and rinsed with 2×25 mL of DCM. The filtrate was washed with 5 mL of 0.5 N NaOH followed by 5 mL of brine. The organic layer was concentrated and the residue was purified by silica gel chromatography (35-95% EtOAc in hexanes) to give 3-(6-(chloromethyl)pyridazin-3-yl)-N-cyclopropyl-4-fluorobenzamide (228 mg, 47% yield). MS (ESI, pos. ion) m/z: 306.2 (M+1). A solution of 3-(6-(chloromethyl)pyridazin-3-yl)-N-cyclopropyl-4-fluorobenzamide (228 mg, 0.75 mmol) in 1 mL of DMF and 1 mL of acetone at RT was treated with NaN$_3$ (68 mg, 1.04 mmol) and the mixture stirred at RT for 5 h. The reaction mixture was filtered through a fritted funnel and the solid was rinsed with 2×5 mL of EtOAc. The solid was discarded and the filtrate was concentrated. The brown residue was purified by silica gel chromatography (55-75% EtOAc in hexanes) to give 3-(6-(azidomethyl)pyridazin-3-yl)-N-cyclopropyl-4-fluorobenzamide (215 mg, 92% yield) as an off white amorphous solid. MS (ESI, pos. ion) m/z: 313.1 (M+1). $^1$H NMR (400 MHz, DMSO-d$_6$) δ ppm 8.65 (1 H, d, J=3.7 Hz), 8.46 (1 H, dd, J=7.3, 2.1 Hz), 8.15 (1 H, dd, J=8.8, 1.8 Hz), 8.07 (1 H, m), 7.90 (1 H, d, J=8.8 Hz), 7.52 (1 H, dd, J=10.5, 8.9 Hz), 4.87

(2 H, s), 2.88 (1 H, m), 0.72 (2 H, m), 0.60 (2 H, m). $^{19}$F NMR (376 MHz, DMSO-$d_6$) δ ppm −114.48.

Preparation XXXI.
3-(azidomethyl)-6-(3-chloropyridin-2-yl)pyridazine

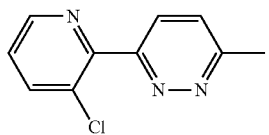

Step 1. 3-(3-chloropyridin-2-yl)-6-methylpyridazine. 3-Chloro-2-(tributylstannyl)pyridine (3.26 g, 8.10 mmol, Synthonix, #C3118G5, Wake Forest, N.C.), 3-iodo-6-methylpyridazine (1.62 g, 7.36 mmol), CuI (140 mg, 0.74 mmol) and Pd(PPh$_3$)$_4$ (511 mg, 0.44 mmol, Strem Chemicals) in DMF (12 mL) was heated at 90° C. for 5 h. The reaction mixture was treated with water and extracted with EtOAc (2×75 mL). The combined organic layers were washed with brine and dried over Na$_2$SO$_4$, filtered and concentrated. The crude compound was purified by silica gel chromatography (50-100% EtOAc in hexanes) to afford 3-(3-chloropyridin-2-yl)-6-methylpyridazine (594 mg, 2.89 mmol, 39% yield) as a viscous orange oil. MS (ESI, pos. ion) m/z: 206.1 (M+1). $^1$H NMR (400 MHz, CDCl$_3$) δ ppm 8.65 (1H, d, J=3.7 Hz), 7.87-7.92 (1 H, m), 7.85 (1 H, d, J=8.6 Hz), 7.46 (1 H, d, J=8.6 Hz), 7.35 (1 H, dd, J=8.2, 4.7 Hz), 2.82 (3 H, s).

Step 2. 3-(chloromethyl)-6-(3-chloropyridin-2-yl)pyridazine. A solution of 3-(3-chloropyridin-2-yl)-6-methylpyridazine (550 mg, 2.67 mmol) in DCE (10 mL) was treated with trichloroisocyanuric acid (249 mg, 1.07 mmol). The reaction was heated at 90° C. for 1 h. The resulting suspension was cooled to RT and filtered through an acrodisc and purified by silica gel chromatography (40-100% EtOAc in hexanes) to give 3-(chloromethyl)-6-(3-chloropyridin-2-yl)pyridazine (293 mg, 1.22 mmol, 46% yield) as a white crystalline solid. MS (ESI, pos. ion) m/z: 241.1 (M+H)$^+$. $^1$H NMR (400 MHz, CDCl$_3$) δ ppm 8.66 (1 H, d, J=3.5 Hz), 8.02 (1 H, d, J=8.6 Hz), 7.88-7.94 (1 H, m), 7.86 (1 H, d, J=8.6 Hz), 7.39 (1 H, dd, J=8.0, 4.7 Hz), 5.00 (2 H, s).

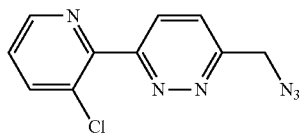 [SMILES: [N-]=[N+]=NCc1ccc(-c2ncccc2Cl)nn1]

Step 3. 3-(azidomethyl)-6-(3-chloropyridin-2-yl)pyridazine. A solution of 3-(chloromethyl)-6-(3-chloropyridin-2-yl)pyridazine (293 mg, 1.22 mmol) in DMF (3 mL) at RT was treated with NaN$_3$ (348 mg, 5.35 mmol) and the mixture stirred at RT for 15 h. The reaction mixture was treated with water and extracted with EtOAc (50 mL). the organic layer was washed with brine (2×25 mL) and dried over Na$_2$SO$_4$, filtered and concentrated. Purification of the crude product by silica gel chromatography (20-90% EtOAc in hexanes) gave 3-(azidomethyl)-6-(3-chloropyridin-2-yl)pyridazine (253 mg, 1.03 mmol, 84% yield) as a colorless viscous oil. MS (ESI, pos. ion) m/z: 247.1 (M+1). $^1$H NMR (400 MHz, CDCl$_3$) δ ppm 8.66 (1 H, dd, J=4.6, 1.1 Hz), 8.01 (1 H, d, J=8.6 Hz), 7.91 (1 H, dd, J=8.2, 1.2 Hz), 7.72 (1 H, d, J=8.6 Hz), 7.39 (1 H, dd, J=8.1, 4.6 Hz), 4.86 (2 H, s).

Preparation XXXII. 3-(6-(azidomethyl)pyridazin-3-yl)-4-fluoro-N,N-dimethylbenzamide

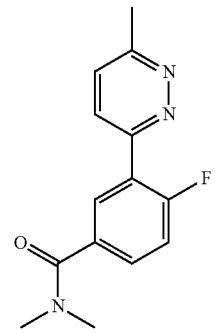 [SMILES: Cc1ccc(-c2cc(C(=O)N(C)C)ccc2F)nn1]

Step 1. 4-fluoro-N,N-dimethyl-3-(6-methylpyridazin-3-yl)benzamide. A mixture of 3-chloro-6-methylpyridazine (500 mg, 3.89 mmol), (5-(dimethylcarbamoyl)-2-fluorophenyl)boronic acid (1.03 g, 4.86 mmol, Combi-Blocks Inc., San Diego, Calif.), Pd(PPh$_3$)$_4$ (225 mg, 0.19 mmol, Strem Chemicals) in dioxane (12 mL) and 2M aqueous Na$_2$CO$_3$ (5.83 mL, 11.67 mmol) was heated in a microwave reactor at 120° C. for 30 min. The reaction mixture was partitioned between 10 mL of 1N NaOH and 50 mL EtOAc.
The organic layer was washed with brine and concentrated. The brown residue was purified by silica gel chromatography (40-100% EtOAc in hexanes) to afford 4-fluoro-N,N-dimethyl-3-(6-methylpyridazin-3-yl)benzamide (480 mg, 1.85 mmol, 47.6% yield) as an off-white amorphous solid. MS (ESI, pos. ion) m/z: 260.1 (M+1). $^1$H NMR (400 MHz, CDCl$_3$) δ ppm 8.26 (1 H, dd, J=7.4, 2.2 Hz), 7.86 (1 H, dd, J=8.7, 1.9 Hz), 7.58 (1 H, ddd, J=8.3, 4.8, 2.2 Hz), 7.40 (1 H, d, J=8.6 Hz), 7.17-7.25 (1 H, m), 3.08 (3 H, s), 3.13 (4 H, s), 2.78 (3 H, s). $^{19}$F NMR (376 MHz, CDCl$_3$) δ ppm −115.61 (1F, s).

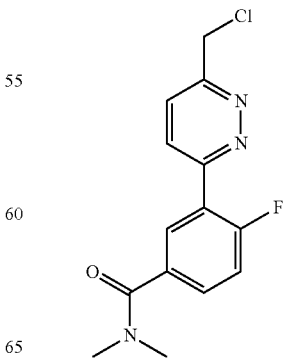

Step 2. 3-(6-(chloromethyl)pyridazin-3-yl)-4-fluoro-N,N-dimethylbenzamide. A solution of 4-fluoro-N,N-dimethyl-3-(6-methylpyridazin-3-yl)benzamide (480 mg, 1.85 mmol) in DCE (25 mL) was treated with trichloroisocyanuric acid (142 mg, 0.61 mmol) and heated at 90° C. for 2.5 h. The reaction mixture was concentrated and purified by silica gel chromatography (30-100% EtOAc in hexanes) to afford 3-(6-(chloromethyl)pyridazin-3-yl)-4-fluoro-N,N-dimethylbenzamide (470 mg, 1.60 mmol, 86% yield) as a white amorphous semi-solid. MS (ESI, pos. ion) m/z: 294.1 (M+1). $^1$H NMR (400 MHz, CDCl$_3$) δ ppm 8.29 (1 H, dd, J=7.4, 2.2 Hz), 8.03 (1 H, dd, J=8.9, 1.7 Hz), 7.78 (1 H, d, J=8.8 Hz), 7.57-7.65 (1 H, m), 7.22-7.31 (2 H, m), 4.95 (2 H, s), 3.08 (3 H, s), 3.13 (3 H, s). $^{19}$F NMR (377 MHz, CDCl$_3$) δ ppm −115.21 (1F, s).

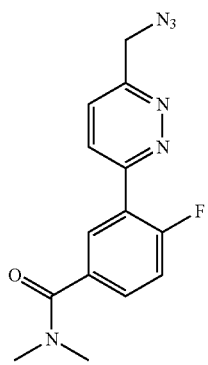 [SMILES: CN(C)C(=O)c1ccc(F)c(-c2ccc(CN=[N+]=[N-])nn2)c1]

Step 3: 3-(6-(azidomethyl)pyridazin-3-yl)-4-fluoro-N,N-dimethylbenzamide. 3-(6-(Chloromethyl)pyridazin-3-yl)-4-fluoro-N,N-dimethylbenzamide (470 mg, 1.60 mmol) was treated with NaN$_3$ (312 mg, 4.80 mmol) and DMF (5 mL) and stirred at RT for 15 h. The reaction mixture was extracted with EtOAc and the organic layer was washed with water and brine (2×30 mL), dried over MgSO$_4$, filtered and concentrated. Purification of the crude material by silica gel chromatography (30-100% EtOAc in hexanes) afforded 3-(6-(azidomethyl)pyridazin-3-yl)-4-fluoro-N,N-dimethylbenzamide (341 mg, 1.14 mmol, 71.0% yield) as a clear colorless film. MS (ESI, pos. ion) m/z: 301.1 (M+1). $^1$H NMR (400 MHz, CDCl$_3$) δ ppm 8.29 (1 H, dd, J=7.3, 2.1 Hz), 8.02 (1 H, dd, J=8.8, 1.6 Hz), 7.57-7.69 (2 H, m), 7.22-7.31 (1 H, m), 4.81 (2 H, s), 3.08 (3 H, s), 3.13 (3 H, s). $^{19}$F NMR (376 MHz, CDCl$_3$) δ ppm −115.30 (1F, s).

Preparation XXXIII. tert-butyl ((3S,5S)-1-(3-isothiocyanatopyridin-4-yl)-5-methylpiperidin-3-yl)carbamate

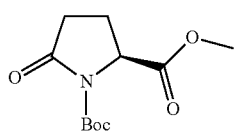 [SMILES: COC(=O)[C@@H]1CCC(=O)N1C(=O)OC(C)(C)C]

Step 1. (S)-1-tert-butyl 2-methyl 5-oxopyrrolidine-1,2-dicarboxylate. In a 1-L RBF, (S)-methyl 5-oxopyrrolidine-2-carboxylate (Aldrich Chemical Company, St. Louis, Mo., 20.00 g, 140 mmol) was treated with EtOAc (200 mL) followed by DMAP (1.71 g, 13.97 mmol) and Boc$_2$O (33.50 g, 154 mmol). The solution was stirred at RT for 2 h. The reaction mixture was cooled to 0° C. and treated with 1N HCl (16 mL) and stirred 10 min. The reaction mixture was transferred to a separatory funnel and the aqueous layer was removed. It was washed with water (25 mL) and concentrated on the rotovap. The residue was treated with MTBE (33 mL) and stirred slowly at 0° C. The crystals that formed were filtered to give (S)-1-tert-butyl 2-methyl 5-oxopyrrolidine-1,2-dicarboxylate (29.52 g, 121 mmol, 87% yield) as a pale yellow crystalline solid after washing two more times with MTBE (2×15 mL) drying under high vacuum. MS (ESI, pos. ion) m/z: 266.1 (M+Na$^+$). $^1$H NMR (400 MHz, CDCl$_3$) δ ppm 4.62 (1 H, dd, J=9.4, 2.9 Hz), 3.79 (3 H, s), 2.64 (1 H, dt, J=17.5, 9.9 Hz), 2.49 (1 H, ddd, J=17.4, 9.4, 3.7 Hz), 2.25-2.39 (1 H, m), 2.04 (1 H, ddt, J=13.1, 9.7, 3.4, 3.4 Hz), 1.50 (9 H, s).

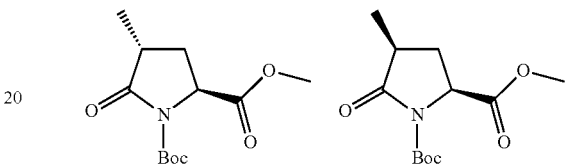

Step 2. (2S,4R and 2S,4S)-1-tert-butyl 2-methyl 4-methyl-5-oxopyrrolidine-1,2-dicarboxylate. In a 1-L flask, (S)-1-tert-butyl 2-methyl 5-oxopyrrolidine-1,2-dicarboxylate (29.52 g, 121 mmol) was treated with THF (300 mL) and cooled to −78° C. and treated with LiHMDS (1.0M in THF, 127 mL, 127 mmol) slowly over 20 min. The solution was stirred at −78° C. for 45 min then treated with iodomethane (18.97 mL, 303 mmol). After stirring for another 2 h at −78° C. the mixture was warmed to RT and stirred 3 h. Glacial HOAc (12 mL) in THF (89 mL) was used to quench the reaction. The solvent was removed on the rotary evaporator and treated with water (200 mL) and EtOAc (140 mL) and stirred for 10 min. The aqueous layer was removed and extracted with EtOAc (85 mL). The combined organic layers were evaporated under reduced pressure to give (2S,4R and 2S,4S)-1-tert-butyl 2-methyl 4-methyl-5-oxopyrrolidine-1,2-dicarboxylate (33.92 g, 132 mmol) as an orange viscous oil along with the bis-methylated material. MS (ESI, pos. ion) m/z: 280.1 (M+Na$^+$). The crude material was used in the subsequent reaction without further purification.

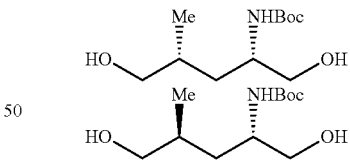

Step 3. tert-butyl ((2S,4R and 2S,4S)-1,5-dihydroxy-4-methylpentan-2-yl)carbamate. In a 1-L flask (2S,4R and 2S,4S)-1-tert-butyl 2-methyl 4-methyl-5-oxopyrrolidine-1,2-dicarboxylate (31.2 g, 121 mmol) was treated with THF (250 mL), cooled to 0° C. in an ice bath and treated with NaBH$_4$ (13.76 g, 364 mmol) in small portions under N$_2$ maintaining the temperature between −5° C. and 5° C. Anh. EtOH (62.5 mL) was then added slowly dropwise and the solution stirred at 0° C. for 5 h. The reaction mixture was then stirred at RT overnight. The reaction mixture was cooled in an ice bath and treated with glacial AcOH (25 mL) followed by water (65 mL) and the solution was stirred for 20 min then EtOAc (100 mL) was added and the solution was stirred for 1 h. The solution was transferred to a separatory funnel and treated with brine (50 mL) and the organic layer separated. The aqueous layer was extracted again with EtOAc (75 mL) and the combined EtOAc extracts were treated with Na$_2$CO$_3$ monohydrate (14 g) and stirred for 15 min along with brine (100 mL). The aqueous layer was removed and the organic layer washed with brine (100 mL). The organic layer was concentrated on the rotovap and azeotroped with toluene (2×75 mL) and EtOAc (75 mL) and dried under high vacuum affording crude tert-butyl ((2S,4R and 2S,4S)-1,5-dihydroxy-4-methylpentan-2-yl)carbamate (31.08 g) as a light yellow foam. The material was used without characterization.

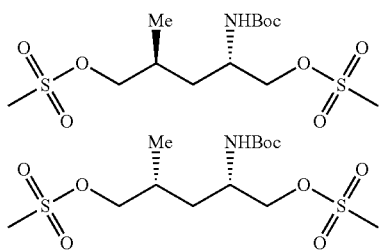

Step 4. (2S,4R and 2S,4S)-2-((tert-butoxycarbonyl) amino)-4-methylpentane-1,5-diyl dimethanesulfonate. In a 1-L flask tert-butyl ((2S,4R and 2S,4S)-1,5-dihydroxy-4-methylpentan-2-yl)carbamate (28.3 g, 121 mmol) was treated with EtOAc (250 mL) and NEt$_3$ (67.2 mL, 482 mmol). Methanesulfonyl chloride (41.26 mL, 529 mmol) was added slowly dropwise at 0° C. resulting in a yellow suspension. The solution was stirred at 0° C. for 1 h. The reaction mixture was treated with a saturated solution of NaHCO$_3$ (aq., 250 mL) and the organic layer was separated and concentrated on the rotovap affording crude (2S,4R and 4S)-2-((tert-butoxycarbonyl)amino)-4-methylpentane-1,5-diyl dimethanesulfonate (43.86 g, 113 mmol, 93% yield) as a viscous oil. MS (ESI, pos. ion) m/z: 412.1 (M+Na$^+$).

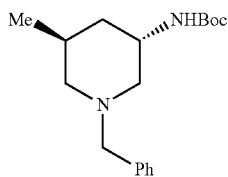

Step 5. tert-butyl ((3S,5S)-1-benzyl-5-methylpiperidin-3-yl)carbamate. In a 500 mL flask, benzylamine (38.6 mL, 353 mmol) was heated to 45° C. and treated with (2S,4R and 2S,4S)-2-((tert-butoxycarbonyl)amino)-4-methylpentane-1,5-diyl dimethanesulfonate (43 g, 110 mmol) in 1,2-dimethoxyethane (43 mL) slowly dropwise via pipette over 30 min. The solution was stirred at 50° C. overnight (15 h). The solution was then treated with K$_2$CO$_3$ (21.5 g) in water (130 mL) and stirred while cooling to RT. It was treated with EtOAc (200 mL) and the aqueous layer was removed and discarded. The organic layer was washed with water (2×130 mL) and concentrated on the rotovap. A small amount of the crude residue was purified by silica gel chromatography (5-30% EtOAc in hexanes) affording tert-butyl ((3S,5S)-1-benzyl-5-methylpiperidin-3-yl)carbamate (555 mg, 1.82 mmol, 1.6% yield) as a clear, colorless oil. MS (ESI, pos. ion) m/z: 305.3 (M+1).

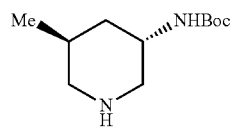

Step 6. tert-butyl ((3S,5S)-5-methylpiperidin-3-yl)carbamate. In a 250 mL round-bottomed flask, tert-butyl ((3S,5S)-1-benzyl-5-methylpiperidin-3-yl)carbamate (555 mg, 1.82 mmol) was treated with EtOH (25 mL) and Pd/C (10 wt %, 146 mg, 0.14 mmol), purged with H$_2$ and stirred under an atmosphere of H$_2$ (balloon) for 12 h. The reaction mixture was filtered through a pad of Celite and the pad was washed with EtOH. The combined filtrates were then concentrated. The crude residue was redissolved in EtOH (25 mL), treated with Pd/C (10 wt %, 150 mg) and heated in a pressurized reactor at 45° C., 39 psi H$_2$ for 10 h. The reaction mixture was filtered through a pad of Celite and the pad was washed with MeOH. The combined filtrates were then concentrated. It was then filtered through a 0.45 uM acrodisc and concentrated again affording crude tert-butyl ((3S,5S)-5-methylpiperidin-3-yl)carbamate (394 mg, 1.84 mmol, 100% yield) as a viscous, colorless oil. MS (ESI, pos. ion) m/z: 215.3 (M+1).

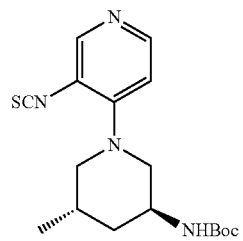

Step 7. tert-butyl ((3S,5S)-1-(3-isothiocyanatopyridin-4-yl)-5-methylpiperidin-3-yl)carbamate. The title compound was prepared and isolated as a clear, colorless viscous oil. from tert-butyl ((3S,5S)-5-methylpiperidin-3-yl)carbamate and 4-chloro-3-nitropyridine (Alfa Aesar) following an analogous procedure to Preparation XIII. as a MS (ESI, pos. ion) m/z: 349.2 (M+1). $^1$H NMR (400 MHz, CDCl$_3$) δ ppm 8.34 (1 H, s), 8.27 (1 H, d, J=5.7 Hz), 6.80 (1 H, d, J=5.7 Hz), 5.24 (1 H, d, J=7.8 Hz), 4.00-4.10 (1 H, m), 3.39-3.51 (2 H, m), 2.95-3.05 (1 H, m), 2.45 (1 H, t, J=11.2 Hz), 2.10-2.24 (1 H, m), 1.93 (1 H, d, J=13.5 Hz), 1.45 (9 H, s), 0.99 (3 H, d, J=6.5 Hz).

Preparation XXXIV. rac-tert-butyl ((cis)-1-(3-isothiocyanatopyridin-4-yl)-5-methylpiperidin-3-yl) carbamate

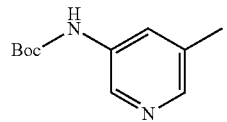

Step 1. tert-butyl (5-methylpyridin-3-yl)carbamate. To a solution of 3-amino-5-methylpyridine (5.11 g, 47.3 mmol, Aldrich) in THF (80 mL) and LiHMDS (1.0M solution in hexanes, 104 mL, 104 mmol) was added dropwise at RT and stirred at this temperature for 15 min. Boc$_2$O (13.00 g, 59.6 mmol) was then added and the solution stirred at RT overnight. The reaction mixture was concentrated on the rotovap and the crude residue was treated with 0.2M HCl (aq., 60 mL) and extracted with EtOAc (2×200 mL). The combined organic layers were washed with a saturated solution of NaHCO₃ (aq.) and brine and dried over Na₂SO₄, filtered and concentrated. The crude material was purified bys silica gel chromatography (30-50% EtOAc in hexanes) affording tert-butyl (5-methylpyridin-3-yl)carbamate (3.83 g, 18.39 mmol, 39% yield) as a yellow solid. MS (ESI, pos. ion) m/z: 209.1 (M+1). ¹H NMR (400 MHz, CDCl₃) δ ppm 8.20 (1 H, s), 8.12 (1 H, s), 7.86 (1 H, br. s.), 6.47 (1 H, br. s.), 2.32 (3 H, s), 1.53 (9 H, s).

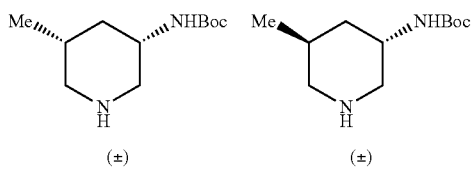

Step 2. tert-butyl (5-methylpiperidin-3-yl)carbamate. In a 150 mL hastalloy metal reactor, tert-butyl (5-methylpyridin-3-yl)carbamate (3.00 g, 14.41 mmol) was treated with glacial HOAc (50 mL), platinum (IV) oxide (500 mg, 2.202 mmol, Aldrich) and rhodium (5 wt. % (dry) on carbon, degussa type, 500 mg, 4.86 mmol, Aldrich) and hydrogenated at 200 psi H₂ at 70° C. for 23 h. The reaction mixture was concentrated on the rotovap and the crude residue was treated with 2N NaOH (aq.) to pH 9 and extracted with EtOAc (2×75 mL). The combined organic layers were washed with brine and dried over Na₂SO₄, filtered and concentrated to yield tert-butyl (5-methylpiperidin-3-yl)carbamate (2.37 g, 11.06 mmol, 77% yield) as a yellow viscous oil. MS (ESI, pos. ion) m/z: 215.3 (M+1). The crude mixture was used in the subsequent step without further purification.

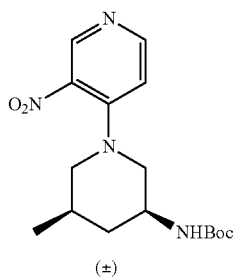

Step 3. rac-tert-butyl ((cis)-5-methyl-1-(3-nitropyridin-4-yl) piperidin-3-yl)carbamate. To a solution of tert-butyl (5-methylpiperidin-3-yl)carbamate (2.37 g, 11.06 mmol) in 2-propanol (60 mL) was added 4-chloro-3-nitropyridine (2.28 g, 14.38 mmol, Alfa Aesar, Ward Hill, Mass.) and Et₃N (6.94 mL, 49.8 mmol). The mixture was heated to 60° C. and stirred for 3 h. The reaction mixture was concentrated on the rotovap, treated with water and extracted with EtOAc (2×100 mL), dried over MgSO₄, filtered and concentrated. Purification by silica gel chromatography (20-80% EtOAc in hexanes) afforded rac-tert-butyl ((cis)-5-methyl-1-(3-nitropyridin-4-yl)piperidin-3-yl) carbamate (1.26 g, 3.75 mmol, 34% yield) with 10% tert-butyl ((3S,5S))-5-methyl-1-(3-nitropyridin-4-yl)piperidin-3-yl)carbamate contamination as a bright yellow crystalline solid. The material was recrystallized from hot EtOAc (ca. 50 mL heating to 70° C.) resulting in diastereomerically pure racemic cis-isomer (1.26 g) as a bright yellow crystalline solid after cooling in the freezer over the weekend. MS (ESI, pos. ion) m/z: 337.2 (M+1). ¹H NMR (400 MHz, CDCl₃) δ ppm 8.85 (1 H, s), 8.34 (1 H, d, J=5.9 Hz), 7.09 (1 H, br. s.), 4.44 (1 H, br. s.), 3.95 (1 H, br. s.), 3.68 (1 H, br. s.), 3.10 (1 H, d, J=11.3 Hz), 2.69 (2 H, q, J=11.6 Hz), 2.10 (1 H, d, J=12.5 Hz), 1.84 (1 H, br. s.), 1.47 (9 H, s), 0.98-1.11 (1 H, m), 0.94 (3 H, d, J=6.7 Hz).

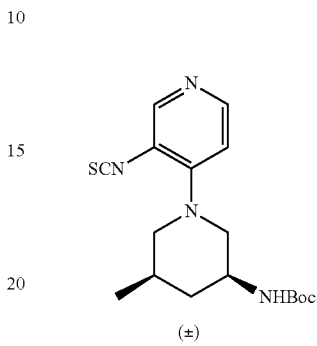

Step 4. rac-tert-butyl ((cis)-1-(3-isothiocyanatopyridin-4-yl)-5-methylpiperidin-3-yl)carbamate. The title compound was prepared as a white crystalline solid from rac-tert-butyl ((cis)-5-methyl-1-(3-nitropyridin-4-yl)piperidin-3-yl)carbamate following an analogous procedure to Preparation XIII. MS (ESI, pos. ion) m/z: 349.1 (M+1). ¹H NMR (400 MHz, CDCl₃) δ ppm 8.30 (1 H, s), 8.23 (1 H, d, J=5.7 Hz), 6.84 (1 H, d, J=5.7 Hz), 4.42 (1 H, br. s.), 3.86 (1 H, d, J=11.7 Hz), 3.70 (2 H, d, J=11.9 Hz), 2.52 (1 H, t, J=11.2 Hz), 2.41 (1 H, t, J=12.0 Hz), 2.11 (1 H, d, J=12.7 Hz), 1.97 (1 H, br. s.), 1.46 (9 H, s), 0.90-1.04 (4 H, m).

Preparation XXXV. tert-butyl ((3R,4S,5R)-4-((tert-butyldimethylsilyl) oxy)-1-(3-isothiocyanatopyridin-4-yl)-5-methylpiperidin-3-yl)carbamate

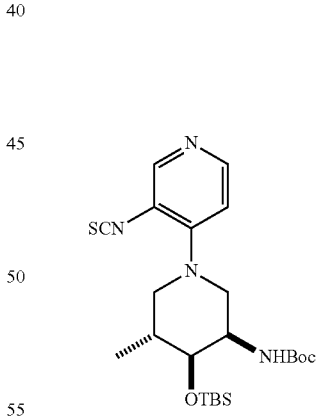

Step 1. tert-butyl ((3R,4S,5R)-4-((tert-butyldimethylsilyl) oxy)-1-(3-isothiocyanatopyridin-4-yl)-5-methylpiperidin-3-yl)carbamate. The title compound was prepared and isolated as a pale yellow foam from tert-butyl ((3R,4S,5R)-4-((tert-butyldimethylsilyl)oxy)-5-methylpiperidin-3-yl)carbamate (prepared in a manner analogous to that described in US2010/005,6576) and 4-chloro-3-nitropyridine following an analogous procedure to Preparation XIII. MS (ESI, pos. ion) m/z: 479.2 (M+1). ¹H NMR (400 MHz, CDCl₃) δ ppm 8.24 (1 H, s), 8.18 (1 H, d, J=5.5 Hz), 6.72 (1 H, d, J=5.5 Hz), 5.15 (1 H, d, J=8.2 Hz), 3.70 (1 H, m), 3.60 (1 H, br.), 3.26-3.14 (2 H, m), 2.94 (1 H, m), 2.65 (1 H, m), 2.11 (1 H, m), 1.35 (9 H, s), 0.81 (12 H, m), 0.09 (3 H, s), 0.07 (3 H, s).

Preparation XXXVI. tert-butyl (3-(3-isothiocyanato-pyridin-4-yl)-5-methylphenyl)carbamate

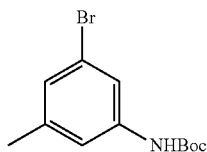 [SMILES: Cc1cc(Br)cc(NC(=O)OC(C)(C)C)c1]

Step 1. tert-butyl (3-bromo-5-methylphenyl)carbamate. A mixture of 3-bromo-5-methylaniline, HCl salt (2.50 g, 11.24 mmol, Sigma-Aldrich), Boc$_2$O (2.57 g, 11.80 mmol), DMAP (137 mg, 1.12 mmol) and triethylamine (1.64 mL, 11.80 mmol) in ACN (23 ml) was stirred at 60° C. overnight. The mixture was concentrated and the crude material was purified by silica gel chromatography (10% EtOAc in hexanes) to provide tert-butyl (3-bromo-5-methylphenyl)carbamate (630 mg, 2.20 mmol, 20% yield) as a tan oil. MS (ESI, pos. ion) m/z: 230.0, 231.0 (M-t-Bu+1). $^1$H NMR (400 MHz, CDCl$_3$) δ ppm 7.39 (t, J=2.05 Hz, 1 H), 7.09 (s, 1 H), 6.96-7.02 (m, 1 H), 6.41 (br. s., 1 H), 2.29 (s, 3 H), 1.51 (s, 9 H).

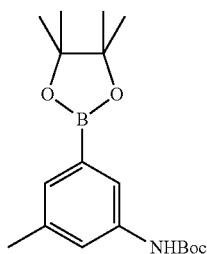 [SMILES: Cc1cc(NC(=O)OC(C)(C)C)cc(B2OC(C)(C)C(C)(C)O2)c1]

Step 2. tert-butyl (3-methyl-5-(4,4,5,5-tetramethyl-1,3,2-dioxaborolan -2-yl)phenyl)carbamate. A mixture of tert-butyl (3-bromo-5-methylphenyl)carbamate (600 mg, 2.10 mmol), bis(pinacolato)diboron (692 mg, 2.73 mmol, Sigma-Aldrich), Pd(dppf)Cl$_2$ (171 mg, 0.21 mmol, Strem Chemicals Inc.) and KOAc (1.03 g, 10.48 mmol) in DMF (7 ml) was stirred at 80° C. overnight. The reaction mixture was cooled to RT and concentrated. The brown residue was diluted in EtOAc and water. The mixture was filtered with a medium glass frit and the layers were separated. The aqueous layer was extracted with EtOAc (2x). The combined organic layers were washed with brine, dried over anh. Na$_2$SO$_4$, filtered and concentrated. The crude material was purified by silica gel chromatography (10% EtOAc in hexanes) to provide tert-butyl (3-methyl-5-(4,4,5,5-tetramethyl-1,3,2-dioxaborolan-2-yl)phenyl)carbamate (620 mg, 1.86 mmol, 89% yield) as an off-white solid. MS (ESI, pos. ion) m/z: 356.1 (M+Na).

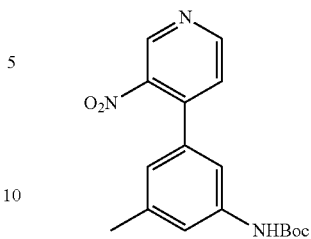

Step 3. tert-butyl (3-methyl-5-(3-nitropyridin-4-yl)phenyl) carbamate. A glass microwave reaction vessel was charged with tert-butyl (3-methyl-5-(4,4,5,5-tetramethyl-1,3,2-dioxaborolan-2-yl)phenyl)carbamate (200 mg, 0.60 mmol), 4-chloro-3-nitropyridine (114 mg, 0.72 mmol, Alfa-Aesar), Pd(dppf)Cl$_2$ (25 mg, 0.030 mmol) and 2 M Na$_2$CO$_3$ (aq., 1.20 mL, 2.40 mmol) in dioxane (3 mL). The reaction mixture was stirred and heated in a Initiator microwave reactor (Personal Chemistry, Biotage AB, Inc., Upssala, Sweden) at 120° C. for 30 min. Water was then added and the mixture was extracted with EtOAc (3x). The combined organic layers were dried over anh. Na$_2$SO$_4$, filtered and concentrated. The crude material was purified by silica gel chromatography (0-50% EtOAc in hexanes) to provide tert-butyl (3-methyl-5-(3-nitropyridin-4-yl)phenyl)carbamate (198 mg, 0.60 mmol, 100% yield) as a tan solid. MS (ESI, pos. ion) m/z: 330.0 (M+1). $^1$H NMR (400 MHz, CDCl$_3$) δ ppm 9.06 (s, 1 H), 8.78 (d, J=4.89 Hz, 1 H), 7.42 (d, J=4.89 Hz, 1 H), 7.24-7.27 (m, 1 H), 6.80 (s, 1 H), 6.53 (s, 1 H), 2.37 (s, 3 H), 1.48-1.55 (m, 9 H).

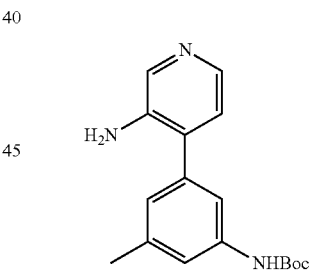

Step 4. tert-butyl (3-(3-aminopyridin-4-yl)-5-methylphenyl) carbamate. A solution of tert-butyl (3-methyl-5-(3-nitro-pyridin-4-yl)phenyl)carbamate (198 mg, 0.60 mmol) in EtOH (5 mL) and EtOAc (5 mL) was degassed by bubbling N$_2$ (g) through the solution for 10 min. Pd/C (10 wt %, 64 mg, 0.060 mmol) was added. A gas bag with a 3-way stopcock filled with H$_2$ was attached to the flask. The flask was evacuated under vacuum and then back-filled with H$_2$ (3x). The mixture was stiffed overnight at RT. The solution was degassed by bubbling N$_2$ (g) through the solution for 10 min and was then filtered through celite. The solution was concentrated to afford tert-butyl (3-(3-aminopyridin-4-yl)-5-methylphenyl)carbamate (200 mg, 0.67 mmol, 111% yield) as an off-white foam. MS (ESI, pos. ion) m/z: 300.0 (M+1).

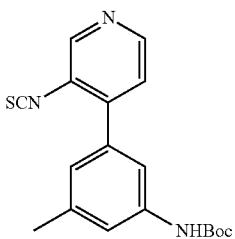 [SMILES: Cc1cc(NC(=O)OC(C)(C)C)cc(-c2ccncc2[N+](=O)[O-])c1]

Step 5. tert-butyl (3-(3-isothiocyanatopyridin-4-yl)-5-methylphenyl) carbamate. 1,1'-thiocarbonyldiimidazole (155 mg, 0.78 mmol, Sigma-Aldrich) was added to a solution of tert-butyl (3-(3-aminopyridin-4-yl)-5-methylphenyl)carbamate (117 mg, 0.39 mmol) in THF (4 mL) at RT. The reaction mixture was heated at 60° C. for 2 h. The mixture was cooled to RT, diluted with EtOAc, washed with water and the organic layer was dried over anh. $Na_2SO_4$, filtered and concentrated. The crude material was purified by silica gel chromatography (0-100% EtOAc in hexanes) to provide tert-butyl (3-(3-isothiocyanatopyridin-4-yl)-5-methylphenyl)carbamate (63 mg, 0.19 mmol, 47% yield) as a white solid. MS (ESI, pos. ion) m/z: 342.0 (M+1). $^1$H NMR (400 MHz, $CDCl_3$) δ ppm 8.58 (s, 1 H), 8.49 (d, J=5.09 Hz, 1 H), 7.32-7.37 (m, 2 H), 7.29 (s, 1 H), 6.98 (s, 1 H), 6.56 (s, 1 H), 2.41 (s, 3 H), 1.53 (s, 9 H).

Preparation XXXVII. rac-tert-butyl ((trans)-4-fluoro-1-(3-isothiocyanatopyridin-4-yl)piperidin-3-yl)carbamate

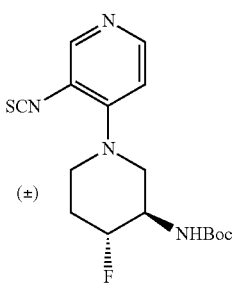

Step 1. rac-tert-butyl ((trans)-4-fluoro-1-(3-isothiocyanatopyridin-4-yl)piperidin-3-yl)carbamate. The title compound was prepared and isolated as a white solid from 4-chloro-3-nitropyridine (Alfa-Aesar) and tert-butyl rac-((trans)-4-fluoropiperidin-3-yl)carbamate (WO 2008/106692) following an analogous procedure to Preparation XII. MS (ESI, pos. ion) m/z: 353.1 (M+1). $^1$H NMR (400 MHz, $CDCl_3$) δ ppm 8.38 (s, 1 H), 8.32 (d, J=5.48 Hz, 1 H), 6.87 (d, J=5.67 Hz, 1 H), 4.62-4.82 (m, 1 H), 4.04 (br. s., 1 H), 3.50 (dt, J=12.32, 3.13 Hz, 1 H), 3.22 (dd, J=7.82, 3.72 Hz, 2 H), 2.18-2.38 (m, 1 H), 1.98-2.09 (m, 2 H), 1.47 (s, 9 H). $^{19}$F NMR (376 MHz, $CDCl_3$) δ ppm −186.21.

Preparation XXXVIII. tert-butyl ((cis)-1-(3-isothiocyanatopyridin-4-yl)-5-methylpiperidin-3-yl)carbamate (enantiomer 1) and tert-butyl ((cis)-1-(3-isothiocyanatopyridin-4-yl)-5-methylpiperidin-3-yl) carbamate (enantiomer 2)

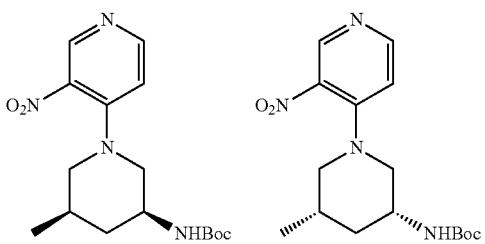

Step 1. tert-butyl ((cis)-5-methyl-1-(3-nitropyridin-4-yl)piperidin-3-yl)carbamate (first eluting enantiomer), tert-butyl ((cis)-5-methyl-1-(3-nitropyridin-4-yl)piperidin-3-yl) carbamate (second eluting enantiomer). A racemic mixture of cis- and trans-tert-butyl-(5-methylpiperidin-3-yl)carbamate (8.36 g, 39.0 mmol) (Preparation XXXIV, step 2) in 2-propanol (100 mL) was treated with 4-chloro-3-nitropyridine (5.11 g, 32.2 mmol, Alfa Aesar, Ward Hill, Mass.) and $Et_3N$ (16.3 mL, 117 mmol). The mixture was heated to 80° C. and stirred for 1.5 h. The reaction mixture was then concentrated under reduced pressure, treated with water and extracted with EtOAc (2×100 mL). The combined organic layers were dried over $MgSO_4$, filtered and concentrated. The crude material was purified by silica gel chromatography (30-80% EtOAc in hexanes) to afford rac-tert-butyl (5-methyl-1-(3-nitropyridin-4-yl)piperidin-3-yl)carbamate (3.11 g, 9.25 mmol, 24% yield) as a 76:24 ratio of cis:trans diastereomers. The mixture was purified by supercritical-fluid chromatography (Chiralcel OJ-H column (21×250 mm, 5 μm), 92% liquid $CO_2$/8% EtOH (20 mM $NH_3$), 70 mL/min). The crude material was repurified by supercritical-fluid chromatography (Chiralcel OZ-H column (21×250 mm, 5 μm), 85% liquid $CO_2$/15% EtOH (20 mM $NH_3$), 70 mL/min) to afford tert-butyl ((cis)-5-methyl-1-(3-nitropyridin-4-yl)piperidin-3-yl)carbamate (first eluting peak) (900 mg, 14% yield), which eluted first from analytical supercritical-fluid chromatography (Chiralcel OZ-H column (4.6×150 mm, 5 μm), 85% liquid $CO_2$/15% EtOH (0.1% diethylamine), 4 mL/min) and was obtained as a bright yellow crystalline solid upon evaporation of the solvent and drying. MS (ESI, pos. ion) m/z: 337.1 (M+1). $^1$H NMR (400 MHz, $CDCl_3$) δ ppm 8.83 (1 H, s), 8.35 (1 H, d, J=6.1 Hz), 7.02 (1 H, br. s.), 4.43 (1 H, br. s.), 3.89 (1 H, d, J=10.2 Hz), 3.69 (1 H, br. s.), 3.09 (1 H, d, J=12.3 Hz), 2.57-2.73 (2 H, m), 2.09 (1 H, d, J=12.1 Hz), 1.84 (1 H, dd, J=11.2, 4.3 Hz), 1.47 (9 H, s), 1.01 (1 H, q, J=12.3 Hz), 0.92 (3 H, d, J=6.5 Hz); and tert-butyl ((cis)-5-methyl-1-(3-nitropyridin-4-yl)piperidin-3-yl)carbamate (second eluting enantiomer) (890 mg, 13.5% yield) eluted second analytical supercritical-fluid chromatography (same conditions as above) as a bright yellow crystalline solid upon evaporation of the solvent and drying. MS (ESI, pos. ion) m/z: 337.1 (M+1). $^1$H NMR (400 MHz, $CDCl_3$) δ ppm 8.83 (1 H, s), 8.35 (1 H, d, J=6.1 Hz), 6.94-7.07 (1 H, m), 4.42 (1 H, br. s.), 3.88 (1 H, br. s.), 3.69 (1 H, br. s.), 3.09 (1 H, d, J=11.2 Hz), 2.57-2.73 (2 H, m), 2.09 (1 H, d, J=12.3 Hz), 1.84 (1 H, dd, J=11.1, 4.4 Hz), 1.47 (9 H, s), 1.01 (1 H, q, J=11.8 Hz), 0.92 (3 H, d, J=6.7 Hz).

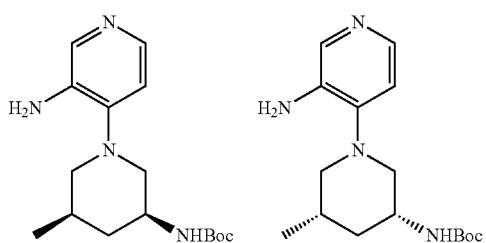

Step 2. tert-butyl ((cis)-1-(3-aminopyridin-4-yl)-5-methylpiperidin-3-yl)carbamate (enantiomer 1) and tert-butyl ((cis)-1-(3-aminopyridin-4-yl)-5-methylpiperidin-3-yl)carbamate (enantiomer 2). tert-Butyl ((cis)-1-(3-aminopyridin-4-yl)-5-methylpiperidin-3-yl)carbamate (enantiomer 1) was prepared from tert-butyl ((cis)-5-methyl-1-(3-nitropyridin-4-yl)piperidin-3-yl)carbamate (first eluting peak) following an analogous procedure to Preparation XIII. MS (ESI, pos. ion) m/z: 307.3 (M+1). tert-Butyl ((cis)-1-(3-aminopyridin-4-yl)-5-methylpiperidin-3-yl)carbamate (enantiomer 2) was prepared from tert-butyl ((cis)-5-methyl-1-(3-nitropyridin-4-yl)piperidin-3-yl)carbamate (second eluting peak) following an analogous procedure to Preparation XIII. MS (ESI, pos. ion) m/z: 307.3 (M+1).

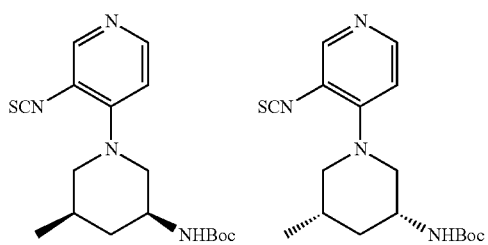

Step 3. tert-butyl ((cis)-1-(3-isothiocyanatopyridin-4-yl)-5-methylpiperidin-3-yl)carbamate (enantiomer 1) and tert-butyl ((cis)-1-(3-isothiocyanatopyridin-4-yl)-5-methylpiperidin-3-yl)carbamate (enantiomer 2). Enantiomerically pure tert-butyl ((cis)-1-(3-aminopyridin-4-yl)-5-methylpiperidin-3-yl)carbamate (enantiomer 1) (820 mg, 2.68 mmol) was treated with 1,1'-thiocarbonyldiimidazole (1.06 g, 5.35 mmol) and THF (30 mL) and heated to 60° C. for 2 h. The reaction mixture was concentrated under reduced pressure and the crude material purified by silica gel chromatography (30-90% EtOAc in hexanes), to provide tert-butyl ((cis)-1-(3-isothiocyanatopyridin-4-yl)-5-methylpiperidin-3-yl)carbamate (enantiomer 1) (690 mg, 1.98 mmol, 74.0% yield) as a white crystalline solid. MS (ESI, pos. ion) m/z: 349.2 (M+1). $^1$H NMR (400 MHz, CDCl$_3$) δ ppm 8.30 (1 H, s), 8.23 (1 H, d, J=5.7 Hz), 6.84 (1 H, d, J=5.7 Hz), 4.41 (1 H, br. s.), 3.87 (1 H, dt, J=11.8, 2.2 Hz), 3.64-3.82 (2 H, m), 2.52 (1 H, t, J=11.2 Hz), 2.35-2.46 (1 H, m), 2.11 (1 H, d, J=12.3 Hz), 1.98 (1 H, dt, J=6.9, 3.8 Hz), 1.46 (9 H, s), 0.90-1.03 (4 H, m). tert-Butyl ((cis)-1-(3-isothiocyanatopyridin-4-yl)-5-methylpiperidin-3-yl)carbamate (enantiomer 2) was prepared from tert-butyl ((cis)-1-(3-aminopyridin-4-yl)-5-methylpiperidin-3-yl)carbamate (enantiomer 2) in an analogous procedure for tert-butyl ((cis)-1-(3-isothiocyanatopyridin-4-yl)-5-methylpiperidin-3-yl)carbamate (enantiomer 1). MS (ESI, pos. ion) m/z: 349.2 (M+1). $^1$H NMR (400 MHz, CDCl$_3$) δ ppm 8.30 (1 H, s), 8.23 (1 H, d, J=5.7 Hz), 6.84 (1 H, d, J=5.7 Hz), 4.41 (1 H, br. s.), 3.87 (1 H, dt, J=11.8, 2.1 Hz), 3.65-3.82 (2 H, m), 2.52 (1 H, t, J=11.2 Hz), 2.36-2.45 (1 H, m), 2.11 (1 H, d, J=12.3 Hz), 1.90-2.04 (1 H, m), 1.46 (9 H, s), 0.91-1.03 (4 H, m).

Preparation XXXIX. tert-butyl ((3S,5R)-5-fluoro-1-(3-isothiocyanatopyridin-4-yl)piperidin-3-yl)carbamate

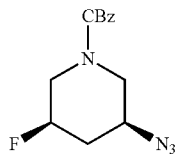

Step 1. (3S,5R)-benzyl 3-azido-5-fluoropiperidine-1-carboxylate. (3R,5R)-Benzyl 3-fluoro-5-((methylsulfonyl)oxy)piperidine-1-carboxylate (1.08 g, 3.26 mmol, US 2010/0216839) was treated with NMP (15 mL) and NaN$_3$ (636 mg, 9.79 mmol) and heated to 80° C. for 16 h. The reaction mixture was diluted with EtOAc (50 mL) and hexanes (25 mL) and washed with water and with brine (2×). The organic layer was dried over MgSO$_4$, filtered and concentrated. Purification by silica gel chromatography (25% EtOAc in hexanes) afforded (3S,5R)-benzyl 3-azido-5-fluoropiperidine-1-carboxylate (780 mg, 2.80 mmol, 86% yield) as a viscous colorless oil. MS (ESI, pos. ion) m/z: 301.0 (M+Na$^+$). $^1$H NMR (400 MHz, CDCl$_3$) δ ppm 7.30-7.41 (5 H, m), 5.15 (2 H, s), 4.64 (1 H, br. s.), 4.52 (1 H, br. s.), 3.97-4.09 (1 H, m), 3.94 (1 H, br. s.), 3.53 (1 H, br. s.), 3.21-3.31 (1 H, m), 3.05-3.17 (1 H, m), 2.31-2.44 (1 H, m), 1.77-1.90 (1 H, m). $^{19}$F NMR (376 MHz, CDCl$_3$) δ ppm −182.84 (1 F, s), −182.95 (1 F, s).

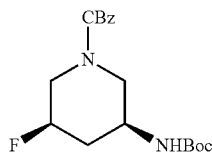

Step 2. (3S,5R)-benzyl 3-((tert-butoxycarbonyl)amino)-5-fluoropiperidine-1-carboxylate. (3S,5R)-benzyl 3-azido-5-fluoropiperidine-1-carboxylate (780 mg, 2.80 mmol) was treated with pyridine (6 mL, 74.2 mmol) and ammonium hydroxide (concentrated, 30% 0.11 mL, 2.80 mmol) followed by PMe3, (1.0M solution in THF, 8.41 mL, 8.41 mmol) and the resulting solution stirred at RT for 2.5 h. The reaction mixture was concentrated, diluted with EtOH and concentrated again. The residue was diluted with dioxane (12 mL) and a saturated solution of NaHCO$_3$ (aq) and cooled to 0° C. A solution of Boc$_2$O (2.45 g, 11.21 mmol) in THF (6 mL) was added and the reaction mixture was removed from the ice bath and stirred at RT for 1.5 h. The reaction mixture was diluted with EtOAc (50 mL), washed with brine (2×), dried over MgSO$_4$, filtered and concentrated. The crude material was purified by silica gel chromatography (10-70% EtOAc in hexanes) to afford (3S,5R)-benzyl 3-((tert-butoxycarbonyl)amino)-5-fluoropiperidine-1-carboxylate (920 mg, 2.61 mmol, 93% yield) as a white crystalline solid. (ESI, pos. ion) m/z: 375.0 (M+1). $^1$H NMR (300 MHz, CDCl$_3$) δ ppm 7.27-7.41 (5 H, m), 5.04-5.30 (2 H, m), 4.89 (1 H, br. s.), 4.73 (1 H, br. s.), 4.32 (1 H, br. s.), 4.08 (1 H, br. s.), 3.88 (1 H, br. s.), 3.15 (2 H, d, J=13.3 Hz), 2.07 (1 H, d, J=14.6 Hz), 1.88 (1 H, d, J=14.8 Hz), 1.40 (9 H, br. s.). ¹⁹F NMR (282 MHz, CDCl₃) δ ppm −180.64 (1 F, s), −181.02 (1 F, s).

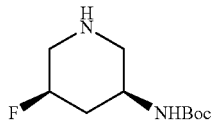

Step 3. tert-butyl ((3S,5R)-5-fluoropiperidin-3-yl)carbamate. (3S,5R)-Benzyl 3-((tert-butoxycarbonyl)amino)-5-fluoropiperidine-1-carboxylate (905 mg, 2.57 mmol) was treated with EtOH (30 mL) and Pd/C (10 wt %, 273 mg, 0.26 mmol), purged with hydrogen and stiffed under an atmosphere of hydrogen (balloon) overnight (16 h). The reaction mixture was filtered through a 0.45 um acrodisc and washed with MeOH and concentrated to afford crude tert-butyl ((3S,5R)-5-fluoropiperidin-3-yl)carbamate (573 mg, 2.63 mmol, 100% yield) as a white crystalline solid. (ESI, pos. ion) m/z: 219.1 (M+1).

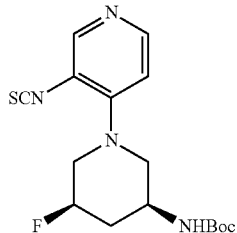

Step 4. tert-butyl ((3S,5R)-5-fluoro-1-(3-isothiocyanatopyridin-4-yl)piperidin-3-yl)carbamate. The title compound was prepared as a white crystalline solid from tert-butyl ((3S,5R)-5-fluoropiperidin-3-yl)carbamate following an analogous procedure to Preparation XIII. MS (ESI, pos. ion) m/z: 353.1 (M+1). ¹H NMR (400 MHz, CDCl₃) δ ppm 8.37 (1 H, s), 8.25 (1 H, d, J=5.5 Hz), 6.82 (1 H, d, J=5.7 Hz), 5.20 (1 H, d, J=6.3 Hz), 4.98 (1 H, br. s.), 4.87 (1 H, br. s.), 4.02 (1 H, br. s.), 3.75 (1 H, br. s.), 3.56 (1 H, d, J=9.4 Hz), 3.23-3.46 (2 H, m), 2.05-2.19 (2 H, m), 1.44 (9 H, s). ¹⁹F NMR (376 MHz, CDCl₃) δ ppm −179.90 (1 F, s).

Preparation XL. (2S,5S)-tert-butyl 4-(3-isothiocyanatopyridin-4-yl)-2,5-dimethylpiperazine-1-carboxylate

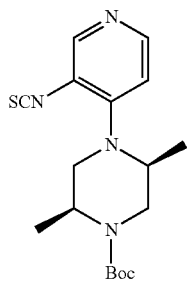

Step 1. (2S,5S)-tert-butyl 2,5-dimethyl-4-(3-nitropyridin-4-yl) piperazine-1-carboxylate. To a solution of (2S,5S)-tert-butyl 2,5-dimethylpiperazine-1-carboxylate hydrochloride (1.17 g, 4.67 mmol, Acesys Pharmatech, A1653, Sample ID 119-99-18) in 2-Propanol (20 mL) was added 4-chloro-3-nitropyridine (1.11 g, 7.00 mmol, Alfa Aesar, Ward Hill, Mass.) and DIPEA (4.06 mL, 23.33 mmol). The mixture was heated and stirred at 85° C. for 2 h. Additional DIPEA (0.81 mL, 4.67 mmol) was added and the heat was raised to 90° C. The mixture was stirred at this temperature for 18 h. The mixture was then cooled to RT and concentrated. The residue was diluted with EtOAc (150 mL) and washed with water (15 mL) followed by brine (15 mL) and then dried over MgSO₄. The crude material was purified by silica gel chromatography (30-70% EtOAc in hexanes) to afford (2S,5S)-tert-butyl 2,5-dimethyl-4-(3-nitropyridin-4-yl)piperazine-1-carboxylate (918 mg, 2.73 mmol, 59% yield) as a yellow solid. MS (ESI, pos. ion) m/z: 337.1 (M+1). ¹H NMR (400 MHz, CDCl₃) δ ppm 8.82 (s, 1 H), 8.38 (d, J=5.9 Hz, 1 H), 6.99 (d, J=6.1 Hz, 1 H), 4.12 (dd, J=14.0, 4.4 Hz, 1 H), 3.99-4.07 (m, 1 H), 3.94 (dt, J=10.8, 5.5 Hz, 1 H), 3.23 (dd, J=13.5, 9.4 Hz, 1 H), 2.98 (dd, J=14.1, 10.8 Hz, 1 H), 2.77 (dd, J=13.5, 5.7 Hz, 1 H), 1.46 (s, 9 H), 1.16 (d, J=6.3 Hz, 3 H), 1.13 (d, J=6.1 Hz, 3 H).

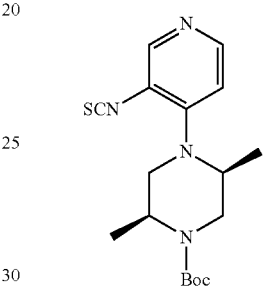

Step 2. (2S,5S)-tert-butyl 4-(3-isothiocyanatopyridin-4-yl)-2,5-dimethylpiperazine-1-carboxylate. The title compound was prepared as a colorless oil from (2S,5S)-tert-butyl 2,5-dimethyl-4-(3-nitropyridin-4-yl)piperazine-1-carboxylate in an analogous manner to Preparation XIII steps 2 and 3. MS (ESI, pos. ion) m/z: 349.1 (M+1). ¹H NMR (400 MHz, CDCl₃d) δ ppm 8.40 (s, 1 H), 8.29 (d, J=5.5 Hz, 1 H), 6.87 (d, J=5.7 Hz, 1 H), 4.23-4.33 (m, 1 H), 4.02 (dd, J=13.8, 4.4 Hz, 1 H), 3.50 (dquin, J=10.9, 5.6, 5.6, 5.6, 5.6 Hz, 1 H), 3.27 (dd, J=12.9, 4.9 Hz, 1 H), 3.03 (dd, J=12.9, 5.5 Hz, 1 H), 2.90 (dd, J=13.8, 10.5 Hz, 1 H), 1.47 (s, 9 H), 1.34 (d, J=6.7 Hz, 3 H), 1.07 (d, J=6.3 Hz, 3 H).

Preparation XLI. rac-tert-butyl 4-(3-isothiocyanatopyridin-4-yl)-trans-2,5-dimethylpiperazine-1-carboxylate

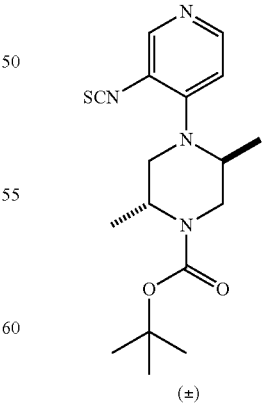

The title compound was prepared and isolated as a brown amorphous solid from rac-trans-N-Boc-2,5-dimethylpiperazine (ACC corp, cat # CCH000523) and 4-chloro-3-nitropy- Preparation XLII. tert-butyl (1-(3-isothiocyanatopyridin-4-yl)-2-methylpiperidin-3-yl)carbamate

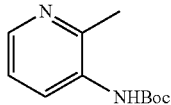

Step 1. tert-butyl (2-methylpyridin-3-yl)carbamate. The title compound was prepared and isolated as a brown crystalline solid from 3-amino-2-methylpyridine (Aldrich, cat #662690) following an analogous procedure to tert-butyl (5-methylpyridin-3-yl)carbamate (Preparation XXXIV step 1). MS (ESI, pos. ion) m/z: 209.1 (M+1). $^1$H NMR (400 MHz, DMSO-$d_6$) δ ppm 8.75 (1 H, s), 8.21 (1 H, dd, J=4.7, 1.6 Hz), 7.75 (1 H, m), 7.19 (1 H, dd, J=8.0, 4.7 Hz), 2.41 (3 H, s), 1.48 (9 H, s).

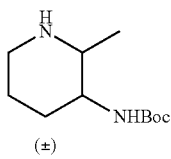

Step 2. tert-butyl (2-methylpiperidin-3-yl)carbamate. In a 150 mL metal reactor, tert-butyl (2-methylpyridin-3-yl)carbamate (2.50 g, 12.00 mmol) was treated with 45 mL of glacial acetic acid, platinum (IV) oxide (420 mg, 1.85 mmol) and rhodium (5 wt %, degussa type, 420 mg, 4.08 mmol) and hydrogenated at 200 psi of hydrogen at 70° C. for 23 h. The reaction mixture was filtered through a pad of Celite and the filter cake was rinsed with 2×20 mL of MeOH. The filtrate was concentrated. The residue was treated with 2 N NaOH (to pH 9) and extracted with EtOAc (3×75 mL). The combined organic extracts were washed with brine and dried over $Na_2SO_4$, filtered and concentrated to give tert-butyl (2-methylpiperidin-3-yl)carbamate (1.67 g, 64.9% yield) as an off white amorphous solid. MS (ESI, pos. ion) m/z: 215.1 (M+1).

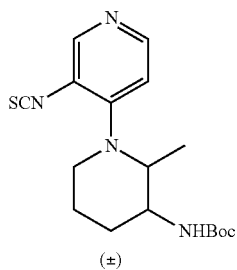

Step 3. tert-butyl (1-(3-isothiocyanatopyridin-4-yl)-2-methylpiperidin-3-yl)carbamate. The title compound was prepared and isolated as a pale yellow amorphous solid from tert-butyl (2-methylpiperidin-3-yl)carbamate and 4-chloro-3-nitropyridine following an analogous procedure to Preparation XIII. MS (ESI, pos. ion) m/z: 349.1 (M+1).

Preparation XLIII. (S)-tert-butyl 4-(3-isothiocyanatopyridin-4-yl)-2-methylpiperazine-1-carboxylate

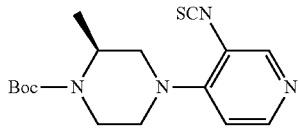

The title compound was prepared as a colorless oil from (S)-1-N-boc-2-methylpiperazine (Oakwood Products Inc., West Columbia, S.C.) and 4-chloro-3-nitropyridine (Alfa Aesar, Ward Hill, Mass.) following an analogous manner to Preparation XIII. MS (ESI, pos. ion) m/z: 335.0 (M+1). $^1$H NMR (400 MHz, CDCl$_3$) δ ppm 8.37 (s, 1 H), 8.28 (d, J=5.5 Hz, 1H), 6.76 (d, J=5.7 Hz, 1 H), 4.40 (br. s., 1 H), 3.98 (d, J=13.3 Hz, 1 H), 3.43-3.54 (m, 2H), 3.38 (td, J=12.7, 3.0 Hz, 1 H), 3.06 (dd, J=12.1, 3.5 Hz, 1 H), 2.84 (td, J=11.8, 3.3 Hz, 1 H), 1.49 (s, 9 H), 1.36 (d, J=6.8 Hz, 3 H).

Preparation XLIV. (S)-tert-butyl (1-(3-isothiocyanatopyridin-4-yl)piperidin-3-yl)(methyl)carbamate

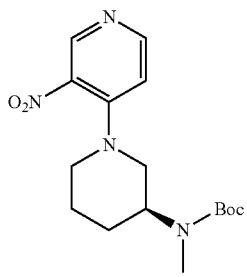 [SMILES: CN(C(=O)OC(C)(C)C)[C@H]1CCCN(c2ccncc2[N+](=O)[O-])C1]

Step 1. (S)-tert-butyl methyl(1-(3-nitropyridin-4-yl)piperidin-3-yl)carbamate. A solution of (S)-tert-butyl (1-(3-nitropyridin-4-yl)piperidin-3-yl)carbamate (1.13 g, 3.49 mmol, WO 2008/106692) in DMF at 0° C. was treated with NaH (60% dispersion in mineral oil, 209 mg, 5.23 mmol). The reaction mixture was stirred at 0° C. for 20 min. Iodomethane (0.24 mL, 3.84 mmol) was added, and the mixture was stirred for a further 30 min at 0° C. A saturated solution of NH$_4$Cl (aq.) was added slowly to the solution at 0° C. The crude material was purified by silica gel chromatography (20-70% EtOAc in hexanes) to afford (S)-tert-butyl methyl(1-(3-nitropyridin-4-yl)piperidin-3-yl)carbamate as a yellow oil. MS (ESI, pos. ion) m/z: 337.1 (M+1). $^1$H NMR (400 MHz, CDCl$_3$) δ ppm 8.83 (s, 1 H), 8.35 (d, J=6.1 Hz, 1 H), 6.90-7.07 (m, 1 H), 4.07 (br. s., 1 H), 3.38-3.52 (m, 1 H), 3.22-3.36 (m, 1 H), 3.09 (t, J=12.0 Hz, 1 H), 2.99 (t, J=11.3 Hz, 1 H), 2.82 (s, 3 H), 1.95 (br. s., 1 H), 1.80-1.90 (m, 1 H), 1.69-1.80 (m, 2 H), 1.48 (s, 9 H).

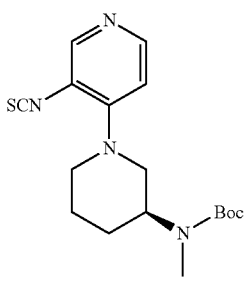

Step 2: (S)-tert-butyl (1-(3-isothiocyanatopyridin-4-yl)piperidin-3-yl)(methyl)carbamate. The title compound was prepared and isolated as a colorless oil from (S)-tert-butyl methyl(1-(3-nitropyridin-4-yl)piperidin-3-yl)carbamate following an analogous procedure to Preparation XIII. MS (ESI, pos. ion) m/z: 349.1 (M+1). $^1$H NMR (400 MHz, CDCl$_3$) δ ppm 8.31 (s, 1 H), 8.24 (d, J=5.7 Hz, 1 H), 6.84 (d, J=5.7 Hz, 1 H), 4.12 (q, J=7.2 Hz, 1 H), 3.72 (d, J=12.5 Hz, 1 H), 3.57 (d, J=11.3 Hz, 1 H), 2.95 (t, J=11.3 Hz, 1 H), 2.84 (s, 3 H), 2.71-2.80 (m, 1 H), 1.80-1.98 (m, 3 H), 1.67-1.78 (m, 1 H), 1.48 (s, 9 H).

Preparation XLV. rac-tert-butyl (1-(3-isothiocyanato-pyridin-4-yl)-5-(trifluoromethyl)piperidin-3-yl)carbamate

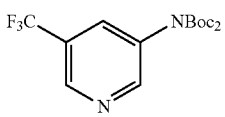

Step 1. bis(tert-butyl (5-(trifluoromethyl)pyridin-3-yl)carbamate). 5-(Trifluoromethyl)pyridin-3-amine (977 mg, 6.03 mmol, Anichem, P20551, North Brunswick, N.J.) was treated with THF (40 mL) and LiHMDS (1.0 M in THF, 13.26 mL, 13.26 mmol) slowly dropwise at RT and stirred at this temperature for 20 min. The solution was then cooled in an ice bath and di-tert-butyl dicarbonate (1.38 g, 6.33 mmol) was added and the solution stirred warming to RT overnight. LC-MS indicated partial conversion to bis(Boc) material (M+1=363.2). The reaction mixture was treated with additional di-tert-butyl dicarbonate (1.38 g, 6.33 mmol) and of 1M LiHMDS and stirred overnight (16 h). The reaction mixture was concentrated and the crude material was treated with 0.2M HCl (aq., 30 mL) and extracted with EtOAc (100 mL). The organic layer was washed with a saturated solution of NaHCO$_3$ (aq.) and brine and dried over MgSO$_4$, filtered and concentrated. The resulting crude product was purified by silica gel chromatography (20-50% EtOAc in hexanes) to afford bis(tert-butyl (5-(trifluoromethyl)pyridin-3-yl)carbamate) (729 mg, 33% yield) as a yellow crystalline solid. MS (ESI, pos. ion) m/z: 363.0 (M+1). $^1$H NMR (400 MHz, CDCl$_3$) δ ppm 8.80 (1H, s), 8.58-8.64 (1 H, m), 7.75 (1 H, s), 1.44 (18 H, s). $^{19}$F NMR (377 MHz, CDCl$_3$) δ ppm -62.36 (3 F, s).

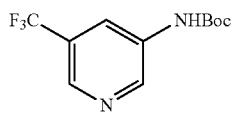

Step 2. tert-butyl (5-(trifluoromethyl)pyridin-3-yl)carbamate. Bis(tert-butyl (5-(trifluoromethyl)pyridin-3-yl)carbamate) (728 mg, 2.01 mmol) was treated with MeOH (5.0 mL), THF (15 mL) and 1N NaOH (aq., 3.0 mL, 3.0 mmol) and stirred at RT for 1 h. The reaction mixture was concentrated, treated with water and extracted with EtOAc (25 mL). The organic layer was washed with brine and dried over MgSO$_4$, filtered and concentrated. The crude material was purified by silica gel chromatography (0-50% EtOAc in hexanes) to afford tert-butyl (5-(trifluoromethyl)pyridin-3-yl)carbamate (363 mg, 1.39 mmol, 68.9% yield) as a white crystalline solid. MS (ESI, pos. ion) m/z: 263.1 (M+1). $^1$H NMR (400 MHz, CDCl$_3$) δ ppm 8.55 (2 H, d, J=3.7 Hz), 8.34 (1 H, br. s.), 6.67 (1 H, br. s.), 1.54 (9 H, s)>95% purity 116517-25-2. $^{19}$F NMR (376 MHz, CDCl$_3$) δ ppm -62.49 (3 F, s).

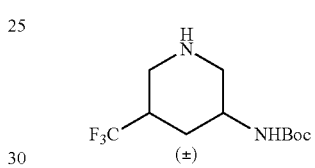

Step 3: rac-tert-butyl (5-(trifluoromethyl)piperidin-3-yl)carbamate. In a 50 mL hastalloy metal reactor, tert-butyl (5-(trifluoromethyl)pyridin-3-yl)carbamate (600 mg, 2.29 mmol) was treated with glacial acetic acid (10 mL), platinum (IV) oxide (250 mg, 1.10 mmol) and rhodium (5 wt. % (dry) on carbon, degussa type, 250 mg, 2.43 mmol) and hydrogenated at 200 psi hydrogen at 70° C. for 23 h. The reaction mixture was cooled to RT and filtered through a 0.45 um acrodisc, washed with MeOH and concentrated under reduced pressure. The residue was treated with EtOAc and 2N NaOH and extracted with EtOAc (3×25 mL). The combined organic layers were washed with brine and dried over MgSO$_4$, filtered and concentrated to afford rac-tert-butyl (5-(trifluoromethyl)piperidin-3-yl)carbamate (490 mg, 1.83 mmol, 80%). MS (ESI, pos. ion) m/z: 269.1 (M+1). The crude material was used in the subsequent step without further purification.

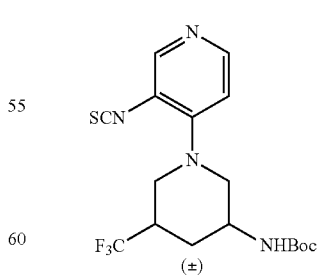

Step 4: rac-tert-butyl (1-(3-isothiocyanatopyridin-4-yl)-5-(trifluoromethyl)piperidin-3-yl)carbamate. The title compound was prepared as a clear, colorless film from rac-tert-butyl (5-(trifluoromethyl)piperidin-3-yl)carbamate following an analogous procedure to Preparation XIII. MS (ESI, pos. ion) m/z: 403.1 (M+1).

Preparation XLVI. (R)-tert-butyl (1-(3-isothiocyanatopyridin-4-yl)piperidin-3-yl)carbamate

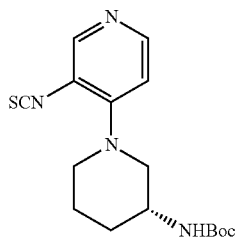

The title compound was prepared from (R)-3-Boc-amino piperidine (CNH Technologies, Woburn, Mass., #: C-3102R) and 4-chloro-3-nitropyridine (Aldrich Chemical Company) following an analogous procedure to Preparation XIII. MS (ESI, pos. ion) m/z: 335.2 (M+1). $^1$H NMR (400 MHz, CDCl$_3$) δ ppm 8.33 (1 H, s), 8.26 (1 H, d, J=5.7 Hz), 6.83 (1 H, d, J=5.7 Hz), 4.88 (1 H, br. s.), 3.89 (1 H, br. s.), 3.44 (1 H, d, J=11.5 Hz), 3.26 (1 H, br. s.), 3.15 (1 H, br. s.), 3.03 (1 H, br. s.), 1.83-1.99 (2 H, m), 1.72-1.83 (1 H, m), 1.62 (1 H, br. s.), 1.46 (9 H, s).

Preparation XLVII. (3-isothiocyanato-4-(piperidin-1-yl)pyridine

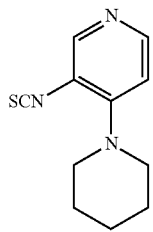

The title compound was prepared from piperidine and 4-chloro-3-nitropyridine (Aldrich Chemical Company) following an analogous procedure to Preparation XIII. MS (ESI, pos. ion) m/z: 220.1 (M+1). $^1$H NMR (400 MHz, CDCl$_3$) δ ppm 8.30 (1 H, s), 8.23 (1 H, d, J=5.7 Hz), 6.76 (1 H, d, J=5.7 Hz), 3.16-3.26 (4 H, m), 1.78 (4 H, quin, J=5.6 Hz), 1.60-1.69 (2 H, m).

Preparation XLVIII. (S)-tert-butyl (1-(2-isothiocyanatophenyl)piperidin-3-yl)carbamate

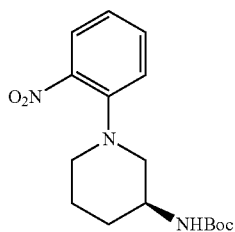

Step 1. (S)-tert-butyl (1-(2-nitrophenyl)piperidin-3-yl)carbamate. A mixture of 1-fluoro-2-nitrobenzene (0.19 mL, 1.77 mmol, Sigma-Aldrich), (s)-3-(boc-amino)piperidine (355 mg, 1.77 mmol, Sigma-Aldrich) and DIPEA (0.62 mL, 3.54 mmol) in EtOH (3.5 mL) was heated at 50° C. and stirred for 20 h. After cooling to RT, the reaction mixture was concentrated. The residue was diluted with EtOAc and saturated NaHCO$_3$ (aq.). The organic layer was washed with water, and brine and dried over Na$_2$SO$_4$, filtered and concentrated to afford (S)-tert-butyl (1-(2-nitrophenyl)piperidin-3-yl)carbamate (536 mg, 1.67 mmol, 94% yield) as an orange oil. MS (ESI, pos. ion) m/z: 322.1 (M+1).

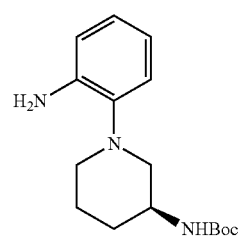

Step 2. (S)-tert-butyl (1-(2-aminophenyl)piperidin-3-yl)carbamate. A solution of (S)-tert-butyl (1-(2-nitrophenyl)piperidin-3-yl)carbamate (536 mg, 1.67 mmol) in EtOH (10 mL) was degassed by bubbling N$_2$ (g) through the solution for 10 min. Pd/C (10 wt. %, 177 mg, 0.17 mmol) was added as a suspension in water (2 mL). A gas bag with a 3-way stopcock filled with H$_2$ was attached to the flask. The flask was evacuated under vacuum and then back-filled with H$_2$ (3×). The mixture was stiffed overnight at RT. The solution was degassed by bubbling N$_2$ (g) through the solution for 10 min and was then filtered through celite. The solution was concentrated to afford (S)-tert-butyl (1-(2-aminophenyl)piperidin-3-yl)carbamate (580 mg, 1.99 mmol, 119% yield) as an off-white foam.

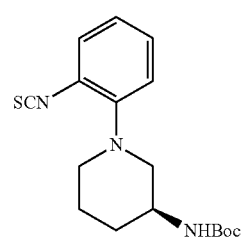

Step 3. (S)-tert-butyl (1-(2-isothiocyanatophenyl)piperidin-3-yl)carbamate. 1,1'-Thiocarbonyldiimidazole (239 mg, 1.34 mmol, Sigma-Aldrich) was added to a solution of (S)-tert-butyl (1-(2-aminophenyl)piperidin-3-yl)carbamate (195 mg, 0.67 mmol) in THF (4 mL) at RT. The reaction was heated at 60° C. for 2 h. The mixture was cooled to RT, diluted with EtOAc, washed with water and the organic layer was dried over anh. Na$_2$SO$_4$, filtered and concentrated. The crude material was purified by silica gel chromatography (0-50% EtOAc in hexanes) to provide (S)-tert-butyl (1-(2-isothiocyanatophenyl)piperidin-3-yl)carbamate (132 mg, 0.40 mmol, 59% yield) as a thick, clear and colorless oil. MS (ESI, pos. ion) m/z: 334.1 (M+1). $^1$H NMR (400 MHz, CDCl$_3$) δ ppm 7.18-7.25 (m, 1 H), 7.14 (dt, J=7.82, 0.88 Hz, 1 H), 6.97-7.06 (m, 2 H), 5.27-5.37 (m, 1 H), 3.98 (br. s., 1 H), 3.14 (d, J=10.56 Hz, 1 H), 3.01 (d, J=10.56 Hz, 1H), 2.92 (d, J=5.87

Hz, 1 H), 2.78 (t, J=9.39 Hz, 1 H), 2.00-2.13 (m, 1 H), 1.68-1.80 (m, 2 H), 1.46 (s, 9 H)

Preparation XLIX. tert-butyl ((3S)-1-(3-isothiocyanatopyridin-4-yl)-2-methylpiperidin-3-yl)carbamate

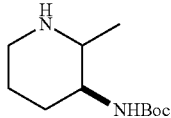

Step 1. tert-butyl ((3S)-2-methylpiperidin-3-yl)carbamate. The title compound was prepared in 2 steps from N-boc-z-l-ornithine (Aldrich, #15565) according to the procedures described in WO06106326.

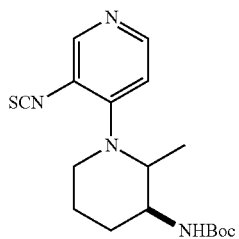

Step 2. tert-butyl ((3S)-1-(3-isothiocyanatopyridin-4-yl)-2-methylpiperidin-3-yl)carbamate. The title compound was prepared and isolated as a brown amorphous solid from tert-butyl ((3S)-2-methylpiperidin-3-yl)carbamate and 4-chloro-3-nitropyridine following an analogous procedure to Preparation XIII. MS (ESI, pos. ion) m/z: 349.1 (M+1).

Preparation L. 3-isothiocyanato-N-(2-methoxypropyl)-N-methylpyridin-4-amine

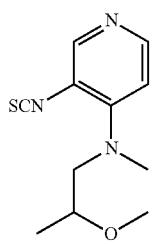

The title compound was prepared from 2-methoxy-N-methylpropan-1-amine hydrochloride (881 mg, 6.31 mmol) (Chembridge, San Diego, Calif.) and 4-chloro-3-nitropyridine (Aldrich Chemical Company) following an analogous procedure to Preparation XIII. MS (ESI, pos. ion) m/z: 238.1 (M+1). $^1$H NMR (400 MHz, CDCl$_3$) δ ppm 8.27 (s, 1 H), 8.11 (d, J=6.1 Hz, 1 H), 6.61 (d, J=5.9 Hz, 1 H), 3.60-3.70 (m, 2 H), 3.35-3.44 (m, 1 H), 3.31 (s, 3 H), 3.12 (s, 3 H), 1.17 (d, J=5.9 Hz, 3 H).

Preparation LI. (S)-tert-butyl (1-(4-isothiocyanatopyridin-3-yl)piperidin-3-yl)carbamate

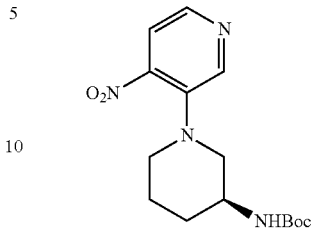

Step 1. (S)-tert-butyl (1-(4-nitropyridin-3-yl)piperidin-3-yl)carbamate. 3-Fluoro-4-nitropyridine (689 mg, 4.85 mmol, Chem Impex International, Wood Dale, Ill.) and (S)-3-(Boc-amino)piperidine (1.17 g, 5.82 mmol, Alfa Aesar, Ward Hill, Mass.) were treated with dioxane (20 mL) and DIPEA (2.12 mL, 12.12 mmol) and heated in a flask with a reflux condenser to 100° C. for 16 h. The reaction mixture was concentrated and the crude material was purified by silica gel chromatography (10-90% EtOAc in hexanes) to afford (S)-tert-butyl (1-(4-nitropyridin-3-yl)piperidin-3-yl)carbamate (1.49 g, 4.62 mmol, 95% yield) as a bright yellow crystalline solid. MS (ESI, pos. ion) m/z: 323.3 (M+1). $^1$H NMR (400 MHz, CDCl$_3$) δ ppm 8.11-8.17 (2 H, m), 7.27 (1 H, br. s.), 4.57 (1 H, br. s.), 3.86 (1 H, d, J=11.9 Hz), 3.73 (1 H, br. s.), 3.64 (1 H, d, J=11.9 Hz), 3.27 (1 H, br. s.), 3.07-3.20 (1 H, m), 1.97-2.06 (1 H, m), 1.81-1.91 (1 H, m), 1.73 (1 H, dtd, J=13.6, 9.1, 9.1, 4.3 Hz), 1.46 (9 H, s).

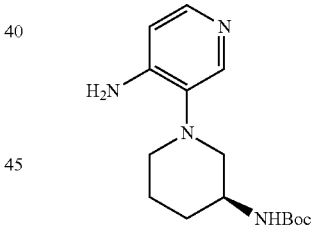

Step 2. (S)-tert-butyl (1-(4-aminopyridin-3-yl)piperidin-3-yl)carbamate. (S)-tert-Butyl (1-(4-nitropyridin-3-yl)piperidin-3-yl)carbamate (1.43 g, 4.44 mmol) was treated with EtOH (50 mL) and Pd/C (10 wt %, 472 mg, 0.44 mmol) and purged with H$_2$ and stiffed overnight under an atmosphere of H$_2$. The reaction mixture was filtered through a 0.45 um acrodisc and concentrated under reduced pressure and dried under high vacuum for 3 h to afford (S)-tert-butyl (1-(4-aminopyridin-3-yl)piperidin-3-yl)carbamate (1.33 g, 4.53 mmol, 100% yield) as a light yellow foam. MS (ESI, pos. ion) m/z: 293.3 (M+1). $^1H NMR$ (400 MHz, CDCl$_3$) δ ppm 7.76 (1 H, d, J=2.7 Hz), 7.16 (1 H, dd, J=8.8, 2.9 Hz), 6.47 (1 H, d, J=8.6 Hz), 4.96 (1 H, br. s.), 4.14 (2 H, d, J=7.0 Hz), 3.86 (1 H, br. s.), 3.16 (1 H, d, J=10.4 Hz), 2.95 (2 H, br. s.), 2.82 (1 H, br. s.), 1.78-1.89 (1 H, m), 1.64-1.78 (3 H, m), 1.57 (3 H, br. s.), 1.46 (9 H, s).

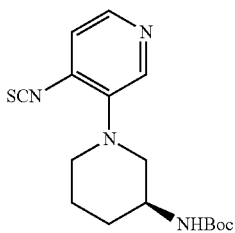 [SMILES: CC(C)(C)OC(=O)N[C@H]1CCCN(c2cnccc2[N+](=O)[O-])C1]

Step 3. (S)-tert-butyl (1-(4-isothiocyanatopyridin-3-yl)piperidin-3-yl)carbamate. (S)-tert-Butyl (1-(4-aminopyridin-3-yl)piperidin-3-yl)carbamate (1.30 g, 4.45 mmol) and 1,1'-thiocarbonyldiimidazole (1.76 g, 8.89 mmol) was treated with THF (30 mL) and heated to 60° C. for 2.5 h. The reaction mixture was concentrated under reduced pressure and the crude material was purified by silica gel chromatography (10-50% EtOAc in hexanes) to provide (S)-tert-butyl (1-(4-isothiocyanatopyridin-3-yl)piperidin-3-yl)carbamate (1.06 g, 3.17 mmol, 71% yield) as a white fibrous solid. MS (ESI, pos. ion) m/z: 335.1 (M+1). $^1$H NMR (400 MHz, CDCl$_3$) δ ppm 8.04 (1 H, d, J=2.9 Hz), 7.15-7.24 (1 H, m), 7.01 (1 H, d, J=8.6 Hz), 4.70 (1 H, br. s.), 3.80 (1 H, br. s.), 3.53 (1 H, d, J=11.5 Hz), 3.27 (1 H, br. s.), 3.02-3.14 (1 H, m), 2.86-2.99 (1 H, m), 1.78-1.94 (2 H, m), 1.65-1.77 (1 H, m), 1.46 (9 H, s).

Preparation LII. N-isobutyl-3-isothiocyanato-N-methylpyridin-4-amine

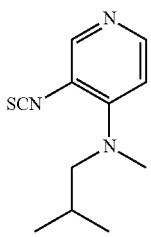

The title compound was prepared from N,2-dimethylpropan-1-amine (Sigma-Aldrich), 4-chloro-3-nitropyridine (Aldrich Chemical Company) following an analogous procedure to Preparation XIII. MS (ESI, pos. ion) m/z: 222.1 (M+1). $^1$H NMR (400 MHz, CDCl$_3$) δ ppm 8.25 (s, 1 H), 8.10 (d, J=6.1 Hz, 1 H), 6.58 (d, J=5.9 Hz, 1 H), 3.30 (d, J=7.6 Hz, 2 H), 3.07 (s, 3 H), 2.04 (dquin, J=13.8, 6.9, 6.9, 6.9, 6.9 Hz, 1 H), 0.93 (d, J=6.7 Hz, 6 H).

Preparation LIII. rac-2-(3-(3-isothiocyanatopyridin-4-yl)cyclohex-2-en-1-yl)isoindoline-1,3-dione

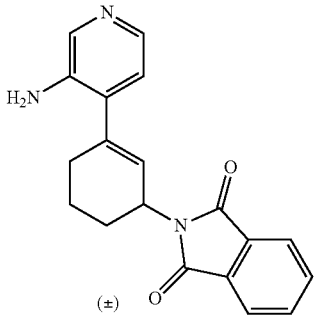

Step 1. rac-2-(3-(3-aminopyridin-4-yl)cyclohex-2-en-1-yl)isoindoline-1,3-dione. A 250 mL Parr shaker was charged with rac-2-(3-(3-nitropyridin-4-yl)cyclohex-2-en-1-yl)isoindoline-1,3-dione (200 g, 0.29 mmol, WO09/109,576) and TFE (20 mL). The shaker was fitted with a vacuum/nitrogen source, and carefully evacuated to <10 mm Hg. The vacuum was released with N$_2$ to complete one degass cycle. The vessel was degassed an additional 2 times, and a slurry of Pd/C (10% wt., 61 mg, 0.06 mmol) in 2 mL TFE was added via pipette. The vessel was degassed an additional 2 times, and transferred to a Parr hydrogenator. The system was carefully evacuated and refilled with N$_2$ (2 cycles). The vessel was once again evacuated, and refilled with H$_2$ to 4 psi. The reaction was agitated for 12 h. The system was de-gassed as described (3 cycles), and the slurry was N$_2$-pressure filtered through a glass frit (10 mL Bohdan) fitted with a 0.22 μm PTFE, 25 mm syringe filter unit (Millipore, SLFG025NK). The carbon was washed with TFE (3×3 mL), and the filtrate was combined with the washes. The solvent was removed in vacuo to afford 199 mg of material. The crude was purified in 2 injections using a Phenominex cyano column (250×20 mm, spherical particle, 5 μm particle size, 120 Å pore size, flow=20 mL/min. A=Heptane, B=THF; isocratic at 45% B). The solvent was removed in vacuo, and the material was dried in a vacuum oven (<1 mm Hg, 60° C.) for 2 h to afford rac-2-(3-(3-aminopyridin-4-yl)cyclohex-2-en-1-yl)isoindoline-1,3-dione (140 mg, 0.22 mmol, 77% yield). MS (ESI, pos. ion) m/z: 320.0 (M+1).

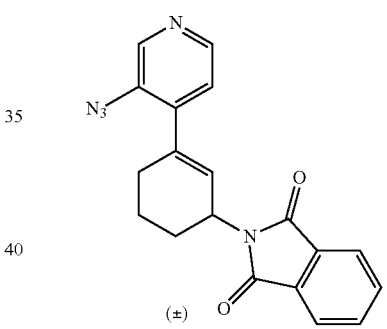

Step 2. rac-(3-(3-azidopyridin-4-yl)cyclohex-2-en-1-yl)isoindoline-1,3-dione. A 30 mL, pressure vessel was charged with rac-2-(3-(3-aminopyridin-4-yl)cyclohex-2-en-1-yl)isoindoline-1,3-dione (140 mg, 0.22 mmol), a stirbar, acetone (10 mL) and water (5 mL). The vessel was immersed into an acetone cooling bath maintained by an external chiller set to −5 C. The solution was stirred for 5 min, afterwhich time, an 8 M solution of H$_2$SO$_4$ (0.27 mL, 2.19 mmol) was added. The solution was stirred for 10 min. The solution was then treated with NaNO$_2$ (43 mg, 0.62 mmol) dissolved in water (0.3 mL). The reaction was stirred for 30 min, and treated with an additional 5 mg of NaNO$_2$. The reaction was stirred an additional 10 min, afterwhich time, a solution of NaN$_3$ (114 mg, 1.75 mmol) dissolved in water (0.4 mL) was cautiously added (N$_2$ evolution). The reaction was stirred cold for 20 min. The vessel was removed from the cooling bath, and concentrated under a stream of N$_2$ to remove the bulk of acetone. The aqueous solution was then treated carefully with Na$_2$CO$_3$ (279 mg, 2.63 mmol) dissolved in water (0.4 mL). The vessel was removed from the cooling bath, and stirred for 30 min. The slurry was N$_2$-pressure filtered through a glass frit (10 mL Bohdan) fitted with a 0.22 μm PTFE, 25 mm syringe filter unit (Millipore, SLFG025NK). The solids were washed with water (3×3 mL), and dried initially under a stream of N$_2$. The material was then dried in a vacuum oven for 1 h (80° C., <1 mm Hg, final pressure=0.06 mm Hg) to afford rac-(3-(3-azidopyridin-4-yl)cyclohex-2-en-1-yl)isoindoline-1,3-dione (140 mg, 0.41 mmol, 92% yield). MS (ESI, pos. ion) m/z: 346.0 (M+1).

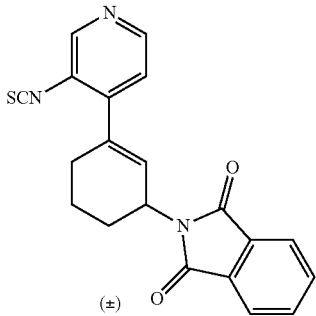

Step 3. rac-2-(3-(3-isothiocyanatopyridin-4-yl)cyclohex-2-en-1-yl)isoindoline-1,3-dione. A dry 15 mL, one neck round bottom flask was charged with 2-(3-(3-azidopyridin-4-yl)cyclohex-2-en-1-yl)isoindoline-1,3-dione (140 mg, 0.41 mmol), dry THF (8 mL), and a stirbar. The flask was fitted with a septa/Ar inlet and immersed into an acetone cooling bath maintained by an external chiller set to −5° C. The solution was stirred for 15 min and then PMe$_3$ (46 µl, 0.45 mmol) was added. The solution was stirred cold for 15 min, and the flask was removed from the cooling bath. The solution was then stirred for 15 min, and charged to a dry 10 mL glass syringe. A dry, 25 mL, one neck round bottom flask was charged with dry THF (5 mL), and a stirbar. The flask was fitted with a septa/Ar inlet and immersed into an acetone cooling bath maintained by an external chiller set to −5° C. The cold solution was then treated with carbon disulfide (0.49 mL, 8.11 mmol). A PTFE addition needle was passed through the septa, and fitted with the 10 mL glass syringe described above. The solution was added via syringe pump over a 1 h period. Upon completion of the addition, the flask was removed from the cooling bath, and stirred for 15 min. The solvent was removed in vacuo, and the residue was further dried in a vacuum oven for 15 min (60° C., <1 mm Hgt, final pressure=0.080 mm Hg). The material was used without characterization.

Preparation LIV. tert-butyl (1-(3-isothiocyanatopyridin-4-yl)-6-methylpiperidin-3-yl)carbamate

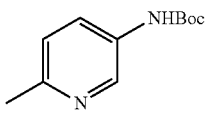

Step 1. tert-butyl (6-methylpyridin-3-yl)carbamate. 5-Amino-2-methylpyridine (3.73 g, 34.5 mmol, Sigma-Aldrich) was treated with THF (65 mL) and LiHMDS (1.0 M in THF, 76 mL, 76 mmol) slowly dropwise at RT and stirred at this temperature for 15 min. Boc$_2$O (7.90 g, 36.2 mmol) was then added and the solution was stirred at RT for 17 h. The reaction mixture was concentrated under reduced pressure and the crude residue was treated with 0.2M HCl (50 mL) and extracted with EtOAc (3×100 mL). The combined organic layers were washed with a saturated solution of NaHCO$_3$, brine, then dried over MgSO$_4$, filtered and concentrated. The crude material was purified by silica gel chromatography (20-50% EtOAc in hexanes) to give tert-butyl (6-methylpyridin-3-yl)carbamate (4.58 g, 21.99 mmol, 64% yield) as a light yellow solid. MS (ESI, pos. ion) m/z: 209.1 (M+1). $^1$H NMR (400 MHz, CDCl$_3$) δ ppm 8.27-8.37 (m, 1 H), 7.86 (br. s., 1H), 7.09 (d, J=8.4 Hz, 1 H), 6.76 (br. s., 1 H), 2.50 (s, 3 H), 1.51 (s, 9 H).

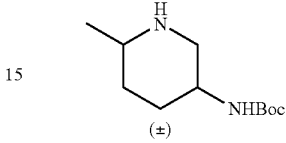

Step 2. tert-butyl (6-methylpiperidin-3-yl)carbamate. In a 150 mL hastalloy metal reactor, tert-butyl (6-methylpyridin-3-yl)carbamate (4.58 g, 21.99 mmol) was treated with HOAc (70 mL), platinum(IV) oxide (0.750 g, 3.30 mmol Aldrich Chemical Company) and rhodium (5 wt. %) (dry) on carbon, wet, degussa 0.77 g, 7.48 mmol, Aldrich Chemical Company) and hydrogenated at 200 psi H$_2$ at 70° C. for 7 h. The catalysts were removed by filtration through a plug of Celite, and the solution was concentrated under reduced pressure. The resulting oil was treated with EtOAc, and washed with a saturated solution of NaHCO$_3$ (aq.). The pH of the organic layer was adjusted to pH 9 with 5N NaOH. The layers were separated and the aqueous layer was extracted with EtOAc (2×100 mL). The combined organic layers were washed with brine, dried over MgSO$_4$, filtered and concentrated to give a mixture of tert-butyl (6-methylpiperidin-3-yl)carbamate isomers (3.41 g, 15.91 mmol, 72% yield). MS (ESI, pos. ion) m/z: 215.1 (M+1).

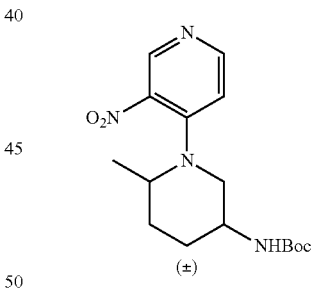

Step 3. tert-butyl (6-methyl-1-(3-nitropyridin-4-yl)piperidin-3-yl)carbamate. To a solution of tert-butyl (6-methylpiperidin-3-yl)carbamate isomers (3.41 g, 15.91 mmol) in 2-propanol (80 mL) was added 4-chloro-3-nitropyridine (Aldrich Chemical Company, 3.78 g, 23.87 mmol) and DIPEA (13.84 mL, 80 mmol). The mixture was heated and stirred at 90° C. for 18 h. The mixture was then cooled to RT and concentrated. The residue was diluted with EtOAc (150 mL) and washed with water (15 mL) followed by brine (15 mL), then dried over MgSO$_4$. The crude material was adsorbed onto silica gel and was purified by silica gel chromatography (30-70% EtOAc in hexanes) to afford tert-butyl (6-methyl-1-(3-nitropyridin-4-yl)piperidin-3-yl)carbamate (2.91 g, 8.65 mmol, 54% yield) as an amorphous yellow solid. MS (ESI, pos. ion) m/z: 337.2 (M+1).

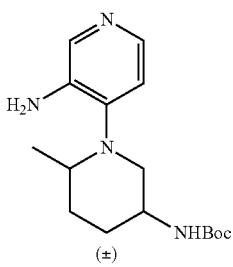

Step 4. tert-butyl-(1-(3-aminopyridin-4-yl)-6-methylpiperidin-3-yl)carbamate. A mixture of tert-butyl-(6-methyl-1-(3-nitropyridin-4-yl)piperidin-3-yl)carbamate isomers (2.91 g, 8.65 mmol) was dissolved in EtOH (100 mL) and purged with $N_2$. Pd/C (10% wt., 921 mg, 0.87 mmol) was added and the flask was evacuated and then filled with $H_2$ four times. The reaction mixture was stirred at RT under an atmosphere of $H_2$ (balloon) for 17 h. The suspension was filtered through a pad of celite to remove the Pd/C residues and the resulting solution was concentrated in vacuo to give tert-butyl-(1-(3-aminopyridin-4-yl)-6-methylpiperidin-3-yl)carbamate (2.47 g, 8.06 mmol, 93% yield) as a beige foam. MS (ESI, pos. ion) m/z: 307.3 (M+1).

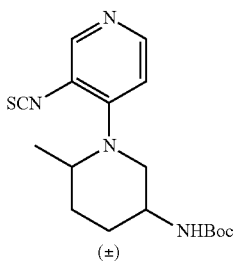 [SMILES: CC1CCC(NC(=O)OC(C)(C)C)CN1c1ccncc1[N+](=O)[O-]]

Step 5. tert-butyl (1-(3-isothiocyanatopyridin-4-yl)-6-methylpiperidin-3-yl)carbamate. Thiocarbonyl diimidazole (2.16 g, 12.14 mmol) was added to a solution of isomers of tert-butyl-1-(3-aminopyridin-4-yl)-6-methylpiperidin-3-yl)carbamate (1.86 g, 6.07 mmol) in THF (60 mL) at RT. The reaction was heated at 60° C. for 1.5 h. One additional equivalent of thiocarbonyl diimidazole (2.16 g, 12.14 mmol) was added, and stirring at 60° C. was continued for another 1.5 h. The mixture was cooled to RT, diluted with EtOAc, washed with water and the organic layer was dried over anh. $MgSO_4$, filtered and concentrated. The crude material was adsorbed onto silica gel and was purified by silica gel chromatography (20-70% EtOAc in hexanes) to give tert-butyl (1-(3-isothiocyanatopyridin-4-yl)-6-methylpiperidin-3-yl)carbamate (1.44 g, 68.1%) above as a light yellow foam. MS (ESI, pos. ion) m/z: 349.2 (M+1).

Preparation LV. rac-2-((trans)-6-fluoro-3-(3-isothiocyanatopyridin-4-yl)cyclohex-2-en-1-yl)isoindoline-1,3-dione

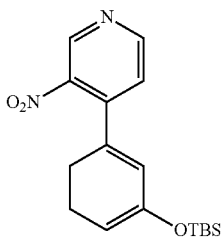 [SMILES: CC(C)(C)[Si](C)(C)OC1=CCCC(c2ccncc2[N+](=O)[O-])=C1]

Step 1. 4-(3-((tert-butyldimethylsilyl)oxy)cyclohexa-1,3-dien-1-yl)-3-nitropyridine. A dry, 25 mL, one neck round bottom flask was charged with 3-(3-nitropyridin-4-yl)cyclohex-2-enone (671 mg, 3.08 mmol, prepared as described in WO 2009/109576), dry $CHCl_3$ (8 mL) and a stirbar. The flask was fitted with a septa/Ar inlet, immersed into an acetone bath maintained by an external chiller set to at −5° C. and stirred for 15 min. The solution was treated with $NEt_3$ (0.65 mL, 4.62 mmol), followed by TBSOTf (0.85 mL, 3.69 mmol). The reaction was stirred at −5° C. overnight and was then treated with 2 pyridylcarbinol (0.12 mL, 1.23 mmol). The cooling bath was removed, and the reaction was stirred for 30 min. The bulk of THF was removed under a stream of $N_2$, and the residue was treated with 10% THF in heptane (5 mL). The slurry was stirred for 20 min and was then loaded onto a 2×80 mm Silicycle diol (R35030B, dried at100° C., <1 mm Hg for 2 h) column slurry packed and eluted with 10% THF in heptane. The initial 500 mL were collected, and the solvent was removed in vacuo. The crude material was purified by preparatory HPLC using a Phenominex cyano column (250× 20 mm, spherical particle, 5 μm particle size, 120 Å pore size, flow=20 mL/min. A=heptane; B=THF; 2% β isocratic) to afford 4-(3-((tert-butyldimethylsilyl)oxy)cyclohexa-1,3-dien-1-yl)-3-nitropyridine (890 mg, 2.68 mmol, 87% yield). $^1$H NMR (400 MHz, ACN-$d_3$) δ ppm 0.16 (s, 6 H) 0.93 (s, 9 H) 2.27-2.34 (m, 4 H) 5.11 (s, 1 H) 5.93 (s, 1 H) 7.40 (d, J=5.09 Hz, 1 H) 8.72 (d, J=5.09 Hz, 1 H) 9.01 (s, 1 H).

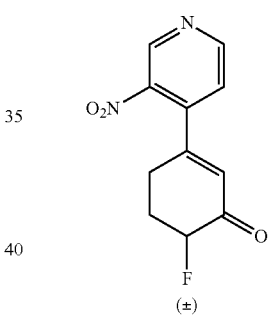

Step 2. 6-fluoro-3-(3-nitropyridin-4-yl)cyclohex-2-enone. A dry, 50 mL, one neck round bottom flask was charged with 1-chloromethyl-4-fluoro-1,4-diazoniabicyclo-(2.2.2)octane bis(tetrafluoroborate) (1.03 g, 2.91 mmol, Alfa Aesar) dried in a vacuum oven for 72 h (0.07 mm Hg, 60° C.), a stirbar, and dry ACN (10 mL). The flask was fitted with a septa/Ar inlet, and stirred and sonicated until a homogenous slurry was produced. The slurry was immersed into a acetone bath maintained by an external chiller set to 5° C., and stirred for 15 min. The slurry was treated with a solution of 4-(3-((tert-butyldimethylsilyl)oxy)cyclohexa-1,3-dien-1-yl)-3-nitropyridine (880 mg, 2.65 mmol) in 4 mL of dry ACN. An additional 5 mL dry ACN was used to assist the transfer. The reaction was stirred at 5° C. for 17 h. The solution was concentrated in vacuo and the crude compound was purified by silica gel chromatography (10% THF in DCE) followed by preparatory HPLC purification using a Phenomenex cyano column (250×20 mm, spherical particle, 5 μm particle size, 120 Å pore size, flow=20 mL/min. A=heptane; B=THF; 20% β isocratic) to afford 6-fluoro-3-(3-nitropyridin-4-yl)cyclohex-2-enone (557 mg, 2.36 mmol, 89%). MS (ESI, pos. ion) m/z: 236.9 (M+1).

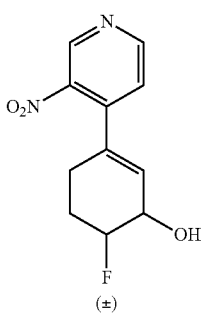 [SMILES: O=[N+]([O-])c1cnccc1C1=CC(O)C(F)CC1]

Step 3. 6-fluoro-3-(3-nitropyridin-4-yl)cyclohex-2-enol. A dry, 100 mL, one neck round bottom flask was charged with 6-fluoro-3-(3-nitropyridin-4-yl)cyclohex-2-enone (557 mg, 2.36 mmol), dry EtOH (50 mL), and a stirbar. The flask was fitted with an Ar inlet, and heated at 45° C. heat transfer block. The solution was stirred until homogenous, and then cerium chloride heptahydrate (942 mg, 2.53 mmol, Fluka) was added. The solution was stirred for 20 min and mixture was cooled in an ice-water bath. The solution was stirred for 5 min, and NaBH₄ (89 mg, 2.36 mmol) was added in portions over 30 min. The reaction was cooled to RT overnight. The mixture was carefully treated with water (10 mL), and stirred at RT for 30 min. The bulk of the EtOH was removed in vacuo, and the aqueous phase was partitioned between water (30 mL) and 1% 1,1,1,3,3,3-hexafluoro-2-propanol—99% CHCl₃ (50 mL). The layers were separated, and the aqueous phase was extracted with 1% 1,1,1,3,3,3-hexafluoro-2-propanol—99% CHCl₃ (4×20 mL). The combined extraction volume was washed with water (1×20 mL), and passed through an unbuffered Varain Chem Elut (CE1010). The extraction tube was washed with 1% 1,1,1,3,3,3-hexafluoro-2-propanol—99% CHCl₃ (2×30 mL). The total elution volume was combined with the wash volume, and the solution was concentrated in vacuo. The oil was then dried in a vacuum oven for 1 h (60° C., <1 mm Hg, final pressure=0.090 mm Hg) to afford 673 mg of material. The crude was purified by preparatory HPLC using a Phenomenex cyano column (250× 20 mm, spherical particle, 5 μm particle size, 120 Å pore size, flow=20 mL/min: A=heptane; B=THF; 20% β isocratic). A band that eluted from 7.4 to 9.6 min was isolated. The solvent was removed in vacuo, and the material was dried in a vacuum oven (<1 mm Hg, 60° C., final pressure=0.080 mm Hg) for 1 h to afford 6-fluoro-3-(3-nitropyridin-4-yl)cyclohex-2-enol (561 mg, 2.36 mmol, 100% yield). The material is a 2:1 mixture of diastereomers. MS (ESI, pos. ion) m/z: 238.9 (M+1).

Step 4. rac-2-((trans)-6-fluoro-3-(3-nitropyridin-4-yl)cyclohex-2-en-1-yl)isoindoline-1,3-dione. A dry 50 mL, one neck round bottom flask was charged with dry THF (5 mL) and a stirbar. The flask was fitted with a septa/Ar inlet and immersed into a cooling bath maintained by an external chiller set to 0° C. The solution was stirred for 5 min, after-which time, tri-n-butylphosphine (0.88 mL, 3.56 mmol, Strem Chemicals Inc.). The reaction was successively treated with 1,1'-(azodicarbonyl)dipiperidine (898 mg, 3.56 mmol, Sigma-Aldrich) dissolved in dry THF (10 mL), 6-fluoro-3-(3-nitropyridin-4-yl)cyclohex-2-enol (565 mg, 2.37 mmol) dissolved in dry THF (10 mL), and phthalimide (523 mg, 3.56 mmol, Sigma-Aldrich) as a slurry in dry THF (8 mL). A precipitate formed within 10 min. The reaction was stirred cold overnight, and the slurry was filtered cold. The solids were washed with cold THF (3×5 mL), and discarded. The filtrate was concentrated in vacuo, and heated into 8 mL EtOH. A precipitate formed over a 48 h period. The slurry was N₂-pressure filtered through a glass frit (10 mL Bohdan) fitted with a 0.22 μm PTFE, 25 mm syringe filter unit (Millipore, SLFG025NK). The solids were washed with cold EtOH (3×3 mL), and discarded. The filtrate was concentrated in vacuo, and the residue was treated with TFE (10 mL). The slurry was N₂-pressure filtered through a glass frit (10 mL Bohdan) fitted with a 0.22 μm PTFE, 25 mm syringe filter unit (Millipore, SLFG025NK). The solids were washed with TFE (3×2 mL), and discarded. The filtrate was concentrated in vacuo. The crude was purified using Prep HPLC method 1. A fraction that eluted from 51.1 to 53.4 min was isolated. The solvent was removed in vacuo. The compound was then dried in a vacuum oven for 2 h (60° C., final pressure=0.090 mm Hg) to afford rac-2-((trans)-6-fluoro-3-(3-nitropyridin-4-yl)cyclohex-2-en-1-yl)isoindoline-1,3-dione (100 mg, 0.27 mmol, 11% yield). MS (ESI, pos. ion) m/z: 368.0 (M+1). ¹H NMR (400 MHz, THF-d8) δ ppm 2.20 (dtd, J=17.61, 11.70, 11.70, 5.70 Hz, 1 H) 2.38 (tq, J=12.06, 4.09 Hz, 1 H) 2.51 (dq, J=17.61, 3.30 Hz, 1 H) 2.58-2.69 (m, 1 H) 5.08-5.18 (m, 1 H) 5.28 (dddd, J=50.50, 11.40, 7.83, 4.11 Hz, 1 H) 5.58 (dt, J=4.30, 2.20 Hz, 1 H) 7.40 (d, J=4.89 Hz, 1 H) 7.74-7.82 (m, 2 H) 7.82-7.88 (m, 2 H) 8.75 (d, J=4.50 Hz, 1 H) 9.11 (s, 1 H)¹⁹F NMR (376 MHz, THF-d8) δ ppm −182.39 (dqt, J=50.72, 10.40, 10.40, 10.40, 5.20, 5.20 Hz, 1 F).

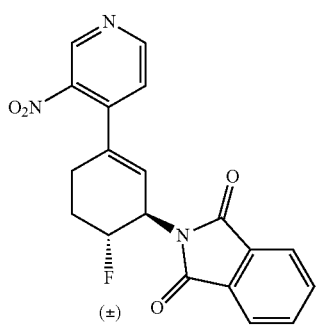 [SMILES: O=C1c2ccccc2C(=O)N1[C@@H]1C=C(c2ccncc2[N+](=O)[O-])CC[C@H]1F]

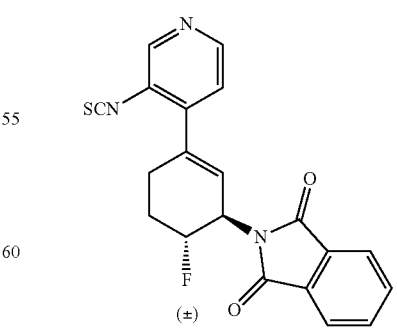

Step 5. rac-2-((trans)-6-fluoro-3-(3-isothiocyanatopyridin-4-yl)cyclohex-2-en-1-yl)isoindoline-1,3-dione. The title compound was prepared and isolated from rac-2-((trans)-6- fluoro-3-(3-nitropyridin-4-yl)cyclohex-2-en-1-yl)isoindoline-1,3-dione following an analogous procedure to Preparation LIII.

Preparation LVI. tert-butyl (1-(3-isothiocyanatopyridin-4-yl)-4-methylpiperidin-3-yl)carbamate

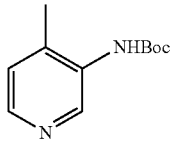

Step 1. tert-butyl (4-methylpyridin-3-yl)carbamate. 3-Amino-4-methylpyridine (5.00 g, 46.2 mmol, Aldrich Chemical Company) was treated with THF (100 mL) and LiHMDS (1.0M in THF, 102 mL, 102 mmol) slowly dropwise at RT and stirred for 30 min. Boc$_2$O (10.60 g, 48.5 mmol) was then added in small portions while cooling in ice and the solution was stirred, warming to RT for 21 h. The reaction mixture was concentrated and the residue was treated with 0.2 M HCl (aq., 100 mL) and extracted with EtOAc (3×150 mL). The combined organic layers were washed with saturated NaHCO$_3$ (aq.) and brine and dried over MgSO$_4$, filtered and concentrated. The crude material was purified by silica gel chromatography (30-50% EtOAc in hexanes) to afford tert-butyl (4-methylpyridin-3-yl)carbamate (4.58 g, 21.99 mmol, 48% yield) as an orange crystalline solid. MS (ESI, pos. ion) m/z: 209.0 (M+1). $^1$H NMR (400 MHz, CDCl$_3$) δ ppm 8.87 (1 H, br. s.), 8.25 (1 H, d, J=4.9 Hz), 7.09 (1 H, d, J=4.9 Hz), 6.17 (1 H, br. s.), 2.27 (3 H, s), 1.53 (9 H, s).

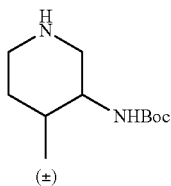

Step 2. tert-butyl (4-methylpiperidin-3-yl)carbamate. In a 150 mL hastalloy metal reactor, tert-butyl (4-methylpyridin-3-yl)carbamate (4.58 g, 21.99 mmol) was treated with glacial HOAc (75 mL), platinum(IV) oxide (764 mg, 3.36 mmol, Aldrich Chemical Company) and rhodium (5 wt. % (dry) on carbon, wet, degussa type, 763 mg, 7.41 mmol, Aldrich Chemical Company) and hydrogenated at 200 psi H$_2$ at 70° C. for 42 h. The catalyst residues were removed by filtration through a Whatman ZAPCAP-CR bottle top filter (0.45 um, teflon), washing with EtOAc, and the solution was then concentrated under reduced pressure. The resulting oil was treated with 5N NaOH (aq.) (to pH 9) and was then extracted with EtOAc. The layers were separated and the aqueous layer was extracted with EtOAc (5×100 mL), adjusting the pH of the former to pH 9 as necessary. The combined organic layers were dried over MgSO$_4$, filtered and concentrated to give tert-butyl (4-methylpiperidin-3-yl)carbamate as a mixture of isomers (2.84 g, 13.25 mmol, 60.3% yield) as a viscous brown oil. The material was used in the subsequent step without further purification.

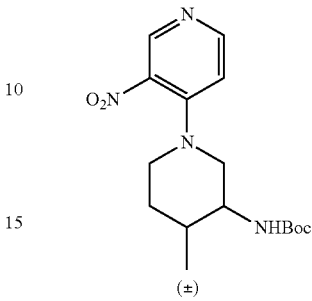

Step 3. tert-butyl (4-methyl-1-(3-nitropyridin-4-yl)piperidin-3-yl)carbamate. To a solution of tert-butyl (4-methylpiperidin-3-yl)carbamate (2.84 g, 13.25 mmol) in 2-propanol (65 mL) was added 4-chloro-3-nitropyridine (3.15 g, 19.88 mmol, Aldrich Chemical Company) and DIPEA (5.76 mL, 33.1 mmol). The mixture was heated and stirred at 60° C. for 5 h. The mixture was then cooled to RT and concentrated. The crude residue was adsorbed onto silica gel and was purified by silica gel chromatography (30-100% EtOAc in hexanes) to afford a tert-butyl (4-methyl-1-(3-nitropyridin-4-yl)piperidin-3-yl)carbamate (1.99 g, 45% yield) as a mixture of isomers as an amorphous yellow solid. MS (ESI, pos. ion) m/z 337.1 (M+1).

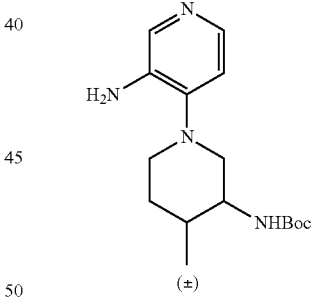

Step 4. tert-butyl (1-(3-aminopyridin-4-yl)-5-methylpiperidin-3-yl)carbamate. A round-bottomed flask was charged with tert-butyl (4-methyl-1-(3-nitropyridin-4-yl)piperidin-3-yl)carbamate isomer (1.87 g, 5.56 mmol) and EtOH (56 mL). The flask was evacuated under vacuum and back-filled with N$_2$. Pd/C (10 wt %, 592 mg, 0.56 mmol) was added and the flask was evacuated under vacuum and back-filled with H$_2$ (4×). The reaction mixture was stirred at RT under an atmosphere of H$_2$ for 56 h. The suspension was filtered through a pad of Celite and the resulting solution was concentrated in vacuo. The crude material was dissolved in EtOAc, and the solvent was removed in vacuo (2×) to give tert-butyl (1-(3-aminopyridin-4-yl)-5-methylpiperidin-3-yl)carbamate (1.02 g, 3.34 mmol, 95% yield) as a mixture of isomers as a brown foam. MS (ESI, pos. ion) m/z 307.1 (M+1).

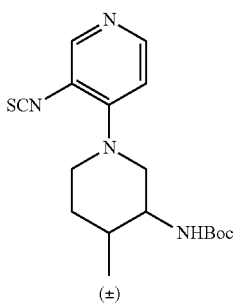 [SMILES: CC1CCN(c2ccncc2[N+](=O)[O-])CC1NC(=O)OC(C)(C)C]

(±)

Step 5. tert-butyl (1-(3-isothiocyanatopyridin-4-yl)-4-methylpiperidin-3-yl)carbamate. 1,1'-Thiocarbonyldiimidazole (2.04 g, 10.31 mmol) was added to a solution of tert-butyl (1-(3-aminopyridin-4-yl)-4-methylpiperidin-3-yl)carbamate (1.58 g, 5.16 mmol) in THF (50 mL) at RT. The reaction was heated at 60° C. for 2 h. The solution was cooled, an additional 0.5 equivalents of 1,1'-thiocarbonyldiimidazole was added and the solution was heated at 60° C. for 2 h. The mixture was cooled to RT and concentrated under reduced pressure. The crude compound was adsorbed onto silica gel and was purified by silica gel chromatography (30-80% EtOAc in hexanes over) to give tert-butyl (1-(3-isothiocyanatopyridin-4-yl)-4-methylpiperidin-3-yl)carbamate as a mixture of isomers (977 mg, 2.80 mmol, 54% yield) as an amorphous white solid. MS (ESI, pos. ion) m/z 349.1 (M+1).

Preparation LVII. 4-(3-isothiocyanatopyridin-4-yl)-5-methylisoxazole.

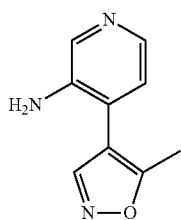

Step 1. 4-(5-methylisoxazol-4-yl)pyridin-3-amine. A dry 100 mL Schlenk-type flask was charged with a suspension of zinc (5 g/0.1 L suspension in THF, 16.37 mL, 12.44 mmol, Rieke Metals Inc.). This material was treated with a solution of 4-iodo-5-methylisoxazole (2.0 g, 9.57 mmol, Maybridge Chemical Co.) dissolved in dry THF (5 mL). The slurry was stirred for 96 h at RT under an Ar atmosphere. The slurry was charged to a dry, 100 mL stainless steel $N_2$ pressure filtration apparatus fitted with a 0.22 μm PTFE syringe filter. A dry, 100 mL, one neck round bottom flask was charged with 3-amino-4-iodopyridine (1.92 g, 8.73 mmol, Alfa Aesar) (vacuum dried at RT for 96 h), a stirbar, A-Phos (1.02 g, 1.44 mmol, Sigma-Aldrich) and THF (20 mL). The flask was fitted with a septa/Ar inlet pierced with a PTFE addition needle. The system was briefly flushed with Ar (the end of the PTFE addition needle was left open). The PFTE addition needle was then fitted to the outlet of the syringe filter/pressure filtration device. The slurry was $N_2$-pressure filtered into the 100 mL round bottom flask over a 5 h period. The reaction was stirred at RT overnight. A second batch of organic zinc reagent was synthesized as described above (4-iodo-5-methyl-isoxazole (3.0 g, 14.36 mmol, Maybridge Chemical Co.), zinc (5 g/0.1 L suspension in THF, 25.2 mL, 19.14 mmol, Rieke Metals Inc.) and stirred for 2 h at RT. This slurry was added using the pressure filtration device described above over a 3 h period. The reaction was cautiously poured onto a stirring, $N_2$ covered, 0.56 M solution of EDTA (pH adjusted to 7.6 with LiOH) (177 mL, 96 mmol, MP Biomedical). The mixture was concentrated under a stream of $N_2$ to remove most of the THF. The mixture was extracted with 1% 1,1,1-3,3,3-hexafluoro-2-propanol in $CHCl_3$ (4×100 mL), and the combined extraction volume was washed with 5% $NaHCO_3$ (1×50 mL). The organic phase was passed through an unbuffered, Varian Chem Elute (CE1020). The solvent was removed in vacuo, and the residue was transferred to a 500 mL, one neck, round bottom flask. The flask was charged with dry THF (150 mL), Si-TAAcONa (0.49 mmol/g loading, 13.0 g, 6.37 mmol, Silicycle), and a stirbar. The flask was fitted with a reflux condenser/Ar inlet and heated at 60° C. overnight. The slurry was cooled, and the solvent was removed in vacuo. The powder was further dried under vacuum at 45° C. for 2 h (final pressure=0.5 mm Hg). The reddish powder was loaded into a 25×300 mm column with 10 μm PTFE support bed. The silica was eluted with $CHCl_3$ (250 mL) and dry THF (250 mL). The total elution volume was combined, and the solvent was removed in vacuo. The residue was purified by silica gel chromatography (11% EtOH in $CHCl_3$) to afford 4-(5-methylisoxazol-4-yl)pyridin-3-amine (1.12 g, 6.38 mmol, 67% yield). MS (ESI, pos. ion) m/z: 176.0 (M+1). $^1$H NMR (400 MHz, THF-d8) δ ppm 2.40 (d, J=0.78 Hz, 3 H) 4.66 (br. s., 2 H) 6.88 (dd, J=4.89, 0.59 Hz, 1 H) 7.84 (d, J=4.70 Hz, 1 H) 8.07 (d, J=0.39 Hz, 1 H) 8.36 (q, J=0.60 Hz, 1 H).

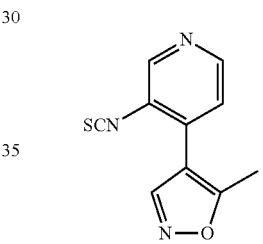

Step 2. 4-(3-isothiocyanatopyridin-4-yl)-5-methylisoxazole. The title compound was prepared and isolated from 4-(5-methylisoxazol-4-yl)pyridin-3-amine following an analogous procedure to Preparation XI. The material was used without characterization.

Preparation LVIII. rac-tert-butyl (1-(3-isothiocyanatopyridin-4-yl)-3-methylpiperidin-3-yl)carbamate

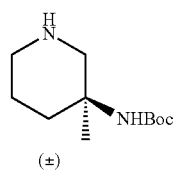

(±)

Step 1. rac-tert-butyl (3-methylpiperidin-3-yl)carbamate. A solution of rac-benzyl 3-((tert-butoxycarbonyl)amino)-3-methylpiperidine-1-carboxylate (78 mg, 0.22 mmol, made as described in WO09/140,320) in EtOH (5 mL) was degassed by bubbling $N_2$ (g) through the solution for 10 min. Pd/C (10 wt. %, 24 mg, 0.022 mmol) was added. A gas bag with a 3-way stopcock filled with $H_2$ was attached to the flask. The flask was evacuated under vacuum and then back-filled with $H_2$ (3×). The mixture was stirred for 2 h at RT. The solution was degassed by bubbling N₂ (g) through the solution for 10 min and filtered through Celite. The solution was concentrated to afford rac-tert-butyl (3-methylpiperidin-3-yl)carbamate (42 mg, 0.20 mmol, 88% yield) as a clear, colorless oil. MS (ESI, pos. ion) m/z: 215.1 (M+1).

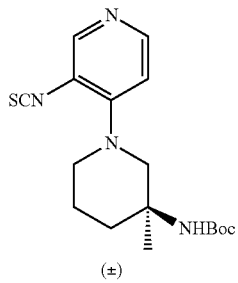

(±)

Step 2. rac-tert-butyl (1-(3-isothiocyanatopyridin-4-yl)-3-methylpiperidin-3-yl)carbamate. The title compound was prepared and isolated as a white solid from 4-chloro-3-nitropyridine (Alfa-Aesar) and rac-tert-butyl (3-methylpiperidin-3-yl)carbamate following an analogous procedure to Preparation XII. MS (ESI, pos. ion) m/z: 337.1 (M+1).

Preparation LIX. tert-butyl 3'-isothiocyanato-5,6-dihydro-[4,4'-bipyridine]-1(2 H)-carboxylate

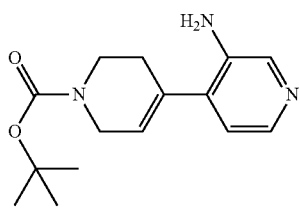 [SMILES: CC(C)(C)OC(=O)N1CC=C(c2ccncc2N)CC1]

Step 1. tert-butyl 3'-amino-5,6-dihydro-[4,4'-bipyridine]-1(2 H)-carboxylate. A 10 mL CEM microwave vessel was charged with 3-amino-4-iodopyridine (139 mg, 0.63 mmol, Alfa Aesar), 3,6-dihydro-2 H-pyridine-1-N-boc-4-boronic acid pinacol ester (236 mg, 0.76 mmol, Frontier Scientific Inc.), NaOAc (155 mg, 1.90 mmol) and a stirbar. The vessel was sealed, and transferred into a glove box using a standard antichamber evacuate-refill cycle (3 times). The vessel was charged with A-Phos (45 mg, 0.063 mmol, Sigma-Aldrich), and sealed. The vessel was then transferred to a standard hood, and treated with dioxane (4 mL), and water (0.4 mL). The slurry was sonicated and was then heated in a microwave using a CEM explorer at 120° C. for 30 min. The solution was treated with a second aliquat of 3,6-dihydro-2H-pyridine-1-N-boc-4-boronic acid pinacol ester (236 mg, 0.76 mmol, Frontier Scientific Inc.) and was then heated in a microwave using a CEM explorer at 120° C. for 30 min The solution was treated with dichlorobis(di-tert-butylphenylphosphine)palladium(II) (20 mg, 0.032 mmol, Alfa Aesar) and was then heated in a microwave using a CEM explorer at 120° C. for 30 min. The solution was cooled to RT overnight under a stream of N₂. The residue was treated with dry THF (5 mL) and SiliaMetS® TAAcOH (1.29 g, 0.63 mmol, Silicycle). The vessel was crimped with a PTFE lined seal, and heated at 60° C. for 3 h. The slurry was N₂-pressure filtered through a glass frit (10 mL Bohdan) fitted with a 0.22 µm PTFE, 25 mm syringe filter unit (Millipore, SLFG025NK). The silica was washed with dry THF (5×5 mL), and concentrated in vacuo. The crude material was purified by silica gel chromatography (10% EtOH in DCE) to afford tert-butyl 3'-amino-5,6-dihydro-[4,4'-bipyridine]-1(2 H)-carboxylate (77 mg, 0.28 mmol, 44% yield). MS (ESI, pos. ion) m/z: 276.0 (M+1).

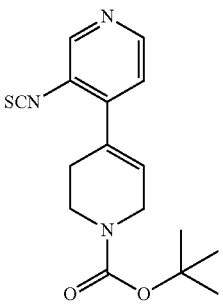

Step 2. tert-butyl 3'-isothiocyanato-5,6-dihydro-[4,4'-bipyridine]-1(2 H)-carboxylate. The title compound was prepared and isolated from tert-butyl 3'-amino-5,6-dihydro-[4,4'-bipyridine]-1(2 H)-carboxylate following an analogous procedure to Preparation XI. MS (ESI, pos. ion) m/z: 317.9 (M+1).

Preparation LX. 4-(3-isothiocyanatopyridin-4-yl)-3,5-dimethylisoxazole

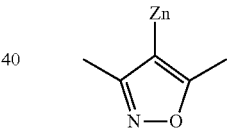

Step 1. (3,5-dimethylisoxazol-4-yl)zinc(II) iodide. A dry. 100 mL 3 neck flask was charged with a stirbar, 3,5-dimethyl-4-iodoisoxazole (5.5 g, 24.7 mmol Afa Aesar) and transferred into a glove box using a standard antichamber vacuum-refill cycle (3 times). A slurry of zinc (5 g/0.1 L suspension in THF, 40 mL, 29.7 mmol, Rieke Metals Inc.) was added. Two of the three openings were sealed with septa, and one was loosely capped. The slurry became warm (~35° C.) within 5 min. The slurry was stirred in the glove box for 1 h and the third opening was sealed with a septa. The flask was transferred to a standard lab hood and one of the septa was pierced with an Ar inlet. The slurry was stirred for 1 h. The slurry was stirred overnight, and N₂ pressure filtered through a 0.22 µm PTFE syringe filter into a dry, closed graduated addition funnel. The filtration took 16 h. The metals were washed with dry THF (1×5 mL), and the wash was combined with the dark filtrate to afford 40 mL of a dark solution. The solution was used without additional characterization to afford a 0.61 M THF solution of (3,5-dimethylisoxazol-4-yl)zinc(II) iodide (7.11 g, 24.7 mmol, 100% yield).

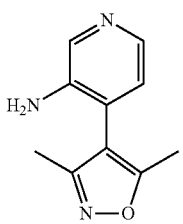

Step 2. 4-(3,5-dimethylisoxazol-4-yl)pyridin-3-amine. A dry, 50 mL, one neck round bottom flask was charged with freshly sublimed 3-amino-4-iodopyridine (1.17 g, 5.32 mmol, Alfa Aesar), A-Phos (565 mg, 0.80 mmol), and a stirbar in a glove box. The flask was sealed with a septa, and moved to a standard fume hood. The septa was pierced with an Ar inlet, and the solids were treated with a 0.61 M THF solution of (3,5-dimethylisoxazol-4-yl)zinc(II) iodide (3.83 g, 13.29 mmol), The reaction was stirred at RT for 48 h. The reaction was carefully poured onto an aqueous 0.54 M EDTA, pH adjusted to 7.6 with LiOH (29.5 ml, 15.95 mmol, MP Biomedicals) solution. The transfer was quantitated with dry THF (3×20 mL). The mixture was stirred for 1 h, and the bulk of organic solvent was removed using a rotary evaporator. The aqueous mixture was extracted with 1% 1,1,1,3,3,3-hexafluoro-2-propanol in CHCl$_3$ (4×60 mL) and each extract was sequentially passed through an unbuffered Varian Chem Elut (CE1010). The total elution volume was concentrated in vacuo. The residue was transferred to a 100 mL round bottom flask, and treated with SiliaMetS® TAAcOH (0.49 mmol/g loading, 10.85 g, 5.32 mmol, Silicycle). The flask was then charged with dry THF (40 mL), and a stirbar. The flask was fitted with a reflux condenser/Ar inlet and heated at 70° C. for 1 h. The solution was cooled over a 30 minute period, and the solvent was removed in vacuo. The powder was further dried at reduced pressure overnight (final pressure=0.10 mm Hg). The silica was loaded onto a silica gel column and the crude material was purified by silica gel chromatography (10% EtOH in DCE). The crude material was treated with acetone (5 mL), and stirred in an ice-water bath. The slurry was N$_2$-pressure filtered through a glass frit (10 mL Bohdan) fitted with a 0.22 μm PTFE, 25 mm syringe filter unit (Millipore, SLFG025NK). The solids were washed with cold acetone (3×2 mL) and discarded. The solvent was removed under reduced pressure, and the oily residue was dried at RT and 0.1 mm Hg vacuum for 2 h to afford 4-(3,5-dimethylisoxazol-4-yl)pyridin-3-amine (1.15 g, 6.08 mmol, 114% yield). MS (ESI, pos. ion) m/z: 190.1 (M+1).

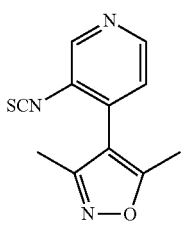

Step 3. 4-(3-isothiocyanatopyridin-4-yl)-3,5-dimethylisoxazole. The title compound was prepared and isolated from 4-(3,5-dimethylisoxazol-4-yl)pyridin-3-amine following an analogous procedure to Preparation XI. The material was used without characterization.

Example 1

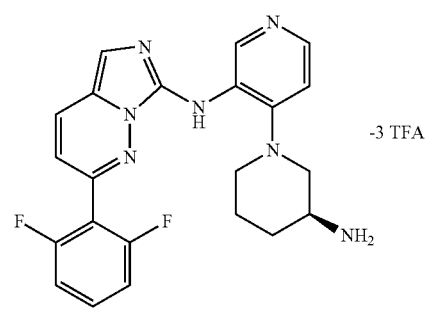 [SMILES: N[C@H]1CCCN(c2ccncc2Nc2ncc3ccc(-c4c(F)cccc4F)nn23)C1]

N-(4-((3S)-3-amino-1-piperidinyl)-3-pyridinyl)-2-(2,6-difluorophenyl)imidazo[1,5-b]pyridazin-7-amine tris(2,2,2-trifluoroacetate)

Step 1. tert-butyl ((3S)-1-(3-((2-(2,6-difluorophenyl)imidazo[1,5-b]pyridazin-7-yl)amino)-4-pyridinyl)-3-piperidinyl)carbamate. A dry, 3 neck, 100 mL Morton flask was configured as follows: opening 1: septa/Ar inlet; opening 2 (center): septa/PTFE addition needle; opening 3: septa. The flask was charged with 3-(azidomethyl)-6-(2,6-difluorophenyl)pyridazine (Preparation I, 2.27 g, 9.17 mmol), a stirbar, and dry THF (20 mL). The flask was immersed into a ice-water bath, and stirred for 15 min. A syringe charged with 1.0M PMe$_3$ in THF (9.63 mL, 9.63 mmol, Aldrich) was fitted to the PTFE addition needle, and added to the stirring solution via syringe pump over 15 min. The mixture was stirred for 15 min. The PTFE addition needle was cleaned with dry THF (1 mL), and fitted with a syringe charged with tert-butyl ((3S)-1-(3-isothiocyanato-4-pyridinyl)-3-piperidinyl)carbamate (Preparation XI, 3.42 g, 10.22 mmol) dissolved in dry THF (20 mL). The solution was added over 15 min via syringe pump. The reaction was warmed to RT overnight. The bulk of the THF was removed in vacuo, and the residue was dissolved in CHCl$_3$ (50 mL). The sample was purified by chromatography (SiliaDiol column (R35030B), Silicycle Inc.) eluted with 10% TFE in CHCl$_3$. The purified material was transferred to a 250 mL one neck round bottom flask. The flask was fitted with a reflux condenser/vacuum/nitrogen source, and carefully evacuated. The flask was placed into an 80° C. heat transfer block. The flask's neck and the lower part of the reflux condenser was wrapped with heating tape and heated to 100° C. The material was heated for 1.5 h and achieved an ultimate vacuum of 0.25 mm Hg. A white material had sublimed on the condenser over the 1.5 h period. The vacuum was released with N$_2$ to afford 5.55 g of material. The sublimed material was discarded (m/z=109; consistent with Me$_3$PS). The residue was dissolved in 25 mL CHCl$_3$. The sample was purified by chromatography (SiliaDiol column (R35030B), Silicycle Inc.) eluted with 1% TFE in CHCl$_3$. The sample was further purified by silica gel chromatography (26-40% TFE in CHCl$_3$) to afford tert-butyl ((3S)-1-(3-((2-(2,6-difluorophenyl)-imidazo[1,5-b]pyridazin-7-yl)amino)-4-pyridinyl)-3-piperidinyl)carbamate (3.94 g, 7.54 mmol, 82% yield). MS (ESI, pos. ion) m/z: 522.0 [M+H]. $^1$H NMR (400 MHz, CDCl$_3$) δ ppm 1.37 (s, 9 H) 1.45 (br. s., 1 H) 1.65-1.82 (m, 3 H) 1.87 (m, J=6.10 Hz, 1 H) 2.80 (br. s., 2 H) 2.93 (br. s., 1H)

3.32 (d, J=9.59 Hz, 1 H) 3.89 (br. s., 0 H) 4.89 (br. s., 1 H) 6.53 (d, J=9.39 Hz, 1 H) 6.91 (d, J=5.09 Hz, 1 H) 7.07 (t, J=8.12 Hz, 2 H) 7.36 (s, 1 H) 7.45 (tt, J=8.40, 6.30 Hz, 1H) 7.68 (br. s., 1 H) 7.76 (d, J=9.39 Hz, 1 H) 8.21 (d, J=5.09 Hz, 1 H) 9.64 (s, 1 H). $^{19}$F NMR (376 MHz, CDCl$_3$) δ ppm −113.05 (t, J=6.50 Hz, 2 F).

The mixture was stirred for 15 min. The PTFE addition needle was cleaned with dry THF (1 mL), and fitted with a syringe charged with tert-butyl ((3S)-1-(3-isothiocyanato-4-pyridinyl)-3-piperidinyl)carbamate (Preparation XI, 3.42 g, 10.22 mmol) dissolved in dry THF (20 mL). The solution was added over 15 min via syringe pump. The reaction was warmed to RT overnight. The bulk of the THF was removed in vacuo, and the residue was dissolved in CHCl$_3$ (50 mL). The sample was purified by chromatography (SiliaDiol column (R35030B), Silicycle Inc.) eluted with 10% TFE in CHCl$_3$. The purified material was transferred to a 250 mL one neck round bottom flask. The flask was fitted with a reflux condenser/vacuum/nitrogen source, and carefully evacuated. The flask was placed into an 80° C. heat transfer block. The flask's neck and the lower part of the reflux condenser was wrapped with heating tape and heated to 100° C. The material was heated for 1.5 h and achieved an ultimate vacuum of 0.25 mm Hg. A white material had sublimed on the condenser over the 1.5 h period. The vacuum was released with N$_2$ to afford 5.55 g of material. The sublimed material was discarded (m/z=109; consistent with Me$_3$PS). The residue was dissolved in 25 mL CHCl$_3$. The sample was purified by chromatography (SiliaDiol column (R35030B), Silicycle Inc.) eluted with 1% TFE in CHCl$_3$. The sample was further purified by silica gel chromatography (26-40% TFE in CHCl$_3$) to afford tert-butyl ((3S)-1-(3-((2-(2,6-difluorophenyl)-imidazo[1,5-b]pyridazin-7-yl)amino)-4-pyridinyl)-3-piperidinyl)carbamate (3.94 g, 7.54 mmol, 82% yield). MS (ESI, pos. ion) m/z: 522.0 [M+H]. $^1$H NMR (400 MHz, CDCl$_3$) δ ppm 1.37 (s, 9 H) 1.45 (br. s., 1 H) 1.65-1.82 (m, 3 H) 1.87 (m, J=6.10 Hz, 1 H) 2.80 (br. s., 2 H) 2.93 (br. s., 1H) 3.32 (d, J=9.59 Hz, 1 H) 3.89 (br. s., 0 H) 4.89 (br. s., 1 H) 6.53 (d, J=9.39 Hz, 1 H) 6.91 (d, J=5.09 Hz, 1 H) 7.07 (t, J=8.12 Hz, 2 H) 7.36 (s, 1 H) 7.45 (tt, J=8.40, 6.30 Hz, 1H) 7.68 (br. s., 1 H) 7.76 (d, J=9.39 Hz, 1 H) 8.21 (d, J=5.09 Hz, 1 H) 9.64 (s, 1 H). $^{19}$F NMR (376 MHz, CDCl$_3$) δ ppm −113.05 (t, J=6.50 Hz, 2 F).

Step 2. N-(4-((3S)-3-amino-1-piperidinyl)-3-pyridinyl)-2-(2,6-difluorophenyl)imidazo[1,5-b]pyridazin-7-amine tris(2,2,2-trifluoroacetate). A 250 mL bottle with a 3-hole top was configured as follows: opening 1: ⅛th" (OD) HDPE tubing connected to a HCl gas cylinder with a gas dispersion frit in the bottle; opening 2: positive pressure nitrogen source; opening three, ⅛th" (OD) HDPE tubing connected to a 25×250 mm column packed with NaOH pellets. The bottle was charged with EtOAc (100 mL), and the volume above the EtOAc was gently purged with N$_2$ from opening 2. HCl gas was introduced at a rate such that a majority of the HCl bubbles were dissolved prior to reaching the top of the EtOAc. The solution was sparged with HCl gas until the amount of HCl bubbles at the gas dispersion tube was approximately equal to the amount of gas that reached the reached the top of the solution. The HCl flow was discontinued, and the system was purged with N$_2$ for 3 min. The bottle was sealed and used directly. The normality was assumed to be 7.5 M (*Tetrahedron Letters*, 1996, 37, 5131). A 250 mL, Schlenk type flask was charged with a stirbar and 7.5 M HCl in EtOAc (100 mL, 750 mmol). The flask was sealed with a septa/Ar inlet/PTFE addition needle. A syringe charged with tert-butyl ((3S)-1-(3-((2-(2,6-difluorophenyl)imidazo[1,5-b]pyridazin-7-yl)amino)-4-pyridinyl)-3-piperidinyl)carbamate (2.61 g, 5.00 mmol) dissolved in EtOAc (40 mL) was fitted to the PTFE addition needle and added via syringe pump over 30 min. The slurry was stirred overnight. The slurry was N$_2$ pressure filtered through a 47 mm, 0.2 µm Fluoropore® membrane (FGLP04700) fitted to a Millipore high pressure filter holder (XX4504700). The solids were washed with EtOAc (4×25 mL), and dried initially under a stream of N$_2$ for 1 h. The solids were further dried in a vacuum oven (80° C., <0.2 mm Hg) for 5 d to afford ~2.4 g of presumably a tris HCl salt. The sample was purified by prep HPLC method 2. The solvent was concentrated to remove the organic solvents, and the aqueous solution was lyophilized. The powder was dissolved in 1% TFA (aq., 40 mL), and N$_2$-pressure filtered through a 28 mL Bohdan reaction vessel glass frit fitted with a 0.22 µm PTFE, 25 mm syringe filter unit (Millipore, SLFG025NK). The filtrate was lyophilized, and the resulting material was further dried in a vacuum oven (80° C., <1 mm Hg) for 30 min. The material was pulverized with a spatula to a consistent particle size. The material was again dried in a vacuum oven (80° C., <1 mm Hg) for 45 min to afford N-(4-((3S)-3-amino-1-piperidinyl)-3-pyridinyl)-2-(2,6-difluorophenyl)-imidazo[1,5-b]pyridazin-7-amine tris(2,2,2-trifluoroacetate) (3.2 g, 4.19 mmol, 84% yield). A ratio of 9:2 fluorines was observed by $^{19}$F NMR; consistent with 3:1 ratio of TFA to N-(4-((3S)-3-amino-1-piperidinyl)-3-pyridinyl)-2-(2,6-difluorophenyl)-imidazo[1,5-b]pyridazin-7-amine. MS (ESI, pos. ion) m/z: 422.0 [M+H]. $^1$H NMR (400 MHz, D$_2$O) δ ppm 1.28 (qq, J=10.80, 3.70 Hz, 1 H) 1.58 (dtd, J=13.30, 10.30, 10.30, 4.10 Hz, 1 H) 1.74 (dt, J=14.18, 3.86 Hz, 1 H) 2.03 (dq, J=12.60, 4.20 Hz, 1H) 3.08 (ddd, J=13.30, 10.95, 2.74 Hz, 1 H) 3.15 (dd, J=12.30, 9.98 Hz, 1 H) 3.23 (tt, J=9.80, 3.70 Hz, 1 H) 3.80 (br. dt, J=13.30, 3.60, 3.60 Hz, 1 H) 4.09 (br. d, J=10.40 Hz, 1H) 6.95 (d, J=9.59 Hz, 1 H) 7.13 (t, J=8.41 Hz, 2 H) 7.35 (d, J=7.04 Hz, 1 H) 7.43 (s, 1H) 7.54 (tt, J=8.40, 6.50 Hz, 1 H) 8.01 (d, J=9.78 Hz, 1 H) 8.23 (dd, J=7.04, 0.98 Hz, 1 H) 8.39 (d, J=0.98 Hz, 1 H). $^{19}$F NMR (377 MHz, D$_2$O) δ ppm −117.35 (t, J=7.44 Hz, 2F) −78.50 (s, 9 F).

Example 2

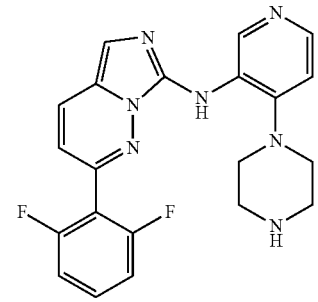 [SMILES: Fc1cccc(F)c1-c1ccc2cnc(Nc3cnccc3N3CCNCC3)n2n1]

2-(2,6-difluorophenyl)-N-(4-(1-piperazinyl)-3-pyridinyl)imidazo[1,5-b]pyridazin-7-amine Step 1. tert-butyl 4-(3-((2-(2,6-difluorophenyl)imidazo[1,5-b]pyridazin-7-yl)amino)-4-pyridinyl)-1-piperazinecarboxylate. PMe$_3$ (1.0 M solution in THF, 0.19 mL, 0.19 mmol) was added dropwise to a solution of 3-(azidomethyl)-6-(2,6-difluorophenyl)pyridazine (Preparation I, 43 mg, 0.17 mmol) in THF (0.5 mL) at RT. The reaction turned light red and an evolution of gas was observed. The reaction was stirred for 15 min at RT. A solution of tert-butyl 4-(3-isothiocyanato-4-pyridinyl)-1-piperazinecarboxylate (Preparation XII, 67 mg, 0.21 mmol) in THF (0.8 mL) was added. After 15 min at RT, the mixture was diluted with EtOAc and washed with H₂O. The aqueous phase was extracted with EtOAc (2×). The combined organic layers were dried over Na₂SO₄, filtered and concentrated to give 100 mg of crude material. The crude was purified by silica gel chromatography (0-5% MeOH in CH₂Cl₂) to provide tert-butyl 4-(3-((2-(2,6-difluorophenyl) imidazo[1,5-b]pyridazin-7-yl)amino)-4-pyridinyl)-1-piperazinecarboxylate (66 mg, 0.13 mmol, 75% yield) as an orange oil. MS (ESI, pos. ion) m/z: 508.3 [M+H]. ¹H NMR (400 MHz, CDCl₃) δ ppm 9.74 (s, 1 H), 8.24 (d, J=5.09 Hz, 1 H), 7.84 (s, 1 H), 7.77 (d, J=9.39 Hz, 1 H), 7.40-7.50 (m, 1 H), 7.37 (s, 1 H), 7.03-7.11 (m, 2 H), 6.95 (d, J=5.09 Hz, 1 H), 6.55 (d, J=9.39 Hz, 1 H), 3.55-3.64 (m, 4 H), 2.96 (t, J=4.99 Hz, 4 H), 1.50 (s, 9 H).

Step 2. 2-(2,6-difluorophenyl)-N-(4-(1-piperazinyl)-3-pyridinyl)imidazo[1,5-b]pyridazin-7-amine. TFA (2.00 mL, 26.0 mmol) was added to a solution of tert-butyl 4-(3-(2-(2, 6-difluorophenyl)imidazo[1,5-b]pyridazin-7-ylamino)pyridin-4-yl)piperazine-1-carboxylate (66 mg, 0.13 mmol) in 1.5 mL of CH₂Cl₂ at RT. After 30 min, MeOH was added and the mixture was concentrated. Saturated NaHCO₃ (aq.) was added to the residue and the mixture was extracted with 10/1 CH₂Cl₂/MeOH (3×). The combined organic layers were dried over anh. Na₂SO₄, filtered and concentrated to afford 2-((2,6-difluorophenyl)-N-(4-(1-piperazinyl)-3-pyridinyl) imidazo[1,5-b]pyridazin-7-amine (50 mg, 0.12 mmol, 94% yield) as an orange amorphous solid. MS (ESI, pos. ion) m/z: 408.2 [M+H]. ¹H NMR (400 MHz, DMSO-d₆) δ ppm 9.37 (s, 1 H), 8.10-8.20 (m, 2 H), 7.92 (s, 1 H), 7.60-7.73 (m, 1 H), 7.44 (s, 1 H), 7.34 (t, J=8.31 Hz, 2 H), 7.09 (d, J=5.09 Hz, 1 H), 6.74 (d, J=9.59 Hz, 1 H), 2.80-2.90 (m, 4 H), 2.71-2.79 (m, 4 H).

Example 3

N-(4-(1-piperazinyl)-3-pyridinyl)-2-(1,3-thiazol-2-yl)imidazo[1,5-b]pyridazin-7-amine The title compound was prepared and isolated as a red amorphous solid from 2-(6-(azidomethyl)pyridazin-3-yl) thiazole (Preparation II) and tert-butyl 4-(3-isothiocyanato-4-pyridinyl)-1-piperazinecarboxylate (Preparation XII) following an analogous procedure to Example 2. MS (ESI, pos. ion) m/z: 379.1 [M+H]. ¹H NMR (400 MHz, DMSO-d₆) δ ppm 9.44 (s, 1 H), 8.13-8.20 (m, 3 H), 8.09 (d, J=3.13 Hz, 1 H), 8.04 (d, J=3.13 Hz, 1 H), 7.43 (s, 1 H), 7.29 (d, J=9.59 Hz, 1 H), 7.14 (d, J=5.09 Hz, 1 H), 2.93-2.98 (m, 4 H), 2.85-2.92 (m, 4 H).

Example 4

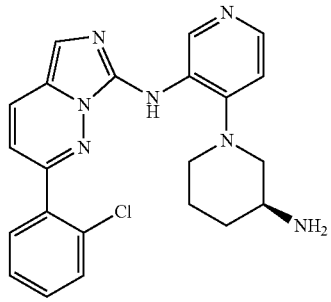 [SMILES: N[C@H]1CCCN(c2ccncc2Nc2ncc3ccc(-c4ccccc4Cl)nn23)C1]

N-(4-((3S)-3-amino-1-piperidinyl)-3-pyridinyl)-2-(2-chlorophenyl)imidazo[1,5-b]pyridazin-7-amine The title compound was prepared and isolated as an orange foam from 3-(azidomethyl)-6-(2-chlorophenyl)pyridazine (Preparation III) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 420.1 (M+1). ¹H NMR (400 MHz, DMSO-d₆) δ ppm 9.38 (1 H, s), 8.06-8.16 (2 H, m), 7.74 (1 H, dd, J=7.1, 2.1 Hz), 7.64-7.70 (1 H, m), 7.50-7.61 (2 H, m), 7.41 (1 H, s), 7.08 (1 H, d, J=5.3 Hz), 6.82 (1H, d, J=9.6 Hz), 3.12 (1 H, d, J=9.2 Hz), 3.02 (1 H, d, J=11.7 Hz), 2.84 (1 H, br. s.), 2.62-2.74 (1 H, m), 2.43 (1 H, t, J=9.7 Hz), 1.66-1.82 (2 H, m), 1.42-1.61 (1 H, m), 1.09-1.27 (2 H, m).

Example 5

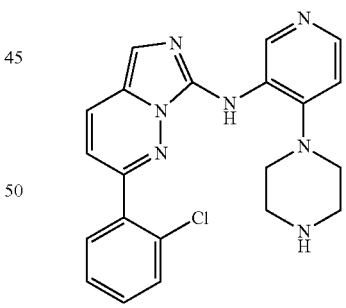

2-(2-chlorophenyl)-N-(4-(1-piperazinyl)-3-pyridinyl) imidazo[1,5-b]pyridazin-7-amine The title compound was prepared and isolated as an orange foam from 3-(azidomethyl)-6-(2-chlorophenyl)pyridazine (Preparation III) and tert-butyl 4-(3-isothiocyanato-4-pyridinyl)-1-piperazinecarboxylate (Preparation XII) following an analogous procedure to Example 2. MS (ESI, pos. ion) m/z: 406.1 [M+H]. ¹H NMR (400 MHz, DMSO-d₆) δ ppm 9.40 (s, 1 H), 8.08-8.16 (m, 2 H), 7.94 (s, 1 H), 7.65-7.75 (m, 2 H), 7.50-7.63 (m, 2 H), 7.42 (s, 1 H), 7.10 (d, J=5.28 Hz, 1 H), 6.81 (d, J=9.39 Hz, 1 H), 2.83-2.91 (m, 4 H), 2.73-2.82 (m, 4 H).

(1 H, m), 2.91 (1H, br.), 2.67 (1 H, m), 2.35 (3 H, m), 1.87-1.71 (2 H, m), 1.59 (1 H, m), 1.23 (2 H, m).

Example 6

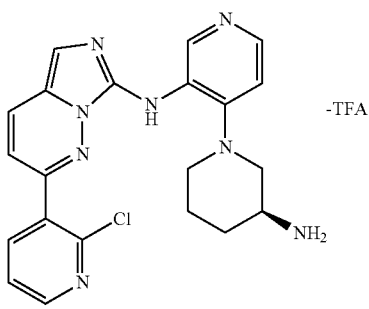 [SMILES: N[C@H]1CCCN(c2ccncc2Nc2ncc3ccc(-c4cccnc4Cl)nn23)C1]

N-(4-((3S)-3-amino-1-piperidinyl)-3-pyridinyl)-2-(2-chloro-3-pyridinyl)imidazo[1,5-b]pyridazin-7-amine (2,2,2-trifluoroacetate)

The title compound was prepared and isolated as an orange amorphous solid from 3-(azidomethyl)-6-(2-chloro-3-pyridinyl)pyridazine (Preparation IV) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 421.1 (M+1). $^1$H NMR (400 MHz, DMSO-$d_6$) δ ppm 9.38 (1 H, s), 8.60 (1 H, dd, J=4.7, 1.8 Hz), 8.20 (1 H, dd, J=7.6, 1.8 Hz), 8.11 (2 H, m), 7.66 (1 H, dd, J=7.5, 4.8 Hz), 7.42 (1 H, s), 7.06 (1 H, d, J=5.1 Hz), 6.86 (1 H, d, J=9.6 Hz), 3.30 (3 H, br.), 3.09 (1 H, m), 3.00 (1 H, m), 2.78 (1 H, m), 2.65 (1 H, m), 2.40 (1 H, m), 1.68 (2 H, m), 1.47 (1 H, m), 1.15(1 H, m).

Example 7

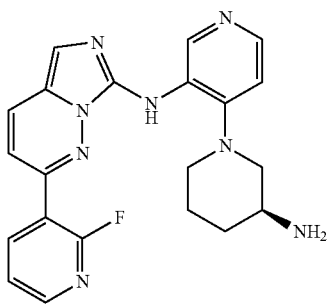 [SMILES: N[C@H]1CCCN(c2ccncc2Nc2ncc3ccc(-c4cccnc4F)nn23)C1]

N-(4-((3S)-3-amino-1-piperidinyl)-3-pyridinyl)-2-(2-fluoro-3-pyridinyl)imidazo[1,5-b]pyridazin-7-amine The title compound was prepared and isolated as an orange amorphous solid from 3-(azidomethyl)-6-(2-fluoro-3-pyridinyl)pyridazine (Preparation VII) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 405.2 (M+1). $^{19}$F NMR (400 MHz, DMSO-$d_6$) δ ppm −68.92. $^1$H NMR (400 MHz, DMSO-$d_6$) δ ppm 9.42 (1 H, s), 8.56-8.36 (2 H, m), 8.25-8.03 (2 H, m), 7.62 (1 H, t, J=5.3 Hz), 7.43 (1 H, s), 7.10 (1 H, d, J=5.3 Hz), 6.98 (1 H, dd, J=9.6, 2.3 Hz), 3.14 (1 H, m), 3.02

Example 8

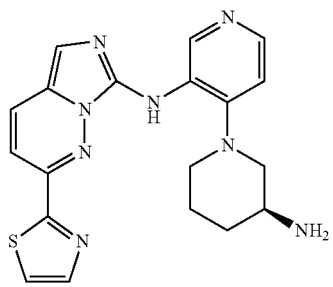 [SMILES: N[C@H]1CCCN(c2ccncc2Nc2ncc3ccc(-c4nccs4)nn23)C1]

N-(4-((3S)-3-amino-1-piperidinyl)-3-pyridinyl)-2-(1,3-thiazol-2-yl)imidazo[1,5-b]pyridazin-7-amine The title compound was prepared and isolated as an orange amorphous solid from 2-(6-(azidomethyl)pyridazin-3-yl)thiazole (Preparation II) and tert-butyl ((3S)-1-(3-isothiocyanato-4-pyridinyl)-3-piperidinyl)carbamate (Preparation XI) following an analogous procedure to Example 2. The crude product was purified by prep HPLC method 3 to afford enriched product as an orange amorphous foam. The sample was repurified by prep HPLC method 5 to afford N-(4-((3S)-3-amino-1-piperidinyl)-3-pyridinyl)-2-(1,3-thiazol-2-yl)imidazo[1,5-b]pyridazin-7-amine as an orange amorphous solid. MS (ESI, pos. ion) m/z: 393.2 (M+1). $^1$H NMR (400 MHz, MeOH d4) δ ppm 9.32 (1 H, s), 8.15 (1 H, d, J=5.3 Hz), 7.99-8.07 (2 H, m), 7.80-7.84 (1 H, m), 7.35-7.42 (2H, m), 7.20 (1 H, d, J=5.3 Hz), 3.38 (1 H, br. s.), 3.06-3.22 (2 H, m), 2.84 (1 H, t, J=11.1 Hz), 2.54-2.65 (1 H, m), 2.03-2.13 (1 H, m), 1.78-2.00 (2 H, m), 1.38 (1 H, d, J=9.6 Hz).

Example 9

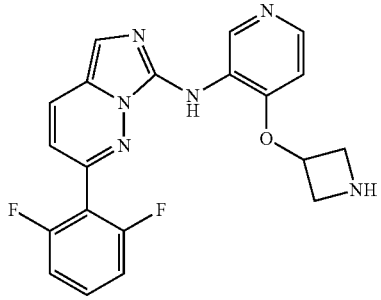 [SMILES: Fc1cccc(F)c1-c1ccc2cnc(Nc3cnccc3OC3CNC3)n2n1]

N-(4-(3-azetidinyloxy)-3-pyridinyl)-2-(2,6-difluorophenyl)imidazo[1,5-b]pyridazin-7-amine The title compound was prepared and isolated as an orange crystalline solid from 3-(azidomethyl)-6-(2,6-difluorophenyl)pyridazine (Preparation I) and tert-butyl 3-((3-isothiocyanato-4-pyridinyl)oxy)-1-azetidinecarboxylate (Preparation XIV) following an analogous procedure to Example 2. The crude material was purified by prep HPLC method 5. MS (ESI, pos. ion) m/z: 395.0 (M+1). ¹H NMR (400 MHz, DMSO-d₆) δ ppm 9.21 (1 H, s), 8.16 (1 H, d, J=9.4 Hz), 8.08 (1 H, d, J=5.5 Hz), 7.78 (1 H, s), 7.66 (1 H, m), 7.44 (1 H, s), 7.35 (2 H, t, J=8.3 Hz), 6.82 (1 H, d, J=5.3 Hz), 6.76 (1 H, d, J=9.4 Hz), 5.14 (1 H, m), 3.82 (2 H, t, J=7.3 Hz), 3.51 (2 H, m), 3.40 (1 H, br.). ¹⁹F NMR (400 MHz, DMSO-d₆) δ ppm −113.57.

Example 10

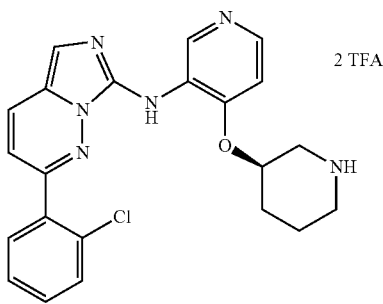 [SMILES: Clc1ccccc1-c1ccc2cnc(Nc3cnccc3O[C@@H]3CCCNC3)n2n1]

2-(2-chlorophenyl)-N-(4-((3R)-3-piperidinyloxy)-3-pyridinyl)imidazo[1,5-b]pyridazin-7-amine bis(2,2,2-trifluoroacetate)

The title compound was prepared and isolated as a bright yellow tar from 3-(azidomethyl)-6-(2-chlorophenyl)pyridazine (Preparation III) and tert-butyl (3R)-3-((3-isothiocyanato-4-pyridinyl)oxy)-1-piperidinecarboxylate (Preparation XV) following an analogous procedure to Example 2. The crude material was purified by prep HPLC method 3. MS (ESI, pos. ion) m/z: 421.1 (M+1). ¹H NMR (400 MHz, MeOH-d4) δ ppm 9.33 (1 H, d, J=1.2 Hz), 8.40 (1 H, dd, J=6.7, 1.2 Hz), 8.08 (1 H, d, J=9.6 Hz), 7.73 (1 H, d, J=6.7 Hz), 7.68 (1 H, dd, J=7.3, 1.9 Hz), 7.58-7.63 (1 H, m), 7.46-7.57 (3 H, m), 6.93 (1 H, d, J=9.4 Hz), 5.39 (1 H, br. s.), 3.66-3.75 (1 H, m), 3.55 (1 H, dd, J=13.8, 2.2 Hz), 3.12-3.26 (1 H, m), 2.17-2.28 (1 H, m), 2.04-2.17 (2 H, m), 1.79-1.89 (1 H, m).

Example 11

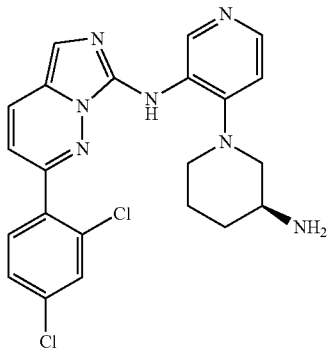 [SMILES: N[C@H]1CCCN(c2ccncc2Nc2ncc3ccc(-c4ccc(Cl)cc4Cl)nn23)C1]

N-(4-((3S)-3-amino-1-piperidinyl)-3-pyridinyl)-2-(2,4-dichlorophenyl)imidazo[1,5-b]pyridazin-7-amine The title compound was prepared and isolated as an orange amorphous solid from 3-(azidomethyl)-6-(2,4-dichlorophenyl)pyridazine (Preparation IX) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 454.0/456.0 (M+1). ¹H NMR (400 MHz, DMSO-d₆) δ ppm 9.46 (1 H, s), 8.17 (2 H, dd, J=7.2, 2.2 Hz), 7.92 (1H, d, J=2.2 Hz), 7.83 (1 H, d, J=8.4 Hz), 7.72 (1 H, dd, J=8.3, 2.1 Hz), 7.47 (1 H, s), 7.13 (1 H, d, J=5.3 Hz), 6.86 (1 H, d, J=9.6 Hz), 3.40 (3 H, br.), 3.19 (1 H, m), 3.08 (1H, m), 2.89 (1 H, m), 2.72 (1 H, m), 2.47 (1 H, m), 1.79 (2 H, m), 1.50 (1 H, m), 1.18 (1H, m).

Example 12

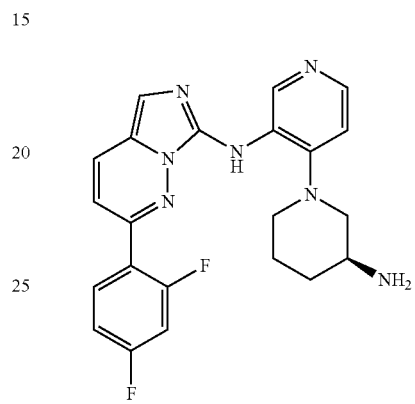

N-(4-((3S)-3-amino-1-piperidinyl)-3-pyridinyl)-2-(2,4-difluorophenyl)imidazo[1,5-b]pyridazin-7-amine The title compound was prepared and isolated as an orange amorphous solid from 3-(azidomethyl)-6-(2,4-difluorophenyl)pyridazine (Preparation X) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 422.0 (M+1). ¹⁹F NMR (400 MHz, DMSO-d₆) δ ppm −106.82 and −110.89. ¹H NMR (400 MHz, DMSO-d₆) δ ppm 9.45 (1 H, s), 8.11 (2 H, m), 7.99 (1 H, td, J=8.8, 6.7 Hz), 7.51 (1 H, ddd, J=11.5, 9.2, 2.5 Hz), 7.41 (1 H, s), 7.35 (1 H, td, J=8.5, 2.2 Hz), 7.10 (1 H, d, J=5.3 Hz), 6.90 (1 H, dd, J=9.6, 2.7 Hz), 3.40 (3 H, br.), 3.13 (1 H, m), 3.03 (1 H, m), 2.89 (1 H, m), 2.69 (1 H, m), 2.43 (1 H, m), 1.79 (2 H, m), 1.59 (1 H, m), 1.18 (1 H, m).

Example 13

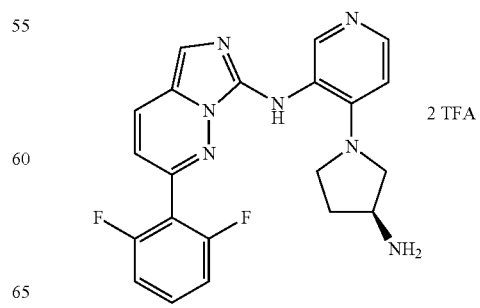

N-(4-((3S)-3-amino-1-pyrrolidinyl)-3-pyridinyl)-2-(2,6-difluorophenyl)imidazo[1,5-b]pyridazin-7-amine bis(2,2,2-trifluoroacetate)

The title compound was prepared and isolated as a yellow amorphous solid from 3-(azidomethyl)-6-(2,6-difluorophenyl)pyridazine (Preparation I) and tert-butyl ((3S)-1-(3-isothiocyanato-4-pyridinyl)-3-pyrrolidinyl)carbamate (Preparation XXVII) following an analogous procedure to Example 2. MS (ESI, pos. ion) m/z: 408.2 (M+1). $^1$H NMR (400 MHz, MeOH-d4) δ ppm 8.38 (1 H, d, J=1.2 Hz), 8.21 (1 H, dd, J=7.0, 1.2 Hz), 7.99 (1 H, d, J=9.6 Hz), 7.56-7.67 (1 H, m), 7.25 (1 H, s), 7.16-7.24 (2 H, m), 7.12 (1 H, d, J=7.2 Hz), 6.67 (1 H, d, J=9.6 Hz), 4.18 (1 H, dd, J=12.3, 6.3 Hz), 3.99-4.05 (1 H, m), 3.86-3.99 (3 H, m), 2.38-2.50 (1 H, m), 2.14-2.25 (1 H, m).

Example 14

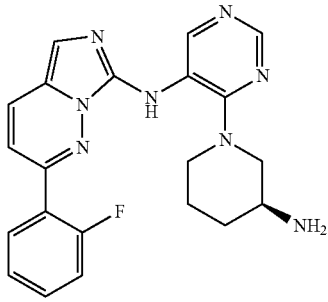 [SMILES: N[C@H]1CCCN(c2ncncc2Nc2ncc3ccc(-c4ccccc4F)nn23)C1]

(S)-N-(4-(3-aminopiperidin-1-yl)pyrimidin-5-yl)-2-(2-fluorophenyl)imidazo[1,5-b]pyridazin-7-amine The title compound was prepared and isolated as an orange amorphous solid from 3-(azidomethyl)-6-(2-fluorophenyl)pyridazine (Preparation VI) and tert-butyl ((3S)-1-(5-isothiocyanato-4-pyrimidinyl)-3-piperidinyl)carbamate (Preparation XVII) following an analogous procedure to Example 2. MS (ESI, pos. ion) m/z: 405.2 (M+1). $^1$H NMR (400 MHz, DMSO-d$_6$) δ ppm 8.73 (1 H, s), 8.40 (1 H, s), 8.06 (1 H, d, J=9.4 Hz), 7.86 (1 H, td, J=7.8, 1.5 Hz), 7.59 (1 H, m), 7.41 (2 H, m), 7.30 (1 H, s), 6.86 (1 H, dd, J=9.4, 2.7 Hz), 3.89 (3 H, br.), 3.70 (2 H, m), 2.92 (1 H, m), 2.65 (2 H, m), 1.69 (1 H, m), 1.57 (1 H, m), 1.29 (1 H, m), 1.14 (1 H, m). $^{19}$F NMR (400 MHz, DMSO-d$_6$) δ ppm −115.66.

Example 15

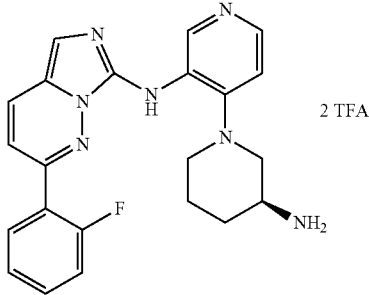 [SMILES: N[C@H]1CCCN(c2ccncc2Nc2ncc3ccc(-c4ccccc4F)nn23)C1]

N-(4-((3S)-3-amino-1-piperidinyl)-3-pyridinyl)-2-(2-fluorophenyl)imidazo[1,5-b]pyridazin-7-amine bis(2,2,2-trifluoroacetate)

Step 1. tert-butyl ((3S)-1-(3-((2-(2-fluorophenyl)imidazo[1,5-b]pyridazin-7-yl)amino)-4-pyridinyl)-3-piperidinyl)carbamate. A 1.0 M solution of PMe$_3$ in THF (0.24 mL, 0.24 mmol) was added dropwise to a solution of 3-(azidomethyl)-6-(2-fluorophenyl)pyridazine (Preparation VI, 50 mg, 0.22 mmol) in THF (1 mL) at RT. The reaction turned pale purple and an evolution of gas was observed. The reaction was stirred for 30 min at RT and a solution of ((3S)-1-(3-isothiocyanato-4-pyridinyl)-3-piperidinyl)carbamate (Preparation XI, 88 mg, 0.26 mmol) in THF (2 mL) was added slowly via it was concentrated and purified by silica gel chromatography (0-10% MeOH in CH$_2$Cl$_2$) to afford tert-butyl ((3S)-1-(3-((2-(2-fluorophenyl)imidazo[1,5-b]pyridazin-7-yl)amino)-4-pyridinyl)-3-piperidinyl)carbamate (64 mg, 58%) as a bright orange viscous oil. MS (ESI, pos. ion) m/z: 504.0 (M+1). $^1$H NMR (400 MHz, CDCl$_3$) δ ppm 9.69 (1 H, s), 8.22 (1 H, d, J=5.1 Hz), 7.90-7.97 (1 H, m), 7.87 (1 H, br. s.), 7.76 (1 H, d, J=9.6 Hz), 7.44-7.53 (1 H, m), 7.28-7.36 (1 H, m), 7.23 (1 H, ddd, J=11.2, 8.3, 0.9 Hz), 6.94 (1 H, d, J=5.1 Hz), 6.83 (1 H, dd, J=9.6, 2.7 Hz), 4.92 (1 H, br. s.), 3.96 (1 H, br. s.), 3.35 (1 H, dd, J=11.0, 3.1 Hz), 2.90 (2 H, d, J=9.2 Hz), 2.79 (1 H, br. s.), 1.88 (2 H, t, J=10.8 Hz), 1.60-1.80 (2 H, m), 1.41-1.56 (2 H, m), 1.30-1.41 (9 H, m).

Step 2. N-(4-((3S)-3-amino-1-piperidinyl)-3-pyridinyl)-2-(2-fluorophenyl)imidazo[1,5-b]pyridazin-7-amine bis(2,2,2-trifluoroacetate). TFA (1.00 mL, 12.98 mmol) was added to a solution of tert-butyl ((3S)-1-(3-((2-(2-fluorophenyl)imidazo[1,5-b]pyridazin-7-yl)amino)-4-pyridinyl)-3-piperidinyl)carbamate (63 mg, 0.13 mmol) in CH$_2$Cl$_2$ (2 mL) at 0° C. After 30 min, the mixture was concentrated under reduced pressure (rotary evaporator) and treated with saturated NaHCO$_3$ (aq.) and extracted with 10:1 CH$_2$Cl$_2$:MeOH (3×). The combined organic layers were dried over anh. Na$_2$SO$_4$, filtered and concentrated to afford the crude product as a yellow amorphous solid. The crude material was purified by prep HPLC method 3 to afford N-(4-((3S)-3-amino-1-piperidinyl)-3-pyridinyl)-2-(2-fluorophenyl)imidazo[1,5-b]pyridazin-7-amine bis(2,2,2-trifluoroacetate) (11 mg, 14%) as a yellow amorphous solid. MS (ESI, pos. ion) m/z: 420.1 (M+1). $^1$H NMR (400 MHz, DMSO-d$_6$) δ ppm 9.09 (1 H, s), 8.74 (1 H, s), 8.38 (1 H, d, J=6.3 Hz), 8.18 (1 H, d, J=9.4 Hz), 8.04 (3 H, br. s.), 7.81-7.91 (1 H, m), 7.56-7.67 (1 H, m), 7.36-7.48 (4 H, m), 7.00 (1 H, dd, J=9.5, 2.6 Hz), 3.39 (1 H, br. s.), 3.28 (2 H, br. s.), 3.18 (1 H, dd, J=12.5, 6.8 Hz), 1.93 (2 H, d, J=7.8 Hz), 1.64-1.77 (1 H, m), 1.58 (1 H, br. s.).

Example 16

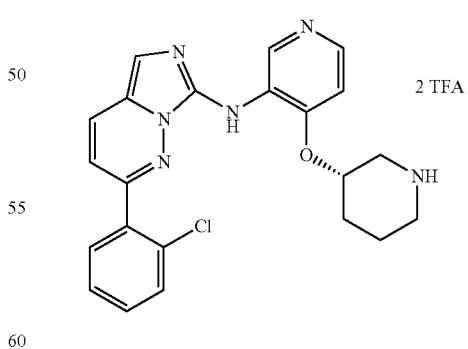

2-(2-chlorophenyl)-N-(4-((3S)-3-piperidinyloxy)-3-pyridinyl)imidazo[1,5-b]pyridazin-7-amine bis(2,2,2-trifluoroacetate)

The title compound was prepared and isolated as a yellow amorphous solid from 3-(azidomethyl)-6-(2-chlorophenyl)

pyridazine (Preparation III) and tert-butyl (3S)-3-((3-isothiocyanato-4-pyridinyl)oxy)-1-piperidinecarboxylate (Preparation XVI) following an analogous procedure to Example 15. The crude material was purified by prep HPLC method 3. MS (ESI, pos. ion) m/z: 421.1 (M+1). ¹H NMR (400 MHz, DMSO-d₆) δ ppm 9.05 (1 H, br. s.), 8.95 (1 H, s), 8.90 (1 H, s), 8.80 (1 H, br. s.), 8.48 (1 H, d, J=6.5 Hz), 8.22 (1 H, d, J=9.4 Hz), 7.75 (1 H, d, J=6.7 Hz), 7.62-7.70 (2 H, m), 7.45-7.61 (3 H, m), 6.97 (1 H, d, J=9.6 Hz), 5.35 (1 H, br. s.), 3.49-3.59 (1 H, m), 3.35-3.46 (1 H, m), 3.25 (1 H, d, J=12.1 Hz), 2.98-3.11 (1 H, m), 2.03 (1 H, d, J=10.0 Hz), 1.83-1.98 (2 H, m).

Example 17

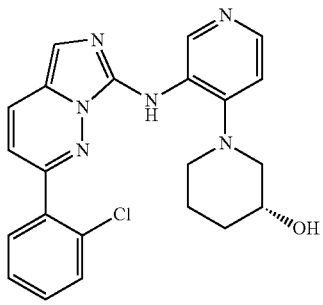 [SMILES: O[C@@H]1CCCN(c2ccncc2Nc2ncc3ccc(-c4ccccc4Cl)nn23)C1]

(3R)-1-(3-((2-(2-chlorophenyl)imidazo[1,5-b]pyridazin-7-yl)amino)-4-pyridinyl)-3-piperidinol Step 1. N-(4-((3R)-3-((tert-butyl(dimethyl)silyl)oxy)-1-piperidinyl)-3-pyridinyl)-2-(2-chlorophenyl)imidazo[1,5-b]pyridazin-7-amine. PMe₃ (1.0 M solution in THF) (0.21 mL, 0.21 mmol) was added dropwise to a solution of 3-(azidomethyl)-6-(2-chlorophenyl)pyridazine (Preparation III, 43 mg, 0.18 mmol) in THF (0.5 mL) at RT. The reaction turned purple and an evolution of gas was observed. The reaction was stirred for 15 min at RT. A solution of 4-((3R)-3-((tert-butyl(dimethyl)silyl)oxy)-1-piperidinyl)-3-isothiocyanatopyridine (Preparation XXI, 67 mg, 0.19 mmol) in THF (0.8 mL) was added. After 30 min at RT, the mixture was diluted with EtOAc and washed with brine. The aqueous phase was extracted with EtOAc (2×). The combined organic layers were dried over anh. Na₂SO₄, filtered and concentrated. The crude material was purified by silica gel chromatography (0-3% MeOH in CH₂Cl₂) to provide N-(4-((3R)-3-((tert-butyl(dimethyl)silyl)oxy)-1-piperidinyl)-3-pyridinyl)-2-(2-chlorophenyl)imidazo[1,5-b]pyridazin-7-amine (55 mg, 0.10 mmol, 59% yield) as an orange oil. MS (ESI, pos. ion) m/z: 421.1 (M+1). ¹H NMR (400 MHz, CDCl₃) δ ppm 9.71 (s, 1 H), 8.24 (d, J=5.09 Hz, 1 H), 7.86 (s, 1 H), 7.75 (d, J=9.39 Hz, 1 H), 7.64 (dd, J=7.34, 1.86 Hz, 1 H), 7.52-7.56 (m, 1 H), 7.38-7.48 (m, 2 H), 7.36 (s, 1 H), 6.98 (d, J=5.09 Hz, 1 H), 6.70 (d, J=9.39 Hz, 1 H), 3.81 (tt, J=9.39, 4.40 Hz, 1 H), 3.21 (dd, J=10.95, 4.30 Hz, 1 H), 3.11 (d, J=11.74 Hz, 1 H), 2.55-2.68 (m, 2 H), 1.88-1.97 (m, 1H), 1.79-1.88 (m, 1 H), 1.63-1.78 (m, 1 H), 1.33-1.45 (m, 1 H), 0.79 (s, 9 H), −0.09 (d, J=3.72 Hz, 6 H).

Step 2. (3R)-1-(3-((2-(2-chlorophenyl)imidazo[1,5-b]pyridazin-7-yl)amino)-4-pyridinyl)-3-piperidinol. A mixture of N-(4-((3R)-3-((tert-butyl(dimethyl)silyl)oxy)-1-piperidinyl)-3-pyridinyl)-2-(2-chlorophenyl)imidazo[1,5-b]pyridazin-7-amine (55 mg, 0.10 mmol) in THF (2 mL), MeOH (1 mL) and 5 M HCl (aq., 1 mL, 5 mmol) was stirred at RT overnight. The reaction mixture was concentrated and saturated NaHCO₃ (aq.) was added. The mixture was extracted with 10/1 CH₂Cl₂/MeOH (3×). The combined organic layers were dried over anh. Na₂SO₄, filtered and concentrated to give (3R)-1-(3-((2-(2-chlorophenyl)imidazo[1,5-b]pyridazin-7-yl)amino)-4-pyridinyl)-3-piperidinol (37 mg, 0.09 mmol, 86% yield) as an orange solid. MS (ESI, pos. ion) m/z: 421.1 (M+1). ¹H NMR (400 MHz, DMSO-d₆) δ ppm 9.33 (s, 1 H), 8.06-8.14 (m, 2 H), 7.92 (s, 1 H), 7.70-7.77 (m, 1 H), 7.63-7.69 (m, 1 H), 7.48-7.61 (m, 2 H), 7.40 (s, 1 H), 7.07 (d, J=5.28 Hz, 1H), 6.81 (d, J=9.39 Hz, 1 H), 4.82 (d, J=4.89 Hz, 1 H), 3.55-3.68 (m, 1 H), 3.14 (dd, J=11.15, 4.30 Hz, 1 H), 3.02 (d, J=11.93 Hz, 1 H), 2.58-2.69 (m, 1 H), 2.52-2.57 (m, 1H), 1.68-1.86 (m, 2 H), 1.19-1.33 (m, 1 H).

Example 18

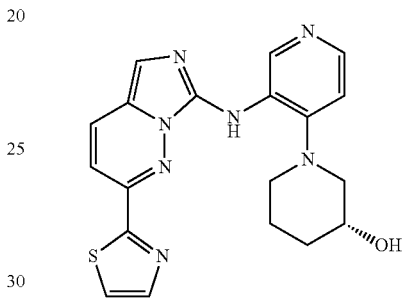

(3R)-1-(3-((2-(1,3-thiazol-2-yl)imidazo[1,5-b]pyridazin-7-yl)amino)-4-pyridinyl)-3-piperidinol The title compound was prepared and isolated as an orange amorphous solid from 2-(6-(azidomethyl)pyridazin-3-yl)thiazole (Preparation II) and 4-((3R)-3-((tert-butyl(dimethyl)silyl)-oxy)-1-piperidinyl)-3-isothiocyanatopyridine (Preparation XXI) following an analogous procedure to Example 17. MS (ESI, pos. ion) m/z: 394.1 (M+1). ¹H NMR (400 MHz, CDCl₃) δ ppm 9.72 (s, 1 H), 8.22 (d, J=5.28 Hz, 1 H), 7.97 (d, J=3.33 Hz, 1 H), 7.92 (s, 1 H), 7.77 (d, J=9.59 Hz, 1 H), 7.53 (d, J=3.13 Hz, 1 H), 7.29-7.32 (m, 1 H), 7.28 (s, 1 H), 6.97 (d, J=5.28 Hz, 1 H), 4.13-4.21 (m, 1 H), 3.20-3.26 (m, 1 H), 2.88-3.04 (m, 3 H), 1.99-2.15 (m, 2 H), 1.84-1.95 (m, 1 H), 1.65-1.77 (m, 2H).

Example 19

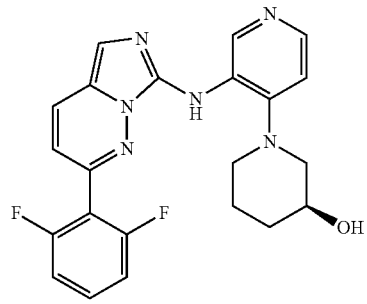 [SMILES: O[C@H]1CCCN(c2ccncc2Nc2ncc3ccc(-c4c(F)cccc4F)nn23)C1]

(3S)-1-(3-((2-(2,6-difluorophenyl)imidazo[1,5-b]pyridazin-7-yl)amino)-4-pyridinyl)-3-piperidinol The title compound was prepared and isolated as an orange amorphous solid from 3-(azidomethyl)-6-(2,6-difluorophenyl)pyridazine (Preparation I) and 4-((3S)-3-((tert-butyl(dimethyl)silyl)oxy)-1-piperidinyl)-3-isothiocyanatopyridine (Preparation XXII) following an analogous procedure to Example 17. MS (ESI, pos. ion) m/z: 422.9 (M+1). $^1$H NMR (400 MHz, CDCl$_3$) δ ppm 9.66 (s, 1 H), 8.20 (d, J=5.28 Hz, 1 H), 7.80 (s, 1 H), 7.76 (d, J=9.39 Hz, 1 H), 7.45 (tt, J=8.48, 6.19 Hz, 1 H), 7.35 (s, 1 H), 7.01-7.13 (m, 2H), 6.93 (d, J=5.28 Hz, 1 H), 6.52 (dt, J=9.39, 1.76 Hz, 1 H), 3.92-4.02 (m, 1 H), 3.08-3.17 (m, 1 H), 2.82-3.00 (m, 3 H), 1.78-2.00 (m, 2 H), 1.51-1.76 (m, 2 H).

Example 20

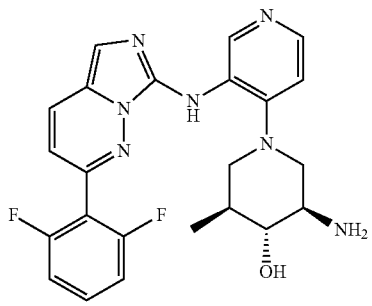 [SMILES: C[C@H]1CN(c2ccncc2Nc2ncc3ccc(-c4c(F)cccc4F)nn23)C[C@@H](N)[C@@H]1O]

(3R,4R,5S)-3-amino-1-(3-((2-(2,6-difluorophenyl)imidazo[1,5-b]pyridazin-7-yl)amino)-4-pyridinyl)-5-methyl-4-piperidinol Step 1. tert-butyl ((3R,4R,5S)-4-((tert-butyl(dimethyl)silyl)oxy)-1-(3-((2-(2,6-difluorophenyl)imidazo[1,5-b]pyridazin-7-yl)amino)-4-pyridinyl)-5-methyl-3-piperidinyl)carbamate PMe$_3$ (1.0 M solution in THF) (0.95 mL, 0.95 mmol) was added dropwise to a solution of 3-(azidomethyl)-6-(2,6-difluorophenyl)pyridazine (Preparation I, 235 mg, 0.95 mmol) in THF (6.0 mL) at RT. The reaction turned purple and an evolution of gas was observed. The reaction was stirred for 15 min at RT. A solution of tert-butyl ((3R,4R,5S)-4-((tert-butyl(dimethyl)silyl)oxy)-1-(3-isothiocyanato-4-pyridinyl)-5-methyl-3-piperidinyl)carbamate (Preparation XIII, 455 mg, 0.95 mmol) in THF (5.0 mL) was added. After 15 min at RT, the mixture was diluted with EtOAc and washed with brine. The aqueous phase was extracted with EtOAc (2×). The combined organic layers were dried over anh. Na$_2$SO$_4$, filtered and concentrated. The crude material was purified by silica gel chromatography (0-3% MeOH in CH$_2$Cl$_2$) to provide tert-butyl ((3R,4R,5S)-4-((tert-butyl(dimethyl)silyl)oxy)-1-(3-((2-(2,6-difluorophenyl)imidazo[1,5-b]pyridazin-7-yl)amino)-4-pyridinyl)-5-methyl-3-piperidinyl)carbamate (450 mg, 0.68 mmol, 71% yield) as an orange solid. MS (ESI, pos. ion) m/z: 666.3 (M+1). $^1$H NMR (400 MHz, CDCl$_3$) δ ppm 9.76 (s, 1 H), 8.21 (d, J=5.09 Hz, 1 H), 7.77 (d, J=9.39 Hz, 1H), 7.70 (br. s., 1 H), 7.34-7.47 (m, 2 H), 7.05 (t, J=8.12 Hz, 2 H), 6.93 (d, J=5.28 Hz, 1H), 6.51 (d, J=9.39 Hz, 1 H), 4.49 (br. s., 1 H), 3.67 (br. s., 1 H), 3.40 (d, J=10.76 Hz, 1H), 3.14-3.28 (m, 2 H), 2.81 (t, J=10.07 Hz, 1 H), 2.29 (t, J=11.15 Hz, 1 H), 1.89-2.03 (m, 1 H), 1.40 (br. s., 9 H), 0.93 (s, 12 H), 0.11 (d, J=11.15 Hz, 6 H).

Step 2. (3R,4R,5S)-3-amino-1-(3-((2-(2,6-difluorophenyl)imidazo[1,5-b]pyridazin-7-yl)amino)-4-pyridinyl)-5-methyl-4-piperidinol.p To a solution of tert-butyl ((3R,4R,5S)-4-((tert-butyl(dimethyl)silyl)oxy)-1-(3-((2-(2,6-difluorophenyl)imidazo[1,5-b]pyridazin-7-yl)amino)-4-pyridinyl)-5-methyl-3-piperidinyl)carbamate (450 mg, 0.68 mmol) in THF (20 mL) and MeOH (10 mL) was added 5 M HCl(aq.) (10 mL). The mixture was heated at 60° C. for 2 h. After cooling to RT, the mixture was concentrated and the diluted with 100 mL of 1 M HCl(aq.). The acidic aqueous layer was extracted with EtOAc (2×50 mL). The aqueous layer was made basic by the addition of saturated NaHCO$_3$ (aq.). The aqueous layer was extracted with 10/1 CH$_2$Cl$_2$/MeOH. The combined organic layers were dried over anh. Na$_2$SO$_4$, filtered and concentrated to afford (3R,4R,5S)-3-amino-1-(3-((2-(2,6-difluorophenyl)imidazo[1,5-b]pyridazin-7-yl)amino)pyridin-4-yl)-5-methylpiperidin-4-ol (298 mg, 0.66 mmol, 98% yield) as an orange solid. MS (ESI, pos. ion) m/z: 452.3 (M+1). $^1$H NMR (400 MHz, CDCl$_3$) δ ppm 9.72 (s, 1 H), 8.20 (d, J=5.09 Hz, 1 H), 7.77 (d, J=9.39 Hz, 2 H), 7.41-7.50 (m, 1 H), 7.36 (s, 1 H), 7.08 (t, J=8.22 Hz, 2 H), 6.93 (d, J=5.28 Hz, 1 H), 6.54 (dt, J=9.44, 1.74 Hz, 1 H), 3.28-3.35 (m, 1 H), 3.10-3.19 (m, 1 H), 2.83-2.95 (m, 2 H), 2.43-2.54 (m, 2 H), 1.87-1.99 (m, 1 H), 0.99 (d, J=6.65 Hz, 3 H).

Example 21

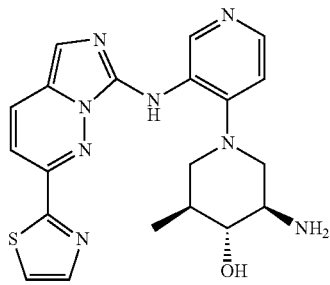 [SMILES: C[C@H]1CN(c2ccncc2Nc2ncc3ccc(-c4nccs4)nn23)C[C@@H](N)[C@@H]1O]

(3R,4R,5S)-3-amino-5-methyl-1-(3-((2-(1,3-thiazol-2-yl)imidazo[1,5-b]pyridazin-7-yl)amino)-4-pyridinyl)-4-piperidinol The title compound was prepared and isolated as a red amorphous solid from 2-(6-(azidomethyl)pyridazin-3-yl)thiazole (Preparation II) and tert-butyl ((3R,4R,5S)-4-((tert-butyl(dimethyl)silyl)oxy)-1-(3-isothiocyanato-4-pyridinyl)-5-methyl-3-piperidinyl)-carbamate (Preparation XIII) following an analogous procedure to Example 20. The crude material was purified by prep HPLC method 4. MS (ESI, pos. ion) m/z: 423.2 (M+1). $^1$H NMR (400 MHz, CDCl$_3$) δ ppm 9.80 (s, 1 H), 8.24 (d, J=5.09 Hz, 1 H), 7.97 (d, J=3.13 Hz, 1 H), 7.93 (s, 1 H), 7.79 (d, J=9.59 Hz, 1 H), 7.55 (d, J=3.13 Hz, 1 H), 7.31-7.36 (m, 2 H), 6.99 (d, J=5.09 Hz, 1 H), 3.31-3.39

(m, 1 H), 3.14-3.24 (m, 2 H), 2.99 (t, J=9.49 Hz, 1 H), 2.57 (t, J=11.25 Hz, 2 H), 2.16-2.28 (m, 1 H), 1.11 (d, J=6.65 Hz, 3 H).

Example 22

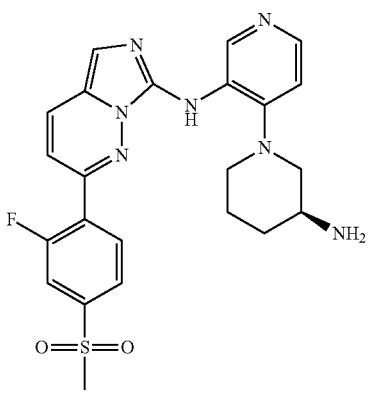 [SMILES: CS(=O)(=O)c1ccc(-c2ccc3cnc(Nc4cnccc4N4CCC[C@H](N)C4)n3n2)c(F)c1]

N-(4-((3S)-3-amino-1-piperidinyl)-3-pyridinyl)-2-(2-fluoro-4-(methylsulfonyl)phenyl)imidazo[1,5-b]pyridazin-7-amine The title compound was prepared and isolated as a red amorphous solid from 3-(azidomethyl)-6-(2-fluoro-4-(methylsulfonyl)phenyl)pyridazine (Preparation VII) and tert-butyl ((3S)-1-(3-isothiocyanato-4-pyridinyl)-3-piperidinyl)carbamate (Preparation XI) following an analogous procedure to Example 20. The crude material was purified by prep HPLC method 4. MS (ESI, pos. ion) m/z: 482.0 (M+1). $^1$H-NMR: $^1$H NMR (400 MHz, CDCl$_3$) δ ppm 9.69 (s, 1 H), 8.21-8.25 (m, 1 H), 8.10 (t, J=7.63 Hz, 1 H), 7.78-7.91 (m, 3 H), 7.39 (s, 1 H), 6.98 (d, J=5.28 Hz, 1 H), 6.74-6.81 (m, 1 H), 3.19 (dd, J=10.66, 3.62 Hz, 1 H), 3.15 (s, 3 H), 3.04-3.13 (m, 2 H), 2.69-2.79 (m, 1 H), 2.54-2.63 (m, 1 H), 1.86-1.99 (m, 2 H), 1.70-1.83 (m, 1 H), 1.32 (dd, J=13.30, 3.72 Hz, 1H).

Example 23

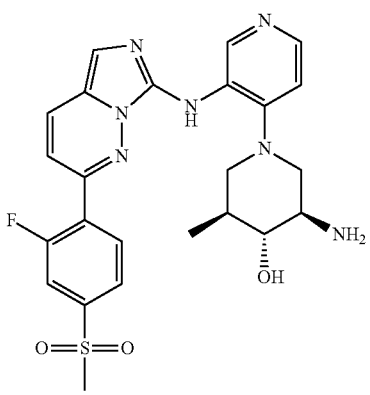 [SMILES: C[C@H]1CN(c2ccncc2Nc2ncc3ccc(-c4ccc(S(C)(=O)=O)cc4F)nn23)C[C@@H](N)[C@@H]1O]

(3R,4R,5S)-3-amino-1-(3-((2-(2-fluoro-4-(methylsulfonyl)phenyl)imidazo[1,5-b]pyridazin-7-yl)amino)-4-pyridinyl)-5-methyl-4-piperidinol The title compound was prepared and isolated as an orange amorphous solid from 3-(azidomethyl)-6-(2-fluoro-4-(methylsulfonyl)phenyl)pyridazine (Preparation VII) and tert-butyl ((3R,4R,5S)-4-((tert-butyl(dimethyl)silyl)oxy)-1-(3-isothiocyanato-4-pyridinyl)-5-methyl-3-piperidinyl)carbamate (Preparation XIII) following an analogous procedure to Example 20. The crude material was purified by prep HPLC method 4. MS (ESI, pos. ion) m/z: 511.9 (M+1). $^1$H NMR (400 MHz, CDCl$_3$) δ ppm 9.69 (s, 1 H), 8.22 (d, J=5.28 Hz, 1 H), 8.10 (t, J=7.53 Hz, 1 H), 7.91-7.96 (m, 1 H), 7.77-7.87 (m, 3 H), 7.37 (s, 1 H), 6.96 (d, J=5.28 Hz, 1 H), 6.77-6.84 (m, 1 H), 3.26-3.33 (m, 1 H), 3.12-3.19 (m, 4 H), 2.88-2.96 (m, 2 H), 2.54-2.62 (m, 1 H), 2.47 (t, J=11.74 Hz, 1 H), 1.90-2.00 (m, 1 H), 0.98 (s, 3 H).

Example 24

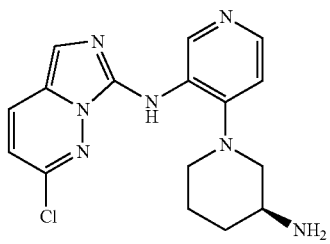 [SMILES: N[C@H]1CCCN(c2ccncc2Nc2ncc3ccc(Cl)nn23)C1]

N-(4-((3S)-3-amino-1-piperidinyl)-3-pyridinyl)-2-chloroimidazo[1,5-b]pyridazin-7-amine The title compound was prepared and isolated as a thick orange oil from 3-(azidomethyl)-6-chloropyridazine (Preparation V) and tert-butyl ((3S)-1-(3-isothiocyanato-4-pyridinyl)-3-piperidinyl)carbamate (Preparation XI) following an analogous procedure to Example 20. The crude material was purified by prep HPLC method 4. MS (ESI, pos. ion) m/z: 344.0 (M+1). $^1$H NMR (400 MHz, CDCl$_3$) δ ppm 9.65 (s, 1 H), 8.23 (d, J=5.28 Hz, 1 H), 7.67 (s, 1 H), 7.35 (s, 1 H), 6.97 (d, J=5.28 Hz, 1 H), 6.34 (d, J=9.39 Hz, 1 H), 3.02-3.28 (m, 3 H), 2.73-2.84 (m, 1 H), 2.58-2.69 (m, 1 H), 1.93-2.06 (m, 3 H), 1.79-1.93 (m, 1 H), 1.35-1.48 (m, 1 H).

Example 25

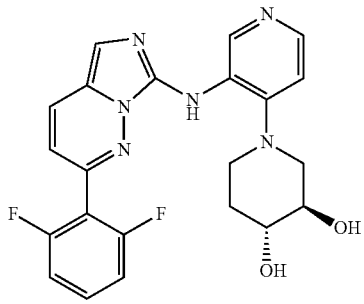

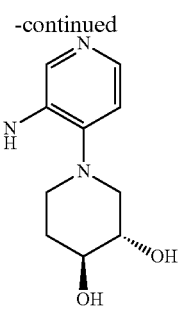

(3S,4S)-1-(3-((2-(2,6-difluorophenyl)imidazo[1,5-b]pyridazin-7-yl)amino)-4-pyridinyl)-3,4-piperidinediol and (3R,4R)-1-(3-((2-(2,6-difluorophenyl)imidazo[1,5-b]pyridazin-7-yl)amino)-4-pyridinyl)-3,4-piperidinediol (1/1)

The title compound was prepared and isolated as a orange amorphous solid from 3-(azidomethyl)-6-(2,6-difluorophenyl)pyridazine (Preparation I) and 4-((3S,4S)-3,4-bis((tert-butyl(dimethyl)silyl)oxy)-1-piperidinyl)-3-isothiocyanato-pyridine and 4-((3R,4R)-3,4-bis((tert-butyl(dimethyl)silyl)oxy)-1-piperidinyl)-3-isothiocyanatopyridine (1/1) (Preparation XXVI) following an analogous procedure to Example 20. The crude material was purified by prep HPLC method 4. MS (ESI, pos. ion) m/z: 439.0 (M+1). $^1$H NMR (400 MHz, CDCl$_3$) δ ppm 9.68 (s, 1 H), 8.20 (d, J=5.09 Hz, 1 H), 7.76 (d, J=9.39 Hz, 1 H), 7.73 (s, 1 H), 7.40-7.50 (m, 1 H), 7.34 (s, 1 H), 7.08 (t, J=8.22 Hz, 2 H), 6.95 (d, J=5.28 Hz, 1 H), 6.54 (dt, J=9.39, 1.76 Hz, 1 H), 3.71-3.80 (m, 1 H), 3.55-3.65 (m, 1 H), 3.33-3.42 (m, 1 H), 3.17-3.27 (m, 1 H), 2.76-2.85 (m, 1 H), 2.68-2.76 (m, 1 H), 2.04-2.13 (m, 1 H), 1.73-1.86 (m, 1 H). MS (ESI, pos. ion) m/z: 439.0 [M+H].

Example 26

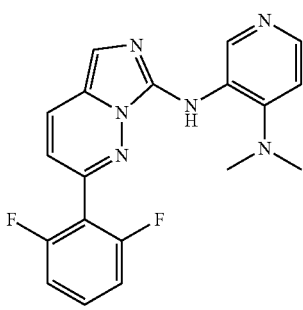 [SMILES: CN(C)c1ccncc1Nc1ncc2ccc(-c3c(F)cccc3F)nn12]

$N^3$-(2-(2,6-difluorophenyl)imidazo[1,5-b]pyridazin-7-yl)-$N^4$,$N^4$-dimethyl-3,4-pyridinediamine The title compound was prepared and isolated as a red amorphous solid from 3-(azidomethyl)-6-(2,6-difluorophenyl)pyridazine (Preparation I) and 3-isothiocyanato-N,N-dimethyl-4-pyridinamine (Preparation XXIII) following an analogous procedure to Example 2, step 1. The crude material was purified by prep HPLC method 4. MS (ESI, pos. ion) m/z: 367.0 (M+1). $^1$H NMR (400 MHz, CDCl$_3$) δ ppm 9.61 (s, 1 H), 8.20 (d, J=5.28 Hz, 1 H), 7.75 (d, J=9.39 Hz, 1 H), 7.53 (s, 1 H), 7.45 (tt, J=8.48, 6.28 Hz, 1 H), 7.34 (s, 1 H), 7.01-7.11 (m, 2 H), 6.95 (d, J=5.09 Hz, 1 H), 6.50 (d, J=9.39 Hz, 1 H), 2.79 (s, 6 H).

Example 27

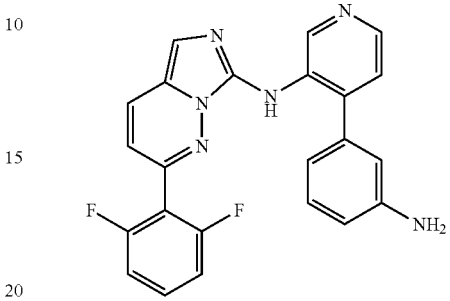

N-(4-(3-aminophenyl)-3-pyridinyl)-2-(2,6-difluorophenyl)imidazo[1,5-b]pyridazin-7-amine Step 1. N-(4-chloro-3-pyridinyl)-2-(2,6-difluorophenyl)imidazo[1,5-b]pyridazin-7-amine PMe$_3$ (0.62 mL of 1.0 M solution in THF, 0.62 mmol) was added dropwise to a solution of 3-(azidomethyl)-6-(2,6-difluorophenyl)pyridazine (Preparation I, 140 mg, 0.57 mmol) in THF (2.5 mL) at RT. The reaction turned purple and an evolution of gas was observed. It was stirred for 15 min at RT. A solution of 4-chloro-3-isothiocyanatopyridine (Preparation XXIV, 106 mg, 0.62 mmol) in THF (1 mL) was added. After 15 min at RT, the reaction was diluted with EtOAc (50 mL) and washed with H$_2$O (10 mL). The aqueous phase was extracted with EtOAc (2×15 mL). The combined organic layers were washed with brine (15 mL), dried over anh. Na$_2$SO$_4$, filtered and concentrated. The crude material was purified by silica gel chromatography (0-3% MeOH in CH$_2$Cl$_2$) to provide N-(4-chloro-3-pyridinyl)-2-(2,6-difluorophenyl)-imidazo[1,5-b]pyridazin-7-amine (110 mg, 54% yield) as an orange crystalline solid. MS (ESI, pos. ion) m/z: 350.8 (M+1). $^1$H NMR (400 MHz, CDCl$_3$) δ ppm 9.90 (s, 1 H), 8.17 (d, J=5.09 Hz, 1 H), 7.79 (d, J=9.59 Hz, 1 H), 7.64 (s, 1 H), 7.40-7.51 (m, 1 H), 7.37 (s, 1 H), 7.32 (d, J=5.09 Hz, 1 H), 7.07 (m, 2 H), 6.57 (dt, J=9.44, 1.64 Hz, 1 H).

Step 2. N-(4-(3-aminophenyl)-3-pyridinyl)-2-(2,6-difluorophenyl)imidazo[1,5-b]pyridazin-7-amine. A mixture of N-(4-chloro-3-pyridinyl)-2-(2,6-difluorophenyl)imidazo[1,5-b]pyridazin-7-amine (49 mg, 0.13 mmol), 3-(4,4,5,5-tetramethyl-1,3,2-dioxaborolan-2-yl)aniline (33 mg, 0.15 mmol), Pd(PPh$_3$)$_4$ (7 mg, 0.6 μmol) and potassium phosphate (87 mg, 0.41 mmol) in 1.5 mL of dioxane and 0.5 mL of H$_2$O was heated in a microwave at 130° C. for 25 min. The organic layer was purified by silica gel chromatography (50-100% EtOAc in hexanes) to provide N-(4-(3-aminophenyl)-3-pyridinyl)-2-(2,6-difluorophenyl)imidazo[1,5-b]pyridazin-7-amine (2 mg, 3% yield) as an orange crystalline solid. MS (ESI, pos. ion) m/z: 415.0 (M+1). $^1$H NMR (400 MHz, DMSO-d$_6$) δ ppm 9.49 (1 H, s), 8.26 (1 H, d, J=4.9 Hz), 8.11 (1 H, d, J=9.4 Hz), 7.86 (1 H, s), 7.681 (1 H, m), 7.42-7.27 (3 H, m), 7.23 (1 H, d, J=4.9 Hz), 7.07 (1 H, t, J=7.7 Hz), 6.73-6.63 (3 H, m), 6.59 (1 H, dd, J=8.0, 1.4 Hz), 5.23 (2 H, br.). $^{19}$F NMR (400 MHz, DMSO-d$_6$) δ ppm −113.34.

Example 28

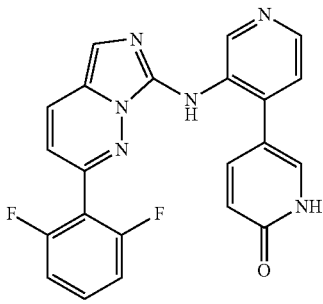 [SMILES: O=c1ccc(-c2ccncc2Nc2ncc3ccc(-c4c(F)cccc4F)nn23)c[nH]1]

3'-((2-(2,6-difluorophenyl)imidazo[1,5-b]pyridazin-7-yl)amino)-3,4'-bipyridin-6(1 H)-one A glass microwave reaction vessel was charged with N-(4-chloro-3-pyridinyl)-2-(2,6-difluorophenyl)imidazo[1,5-b]pyridazin-7-amine (Example 27, Step 1, 40 mg, 0.11 mmol), 6-hydroxypyridin-3-ylboronic acid (19 mg, 0.13 mmol, Combi-Blocks, Inc.), Pd(PPh$_3$)$_4$ (13 mg, 0.01 mmol) and 2 M Na$_2$CO$_3$ (aq., 0.17 mL, 0.34 mmol) in dioxane (1.00 mL). The reaction was stirred and heated in a microwave at 120° C. for 20 min. H$_2$O was added and the mixture was extracted with EtOAc (3×). The combined organic layers were dried over anh. Na$_2$SO$_4$, filtered and concentrated. The crude material was purified by silica gel chromatography (0-5% MeOH in CH$_2$Cl$_2$) to provide 3'-((2-(2,6-difluorophenyl)imidazo[1,5-b]pyridazin-7-yl)amino)-3,4'-bipyridin-6(1 H)-one (1 mg, 2.40 μmol, 2% yield) as a yellow solid. MS (ESI, pos. ion) m/z: 416.9 (M+1). $^1$H NMR (400 MHz, MeOH-d4) δ ppm 8.82 (s, 1 H), 8.30 (d, J=5.09 Hz, 1 H), 7.96 (d, J=9.39 Hz, 1 H), 7.74 (dd, J=9.59, 2.54 Hz, 1 H), 7.55-7.64 (m, 2 H), 7.37 (d, J=5.09 Hz, 1 H), 7.24 (s, 1 H), 6.69 (d, J=9.39 Hz, 1 H), 6.44 (d, J=9.39 Hz, 1 H).

Example 29

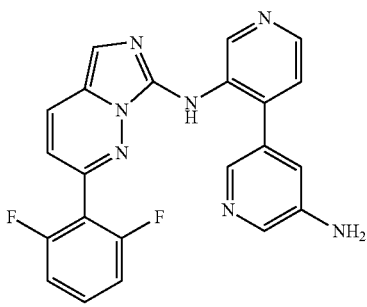 [SMILES: Nc1cncc(-c2ccncc2Nc2ncc3ccc(-c4c(F)cccc4F)nn23)c1]

N3'-(2-(2,6-difluorophenyl)imidazo[1,5-b]pyridazin-7-yl)-3,4'-bipyridine-3',5-diamine Step 1. N-(4-Bromopyridin-3-yl)-2-(2,6-difluorophenyl) imidazo[1,5-b]pyridazin-7-amine and N-(4-chloropyridin-3-yl)-2-(2,6-difluorophenyl)imidazo[1,5-b]pyridazin-7-amine (1/1). To a solution of 3-(azidomethyl)-6-(2,6-difluorophenyl)pyridazine (Preparation I, 350 mg, 1.42 mmol) in 2 mL of THF at RT was added PMe$_3$ (1.55 mL of 1 M in THF solution, 1.55 mmol). The resulting brown solution was stirred at RT for 15 min. It was treated with a suspension of 4-bromo-3-isothiocyanatopyridine and 4-chloro-3-isothiocyanatopyridine (1/1) (Preparation XXV, 338 mg) in 3 mL of THF. After stirring for 1 h at RT, the mixture was concentrated at reduced pressure to half of the volume and the remaining suspension was purified by silica gel chromatography (25-75% EtOAc in hexanes) to give 353 mg of brown solid as a 1/1 mixture of N-(4-bromopyridin-3-yl)-2-(2,6-difluorophenyl)imidazo[1,5-b]pyridazin-7-amine and N-(4-chloropyridin-3-yl)-2-(2,6-difluorophenyl)imidazo[1,5-b]pyridazin-7-amine. This material was used in next step without further purification. MS (ESI, pos. ion) m/z: 401.9/403.9 (M+1), and 358.0 (M+1).

Step 2. N3'-(2-(2,6-difluorophenyl)imidazo[1,5-b]pyridazin-7-yl)-3,4'-bipyridine-3',5-diamine. A mixture of N-(4-bromopyridin-3-yl)-2-(2,6-difluorophenyl)imidazo[1,5-b]pyridazin-7-amine and N-(4-chloropyridin-3-yl)-2-(2,6-difluorophenyl)imidazo[1,5-b]pyridazin-7-amine (1/1, 71 mg), 5-(4,4,5,5-tetramethyl-1,3,2-dioxaborolan-2-yl)pyridin-3-amine (58.3 mg, 0.26 mmol, Boron Molecular, Research Triangle, N.C.), Pd(PPh$_3$)$_4$ (10.2 mg, 8.8 μmol) in 1.5 mL of dioxane and 2 N Na$_2$CO$_3$ (0.5 mL) in a sealed glass tube was heated in a microwave at 130° C. for 25 min. The organic phase of the reaction mixture was purified by silica gel chromatography (1-10% MeOH in EtOAc) to give an orange solid (about 80% pure) which was recrystallized from ether to give N3'-(2-(2,6-difluorophenyl)imidazo[1,5-b]pyridazin-7-yl)-3,4'-bipyridine-3',5-diamine (27 mg, 37% yield) as an orange crystalline solid. MS (ESI, pos. ion) m/z: 416.0 (M+1). $^1$H NMR (400 MHz, DMSO-d$_6$) δ ppm 9.04 (1 H, s), 8.29 (1 H, d, J=4.9 Hz), 8.13 (1 H, s), 8.07 (1 H, d, J=9.4 Hz), 7.88 (1 H, d, J=2.7 Hz), 7.80 (1 H, d, J=2.0 Hz), 7.63 (1 H, m), 7.25 (4 H, m), 6.98 (1 H, t, J=2.2 Hz), 6.66 (1 H, d, J=9.4 Hz), 5.77 (1 H, s), 5.38 (2 H, br. s). $^{19}$F NMR (400 MHz, DMSO-d$_6$) δ ppm −113.34.

Example 30

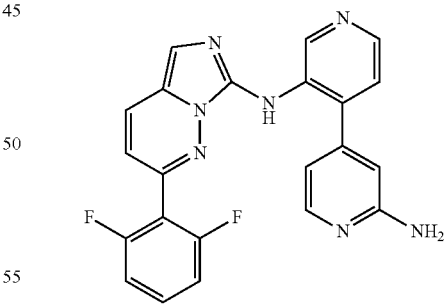

N3'-(2-(2,6-difluorophenyl)imidazo[1,5-b]pyridazin-7-yl)-4,4'-bipyridine-2,3'-diamine A glass microwave reaction vessel was charged with a 1:1 mixture of N-(4-bromopyridin-3-yl)-2-(2,6-difluorophenyl) imidazo[1,5-b]pyridazin-7-amine and N-(4-chloropyridin-3-yl)-2-(2,6-difluorophenyl)imidazo[1,5-b]pyridazin-7-amine (Example 29, step 1, 85 mg), (2-aminopyridin-4-yl)boronic acid (44 mg, 0.31 mmol, CombiPhos Catalysis, Inc., Princeton, N.J.), Pd(PPh₃)₄ (12 mg, 10.6 µmol) and 2 M Na₂CO₃ (0.33 mL) in dioxane (1.5 mL). The reaction was stirred and heated in a microwave at 130° C. for 25 min. The mixture was diluted with EtOAc and water. The layers were separated and the aqueous layer was extracted with EtOAc (2×). The combined organic layers were dried over anh. Na₂SO₄, filtered and concentrated. The crude material was purified by prep HPLC method 4. The desired fractions were collected and concentrated. The residue was partitioned between 30 mL of EtOAc and 5 mL of 0.5 M NaOH. The organic solution was washed with brine (5 mL), dried over Na₂SO₄ and concentrated to afford N3'-(2-(2,6-difluorophenyl)imidazo[1,5-b]pyridazin-7-yl)-[4,4'-bipyridine]-2,3'-diamine (15 mg, 17% yield) as an orange solid. MS (ESI, pos. ion) m/z: 415.9 (M+1). ¹H NMR (400 MHz, CDCl₃) δ ppm 9.88 (s, 1 H), 8.34 (d, J=4.89 Hz, 1 H), 8.16 (d, J=5.09 Hz, 1 H), 7.75 (d, J=9.39 Hz, 1 H), 7.39 (m, 2 H), 7.34 (s, 1 H), 7.14 (d, J=4.89 Hz, 1 H), 7.05 (t, J=8.22 Hz, 2 H), 6.78-6.85 (m, 1 H), 6.63 (s, 1 H), 6.53 (dt, J=9.39, 1.76 Hz, 1 H), 4.55 (br., 2 H).

Example 31

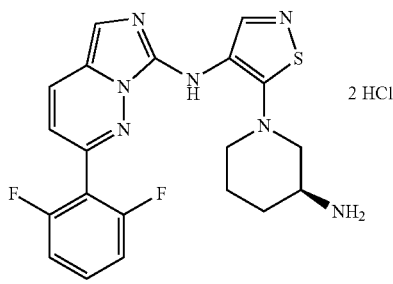 [SMILES: N[C@H]1CCCN(c2sncc2Nc2ncc3ccc(-c4c(F)cccc4F)nn23)C1]

N-(5-((3S)-3-amino-1-piperidinyl)-4-isothiazolyl)-2-(2,6-difluorophenyl)imidazo[1,5-b]pyridazin-7-amine dihydrochloride Step 1. tert-butyl ((3S)-1-(4-((2-(2,6-difluorophenyl)imidazo[1,5-b]pyridazin-7-yl)amino)-5-isothiazolyl)-3-piperidinyl)carbamate. A dry, 50 mL, one neck round bottom flask was charged with 3-(azidomethyl)-6-(2,6-difluorophenyl)pyridazine (Preparation I, 156 mg, 0.63 mmol), a stirbar and dry THF (4 mL). The flask was fitted with a septa/Ar inlet and immersed into a ice-water bath. A 1.0 M PMe₃ solution in THF (0.67 mL, 0.67 mmol, Aldrich) was added dropwise via syringe. The solution was stirred cold for 15 min following the addition. A solution of tert-butyl ((3S)-1-(4-isothiocyanato-5-isothiazolyl)-3-piperidinyl)carbamate (Preparation XVIII, 223 mg, 0.66 mmol) in dry THF (4 mL) was added. The reaction was warmed to RT overnight. The solvent was removed in vacuo. The crude material was purified by prep HPLC method 1. The combined fractions were concentrated to ~30 mL, at which point a precipitate formed. The slurry was N₂-pressure filtered through a 10 mL Bohdan reaction vessel glass frit fitted with a 0.22 µm PTFE, 25 mm syringe filter unit (Millipore, SLFG025NK). The solids were washed with H₂O (3×5 mL), and dried initially under a stream of N₂. The material was further dried in a vacuum oven (80° C., <1 mm Hg) to afford tert-butyl ((3S)-1-(4-((2-(2,6-difluorophenyl)imidazo[1,5-b]pyridazin-7-yl)amino)-5-isothiazolyl)-3-piperidinyl)carbamate (250 mg, 0.39 mmol, 62% yield). The filtrate was combined with the water washes, and concentrated in vacuo. The material was purified by prep HPLC method 1. The solvent was removed in vacuo, and the residue was dissolved in H₂O (4 mL). The solution was N₂-pressure filtered through a 4 mL Bohdan glass frit fitted with a 0.22 µm PTFE, 25 mm syringe filter unit (Millipore, SLFG025NK). The transfer was quantitated with H₂O (2×2 mL), and the filtrate was lyophilized for 72 h to afford a second portion of tert-butyl ((3S)-1-(4-((2-(2,6-difluorophenyl)imidazo[1,5-b]pyridazin-7-yl)amino)-5-isothiazolyl)-3-piperidinyl)carbamate (29 mg, 0.05 mmol, 7% yield; combined yield=69%). MS (ESI, pos. ion) m/z: 527.9 (M+1). ¹H NMR (400 MHz, CDCl₃) δ ppm 1.37 (s, 9 H) 1.47-1.64 (m, 2 H) 1.75 (m, J=9.80 Hz, 2 H) 3.01 (dd, J=11.74, 6.65 Hz, 1 H) 3.13 (br. s., 2 H) 3.51 (d, J=12.72 Hz, 1 H) 3.65 (br. s., 1 H) 4.72 (br. s., 2 H) 4.97 (br. s., 1 H) 6.62 (d, J=9.78 Hz, 1 H) 7.04 (t, J=8.22 Hz, 2 H) 7.45 (tt, J=8.20, 6.30 Hz, 1 H) 7.71 (d, J=9.59 Hz, 1 H) 8.22 (br. s., 1 H) 8.74 (br. s., 1 H). ¹⁹F NMR (376 MHz, CDCl₃) δ ppm −113.06-112.76 (m, 2 F) −76.35 (s, 3 F).

Step 2. N-(5-((3S)-3-amino-1-piperidinyl)-4-isothiazolyl)-2-(2,6-difluorophenyl)imidazo[1,5-b]pyridazin-7-amine dihydrochloride. A solution of HCl in EtOAc was prepared as described in step 2 in the preparation of Example 1. A dry, three neck 100 mL Morton flask was configured as follows: opening 1: septa/PTFE addition needle; opening 2: septa, opening 3: septa/18 gauge needle. The flask was charged with the HCl saturated EtOAc (30 mL), and a stirbar. The flask was immersed into an ice-water bath and stirred for 10 min. A syringe charged with tert-butyl ((3S)-1-(4-((2-(2,6-difluorophenyl)imidazo[1,5-b]pyridazin-7-yl)amino)-5-isothiazolyl)-3-piperidinyl)carbamate (250 mg, 0.47 mmol) dissolved in EtOAc (10 mL) was fitted to the PTFE addition needle. The solution was added via syringe pump over 30 min to the vigorously stirred acid solution. The PTFE addition needle was withdrawn, and the flask was placed into a 5° C. refrigerator overnight. The slurry was N₂-pressure filtered through a 10 mL Bohdan reaction vessel glass frit fitted with a 0.22 µm PTFE, 25 mm syringe filter unit (Millipore, SLFG025NK). The yellow solid was washed with EtOAc (3×5 mL), and dried briefly under a stream of N₂. The solid was dried in a vacuum oven (80° C., <1 mm Hg) for 10 min. The solid was dissolved in H₂O (5 mL), and N₂ pressure filtered through the PTFE frit. The transfer was quantitated with a second portion of water (5 mL). The filtrate was lyophilized, and the solid was dried in a vacuum oven (80° C., <1 mm Hg) for 1 h to afford N-(5-((3S)-3-amino-1-piperidinyl)-4-isothiazolyl)-2-(2,6-difluorophenyl)imidazo[1,5-b]pyridazin-7-amine dihydrochloride (137 mg, 0.27 mmol, 58% yield). MS (ESI, pos. ion) m/z: 428.0 (M+1). ¹H NMR (400 MHz, DMF-d6) δ ppm 1.62 (qq, J=9.00, 4.10 Hz, 1 H) 1.83-2.00 (m, 2 H) 2.08-2.19 (m, 1 H) 3.18 (ddd, J=12.40, 9.19, 2.93 Hz, 1 H) 3.43-3.60 (m, 3 H) 4.02 (d, J=9.39 Hz, 1 H) 7.03 (d, J=9.59 Hz, 1 H) 7.40 (t, J=8.31 Hz, 2 H) 7.68 (s, 1 H) 7.77 (tt, J=8.40, 6.50 Hz, 1 H) 8.27 (d, J=9.78 Hz, 1 H) 8.37 (s, 1

H) 9.11 (br. s., 3 H) 10.37 (br. s., 1 H). $^{19}$F NMR (377 MHz, DMF-d6) δ ppm -112.79 (t, J=6.87 Hz, 2 F).

Example 32

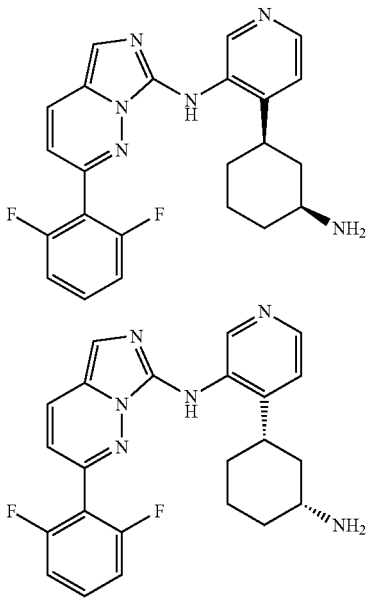

N-(4-((1R,3S)-3-aminocyclohexyl)-3-pyridinyl)-2-(2,6-difluorophenyl)imidazo[1,5-b]pyridazin-7-amine and N-(4-((1S,3R)-3-aminocyclohexyl)-3-pyridinyl)-2-(2,6-difluorophenyl)imidazo[1,5-b]pyridazin-7-amine (1/1)

Step 1. 2-((1R,3S)-3-(3-((2-(2,6-difluorophenyl)imidazo[1,5-b]pyridazin-7-yl)amino)-4-pyridinyl)cyclohexyl)-1H-isoindole-1,3(2 H)-dione and 2-((1S,3R)-3-(3-(2-(2,6-difluorophenyl)imidazo[1,5-b]pyridazin-7-yl)amino)-4-pyridinyl)cyclohexyl)-1H-isoindole-1,3(2 H)-dione bis(2,2,2-trifluoroacetate) (1/1). A dry, 15 mL one neck round bottom flask was charged with 3-(azidomethyl)-6-(2,6-difluorophenyl)pyridazine (Preparation I, 124 mg, 0.50 mmol), dry THF (5 mL), and a stirbar. The flask was fitted with a septa/Ar inlet and immersed into an ice water bath. The solution was stirred for 15 min, and a 1.0 M solution of PMe$_3$ in THF (0.55 mL, 0.55 mmol, Aldrich) was added dropwise. The solution was stirred an additional 15 min and was treated with 2-((1R,3S)-3-(3-isothiocyanatopyridin-4-yl)cyclohexyl)isoindoline-1,3-dione and 2-((1S,3R)-3-(3-isothiocyanatopyridin-4-yl)cyclohexyl)isoindoline-1,3-dione (Preparation XIX, 200 mg, 0.28 mmol) dissolved in 5 mL of dry THF. The reaction was stirred overnight at RT and the solvent was removed in vacuo. The crude was purified by prep HPLC method 1. The solvent was removed in vacuo, and the residue was treated with CHCl$_3$ (5 mL). The organic solution was treated with MgSO$_4$, and N$_2$-pressure filtered through a 10 mL Bohdan glass frit fitted with a 0.22 μm PTFE, 25 mm syringe filter unit (Millipore, PN SLFG025NK). The transfer was quantitated with CHCl$_3$ (3×2 mL). The combined filtrates were concentrated in vacuo, and dried in a vacuum oven (60° C., <1 mm Hg) to afford 2-((1R,3S)-3-(3-((2-(2,6-difluorophenyl)imidazo[1,5-b]pyridazin-7-yl)amino)-4-pyridinyl)cyclohexyl)-1H-isoindole-1,3(2 H)-dione bis(2,2,2-trifluoroacetate) and 2-((1S,3R)-3-(3-((2-(2,6-difluorophenyl)imidazo[1,5-b]pyridazin-7-yl)amino)-4-pyridinyl)cyclohexyl)-1H-isoindole-1,3(2 H)-dione bis(2,2,2-trifluoroacetate) (1/1, 86 mg, 0.06 mmol, 11% yield). MS (ESI, pos. ion) m/z: 550.8 (M+1). $^1$H NMR (400 MHz, CDCl$_3$)$_8$ ppm 1.44-1.59 (m, 1 H) 1.59-1.80 (m, 2 H) 1.90 (d, J=12.72 Hz, 1 H) 2.00-2.24 (m, 3 H) 2.31 (q, J=12.98 Hz, 1 H) 2.68 (q, J=12.06 Hz, 1 H) 3.20 (t, J=11.15 Hz, 1H) 4.39 (t, J=12.13 Hz, 1 H) 6.80 (d, J=9.19 Hz, 1 H) 7.04 (t, J=8.41 Hz, 2 H) 7.45 (dt, J=14.70, 7.60 Hz, 2 H) 7.71 (ddd, J=4.50, 3.33, 1.40 Hz, 3 H) 7.67 (d, J=8.61 Hz, 1 H) 7.79-7.84 (m, 2 H) 7.89 (d, J=9.78 Hz, 1 H) 8.48 (d, J=5.48 Hz, 1 H) 9.26 (br. s., 1 H) 9.58 (br. s., 1 H). $^{19}$F NMR (377 MHz, CDCl$_3$) δ ppm -113.31 (t, J=7.15 Hz, 2 F) -76.33 (br. s., 6 F).

Step 2. N-(4-((1R,3S)-3-aminocyclohexyl)pyridin-3-yl)-2-(2,6-difluorophenyl)imidazo[1,5-b]pyridazin-7-amine bis(2,2,2-trifluoroacetate) and N-(4-((1S,3R)-3-aminocyclohexyl)pyridin-3-3-yl)-2-(2,6-difluorophenyl)imidazo[1,5-b]pyridazin-7-amine bis(2,2,2-trifluoroacetate) (1/1). A dry, 5 mL microwave pressure vessel was charged with 2-((1R,3S)-3-(3-((2-(2,6-difluorophenyl)imidazo[1,5-b]pyridazin-7-yl)amino)-4-pyridinyl)cyclohexyl)-1H-isoindole-1,3(2 H)-dione bis(2,2,2-trifluoroacetate) and 2-((1S,3R)-3-(3-((2-(2,6-difluorophenyl)imidazo[1,5-b]pyridazin-7-yl)amino)-4-pyridinyl)cyclohexyl)-1H-isoindole-1,3(2 H)-dione bis(2,2,2-trifluoroacetate) (1/1, 86 mg, 0.06 mmol), a stirbar, EtOH (3 mL) and methylamine (33% wt. solution in absolute EtOH) (0.07 mL, 0.55 mmol). The vessel was crimped with a PTFE-lined seal and placed in a 45° C. heat transfer block for 3 h. The solution was concentrated under a stream of N$_2$ to a volume of 1 mL. The solution was treated with hydrazine, anh. (3.47 μl, 0.11 mmol), and the vessel was crimped with a PTFE line seal. The vessel was placed into a 45° C. heat transfer block for 2 h and was cooled to RT. The solution was concentrated in vacuo. The crude material was purified using prep HPLC method 1 to afford N-(4-((1R,3S)-3-aminocyclohexyl)pyridin-3-yl)-2-(2,6-difluorophenyl)-imidazo[1,5-b] pyridazin-7-amine bis(2,2,2-trifluoroacetate) and N-(4-((1S,3R)-3-aminocyclohexyl)pyridin-3-yl)-2-(2,6-difluorophenyl)imidazo[1,5-b]pyridazin-7-amine bis(2,2,2-trifluoroacetate) (1/1) (33 mg, 0.03 mmol, 46% yield). MS (ESI, pos. ion) m/z: 421.0 (M+1). $^1$H NMR (400 MHz, DMF-d6) δ ppm 1.51 (m, J=10.76 Hz, 2 H) 1.62 (q, J=11.70 Hz, 1 H) 1.85 (q, J=12.00 Hz, 1 H) 1.95 (m, J=6.00, 2.90 Hz, 1 H) 2.02 (d, J=9.78 Hz, 1 H) 2.20 (d, J=11.35 Hz, 1 H) 2.43 (d, J=11.93 Hz, 1 H) 3.44 (q, J=10.40 Hz, 2 H) 7.01 (br. s, 2 H) 6.85 (d, J=9.39 Hz, 1 H) 7.36 (t, J=8.31 Hz, 2 H) 7.47 (s, 1 H) 7.65 7.77 (m, 1 H) 7.72 (tt, J=8.40, 6.70 Hz, 1 H) 8.25 (d, J=9.39 Hz, 1 H) 8.42-8.65 (m, 4 H) 9.02 (br. s., 1 H) 9.07 (br. s., 1 H). $^{19}$F NMR (376 MHz, DMF-d) δ ppm -113.30 (t, J=7.15 Hz, 2 F) -74.60 (br. s., 9 F). The DMF from the NMR sample was concentrated in vacuo, and the sample was dried in a vacuum oven (60° C., <1 mm Hg) overnight. Approximately 6 mg was analyzed in D$_2$O to check whether the TFA—aromatic fluorine ratio changed. Sample was a bis-TFA salt by $^{19}$F NMR. $^1$H NMR (400 MHz, D$_2$O) δ ppm 1.38-1.59 (m, 3 H) 1.69 (q, J=11.93 Hz, 1 H) 2.00 (d, J=10.56 Hz, 2 H) 2.10 (d, J=11.15 Hz, 1 H) 2.29 (d, J=11.74 Hz, 1 H) 3.20 (t, J=11.44 Hz, 1 H) 3.35 (t, J=11.15 Hz, 1 H) 6.95 (d, J=9.59 Hz, 1 H) 7.12 (t, J=8.41 Hz, 1 H) 7.54 (tt, J=8.60, 6.50 Hz, 1 H) 7.53 (s, 1 H) 7.90 (d, J=6.06 Hz, 1 H) 8.12 (d, J=9.59

Hz, 1 H) 8.29 (s, 1 H) 8.32 (d, J=6.06 Hz, 1 H). $^{19}$F NMR (376 MHz, D$_2$O) δ ppm −117.58 (t, J=7.15 Hz, 2 F) −78.50 (s, 6 F).

Example 33

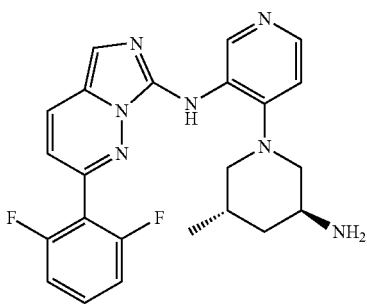 [SMILES: C[C@H]1C[C@H](N)CN(c2ccncc2Nc2ncc3ccc(-c4c(F)cccc4F)nn23)C1]

N-(4-((3S,5S)-3-amino-5-methylpiperidin-1-yl)pyridin-3-yl)-2-(2,6-difluorophenyl) imidazo[1,5-b]pyridazin-7-amine The title compound was prepared and isolated as a bright orange foam from 3-(azidomethyl)-6-(2,6-difluorophenyl) pyridazine (Preparation I) and tert-butyl ((3S,5S)-1-(3-isothiocyanatopyridin-4-yl)-5-methylpiperidin-3-yl)carbamate (Preparation XXXIII) following an analogous procedure to Example 2. MS (ESI, pos. ion) m/z: 436.2 (M+1). $^1$H NMR (400 MHz, DMSO-d$_6$) δ ppm 9.33 (1 H, s), 8.16 (1 H, d, J=9.4 Hz), 8.12 (1 H, d, J=5.1 Hz), 7.62-7.72 (1 H, m), 7.44 (1 H, s), 7.34 (2 H, t, J=8.2 Hz), 7.07 (1 H, d, J=5.3 Hz), 6.74 (1 H, d, J=9.6 Hz), 2.98-3.10 (2 H, m), 2.83-2.91 (1 H, m), 2.73-2.82 (1 H, m), 2.41 (1 H, dd, J=11.1, 8.5 Hz), 1.94 (1 H, br. s.), 1.42-1.51 (1 H, m), 1.28-1.37 (1 H, m), 0.82 (3 H, d, J=6.8 Hz). $^{19}$F NMR (377 MHz, DMSO-d$_6$) δ ppm −113.58 (1 F, s).

Example 34 and 35

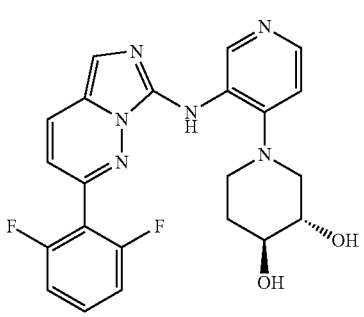

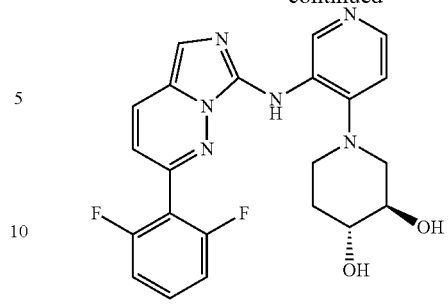

1-(3-((2-(2,6-difluorophenyl)imidazo[1,5-b]pyridazin-7-yl)amino)-4-pyridinyl)-3,4-trans-piperidinediol (first eluting enantiomer) and 1-(3-((2-(2, 6-difluorophenyl)imidazo[1,5-b]pyridazin-7-yl) amino)-4-pyridinyl)-3,4-trans-piperidinediol (second eluting enantiomer)

A portion of Example 25 was purified by supercritical-fluid chromatography (Chiralpak AS-H (250×21 mm, 5 μm), 70% liquid CO$_2$/30% MeOH (40 mM NH$_3$), 70 mL/min) followed by repurification of Example 35 by Princeton pyridine column (250×21 mm, 5 μm), 72% liquid CO$_2$/28% MeOH (40 mM NH$_3$) gave 1-(3-((2-(2,6-difluorophenyl)imidazo[1,5-b] pyridazin-7-yl)amino)-4-pyridinyl)-3,4-trans-piperidinediol, first eluting enantiomer (Example 34, 210 mg, 0.48 mmol) as an orange solid: MS (ESI, pos. ion) m/z: 439.1 (M+1). $^1$H NMR (400 MHz, CDCl$_3$) δ ppm 9.68 (s, 1H), 8.21 (d, J=5.09 Hz, 1 H), 7.68-7.81 (m, 2 H), 7.40-7.51 (m, 1 H), 7.34 (s, 1 H), 7.09 (t, J=8.22 Hz, 2 H), 6.96 (d, J=5.09 Hz, 1 H), 6.55 (d, J=9.59 Hz, 1 H), 3.77 (td, J=8.41, 4.30 Hz, 1 H), 3.56-3.65 (m, 1 H), 3.39 (dd, J=11.54, 2.35 Hz, 1 H), 3.16-3.27 (m, 1H), 2.81 (td, J=11.44, 2.35 Hz, 1 H), 2.67-2.76 (m, 1 H), 2.05-2.15 (m, 1 H), 1.73-1.87 (m, 1 H); and 1-(3-((2-(2,6-difluorophenyl)imidazo[1,5-b]pyridazin-7-yl)amino)-4-pyridinyl)-3,4-trans-piperidinediol, second eluting enantiomer (Example 35, 180 mg, 0.41 mmol) as an orange solid: MS (ESI, pos. ion) m/z: 439.1 (M+1). $^1$H NMR (400 MHz, CDCl$_3$) δ ppm 9.68 (s, 1 H), 8.21 (d, J=5.09 Hz, 1 H), 7.68-7.83 (m, 2 H), 7.41-7.52 (m, 1 H), 7.35 (s, 1 H), 7.04-7.14 (m, 2 H), 6.96 (d, J=5.28 Hz, 1 H), 6.55 (d, J=9.39 Hz, 1 H), 3.77 (td, J=8.51, 4.30 Hz, 1 H), 3.61 (td, J=8.90, 5.09 Hz, 1 H), 3.39 (dd, J=11.44, 2.45 Hz, 1 H), 3.23 (d, J=12.13 Hz, 1 H), 2.82 (td, J=11.44, 2.35 Hz, 1 H), 2.68-2.76 (m, 1 H), 2.04-2.15 (m, 1 H), 1.74-1.86 (m, 1 H).

Example 36

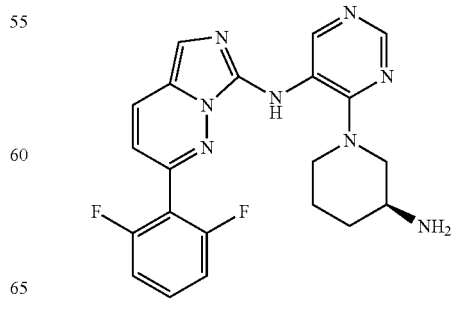

(S)-N-(4-((3S)-3-amino-1-piperidinyl)-5-pyrimidinyl)-2-(2,6-difluorophenyl)imidazo[1,5-b]pyridazin-7-amine The title compound was prepared and isolated as an orange amorphous solid from 3-(azidomethyl)-6-(2,6-difluorophenyl)pyridazine (Preparation I) and tert-butyl ((3S)-1-(5-isothiocyanato-4-pyrimidinyl)-3-piperidinyl)carbamate (Preparation XVII) following an analogous procedure to Example 2. MS (ESI, pos. ion) m/z: 423.0 (M+1). $^1$H NMR (400 MHz, DMSO-d$_6$) δ ppm 8.55 (1 H, s), 8.38 (1 H, s), 8.10 (1 H, d, J=9.4 Hz), 7.65 (1H, m), 7.32 (3 H, m), 6.67 (1 H, d, J=9.4 Hz), 3.89 (3 H, br.), 3.74 (3 H, m), 2.91 (1 H, m), 2.72 (1 H, m), 1.69 (1 H, m), 1.49 (1 H, m), 1.16 (2 H, m). $^{19}$F NMR (376 MHz, DMSO-d$_6$) δ ppm −113.51.

Example 37

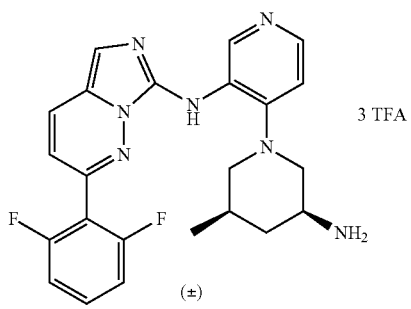 [SMILES: C[C@@H]1C[C@H](N)CN(c2ccncc2Nc2ncc3ccc(-c4c(F)cccc4F)nn23)C1]

(±)

rac-N-(4-((cis)-3-amino-5-methylpiperidin-1-yl)pyridin-3-yl)-2-(2,6-difluorophenyl)imidazo[1,5-b]pyridazin-7-amine tris(2,2,2-trifluoroacetate)

Step 1. rac-tert-butyl ((cis)-1-(3-((2-(2,6-difluorophenyl)imidazo[1,5-b]pyridazin-7-yl)amino)pyridin-4-yl)-5-methylpiperidin-3-yl)carbamate. The title compound was prepared and isolated as a bright orange foam from 3-(azidomethyl)-6-(2,6-difluorophenyl)pyridazine (Preparation I) and rac-tert-butyl ((cis)-1-(3-isothiocyanatopyridin-4-yl)-5-methylpiperidin-3-yl)carbamate (Preparation XXXIV) following an analogous procedure to Example 2, step 1 and 2. MS (ESI, pos. ion) m/z: 536.3 (M+1). $^1$H NMR (400 MHz, CDCl$_3$) δ ppm 9.72 (1 H, s), 8.16-8.23 (1 H, m), 7.76 (1 H, d, J=9.4 Hz), 7.69 (1 H, br. s.), 7.45 (1 H, quin, J=7.4 Hz), 7.35 (1 H, s), 7.06 (2 H, t, J=8.1 Hz), 6.92 (1 H, d, J=5.1 Hz), 6.51 (1 H, d, J=9.6 Hz), 4.40 (1 H, br. s.), 3.77 (1 H, d, J=16.0 Hz), 3.42 (1 H, d, J=7.6 Hz), 3.23 (1 H, br. s.), 2.49 (1 H, br. s.), 2.00-2.11 (2H, m), 1.77 (4 H, s), 1.80 (4 H, s), 0.85-0.94 (1 H, m), 0.76-0.85 (3 H, m).

Step 2. rac-N-(4-((cis)-3-amino-5-methylpiperidin-1-yl)pyridin-3-yl)-2-(2,6-difluorophenyl)imidazo[1,5-b]pyridazin-7-amine tris(2,2,2-trifluoroacetate). The title compound was prepared and isolated as a bright orange foam from rac-tert-butyl ((cis)-1-(3-((2-(2,6-difluorophenyl)imidazo[1,5-b]pyridazin-7-yl)amino)pyridin-4-yl)-5-methylpiperidin-3-yl)carbamate following an analogous procedure to Example 2, step 3. MS (ESI, pos. ion) m/z: 436.2 (M+1). $^1$H NMR (400 MHz, MeOH-d4) δ ppm 9.01 (1 H, s), 8.31 (1 H, d, J=6.7 Hz), 8.09 (1 H, d, J=9.6 Hz), 7.56-7.66 (1 H, m), 7.48 (1 H, d, J=6.7 Hz), 7.43 (1 H, s), 7.21 (2 H, t, J=8.3 Hz), 6.79 (1 H, d, J=9.6 Hz), 4.15 (1 H, d, J=7.6 Hz), 4.00 (1 H, d, J=12.7 Hz), 2.93 (1 H, t, J=11.5 Hz), 2.46 (1 H, t, J=12.2 Hz), 2.14 (1 H, d, J=12.9 Hz), 1.63 (1 H, d, J=6.7 Hz), 1.23 (1 H, q, J=12.1 Hz), 0.89 (3 H, d, J=6.7 Hz). $^{19}$F NMR (376 MHz, MeOH-d4) δ ppm −115.28 (1 F, s).

Example 38 and 39

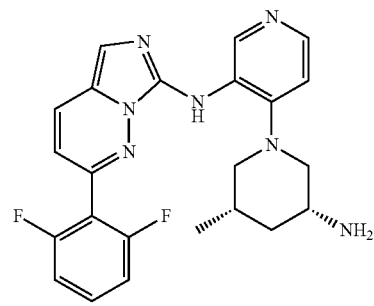

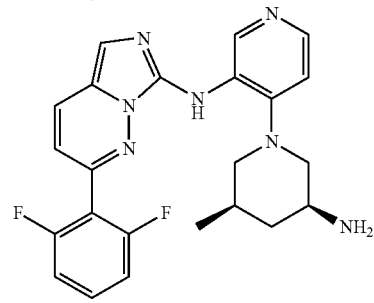

N-(4-((cis)-3-amino-5-methylpiperidin-1-yl)pyridin-3-yl)-2-(2,6-difluorophenyl)imidazo[1,5-b]pyridazin-7-amine (enantiomer 1) and N-(4-((cis)-3-amino-5-methylpiperidin-1-yl)pyridin-3-yl)-2-(2,6-difluorophenyl)imidazo[1,5-b]pyridazin-7-amine (enantiomer 2)

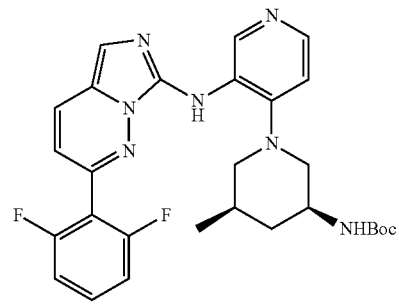

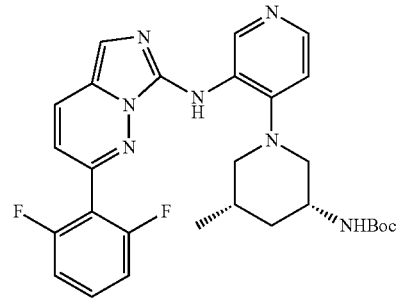

Step 1. tert-butyl ((cis)-1-(3-((2-(2,6-difluorophenyl)imidazo[1,5-b]pyridazin-7-yl)amino)pyridin-4-yl)-5-methylpiperidin-3-yl)carbamate (first eluting enantiomer) and tert-butyl ((cis)-1-(3-((2-(2,6-difluorophenyl)imidazo[1,5-b]pyridazin-7-yl)amino)pyridin-4-yl)-5-methylpiperidin-3-yl)carbamate (second eluting enantiomer). A portion of rac-tert-butyl ((cis)-1-(3-((2-(2,6-difluorophenyl)imidazo[1,5-b]pyridazin-7-yl)amino)pyridin-4-yl)-5-methylpiperidin-3-yl)carbamate (Step 1, Example 37) was purified by SFC (Chiralcel OZ-H column (250×30 mm i.d.; 5 μm), 65% liquid $CO_2$, 35% MeOH (20 mM $NH_3$), 120 mL/min) to give tert-butyl ((cis)-1-(3-((2-(2,6-difluorophenyl)imidazo[1,5-b]pyridazin-7-yl)amino)pyridin-4-yl)-5-methylpiperidin-3-yl)carbamate (first eluting enantiomer) which eluted first from an analytical SFC column (Chiralcel OZ column, 70% liquid $CO_2$, 30% MeOH (0.1% diethylamine), 4 mL/min) and tert-butyl ((cis)-1-(3-((2-(2,6-difluorophenyl)imidazo[1,5-b]pyridazin-7-yl)amino)pyridin-4-yl)-5-methylpiperidin-3-yl)carbamate (second eluting enantiomer) which eluted second from an analytical SFC column (Chiralcel OZ column, 70% liquid $CO_2$, 30% MeOH (0.1% diethylamine), 4 mL/min).

Step 2. N-(4-((cis)-3-amino-5-methylpiperidin-1-yl)pyridin-3-yl)-2-(2,6-difluorophenyl)imidazo[1,5-b]pyridazin-7-amine (enantiomer 1) and N-(4-((cis)-3-amino-5-methylpiperidin-1-yl)pyridin-3-yl)-2-(2,6-difluorophenyl)imidazo[1,5-b]pyridazin-7-amine (enantiomer 2). tert-Butyl ((3R,5S)-1-(3-((2-(2,6-difluorophenyl)imidazo[1,5-b]pyridazin-7-yl)amino)pyridin-4-yl)-5-methylpiperidin-3-yl)carbamate (second eluting peak) (470 mg, 0.878 mmol) was diluted in DCM (5 mL) and then cooled to 0° C. The mixture was treated with TFA (2.00 mL, 26.0 mmol). The mixture was removed from the cooling bath and stirred at RT for 30 min. The reaction mixture was concentrated under reduced pressure and the residue was treated with DCM and shaken with 1N NaOH (ca. pH 10) in a separatory funnel until the solution turned bright orange. The mixture was then extracted with DCM (4×30 mL). The combined organic layers were dried over $Na_2SO_4$, filtered and concentrated to afford N-(4-((cis)-3-amino-5-methylpiperidin-1-yl)pyridin-3-yl)-2-(2,6-difluorophenyl)imidazo[1,5-b]pyridazin-7-amine (cis enantiomer 2, Example 39) (335 mg, 0.77 mmol, 88% yield) as an orange amorphous foam. MS (ESI, pos. ion) m/z: 436.2 (M+1). $^1$H NMR (400 MHz, MeOH-d4) δ ppm 9.27 (1 H, s), 8.11 (1 H, d, J=5.3 Hz), 8.00 (1 H, d, J=9.4 Hz), 7.54-7.65 (1 H, m), 7.36 (1 H, s), 7.20 (2 H, t, J=8.3 Hz), 7.13 (1 H, d, J=5.5 Hz), 6.67 (1 H, d, J=9.4 Hz), 3.35-3.41 (1 H, m), 3.25 (1 H, d, J=8.2 Hz), 2.83-2.95 (1 H, m), 2.40 (1 H, t, J=10.7 Hz), 2.20 (1 H, t, J=11.3 Hz), 1.96 (1 H, d, J=12.5 Hz), 1.71-1.86 (1 H, m), 0.88-0.99 (1 H, m), 0.84 (3 H, d, J=6.7 Hz). $^{19}$F NMR (377 MHz, MeOH-d4) δ ppm −115.14 (1 F, s). N-(4-((cis)-3-amino-5-methylpiperidin-1-yl)pyridin-3-yl)-2-(2,6-difluorophenyl)imidazo[1,5-b]pyridazin-7-amine (enantiomer 1, Example 38) was isolated an orange amorphous solid prepared in an analogous manner from tert-butyl ((cis)-1-(3-((2-(2,6-difluorophenyl)imidazo[1,5-b]pyridazin-7-yl)amino)pyridin-4-yl)-5-methylpiperidin-3-yl)carbamate (first eluting peak). MS (ESI, pos. ion) m/z: 436.2 (M+1). $^1$H NMR (400 MHz, MeOH-d4) δ ppm 9.27 (1 H, s), 8.12 (1 H, d, J=5.3 Hz), 8.01 (1 H, d, J=9.6 Hz), 7.54-7.66 (1 H, m), 7.37 (1 H, s), 7.17-7.25 (2 H, m), 7.14 (1 H, d, J=5.3 Hz), 6.69 (1 H, d, J=9.4 Hz), 3.38-3.44 (1 H, m), 3.28 (1 H, d, J=9.8 Hz), 2.89-3.01 (1 H, m), 2.45 (1 H, t, J=10.7 Hz), 2.21 (1 H, t, J=11.3 Hz), 1.99 (1 H, d, J=12.9 Hz), 1.72-1.88 (1 H, m), 0.89-0.99 (1 H, m), 0.81-0.88 (3 H, m). $^{19}$F NMR (376 MHz, MeOH-d4) δ ppm −115.13 (1 F, s).

Example 40

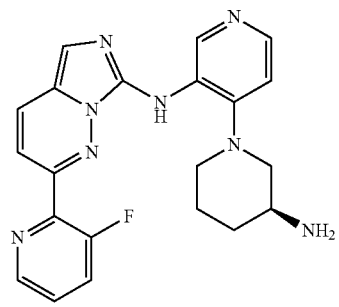 [SMILES: N[C@H]1CCCN(c2ccncc2Nc2ncc3ccc(-c4ncccc4F)nn23)C1]

N-(4-((3S)-3-amino-1-piperidinyl)-3-pyridinyl)-2-(3-fluoro-2-pyridinyl)imidazo [1,5-b]pyridazin-7-amine The title compound was prepared and isolated as an orange amorphous solid from 3-(azidomethyl)-6-(3-fluoropyridin-2-yl)pyridazine (Preparation XXVIII) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 405.0 (M+1). $^1$H NMR (400 MHz, DMSO-$d_6$) δ ppm 9.33 (1 H, s), 8.49 (1 H, m), 7.93-8.03 (2 H, m), 7.79 (1 H, m), 7.52 (1 H, dt, J=8.4, 4.1 Hz), 7.25 (1 H, s), 7.08 (1 H, d, J=9.6 Hz), 6.95 (1H, d, J=5.1 Hz), 3.15 (3 H, br.), 2.93 (1 H, m), 2.86 (1 H, m), 2.78 (1 H, m), 2.49 (1 H, m), 2.25 (2 H, m), 1.70 (1 H, m), 1.55 (2 H, m). $^{19}$F NMR (376 MHz, DMSO-$d_6$) δ ppm −119.07.

Example 41

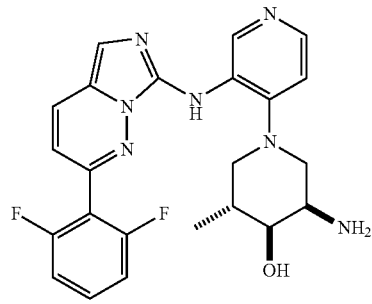 [SMILES: C[C@@H]1CN(c2ccncc2Nc2ncc3ccc(-c4c(F)cccc4F)nn23)C[C@@H](N)[C@H]1O]

(3R,4S,5R)-3-amino-1-(3-((2-(2,6-difluorophenyl)imidazo[1,5-b]pyridazin-7-yl)amino)-4-pyridinyl)-5-methyl-4-piperidinol The title compound was prepared and isolated as an orange amorphous solid from 3-(azidomethyl)-6-(2,6-difluorophenyl)pyridazine (Preparation I) and tert-butyl ((3R,4S,5R)-4-((tert-butyldimethylsilyl)oxy)-1-(3-isothiocyanatopyridin-4-yl)-5-methylpiperidin-3-yl)carbamate (Preparation XXXV) following an analogous procedure to Example 20. MS (ESI, pos. ion) m/z: 452.3 (M+1). $^1$H NMR (400 MHz, DMSO-$d_6$) δ ppm 9.09 (1 H, s), 7.90 (2 H, m), 7.44 (1 H, m), 7.19 (1 H, s), 7.08 (2 H, t, J=8.2 Hz), 6.84 (1 H, d, J=5.1 Hz), 6.49 (1 H, d, J=9.2 Hz), 4.43 (1 H, m), 4.10 (1 H, br.), 3.18 (2 H, m), 3.01 (1 H, m), 2.85 (1 H, m), 2.58 (3 H, m), 2.51 (1 H, m), 1.69 (1 H, m), 0.58 (3 H, d, J=6.7 Hz). $^{19}$F NMR (376 MHz, DMSO-$d_6$) δ ppm −113.56.

Example 42

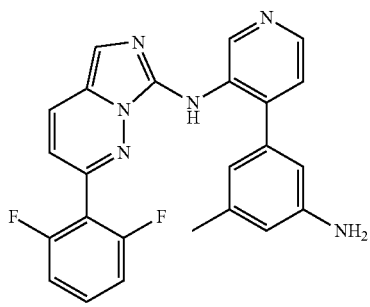

N-(4-(3-amino-5-methylphenyl)-3-pyridinyl)-2-(2,6-difluorophenyl)imidazo[1,5-b]pyridazin-7-amine The title compound was prepared and isolated as an orange solid from 3-(azidomethyl)-6-(2,6-difluorophenyl)pyridazine (Preparation I) and tert-butyl (3-(3-isothiocyanato-pyridin-4-yl)-5-methylphenyl)carbamate (Preparation XXXVI) following an analogous procedure to Example 20. MS (ESI, pos. ion) m/z: 429.0 (M+1). $^1$H NMR (400 MHz, CDCl$_3$) δ ppm 9.86 (s, 1 H), 8.30 (d, J=4.70 Hz, 1 H), 7.74 (d, J=9.39 Hz, 1H), 7.64 (s, 1 H), 7.44 (tt, J=8.46, 6.21 Hz, 1 H), 7.34 (s, 1 H), 7.15 (d, J=4.69 Hz, 1 H), 6.98-7.08 (m, 2 H), 6.73 (s, 1 H), 6.60 (t, J=2.05 Hz, 1 H), 6.52 (t, J=1.86 Hz, 1 H), 6.48 (dt, J=9.44, 1.74 Hz, 1 H), 3.68 (d, J=0.59 Hz, 2 H), 2.22 (s, 3 H).

Example 43, 44 and 45

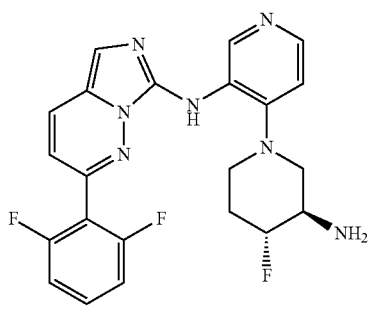

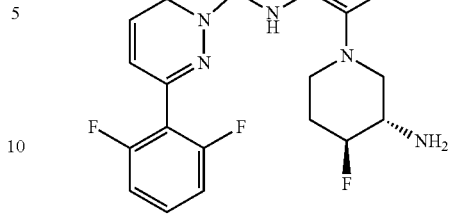

rac-N-(4-(trans-3-amino-4-fluoropiperidin-1-yl)pyridin-3-yl)-2-(2,6-difluorophenyl)imidazo[1,5-b]pyridazin-7-amine, N-(4-(trans-3-amino-4-fluoropiperidin-1-yl)pyridin-3-yl)-2-(2,6-difluorophenyl)imidazo[1,5-b]pyridazin-7-amine (first eluting enantiomer), and N-(4-(trans-3-amino-4-fluoropiperidin-1-yl)pyridin-3-yl)-2-(2,6-difluorophenyl)imidazo[1,5-b]pyridazin-7-amine (second eluting enantiomer)

Step 1. rac-N-(4-(trans-3-amino-4-fluoropiperidin-1-yl)pyridin-3-yl)-2-(2,6-difluorophenyl)imidazo[1,5-b]pyridazin-7-amine (Example 43). The title compound was prepared and isolated as an orange solid from 3-(azidomethyl)-6-(2,6-difluorophenyl)pyridazine (Preparation I) and rac-tert-butyl ((trans)-4-fluoro-1-(3-isothiocyanatopyridin-4-yl)piperidin-3-yl)carbamate (Preparation XXXVII) following an analogous procedure to Example 20. MS (ESI, pos. ion) m/z: 440.1 (M+1). $^1$H NMR (400 MHz, CDCl$_3$) δ ppm 9.73 (s, 1 H), 8.22 (d, J=5.28 Hz, 1 H), 7.84 (s, 1 H), 7.78 (d, J=9.39 Hz, 1 H), 7.46 (tt, J=8.41, 6.26 Hz, 1 H), 7.37 (s, 1 H), 7.03-7.13 (m, 2H), 6.96 (d, J=5.09 Hz, 1 H), 6.55 (dt, J=9.39, 1.76 Hz, 1 H), 4.25-4.46 (m, 1 H), 3.16-3.33 (m, 3 H), 2.78-2.89 (m, 1 H), 2.68 (dd, J=11.35, 7.82 Hz, 1 H), 2.12-2.26 (m, 1H), 1.93-2.07 (m, 1 H). $^{19}$F NMR (376 MHz, CDCl$_3$) δ ppm −112.78, −185.17.

Step 3. N-(4-(trans-3-amino-4-fluoropiperidin-1-yl)pyridin-3-yl)-2-(2,6-difluorophenyl)imidazo[1,5-b]pyridazin-7-amine (first eluting enantiomer), and N-(4-(trans-3-amino-4-fluoropiperidin-1-yl)pyridin-3-yl)-2-(2,6-difluorophenyl) imidazo[1,5-b]pyridazin-7-amine (second eluting enantiomer). A portion of rac-N-(4-(trans-3-amino-4-fluoropiperidin-1-yl)pyridin-3-yl)-2-(2,6-difluorophenyl)imidazo[1,5-b]pyridazin-7-amine (Example 43) was purified by SFC (ChiralpakAS-H (2×15 cm, 5 μm), 80% liquid CO$_2$/20% EtOH (0.1% DEA, 5% CH$_2$Cl$_2$), 60 mL/min) gave N-(4-(trans-3-amino-4-fluoropiperidin-1-yl)pyridin-3-yl)-2-(2,6-difluorophenyl)imidazo[1,5-b]pyridazin-7-amine, first eluting enantiomer (Example 44, 130 mg, 0.30 mmol) as an orange solid. This material eluted first by analytical SFC (Chiralpak AS-H (0.46×25 cm, 5 μm), 80% liquid CO$_2$/20% EtOH (0.1% DEA), 3 mL/min): MS (ESI, pos. ion) m/z: 440.1 (M+1). $^1$H NMR (400 MHz, CDCl$_3$) δ ppm 9.73 (s, 1 H), 8.22 (d, J=5.09 Hz, 1 H), 7.84 (s, 1 H), 7.78 (d, J=9.39 Hz, 1 H), 7.41-7.51 (m, 1 H), 7.37 (s, 1 H), 7.03-7.14 (m, 2 H), 6.96 (d, J=5.09 Hz, 1 H), 6.55 (dt, J=9.39, 1.76 Hz, 1 H), 4.23-4.47 (m, 1 H), 3.15-3.33 (m, 3 H), 2.79-2.89 (m, 1 H), 2.68 (dd, J=11.35, 7.82 Hz, 1 H), 2.12-2.25 (m, 1 H), 1.92-2.07 (m, 1 H). $^{19}$F NMR (376 MHz, CDCl$_3$) δ ppm −112.78, −184.17; and N-(4-(trans-3-amino-4-fluoropiperidin-1-yl) pyridin-3-yl)-2-(2,6-difluorophenyl)imidazo[1,5-b]pyridazin-7-amine, second eluting enantiomer (Example 45, 110 mg, 0.25 mmol) as an orange solid. This material eluted second by analytical SFC (Chiralpak AS-H (0.46×25 cm, 5 μm), 80% liquid $CO_2$/20% EtOH (0.1% DEA), 3 mL/min): MS (ESI, pos. ion) m/z: 440.1 (M+1). $^1$H NMR (400 MHz, CDCl$_3$) δ ppm 9.73 (s, 1 H), 8.22 (d, J=5.28 Hz, 1 H), 7.84 (s, 1 H), 7.78 (d, J=9.39 Hz, 1H), 7.46 (tt, J=8.41, 6.26 Hz, 1 H), 7.37 (s, 1 H), 7.03-7.12 (m, 2 H), 6.96 (d, J=5.09 Hz, 1 H), 6.55 (dt, J=9.39, 1.76 Hz, 1 H), 4.25-4.46 (m, 1 H), 3.15-3.33 (m, 3 H), 2.78-2.89 (m, 1 H), 2.68 (dd, J=11.35, 7.82 Hz, 1 H), 2.12-2.25 (m, 1 H), 1.93-2.07 (m, 1H). $^{19}$F NMR (376 MHz, CDCl$_3$) δ ppm −112.78, −184.18.

Example 46 and 47

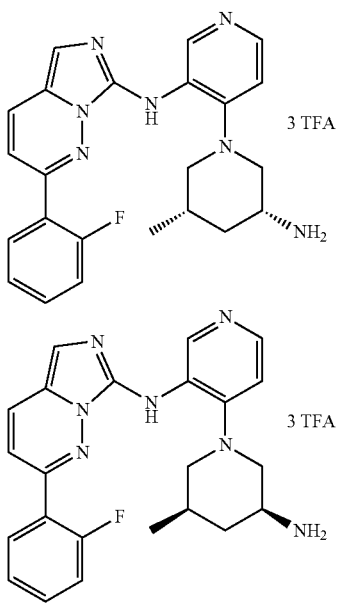

N-(4-((cis)-3-amino-5-methylpiperidin-1-yl)pyridin-3-yl)-2-(2-fluorophenyl)imidazo[1,5-b]pyridazin-7-amine tris(2,2,2-trifluoroacetate) (enantiomer 1) and N-(4-((cis)-3-amino-5-methylpiperidin-1-yl)pyridin-3-yl)-2-(2-fluorophenyl)imidazo[1,5-b]pyridazin-7-amine tris(2,2,2-trifluoroacetate) (enantiomer 2)

N-(4-((cis)-3-Amino-5-methylpiperidin-1-yl)pyridin-3-yl)-2-(2-fluorophenyl)imidazo[1,5-b]pyridazin-7-amine tris(2,2,2-trifluoroacetate) (enantiomer 1) (Example 46) was prepared and isolated as a bright yellow amorphous solid from 3-(azidomethyl)-6-(2-fluorophenyl)pyridazine (Preparation VI) and tert-butyl ((cis)-1-(3-isothiocyanatopyridin-4-yl)-5-methylpiperidin-3-yl)carbamate (enantiomer 1) (Preparation XXXVIII) following an analogous procedure to Example 2. MS (ESI, pos. ion) m/z: 418.2 (M+1). $^1$H NMR (400 MHz, MeOH-d4) δ ppm 9.09 (1 H, s), 8.32 (1 H, d, J=6.7 Hz), 8.06 (1 H, d, J=9.6 Hz), 7.87 (1 H, t, J=7.7 Hz), 7.56-7.65 (1 H, m), 7.50 (1H, d, J=6.7 Hz), 7.29-7.43 (3 H, m), 7.02 (1 H, dd, J=9.6, 2.5 Hz), 4.15 (1 H, d, J=7.8 Hz), 4.02 (1 H, d, J=12.5 Hz), 2.94 (1 H, t, J=11.3 Hz), 2.48 (1 H, t, J=12.1 Hz), 2.16 (1H, d, J=11.9 Hz), 1.72 (1 H, br. s.), 1.24 (1 H, q, J=12.1 Hz), 0.88 (3 H, d, J=6.7 Hz). $^{19}$F NMR (376 MHz, MeOH-d4) δ ppm −117.38 (1 F, s). N-(4-((cis)-3-amino-5-methylpiperidin-1-yl)pyridin-3-yl)-2-(2-fluorophenyl)imidazo[1,5-b]pyridazin-7-amine tris(2,2,2-trifluoroacetate) (enantiomer 2) (Example 47) was prepared and isolated as a bright yellow amorphous solid from 3-(azidomethyl)-6-(2-fluorophenyl)pyridazine (Preparation VI) and tert-butyl ((cis)-1-(3-isothiocyanatopyridin-4-yl)-5-methylpiperidin-3-yl)carbamate (enantiomer 2) (Preparation XXXVIII) following an analogous procedure to Example 2. MS (ESI, pos. ion) m/z: 418.2 (M+1). $^1$H NMR (400 MHz, MeOH-d4) δ ppm 9.02-9.09 (1 H, m), 8.31 (1 H, dd, J=6.7, 1.0 Hz), 8.05 (1 H, d, J=9.6 Hz), 7.87 (1H, td, J=7.7, 1.6 Hz), 7.56-7.64 (1 H, m), 7.49 (1 H, d, J=6.7 Hz), 7.27-7.43 (3 H, m), 7.03 (1 H, dd, J=9.7, 2.4 Hz), 4.12-4.21 (1 H, m), 4.02 (1 H, d, J=12.7 Hz), 2.96 (1 H, t, J=11.4 Hz), 2.48 (1 H, t, J=12.3 Hz), 2.15 (1 H, d, J=12.3 Hz), 1.61-1.77 (1 H, m), 1.24 (1 H, q, J=12.1 Hz), 0.87 (3 H, d, J=6.7 Hz). $^{19}$F NMR (377 MHz, MeOH-d4) δ ppm −117.33 (1 F, s).

Example 48

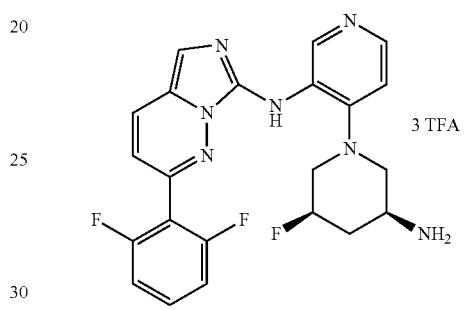

N-(4-((3S,5R)-3-amino-5-fluoropiperidin-1-yl)pyridin-3-yl)-2-(2,6-difluorophenyl)imidazo[1,5-b]pyridazin-7-amine tris(2,2,2-trifluoroacetate)

The title compound was prepared and as a yellow foam from 3-(azidomethyl)-6-(2,6-difluorophenyl)pyridazine (Preparation I) and tert-butyl ((3S,5R)-5-fluoro-1-(3-isothiocyanatopyridin-4-yl)piperidin-3-yl)carbamate (Preparation XXXIX) following an analogous procedure to Example 2. MS (ESI, pos. ion) m/z: 440.1 (M+1). $^1$H NMR (400 MHz, MeOH-d4) δ ppm 9.21-9.28 (1 H, m), 8.37 (1 H, dd, J=6.6, 0.9 Hz), 8.08 (1 H, d, J=9.6 Hz), 7.53-7.64 (2 H, m), 7.45 (1 H, s), 7.12-7.22 (2 H, m), 6.77 (1 H, d, J=9.4 Hz), 5.09 (1 H, d, J=2.5 Hz), 4.97 (1 H, br. s.), 4.18-4.31 (1 H, m), 3.66-3.83 (3 H, m), 3.23 (1 H, d, J=14.1 Hz), 2.35 (1 H, br. s.), 2.21-2.33 (1 H, m). $^{19}$F NMR (377 MHz, MeOH-d4) δ ppm −115.30 (2 F, s), −181.93 (1 F, s).

Example 49

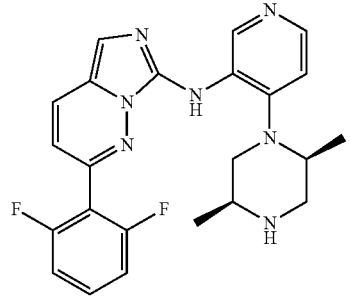 [SMILES: C[C@H]1CN(c2ccncc2Nc2ncc3ccc(-c4c(F)cccc4F)nn23)[C@@H](C)CN1]

2-(2,6-difluorophenyl)-N-(4-((2S,5S)-2,5-dimethylpiperazin-1-yl)pyridin-3-yl)imidazo[1,5-b]pyridazin-7-amine The title compound was prepared and isolated as a red amorphous solid from 3-(azidomethyl)-6-(2,6-difluorophenyl)pyridazine (Preparation I) and (2S,5S)-tert-butyl 4-(3-isothiocyanatopyridin-4-yl)-2,5-dimethylpiperazine-1-carboxylate (Preparation XL) following an analogous procedure to Example 2. MS (ESI, pos. ion) m/z: 436.1 (M+1). $^1$H NMR (400 MHz, MeOH-d4) δ ppm 9.27 (s, 1 H), 8.11 (d, J=5.5 Hz, 1 H), 7.98 (d, J=9.4 Hz, 1 H), 7.52-7.63 (m, 1 H), 7.35 (s, 1 H), 7.10-7.23 (m, 3 H), 6.65 (d, J=9.6 Hz, 1 H), 3.53-3.63 (m, 1 H), 2.84-2.99 (m, 4 H), 2.80 (dd, J=12.9, 4.1 Hz, 1 H), 1.17 (d, J=6.3 Hz, 3 H), 0.98 (d, J=6.7 Hz, 3 H). $^{19}$F NMR (376 MHz, MeOH-d4) δ ppm −115.12 (s, 2 F).

Example 50, 51, and 52

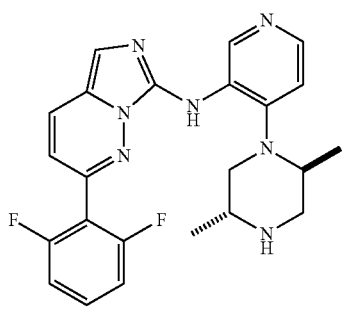

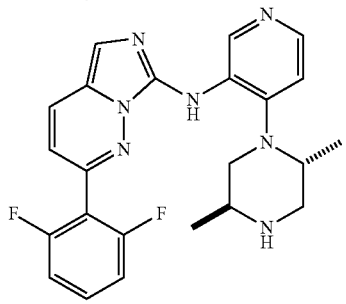

rac-2-(2,6-difluorophenyl)-N-(4-((trans)-2,5-dimethyl-1-piperazinyl)-3-pyridinyl)imidazo[1,5-b]pyridazin-7-amine and 2-(2,6-difluorophenyl)-N-(4-((trans)-2,5-dimethyl-1-piperazinyl)-3-pyridinyl)imidazo[1,5-b]pyridazin-7-amine (first eluting enantiomer) and 2-(2,6-difluorophenyl)-N-(4-((trans)-2,5-dimethyl-1-piperazinyl)-3-pyridinyl)imidazo[1,5-b]pyridazin-7-amine (second eluting enantiomer)

rac-2-(2,6-Difluorophenyl)-N-(4-((trans)-2,5-dimethyl-1-piperazinyl)-3-pyridinyl)imidazo[1,5-b]pyridazin-7-amine (Example 50) was prepared and isolated as an orange amorphous solid from 3-(azidomethyl)-6-(2,6-difluorophenyl)pyridazine (Preparation I) and rac-tert-butyl 4-(3-isothiocyanatopyridin-4-yl)-trans-2,5-dimethylpiperazine-1-carboxylate (Preparation XLI) following an analogous procedure to Example 2 MS (ESI, pos. ion) m/z: 436.1 (M+1). $^1$H NMR (400 MHz, DMSO-d$_6$) δ ppm 9.59 (1 H, s), 8.52 (1 H, s), 8.16 (2 H, m), 7.67 (1 H, m), 7.44 (1 H, s), 7.16-7.37 (3H, m), 6.74 (1 H, d, J=9.4 Hz), 3.39 (1 H, br.), 2.03 (2 H, m), 2.77 (2 H, m), 2.40 (1 H, m), 2.19 (1 H, t, J=11.0 Hz), 0.85 (3 H, d, J=5.9 Hz), 0.73 (3 H, d, J=5.9 Hz). $^{19}$F NMR (376 MHz, DMSO-d$_6$) δ ppm −113.70. A 315 mg portion of rac-2-(2,6-difluorophenyl)-N-(4-((trans)-2,5-dimethyl-1-piperazinyl)-3-pyridinyl)imidazo[1,5-b]pyridazin-7-amine (Example 50) was purified by SFC (LUX2 (2×15 cm×5 µM, 60% liquid CO$_2$/40% MeOH (0.1% NH$_4$OH), 60 mL/min) to afford 123 mg of 2-(2,6-difluorophenyl)-N-(4-((trans)-2,5-dimethyl-1-piperazinyl)-3-pyridinyl)imidazo[1,5-b]pyridazin-7-amine (first eluting enantiomer, Example 51), which eluted at 9.66 min by analytical SFC chromatography (LUX2 (0.46×10 cm, 0.5 µm) 65% liquid CO$_2$/35% MeOH (0.2% DEA), 4 mL/min). MS (ESI, pos. ion) m/z: 436.1 (M+1); and 131 mg of 2-(2,6-difluorophenyl)-N-(4-((trans)-2,5-dimethyl-1-piperazinyl)-3-pyridinyl)imidazo[1,5-b]pyridazin-7-amine (second eluting enantiomer, Example 52), which eluted at 13.10 min by analytical SFC chromatography (same conditions as above).

Example 53

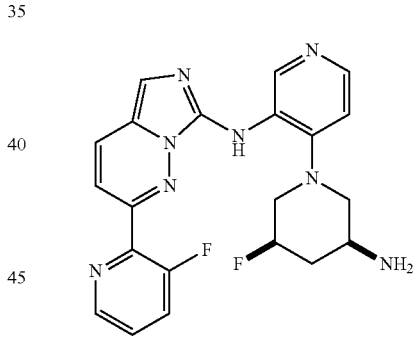

N-(4-((3S,5R)-3-amino-5-fluoro-1-piperidinyl)-3-pyridinyl)-2-(3-fluoro-2-pyridinyl)imidazo[1,5-b]pyridazin-7-amine The title compound was prepared and isolated as an orange amorphous solid from 3-(azidomethyl)-6-(3-fluoropyridin-2-yl)pyridazine (Preparation XXVIII) and tert-butyl ((3S,5R)-5-fluoro-1-(3-isothiocyanatopyridin-4-yl)piperidin-3-yl)carbamate (Preparation XXXIX) following an analogous procedure to Example 2. MS (ESI, pos. ion) m/z: 423.0 (M+1). $^1$H NMR (400 MHz, DMSO-d$_6$) δ ppm 9.24 (1 H, s), 8.47 (1 H, s), 7.97 (2 H, m), 7.82 (1 H, t, J=9.7 Hz), 7.52 (1 H, m), 7.24 (1 H, s), 7.08 (1 H, m), 7.00 (1 H, m.), 4.69 (1 H, br.), 4.57 (1 H, br.), 3.85 (1 H, m), 3.80 (1 H, br.), 3.21 (1 H, m), 2.90 (1 H, m), 2.80 (1 H, m), 2.64 (1 H, m), 2.13 (2 H, m), 1.33 (1 H, m). $^{19}$F NMR (376 MHz, DMSO-d$_6$) δ ppm −119.38 and −178.83.

Example 54, 55, 56, 57

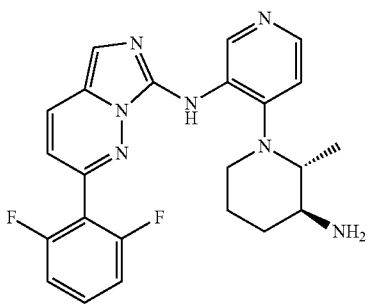

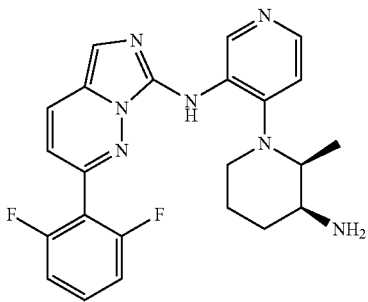

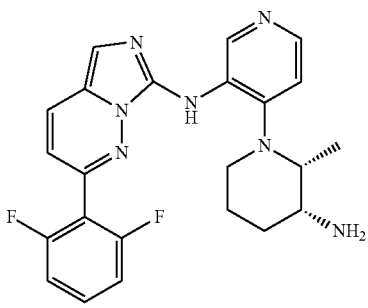

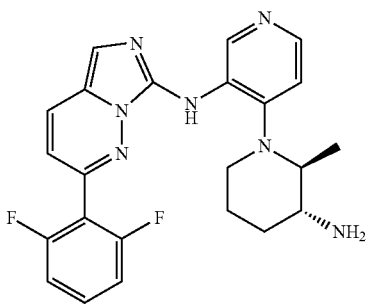

N-(4-((trans)-3-amino-2-methyl-1-piperidinyl)-3-pyridinyl)-2-(3-fluoro-2-pyridinyl)imidazo[1,5-b]pyridazin-7-amine (enantiomer 1) (Example 54)

N-(4-((trans)-3-amino-2-methyl-1-piperidinyl)-3-pyridinyl)-2-(3-fluoro-2-pyridinyl)imidazo[1,5-b]pyridazin-7-amine (enantiomer 2) (Example 55)

N-(4-((cis)-3-amino-2-methyl-1-piperidinyl)-3-pyridinyl)-2-(3-fluoro-2-pyridinyl)imidazo[1,5-b]pyridazin-7-amine (enantiomer 3) (Example 56)

N-(4-((cis)-3-amino-2-methyl-1-piperidinyl)-3-pyridinyl)-2-(3-fluoro-2-pyridinyl)imidazo[1,5-b]pyridazin-7-amine (enantiomer 4) (Example 57)

Step 1. tert-butyl (1-(3-((2-(2,6-difluorophenyl)imidazo[1,5-b]pyridazin-7-yl)amino)pyridin-4-yl)-2-methylpiperidin-3-yl)carbamate (first eluting enantiomer), tert-butyl (1-(3-((2-(2,6-difluorophenyl)imidazo[1,5-b]pyridazin-7-yl)amino)pyridin-4-yl)-2-methylpiperidin-3-yl)carbamate (second eluting enantiomer), tert-butyl (1-(3-((2-(2,6-difluorophenyl)imidazo[1,5-b]pyridazin-7-yl)amino)pyridin-4-yl)-2-methylpiperidin-3-yl)carbamate (third eluting enantiomer), tert-butyl (1-(3-((2-(2,6-difluorophenyl)imidazo[1,5-b]pyridazin-7-yl)amino)pyridin-4-yl)-2-methylpiperidin-3-yl)carbamate (fourth eluting enantiomer). PMe$_3$ (1.12 mL of 1.0 M solution in THF, 1.12 mmol) was added drop wise to a solution of 3-(azidomethyl)-6-(2,6-difluorophenyl)pyridazine (264 mg, 1.06 mmol, Preparation I) in THF (1.5 mL) at RT. The resulting purple mixture was stirred for 15 min at RT. A solution of tert-butyl (1-(3-isothiocyanatopyridin-4-yl)-2-methylpiperidin-3-yl)carbamate (391 mg, 1.12 mmol, Preparation XLII) in THF (2+1 mL) was added. After 15 min at RT, the reaction mixture was diluted with EtOAc (80 mL) and washed with water (5 mL) followed by brine (5 mL). The organic layer was dried over Na$_2$SO$_4$, and concentrated. The crude material was purified by silica gel chromatography (50-100% EtOAc in CH$_2$Cl$_2$) to provide tert-butyl (1-(3-((2-(2,6-difluorophenyl)imidazo[1,5-b]pyridazin-7-yl)amino)pyridin-4-yl)-2-methylpiperidin-3-yl)carbamate (465 mg, 81% yield) as an orange amorphous solid. MS (ESI, pos. ion) m/z: 536.2 (M+1). Chiral separation: A ca. 3:1 ratio of cis:trans diastereomers from above (465 mg) was subjected to chiral separation using a preparatory SFC (Chiralcel OZ-H column (21×250 mm i.d., 5 μm) 75% liquid CO$_2$/25% MeOH (20 mM NH$_3$), 75 mL/min). This separation resulted in 4 peaks, with de % values of greater than 99% for each peak. The 4 peaks were further characterized on an analytical SFC column (Chiralcel OZ-H (150×4.6 mm, 5 μm), 75% liquid CO$_2$/25% methanol (0.2% DEA), 4 mL/min): tert-butyl (1-(3-((2-(2,6-difluorophenyl)imidazo[1,5-b]pyridazin-7-yl)amino)pyridin-4-yl)-2-methylpiperidin-3-yl)carbamate (first eluting enantiomer) (53 mg of orange amorphous solid) with a retention time of 9.32 min; tert-butyl (1-(3-((2-(2,6-difluorophenyl)imidazo[1,5-b]pyridazin-7-yl)amino)pyridin-4-yl)-2-methylpiperidin-3-yl)carbamate (second eluting enantiomer) (52 mg of orange amorphous solid) with a retention time of 11.48 min; tert-butyl (1-(3-((2-(2,6-difluorophenyl)imidazo[1,5-b]pyridazin-7-yl)amino)pyridin-4-yl)-2-methylpiperidin-3-yl)carbamate (third eluting enantiomer) (145 mg of orange amorphous solid) with a retention time of 12.92 min; tert-butyl (1-(3-((2-(2,6-difluorophenyl)imidazo[1,5-b]pyridazin-7-yl)amino)pyridin-4-yl)-2-methylpiperidin-3-yl)carbamate (fourth eluting enantiomer) (145 mg of orange amorphous solid) with a retention time of 14.97 min.

Step 2. N-(4-((trans)-3-amino-2-methyl-1-piperidinyl)-3-pyridinyl)-2-(3-fluoro-2-pyridinyl)imidazo[1,5-b]pyridazin-7-amine (enantiomer 1) (Example 54). tert-Butyl (1-(3-((2-(2,6-difluorophenyl)imidazo[1,5-b]pyridazin-7-yl)amino)pyridin-4-yl)-2-methylpiperidin-3-yl)carbamate (first eluting enantiomer) (53 mg, 0.09 mmol) in 2 mL of DCM was treated with 0.5 mL of TFA and stirred at RT for 1 h. Volatiles were removed under reduced pressure. The residue was treated with 10 mL of 1 N NaOH, and the mixture was extracted with 3×15 mL of EtOAc. The combined organic extracts were washed with 2×5 mL of water followed by 2×5 mL of brine, dried over sodium sulfate and concentrated to give the title compound (39 mg, 96% yield) as an orange amorphous solid. MS (ESI, pos. ion) m/z: 436.1 (M+1). $^1$H NMR (400 MHz, DMSO-$d_6$) δ ppm 9.47 (1 H, s), 8.00-8.17 (2 H, m), 7.63 (1 H, tt, J=8.5, 6.5 Hz), 7.39 (1 H, s), 7.30 (2 H, m), 7.16 (1 H, d, J=5.1 Hz), 6.70 (1 H, d, J=9.4 Hz), 3.37 (3 H, br.), 2.78 (2 H, m), 2.56 (1 H, m), 2.36 (1 H, m), 1.76 (1 H, m), 1.59 (2 H, m), 1.23 (1 H, m), 0.84 (3 H, d, J=6.3 Hz). $^{19}$F NMR (376 MHz, DMSO-$d_6$) δ ppm −113.35. The relative stereochemistry was confirmed by $^1$H-NMR studies.

N-(4-((trans)-3-amino-2-methyl-1-piperidinyl)-3-pyridinyl)-2-(3-fluoro-2-pyridinyl)imidazo[1,5-b]pyridazin-7-amine (enantiomer 2) (Example 55). tert-Butyl (1-(3-((2-(2,6-difluorophenyl)imidazo[1,5-b]pyridazin-7-yl)amino)pyridin-4-yl)-2-methylpiperidin-3-yl)carbamate (second eluting enantiomer) (52 mg, 0.09 mmol) in 2 mL of DCM was treated with 0.5 mL of TFA and stirred at RT for 1 h. Volatiles were removed under reduced pressure. The residue was treated with 10 mL of 1 N NaOH, extracted with 3×15 mL of EtOAc. The combined organic extracts were washed with 2×5 mL of water followed by 2×5 mL of brine, dried over sodium sulfate and concentrated to give the title compound (38 mg, 96% yield) as an orange amorphous solid. MS (ESI, pos. ion) m/z: 436.1 (M+1). $^1$H NMR (400 MHz, DMSO-$d_6$) δ ppm 9.47 (1 H, s), 8.00-8.17 (2 H, m), 7.63 (1 H, tt, J=8.5, 6.5 Hz), 7.39 (1 H, s), 7.30 (2 H, m), 7.16 (1 H, d, J=5.1 Hz), 6.70 (1 H, d, J=9.4 Hz), 3.37 (3 H, br.), 2.78 (2 H, m), 2.56 (1 H, m), 2.36 (1 H, m), 1.76 (1 H, m), 1.59 (2 H, m), 1.23 (1 H, m), 0.84 (3 H, d, J=6.3 Hz). $^{19}$F NMR (376 MHz, DMSO-$d_6$) δ ppm −113.35. The relative stereochemistry was confirmed by $^1$H-NMR studies.

N-(4-((cis)-3-amino-2-methyl-1-piperidinyl)-3-pyridinyl)-2-(3-fluoro-2-pyridinyl)imidazo[1,5-b]pyridazin-7-amine (enantiomer 3) (Example 56). tert-Butyl (1-(3-((2-(2,6-difluorophenyl)imidazo[1,5-b]pyridazin-7-yl)amino)pyridin-4-yl)-2-methylpiperidin-3-yl)carbamate (third eluting enantiomer) (145 mg, 0.27 mmol) in 5 mL of DCM was treated with 1.5 mL of TFA and stirred at RT for 1 h. Volatiles were removed under reduced pressure. The residue was treated with 10 mL of 1 N NaOH, extracted with 3×25 mL of EtOAc. The combined organic layers were washed with 2×5 mL of water followed by 2×5 mL of brine, dried with Na$_2$SO$_4$ and concentrated to give the title compound (109 mg, 92% yield) as an orange amorphous solid. MS (ESI, pos. ion) m/z: 436.1 (M+1). $^1$H NMR (400 MHz, DMSO-$d_6$) δ ppm 9.40 (1 H, s), 8.25 (1 H, br.), 8.09 (2 H, m), 7.65 (1 H, m), 7.43 (1 H, s), 7.33 (2 H, m), 7.13 (1H, d, J=5.3 Hz), 6.74 (1 H, d, J=9.4 Hz), 3.24-3.31 (3 H, m), 3.00 (1 H, m), 2.89 (1 H, m), 2.63 (1 H, m), 1.71 (1 H, m), 1.50 (3 H, m), 0.81 (3 H, d, J=6.3 Hz). $^{19}$F NMR (376 MHz, DMSO-$d_6$) δ ppm −113.39. The relative stereochemistry was confirmed by $^1$H-NMR studies and the absolute stereochemistry was arbitrarily assigned.

N-(4-((cis)-3-amino-2-methyl-1-piperidinyl)-3-pyridinyl)-2-(3-fluoro-2-pyridinyl)imidazo[1,5-b]pyridazin-7-amine (enantiomer 4) (Example 57). tert-Butyl (1-(3-((2-(2,6-difluorophenyl)imidazo[1,5-b]pyridazin-7-yl)amino)pyridin-4-yl)-2-methylpiperidin-3-yl)carbamate (fourth eluting enantiomer) (145 mg, 0.27 mmol) in 5 mL of DCM was treated with 1.5 mL of TFA and stirred at RT for 1 h. Volatiles were removed under reduced pressure. The residue was treated with 10 mL of 1 N NaOH (aq.), extracted with 3×25 mL of EtOAc. The combined organic layers were washed with 2×5 mL of water followed by 2×5 mL of brine, dried with sodium sulfate and concentrated to give the title compound (110 mg, 93% yield) as an orange amorphous solid. MS (ESI, pos. ion) m/z: 436.1 (M+1). $^1$H NMR (400 MHz, DMSO-$d_6$) δ ppm 9.40 (1 H, s), 8.25 (1 H, br.), 8.09 (2 H, m), 7.65 (1 H, m), 7.43 (1 H, s), 7.33 (2 H, m), 7.13 (1 H, d, J=5.3 Hz), 6.74 (1 H, d, J=9.4 Hz), 3.24-3.31 (3 H, m), 3.00 (1 H, m), 2.89 (1 H, m), 2.63 (1 H, m), 1.71 (1 H, m), 1.50 (3 H, m), 0.81 (3 H, d, J=6.3 Hz). $^{19}$F NMR (376 MHz, DMSO-$d_6$) δ ppm −113.39. The relative stereochemistry was confirmed by $^1$H-NMR studies.

Example 58

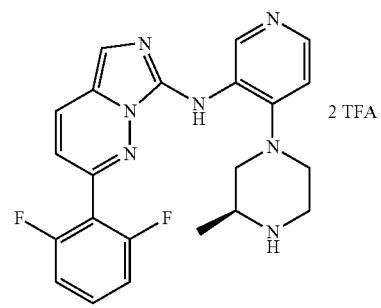 [SMILES: C[C@H]1CN(c2ccncc2Nc2ncc3ccc(-c4c(F)cccc4F)nn23)CCN1]

(S)-2-(2,6-difluorophenyl)-N-(4-(3-methylpiperazin-1-yl)pyridin-3-yl)imidazo[1,5-b]pyridazin-7-amine bis(2,2,2-trifluoroacetate)

The title compound was prepared and isolated as a tan amorphous solid from 3-(azidomethyl)-6-(2,6-difluorophenyl)pyridazine (Preparation I) and (S)-tert-butyl 4-(3-isothiocyanatopyridin-4-yl)-2-methylpiperazine-1-carboxylate (Preparation XLIII) following an analogous procedure to Example 2. MS (ESI, pos. ion) m/z: 422.0 (M+1). $^1$H NMR (400 MHz, MeOH-d4) δ ppm 9.09 (s, 1 H), 8.32 (d, J=6.7 Hz, 1 H), 8.08 (d, J=9.6 Hz, 1 H), 7.55-7.65 (m, 1 H), 7.53 (d, J=6.5 Hz, 1 H), 7.45 (s, 1 H), 7.20 (t, J=8.3 Hz, 2 H), 6.78 (d, J=9.6 Hz, 1 H), 4.03-4.16 (m, 2 H), 3.48 (d, J=12.7 Hz, 1 H), 3.32-3.41 (m, 2 H), 3.15-3.26 (m, 1 H), 3.02-3.12 (m, 1 H), 1.27 (d, J=6.7 Hz, 3 H). $^{19}$F NMR (376 MHz, MeOH-d4) δ ppm −77.09 (br. s., 6 F), −115.28 (s, 2 F).

Example 59

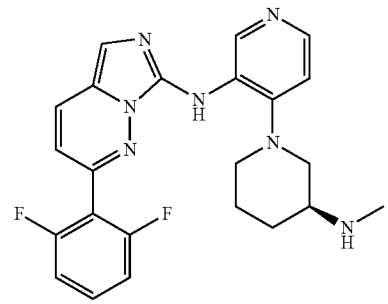 [SMILES: CN[C@H]1CCCN(c2ccncc2Nc2ncc3ccc(-c4c(F)cccc4F)nn23)C1]

(S)-2-(2,6-difluorophenyl)-N-(4-(3-(methylamino)
piperidin-1-yl)pyridin-3-yl)imidazo[1,5-b]pyridazin-
7-amine The title compound was prepared and isolated as a bright orange amorphous solid from 3-(azidomethyl)-6-(2,6-difluorophenyl)pyridazine (Preparation I) and (S)-tert-butyl (1-(3-isothiocyanatopyridin-4-yl)piperidin-3-yl)(methyl)carbamate ((Preparation XLIV) following an analogous procedure to Example 2. MS (ESI, pos. ion) m/z: 436.1 (M+1). $^1$H NMR (400 MHz, MeOH-d4) δ ppm 9.19 (s, 1 H), 8.11 (d, J=5.5 Hz, 1 H), 7.99 (d, J=9.6 Hz, 1 H), 7.58 (tt, J=8.5, 6.4 Hz, 1 H), 7.35 (s, 1 H), 7.10-7.24 (m, 3 H), 6.67 (d, J=9.4 Hz, 1 H), 3.42 (d, J=8.2 Hz, 1 H), 3.08-3.18 (m, 1 H), 2.80-2.91 (m, 1 H), 2.64-2.74 (m, 1 H), 2.55-2.63 (m, 1 H), 2.25 (s, 3 H), 1.90-2.01 (m, 1 H), 1.75-1.86 (m, 1H), 1.58-1.73 (m, 1 H), 1.29-1.39 (m, 1 H). $^{19}$F NMR (377 MHz, MeOH-d4) δ ppm −115.01 (s, 2 F).

Example 60 and 61

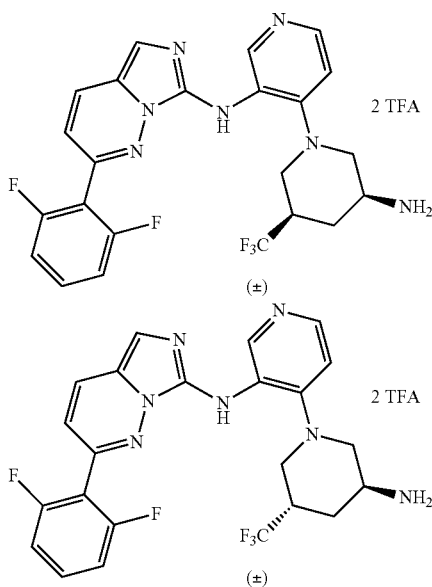

rac-N-(4-((cis)-3-amino-5-(trifluoromethyl)piperi-
din-1-yl)pyridin-3-yl)-2-(2,6-difluorophenyl)imidazo
[1,5-b]pyridazin-7-amine bis(2,2,2-trifluoroacetate)
and rac-N-(4-((trans)-3-amino-5-(trifluoromethyl)
piperidin-1-yl)pyridin-3-yl)-2-(2,6-difluorophenyl)
imidazo[1,5-b]pyridazin-7-amine bis(2,2,2-trifluoro-
acetate)

The title compounds were prepared from 3-(azidomethyl)-6-(2,6-difluorophenyl)pyridazine (Preparation I) and rac-tert-butyl (1-(3-isothiocyanatopyridin-4-yl)-5-(trifluoromethyl)piperidin-3-yl)carbamate (Preparation XLV) following an analogous procedure to Example 2 steps 1 and 2. The diasteromers were separated by silica gel chromatography (0-10% MeOH in DCM) followed by purification by preparatory HPLC performed on a Gilson GX-281 equipped with a SiliaChrom XT C18 column with UV detection at 254 nm eluting with 20-95% CH$_3$CN in water with 0.1% TFA for 11 min at 45 mL/min to afford rac-tert-butyl ((cis)-1-(3-((2-(2, 6-difluorophenyl)imidazo[1,5-b]pyridazin-7-yl)amino)pyridin-4-yl)-5-(trifluoromethyl)piperidin-3-yl)carbamate 2,2,2-trifluoroacetate (34 mg, 0.048 mmol, 26%) as a yellow solid. MS (ESI, pos. ion) m/z: 590.2 (M+1); and rac-tert-butyl ((trans)-1-(3-((2-(2,6-difluorophenyl)imidazo[1,5-b]pyridazin-7-yl)amino)pyridin-4-yl)-5-(trifluoromethyl)piperidin-3-yl)carbamate 2,2,2-trifluoroacetate (44 mg, 0.062 mmol, 34%) as a yellow solid. MS (ESI, pos. ion) m/z: 590.2 (M+1).

Step 2. rac-N-(4-((cis)-3-amino-5-(trifluoromethyl)piperidin-1-yl)pyridin-3-yl)-2-(2,6-difluorophenyl)imidazo[1,5-b]pyridazin-7-amine bis(2,2,2-trifluoroacetate), Example 60. The title compound was prepared and isolated as a bright yellow amorphous solid from and rac-tert-butyl ((cis)-1-(3-((2-(2,6-difluorophenyl)imidazo[1,5-b]pyridazin-7-yl)amino)pyridin-4-yl)-5-(trifluoromethyl)piperidin-3-yl)carbamate 2,2,2-trifluoroacetate following an analogous procedure to Example 2 step 3. MS (ESI, pos. ion) m/z: 490.2 (M+1). $^1$H NMR (400 MHz, MeOH-d4) δ ppm 9.03 (1 H, s), 8.35 (1 H, d, J=6.7 Hz), 8.09 (1 H, d, J=9.4 Hz), 7.57-7.65 (1 H, m), 7.52-7.57 (1 H, m), 7.44 (1 H, s), 7.18 (2 H, t, J=8.3 Hz), 6.79 (1H, d, J=9.6 Hz), 4.10-4.22 (2 H, m), 3.44-3.55 (2 H, m), 2.86-3.04 (2 H, m), 2.60 (1H, br. s.), 2.40 (1 H, d, J=12.5 Hz), 1.67 (1 H, q, J=12.3 Hz). $^{19}$F NMR (377 MHz, MeOH-d4) δ ppm −73.9 (3 F, s), −115.38 (2 F, s).

rac-N-(4-((trans)-3-amino-5-(trifluoromethyl)piperidin-1-yl)pyridin-3-yl)-2-(2,6-difluorophenyl)imidazo[1,5-b]pyridazin-7-amine bis(2,2,2-trifluoroacetate), Example 61. The title compound was prepared and isolated as a bright orange amorphous solid from 3-(azidomethyl)-6-(2,6-difluorophenyl)pyridazine and rac-tert-butyl ((trans)-1-(3-((2-(2,6-difluorophenyl)imidazo[1,5-b]pyridazin-7-yl)amino)pyridin-4-yl)-5-(trifluoromethyl)piperidin-3-yl)carbamate 2,2,2-trifluoroacetate following an analogous procedure to Example 2. MS (ESI, pos. ion) m/z: 490.2 (M+1). $^1$H NMR (400 MHz, MeOH-d4) δ ppm 9.18 (1 H, s), 8.39 (1 H, dd, J=6.7, 1.0 Hz), 8.07-8.14 (1 H, m), 7.55-7.67 (2 H, m), 7.46 (1 H, s), 7.20 (2 H, t, J=8.2 Hz), 6.80 (1 H, d, J=9.6 Hz), 4.10-4.20 (1 H, m), 3.92 (1 H, d, J=3.7 Hz), 3.73 (1 H, d, J=13.5 Hz), 3.63 (1 H, dd, J=13.2, 2.6 Hz), 3.09-3.19 (1 H, m), 2.66-2.82 (1 H, m), 2.13-2.29 (2 H, m). $^{19}$F NMR (377 MHz, MeOH-d4) δ ppm −73.18 (3 F, s), −115.27 (2 F, s).

Example 62

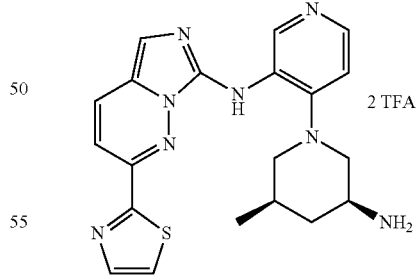

N-(4-((3S,5R)-3-amino-5-methylpiperidin-1-yl)pyridin-3-yl)-2-(thiazol-2-yl)imidazo[1,5-b]pyridazin-7-amine bis(2,2,2-trifluoroacetate)

The title compound was prepared and isolated as a tan amorphous solid from 2-(6-azidomethyl)pyridazin-3-yl)thiazole (Preparation II) and tert-butyl ((cis)-1-(3-isothiocyanatopyridin-4-yl)-5-methylpiperidin-3-yl)carbamate (Preparation XXVIII, enantiomer 1) following an analogous procedure to Example 2. MS (ESI, pos. ion) m/z: 407.0 (M+1). ¹H NMR (400 MHz, DMSO-d₆) δ ppm 8.73 (1 H, s), 8.62 (1 H, br. s.), 8.15 (1 H, d, J=6.5 Hz), 7.99 (1 H, d, J=9.6 Hz), 7.87 (1 H, d, J=3.1 Hz), 7.79 (4 H, d, J=3.1 Hz), 7.18-7.26 (2 H, m), 7.13 (1 H, d, J=9.6 Hz), 3.73-3.86 (4 H, m), 3.60 (3 H, d, J=12.3 Hz), 3.00 (1 H, br. s.), 2.55 (1 H, t, J=11.3 Hz), 2.18-2.25 (1 H, m), 1.84 (1 H, d, J=12.1 Hz), 1.41 (1 H, br. s.), 0.92 (1 H, q, J=12.2 Hz), 0.63 (3 H, d, J=6.5 Hz).

Example 63

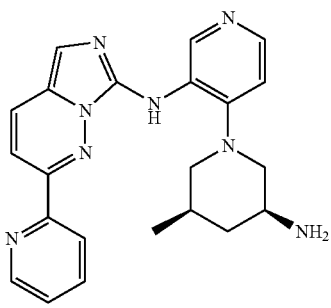 [SMILES: C[C@@H]1C[C@H](N)CN(c2ccncc2Nc2ncc3ccc(-c4ccccn4)nn23)C1]

N-(4-((cis)-3-amino-5-methylpiperidin-1-yl)pyridin-3-yl)-2-(pyridin-2-yl)imidazo[1,5-b]pyridazin-7-amine The title compound was prepared and isolated as a bright orange amorphous solid from 3-(azidomethyl)-6-(pyridin-2-yl)pyridazine (Preparation XXIX) and tert-butyl ((cis)-1-(3-isothiocyanatopyridin-4-yl)-5-methylpiperidin-3-yl)carbamate (Preparation XXXVIII, enantiomer 1) following an analogous procedure to Example 2. MS (ESI, pos. ion) m/z: 401.1 (M+1). ¹H NMR (400 MHz, MeOH-d4) δ ppm 9.17 (1 H, s), 8.74 (1 H, d, J=4.5 Hz), 8.29 (1 H, d, J=8.0 Hz), 8.15 (1 H, d, J=5.5 Hz), 7.95-8.07 (2 H, m), 7.50-7.58 (2 H, m), 7.33 (1 H, s), 7.17 (1 H, d, J=5.5 Hz), 3.43-3.52 (1 H, m), 2.88-3.01 (1H, m), 2.40 (1 H, t, J=10.8 Hz), 2.27 (1 H, t, J=11.2 Hz), 2.05 (1 H, d, J=12.5 Hz), 1.83 (1 H, br. s.), 0.87-0.99 (4 H, m).

Example 64

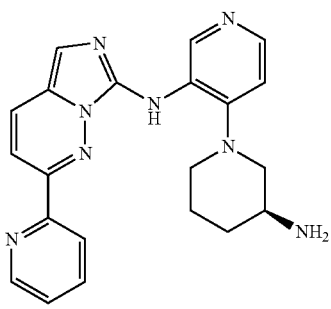 [SMILES: N[C@H]1CCCN(c2ccncc2Nc2ncc3ccc(-c4ccccn4)nn23)C1]

Example 65

(S)-N-(4-(3-aminopiperidin-1-yl)pyridin-3-yl)-2-(pyridin-2-yl)imidazo[1,5-b]pyridazin-7-amine The title compound was prepared and isolated as a bright orange amorphous solid from 3-(azidomethyl)-6-(pyridin-2-yl)pyridazine (Preparation XXIX) and (S)-tert-butyl (1-(3-isothiocyanatopyridin-4-yl)piperidin-3-yl)carbamate (Preparation XI) following an analogous procedure to Example 2. MS (ESI, pos. ion) m/z: 387.0 (M+1). ¹H NMR (400 MHz, MeOH-d4 δ ppm 9.15 (1 H, s), 8.73 (1 H, d, J=4.7 Hz), 8.29 (1 H, d, J=8.0 Hz), 8.14 (1 H, d, J=5.5 Hz), 7.95-8.05 (2 H, m), 7.48-7.58 (2 H, m), 7.32 (1 H, s), 7.16 (1H, d, J=5.5 Hz), 3.34-3.41 (2 H, m), 3.12-3.23 (1 H, m), 2.92-3.03 (1 H, m), 2.84 (1H, t, J=11.8 Hz), 2.54-2.66 (1 H, m), 2.00 (1 H, dd, J=13.1, 4.3 Hz), 1.82-1.92 (1 H, m), 1.65-1.79 (1 H, m), 1.28-1.42 (1 H, m).

Example 65

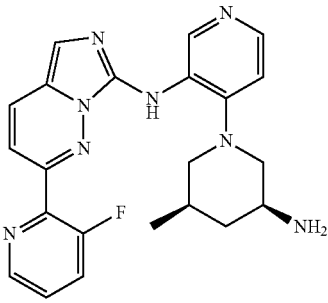 [SMILES: C[C@@H]1C[C@H](N)CN(c2ccncc2Nc2ncc3ccc(-c4ncccc4F)nn23)C1]

N-(4-((cis)-3-amino-5-methylpiperidin-1-yl)pyridin-3-yl)-2-(3-fluoropyridin-2-yl)imidazo[1,5-b]pyridazin-7-amine The title compound was prepared and isolated as a bright orange amorphous solid from 3-(azidomethyl)-6-(3-fluoropyridin-2-yl)pyridazine (Preparation XXVIII) and 3-(azidomethyl)-6-(pyridin-2-yl)pyridazine and tert-butyl ((cis)-1-(3-isothiocyanatopyridin-4-yl)-5-methylpiperidin-3-yl)carbamate (Preparation XXXVIII, enantiomer 1) following an analogous procedure to Example 2. MS (ESI, pos. ion) m/z: 419.0 (M+1). ¹H NMR (400 MHz, MeOH-d4) δ ppm 9.36 (1 H, s), 8.62 (1 H, dt, J=4.5, 1.4 Hz), 8.15 (1 H, d, J=5.3 Hz), 8.05 (1 H, d, J=9.6 Hz), 7.86 (1 H, ddd, J=11.1, 8.4, 1.3 Hz), 7.64 (1 H, dt, J=8.7, 4.1 Hz), 7.36 (1 H, s), 7.29 (1 H, d, J=9.8 Hz), 7.19 (1 H, d, J=5.3 Hz), 3.40-3.46 (1 H, m), 3.23-3.30 (1 H, m), 3.01-3.11 (1 H, m), 2.41 (1 H, t, J=10.8 Hz), 2.30 (1 H, t, J=11.2 Hz), 2.07 (1 H, d, J=12.5 Hz), 1.87-2.03 (1 H, m), 0.94-1.00 (1 H, m), 0.87-0.94 (3 H, m). ¹⁹F NMR (377 MHz, MeOH-d4) δ ppm −120.62 (1 F, s).

Example 66

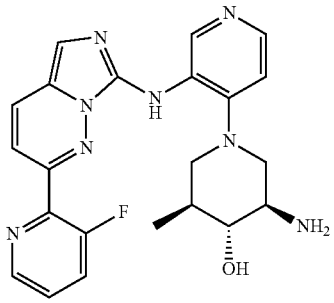 [SMILES: C[C@H]1CN(c2ccncc2Nc2ncc3ccc(-c4ncccc4F)nn23)C[C@@H](N)[C@@H]1O]

(3R,4R,5S)-3-amino-1-(3-((2-(3-fluoropyridin-2-yl)imidazo[1,5-b]pyridazin-7-yl)amino)pyridin-4-yl)-5-methylpiperidin-4-ol The title compound was prepared and isolated as an orange amorphous solid from 3-(azidomethyl)-6-(3-fluoropyridin-2-yl)pyridazine (Preparation XXVIII) and tert-butyl ((3R,4R,5S)-4-((tert-butyldimethylsilyl)oxy)-1-(3-isothiocyanatopyridin-4-yl)-5-methylpiperidin-3-yl)carbamate (Preparation XIII) following an analogous procedure to Example 20. MS (ESI, pos. ion) m/z: 435.0 (M+1). $^1$H NMR (400 MHz, MeOH-d4) δ ppm 9.29 (1 H, s), 8.60 (1 H, d, J=4.7 Hz), 8.12 (1 H, d, J=5.3 Hz), 8.03 (1 H, d, J=9.8 Hz), 7.81-7.90 (1 H, m), 7.61 (1 H, dt, J=8.5, 4.2 Hz), 7.34 (1 H, s), 7.26 (1 H, d, J=9.6 Hz), 7.17 (1 H, d, J=5.5 Hz), 3.41-3.52 (1 H, m), 2.86-2.98 (2 H, m), 2.59 (1 H, t, J=10.8 Hz), 2.51 (1 H, t, J=11.6 Hz), 1.90 (1 H, s), 1.77-1.89 (1 H, m), 0.97 (3 H, d, J=6.7 Hz). $^{19}$F NMR (377 MHz, MeOH-d4) δ ppm −120.32 (1 F, s).

Examples 67 and 68

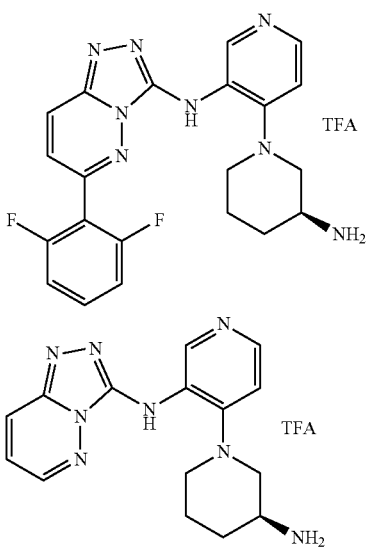

(S)-N-(4-(3-aminopiperidin-1-yl)pyridin-3-yl)-6-(2,6-difluorophenyl)-[1,2,4]triazolo[4,3-b]pyridazin-3-amine 2,2,2-trifluoroacetate and (S)-N-(4-(3-aminopiperidin-1-yl)pyridin-3-yl)-[1,2,4]triazolo[4,3-a]pyridin-3-amine 2,2,2-trifluoroacetate Step 1. (S)-tert-butyl (1-(3-((6-chloro-[1,2,4]triazolo[4,3-b]pyridazin-3-yl)amino)pyridin-4-yl)piperidin-3-yl)carbamate. A glass microwave reaction vessel was charged with (S)-tert-butyl (1-(3-isothiocyanatopyridin-4-yl)piperidin-3-yl)carbamate (400 mg, 1.20 mmol, Preparation XI) and 3-chloro-6-hydrazinopyridazine (173 mg, 1.2 mmol, Sigma-Aldrich) in acetonitrile (8 mL). The reaction mixture was stirred and heated at 90° C. for 1 h. DCC (271 mg, 1.32 mmol) was added and the reaction was stirred at 90° C. for another 3 h. The mixture was cooled to RT and diluted with water. The aqueous layer was extracted with CH$_2$Cl$_2$ (3×). The combined organic layers were dried (MgSO$_4$), filtered and concentrated. The residue was purified by silica gel chromatography (3-5% MeOH in CH$_2$Cl$_2$) to give (S)-tert-butyl (1-(3-((6-chloro-[1,2,4]triazolo[4,3-b]pyridazin-3-yl)amino)pyridin-4-yl)piperidin-3-yl)carbamate (520 mg, 1.17 mmol, 98% yield) as an orange solid. MS (ESI, pos. ion) m/z: 445.1 (M+1). $^1$H NMR (400 MHz, CDCl$_3$) δ ppm 9.65 (1 H, s), 8.31 (1 H, d, J=5.3 Hz), 7.98 (1 H, d, J=9.6 Hz), 7.67 (1 H, br. s.), 6.98-7.06 (2 H, m), 4.67 (1 H, br. s.), 3.92 (1 H, br. s.), 3.38-3.50 (1 H, m), 3.10 (1 H, d, J=11.3 Hz), 2.65-2.82 (2 H, m), 2.05-2.12 (1 H, m), 1.93 (2 H, qt, J=9.0, 4.5 Hz), 1.39 (9 H, s).

Step 2. (S)-N-(4-(3-aminopiperidin-1-yl)pyridin-3-yl)-6-(2,6-difluorophenyl)-[1,2,4]triazolo[4,3-b]pyridazin-3-amine 2,2,2-trifluoroacetate (Example 67) and (S)-N-(4-(3-aminopiperidin-1-yl)pyridin-3-yl)-[1,2,4]triazolo[4,3-a]pyridin-3-amine 2,2,2-trifluoroacetate (Example 68). A glass microwave reaction vessel was charged with (S)-tert-butyl (1-(3-((6-chloro-[1,2,4]triazolo[4,3-b]pyridazin-3-yl)amino)pyridin-4-yl)piperidin-3-yl)carbamate (175 mg, 0.39 mmol) and 2,6-difluorophenylzinc bromide (0.5 M in THF, 2.36 mL, 1.18 mmol, Rieke Metals, Inc.) followed by A-Phos (14 mg, 0.020 mmol, Sigma-Aldrich). The reaction mixture was stirred and heated at 90° C. for 2 h. The mixture was cooled to RT and quenched with EDTA solution (pH 7.4) and extracted with CHCl$_3$/i-PrOH (4/1). The combined organic layers were dried over MgSO$_4$, filtered and concentrated to give (S)-tert-butyl (1-(3-((6-(2,6-difluorophenyl)-[1,2,4]triazolo[4,3-b]pyridazin-3-yl)amino)pyridin-4-yl)piperidin-3-yl)carbamate (206 mg), which was used in the next reaction without further purification. A mixture of (S)-tert-butyl (1-(3-((6-(2,6-difluorophenyl)-[1,2,4]triazolo[4,3-b]pyridazin-3-yl)amino)pyridin-4-yl)piperidin-3-yl)carbamate (206 mg, 0.39 mmol) and TFA (0.2 mL, 2.69 mmol) in DCM (1 mL) was stirred for 15 min at RT. The mixture was concentrated and the residue was purified with prep HPLC (5-30% MeCN in water with 0.1% TFA for 30 min) using Phenomenex Gemini C$_{18}$ column (100×50 mm, 10 μm) at 90 mL/min. with UV detection at 254 nm to give (S)-N-(4-(3-aminopiperidin-1-yl)pyridin-3-yl)-6-(2,6-difluorophenyl)-[1,2,4]triazolo[4,3-b]pyridazin-3-amine 2,2,2-trifluoroacetate (70 mg, 0.13 mmol, 33% yield, Example 67) as a yellow solid. MS (ESI, pos. ion) m/z: 422.9 (M+1). $^1$H NMR (400 MHz, DMSO-d$_6$) δ ppm 9.24 (1 H, br. s.), 8.84 (1 H, s), 8.45 (1 H, d, J=9.6 Hz), 8.39 (1 H, d, J=6.5 Hz), 8.02 (3 H, br. s.), 7.67-7.77 (1 H, m), 7.53 (1 H, d, J=9.8 Hz), 7.33-7.44 (3 H, m), 3.82 (1 H, d, J=12.5 Hz), 3.30-3.38 (3 H, m), 3.21 (1 H, dd, J=11.8, 6.9 Hz), 1.93 (1 H, dd, J=8.2, 4.1 Hz), 1.73-1.85 (1 H, m), 1.61-1.71 (1 H, m), 1.41-1.53 (1 H, m). $^{19}$F NMR (376 MHz, DMSO-d$_6$) δ ppm −74.04, −113.49; and (S)-N-(4-(3-aminopiperidin-1-yl)pyridin-3-yl)-[1,2,4]triazolo[4,3-a]pyridin-3-amine 2,2,2-trifluoroacetate (27 mg, 0.09 mmol, Example 68) as a light yellow solid. MS (ESI, pos. ion) m/z: 311.1 (M+1). ¹H NMR (400 MHz, DMSO-d₆) δ ppm 9.22 (1 H, s), 8.36 (1 H, d, J=6.5 Hz), 8.09 (3 H, br. s.), 7.43 (1 H, d, J=6.5 Hz), 7.24 (1 H, d, J=11.7 Hz), 5.92-6.13 (1 H, m), 3.76 (1 H, d, J=12.5 Hz), 3.43-3.59 (1 H, m), 2.99-3.30 (3 H, m), 1.88-2.04 (2 H, m), 1.54-1.78 (2 H, m).

Example 69

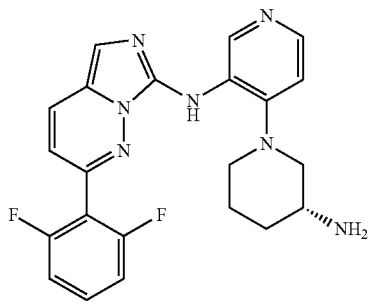 [SMILES: N[C@@H]1CCCN(c2ccncc2Nc2ncc3ccc(-c4c(F)cccc4F)nn23)C1]

(R)-N-(4-(3-aminopiperidin-1-yl)pyridin-3-yl)-2-(2,6-difluorophenyl)imidazo[1,5-b]pyridazin-7-amine The title compound was prepared and isolated as a bright orange amorphous solid from 3-(azidomethyl)-6-(2,6-difluorophenyl)pyridazine (Preparation I) and (R)-tert-butyl (1-(3-isothiocyanatopyridin-4-yl)piperidin-3-yl)carbamate (Preparation XLVI) following an analogous procedure to Example 2. MS (ESI, pos. ion) m/z: 422.0 (M+1). ¹H NMR (400 MHz, CDCl₃) δ ppm 9.70 (1 H, s), 8.22 (1 H, d, J=5.3 Hz), 7.76 (1 H, d, J=9.4 Hz), 7.41-7.48 (1 H, m), 7.36 (1 H, s), 7.07 (2 H, t, J=8.0 Hz), 6.95 (1 H, d, J=5.3 Hz), 6.52 (1 H, d, J=9.4 Hz), 3.17 (1 H, d, J=12.3 Hz), 3.02-3.11 (2 H, m), 2.73 (1 H, t, J=9.4 Hz), 2.56 (1 H, t, J=9.7 Hz), 1.75-1.97 (4 H, m), 1.23-1.35 (2 H, m). ¹⁹F NMR (377 MHz, CDCl₃) δ ppm −112.71 (2 F, s).

Example 70

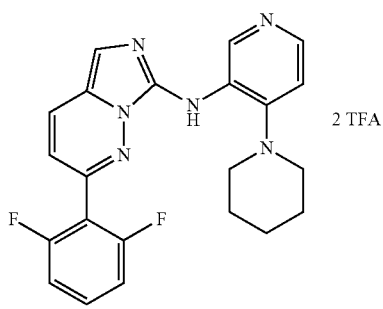 [SMILES: Fc1cccc(F)c1-c1ccc2cnc(Nc3cnccc3N3CCCCC3)n2n1]

2-(2,6-difluorophenyl)-N-(4-(piperidin-1-yl)pyridin-3-yl)imidazo[1,5-b]pyridazin-7-amine bis(2,2,2-trifluoroacetate)

The title compound was prepared and isolated as a bright orange foam from 3-(azidomethyl)-6-(2,6-difluorophenyl)pyridazine (Preparation I) and (3-isothiocyanato-4-(piperidin-1-yl)pyridine (Preparation XLVII) following an analogous procedure to Example 2. MS (ESI, pos. ion) m/z: 407.0 (M+1). ¹H NMR (400 MHz, CDCl₃) δ ppm 9.48 (1 H, s), 8.35 (1 H, d, J=6.5 Hz), 7.85 (1 H, d, J=9.6 Hz), 7.43-7.54 (1 H, m), 7.39 (1 H, s), 7.15 (1 H, d, J=6.5 Hz), 7.06 (2 H, t, J=8.2 Hz), 6.70 (1 H, d, J=9.6 Hz), 3.24-3.36 (4 H, m), 1.78 (4 H, br. s.), 1.69 (2 H, d, J=4.7 Hz). ¹⁹F NMR (376 MHz, CDCl₃) δ ppm −112.70 (1 F, s).

Example 71

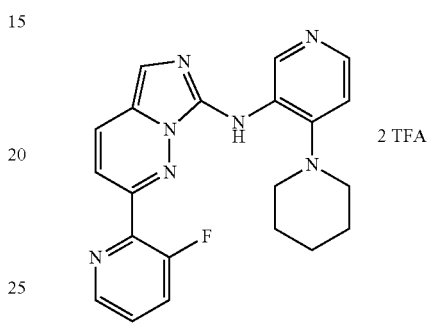

2-(3-Fluoropyridin-2-yl)-N-(4-(piperidin-1-yl)pyridin-3-yl)imidazo[1,5-b]pyridazin-7-amine bis(2,2,2-trifluoroacetate)

The title compound was prepared and isolated as an orange amorphous solid from 3-(azidomethyl)-6-(3-fluoropyridin-2-yl)pyridazine (Preparation XXVIII) and (3-isothiocyanato-4-(piperidin-1-yl)pyridine (Preparation XLVII) following an analogous procedure to Example 2. MS (ESI, pos. ion) m/z: 390.0 (M+1). ¹H NMR (400 MHz, MeOH-d4) δ ppm 9.04 (s, 1 H), 8.61 (d, J=4.5 Hz, 1 H), 8.19 (d, J=6.8 Hz, 1 H), 8.07 (d, J=9.6 Hz, 1 H), 7.79-7.88 (m, 1 H), 7.63 (dt, J=8.4, 4.2 Hz, 1 H), 7.36-7.43 (m, 2 H), 7.31 (d, J=9.8 Hz, 1 H), 3.48 (br. s., 4 H), 1.67 (br. s., 6 H). ¹⁹F NMR (377 MHz, MeOH-d4) δ ppm −121.01 (s, 1 F).

Example 72

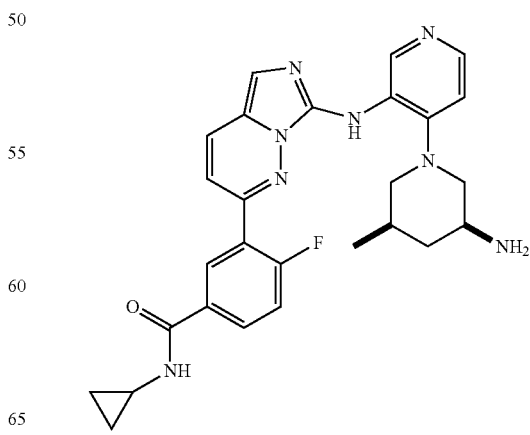

3-(7-((4-((3S,5R)-3-amino-5-methyl-1-piperidinyl)-3-pyridinyl)amino)imidazo[1,5-b]pyridazin-2-yl)-N-cyclopropyl-4-fluorobenzamide The title compound was prepared and isolated as an orange amorphous solid from 3-(6-(azidomethyl)pyridazin-3-yl)-N-cyclopropyl-4-fluorobenzamide (Preparation XXX) and tert-butyl ((cis)-1-(3-isothiocyanatopyridin-4-yl)-5-methylpiperidin-3-yl)carbamate (Preparation XXXVIII, enantiomer 1) following an analogous procedure to Example 2. MS (ESI, pos. ion) m/z: 501.4 (M+1). $^1$H NMR (400 MHz, DMSO-$d_6$) δ ppm 9.51 (1 H, s), 8.68 (1 H, d, J=4.1 Hz), 8.36 (1 H, dd, J=7.3, 2.2 Hz), 8.15 (2 H, m), 8.06 (1 H, m), 7.89 (1 H, br.), 7.53 (1 H, dd, J=10.7, 8.7 Hz), 7.43 (1 H, s), 7.10 (1 H, d, J=5.1 Hz), 6.94 (1 H, dd, J=9.5, 2.6 Hz), 3.20 (1 H, m), 3.10 (1 H, m), 2.90 (2 H, tt, J=7.4, 3.9 Hz), 2.21 (2 H, m), 1.84 (2 H, m), 1.53 (2 H, br.), 0.75 (6 H, m), 0.62 (2 H, m). $^{19}$F NMR (376 MHz, DMSO-$d_6$) δ ppm −112.33.

Example 73

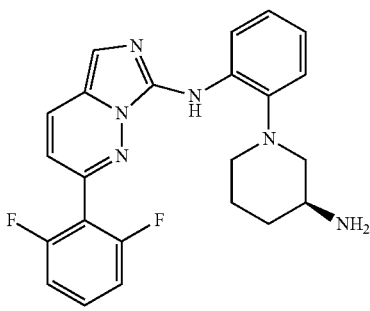 [SMILES: N[C@H]1CCCN(c2ccccc2Nc2ncc3ccc(-c4c(F)cccc4F)nn23)C1]

(S)-N-(2-(3-aminopiperidin-1-yl)phenyl)-2-(2,6-difluorophenyl)imidazo[1,5-b]pyridazin-7-amine The title compound was prepared and isolated as an orange solid from 3-(azidomethyl)-6-(2,6-difluorophenyl)pyridazine (Preparation I) and (S)-tert-butyl (1-(2-isothiocyanatophenyl)piperidin-3-yl)carbamate (Preparation XLVIII) following an analogous procedure to Example 20. MS (ESI, pos. ion) m/z: 421.1 (M+1). $^1$H NMR (400 MHz, CDCl$_3$) δ ppm 8.64 (s, 1 H), 8.49 (d, J=8.02 Hz, 1 H), 7.73 (d, J=9.39 Hz, 1H), 7.38-7.50 (m, 1 H), 7.33 (s, 1 H), 7.16-7.23 (m, 1 H), 7.13 (d, J=7.83 Hz, 1 H), 7.01-7.10 (m, 2 H), 6.92 (tt, J=7.63, 0.78 Hz, 1 H), 6.48 (dt, J=9.39, 1.66 Hz, 1 H), 3.00-3.14 (m, 2 H), 1.79-1.92 (m, 2 H), 1.70-1.78 (m, 1 H), 1.51 (br s, 4 H). $^{19}$F NMR (376 MHz, CDCl$_3$) δ ppm −112.63.

Example 74

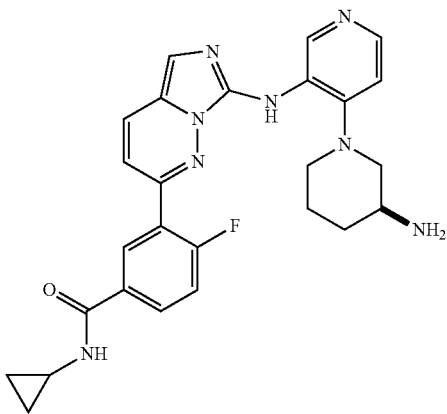 [SMILES: N[C@H]1CCCN(c2ccncc2Nc2ncc3ccc(-c4cc(C(=O)NC5CC5)ccc4F)nn23)C1]

3-(7-((4-((3S)-3-amino-1-piperidinyl)-3-pyridinyl)amino)imidazo[1,5-b]pyridazin-2-yl)-N-cyclopropyl-4-fluorobenzamide The title compound was prepared and isolated as an orange amorphous solid from 3-(6-(azidomethyl)pyridazin-3-yl)-N-cyclopropyl-4-fluorobenzamide (Preparation XXX) and tert-butyl ((3S)-1-(3-isothiocyanato-4-pyridinyl)-3-piperidinyl)carbamate (Preparation XI) following an analogous procedure to Example 2. MS (ESI, pos. ion) m/z: 487.3 (M+1). $^1$H NMR (400 MHz, DMSO-$d_6$) δ ppm 9.43 (1 H, s), 8.74 (1 H, d, J=4.1 Hz), 8.36 (2 H, m), 8.14 (2 H, br.), 8.05 (1 H, m), 7.52 (1 H, m), 7.44 (1 H, s.), 7.11 (1 H, m), 6.95 (1 H, m), 3.20 (3 H, m), 3.08 (2 H, m), 2.97 (1 H, m), 2.88 (3 H, m), 1.91 (1 H, m), 1.81 (2 H, m.), 1.64 (1 H, m), 1.35 (1 H, m), 0.73 (2 H, m), 0.59 (2 H, m). $^{19}$F NMR (376 MHz, DMSO-$d_6$) δ ppm −112.21.

Example 75 and 76

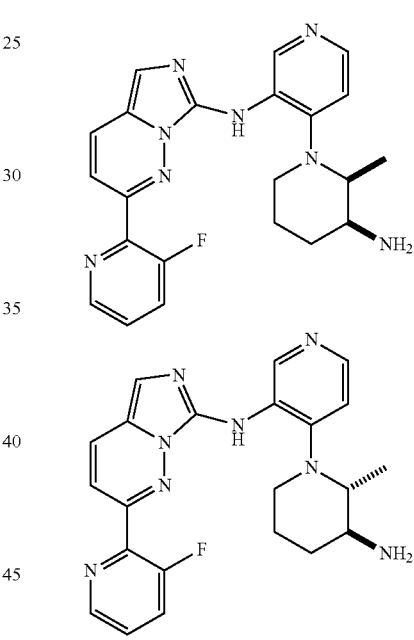

Step 1. tert-butyl ((2S,3S)-1-(3-((2-(3-fluoropyridin-2-yl)imidazo[1,5-b]pyridazin-7-yl)amino)pyridin-4-yl)-2-methylpiperidin-3-yl)carbamate (first eluting diastereomer) and tert-butyl ((2R,3S)-1-(3-((2-(3-fluoropyridin-2-yl)imidazo[1,5-b]pyridazin-7-yl)amino)pyridin-4-yl)-2-methylpiperidin-3-yl)carbamate (second eluting diastereomer). PMe$_3$ (0.86 mL of 1.0 M solution in THF, 0.86 mmol) was added drop wise to a solution of 3-(azidomethyl)-6-(3-fluoropyridin-2-yl)pyridazine (Preparation XXVIII, 190 mg, 0.82 mmol) in THF (2 mL) at RT. After the reaction mixture stirred for 15 min at RT, it was treated with a suspension of tert-butyl ((3S)-1-(3-isothiocyanatopyridin-4-yl)-2-methylpiperidin-3-yl)carbamate (Preparation XLIX, 288 mg, 0.82 mmol) in THF (2.5 mL) at RT. The resulting mixture was stirred at RT for 15 min; then concentrated to half of its volume. The solution purified by silica gel chromatography (50-100% EtOAc in hexanes followed by 1-3% MeOH in EtOAc) to provide tert-butyl ((3S)-1-(3-((2-(3-fluoropyridin-2-yl)imidazo[1,5-b]pyridazin-7-yl)amino)pyridin-4-yl)-2-methylpiperidin-3-yl)carbamate as an orange amorphous solid. MS (ESI, pos. ion) m/z: 519.1 (M+1). LCMS indicated the presence of 2 peaks with the same mass at about 1:3 ratio. The above obtained orange amorphous solid was dissolved in 10 mL of DMSO and purified on a preparative reverse-phase HPLC (using Prep HPLC method 3) to provide tert-butyl ((2S,3S)-1-(3-((2-(3-fluoropyridin-2-yl)imidazo[1,5-b]pyridazin-7-yl)amino)pyridin-4-yl)-2-methylpiperidin-3-yl)carbamate (first eluting diastereomer) and tert-butyl ((2R,3S)-1-(3-((2-(3-fluoropyridin-2-yl)imidazo[1,5-b]pyridazin-7-yl)amino)pyridin-4-yl)-2-methylpiperidin-3-yl)carbamate (second eluting diastereomer).

Step 2. N-(4-((2S,3S)-3-amino-2-methyl-1-piperidinyl)-3-pyridinyl)-2-(3-fluoro-2-pyridinyl)imidazo[1,5-t]pyridazin-7-amine (Example 75). The above obtained tert-butyl ((2S,3S)-1-(3-((2-(3-fluoropyridin-2-yl)imidazo[1,5-b]pyridazin-7-yl)amino)pyridin-4-yl)-2-methylpiperidin-3-yl)carbamate (first eluting diastereomer) in 2 mL of DCM at RT was treated with 0.5 mL of TFA and the mixture was stirred for 1 h at RT. It was concentrated under reduced pressure. The orange residue was partitioned between 5 mL of 1 N NaOH and 35 mL of EtOAc. The organic layer was separated, washed with 5 mL of brine, dried over sodium sulfate and concentrated to give N-(4-((2S,3S)-3-amino-2-methylpiperidin-1-yl)pyridin-3-yl)-2-(3-fluoropyridin-2-yl)imidazo[1,5-b]pyridazin-7-amine (48 mg) as an orange amorphous solid. The relative stereochemistry was confirmed by $^1$H-NMR studies. MS (ESI, pos. ion) m/z: 419.0 (M+1). $^1$H NMR (400 MHz, DMSO-$d_6$) δ ppm 9.59 (1 H, s), 8.71 (1 H, m), 8.30 (1 H, br.), 8.22 (2 H, m), 8.04 (1 H, ddd, J=11.3, 8.5, 1.0 Hz), 7.75 (1 H, dt, J=8.4, 4.2 Hz), 7.48 (1 H, s), 7.29 (1 H, d, J=9.6 Hz), 7.22 (1 H, d, J=5.1 Hz), 3.36 (2 H, br.), 3.15 (2 H, m), 2.76 (1 H, m), 1.70 (1 H, m), 1.58 (2 H, m), 1.68 (2 H, m), 0.88 (3 H, d, J=6.5 Hz). $^{19}$F NMR (376 MHz, DMSO-$d_6$) δ ppm −119.57.

N-(4-((2R,3S)-3-amino-2-methyl-1-piperidinyl)-3-pyridinyl)-2-(3-fluoro-2-pyridinyl)imidazo[1,5-b]pyridazin-7-amine (Example 76). The above obtained tert-butyl ((2R,3S)-1-(3-((2-(3-fluoropyridin-2-yl)imidazo[1,5-b]pyridazin-7-yl)amino)pyridin-4-yl)-2-methylpiperidin-3-yl)carbamate (second eluting diastereomer) in 4 mL of DCM at RT was treated with 0.8 mL of TFA and the mixture was stirred for 1 h at RT. It was concentrated under reduced pressure. The orange residue was partitioned between 10 mL of 1 N NaOH and 55 mL of EtOAc. The organic layer was separated, washed with 5 mL of brine, dried over sodium sulfate and concentrated to give N-(4-((2R,3S)-3-amino-2-methylpiperidin-1-yl)pyridin-3-yl)-2-(3-fluoropyridin-2-yl)imidazo[1,5-b]pyridazin-7-amine (160 mg) as an orange amorphous solid. The relative stereochemistry was confirmed by $^1$H-NMR studies. MS (ESI, pos. ion) m/z: 419.0 (M+1). $^1$H NMR (400 MHz, DMSO-$d_6$) δ ppm 9.63 (1 H, s), 8.65 (1 H, d, J=4.5 Hz), 8.31 (1 H, br.), 8.17 (2 H, m), 7.99 (1 H, dd, J=10.9, 9.1 Hz), 7.70 (1 H, dt, J=8.4, 4.1 Hz), 7.41 (1 H, s), 7.26 (2 H, m), 3.39 (2 H, br.), 2.89 (1 H, m), 2.78 (1 H, m), 2.65 (1 H, m), 2.58 (1 H, m), 1.94 (1 H, m), 1.76 (2 H, m), 1.33 (1 H, m), 0.90 (3 H, d, J=6.1 Hz). $^{19}$F NMR (376 MHz, DMSO-$d_6$) δ ppm −118.94.

Example 77

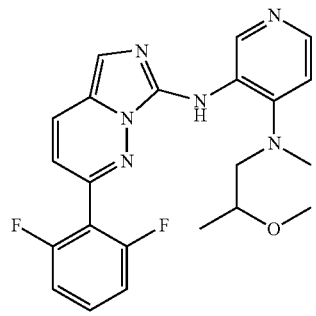 [SMILES: COC(C)CN(C)c1ccncc1Nc1ncc2ccc(-c3c(F)cccc3F)nn12]

N3-(2-(2,6-difluorophenyl)imidazo[1,5-b]pyridazin-7-yl)-N4-(2-methoxypropyl)-N4-methylpyridine-3,4-diamine The title compound was prepared and isolated as an orange solid from 3-(azidomethyl)-6-(2,6-difluorophenyl)pyridazine (Preparation I) and 3-isothiocyanato-N-(2-methoxypropyl)-N-methylpyridin-4-amine (Preparation L) following an analogous procedure to Example 2. MS (ESI, pos. ion) m/z: 425.0 (M+1). $^1$H NMR (400 MHz, MeOH-d4) δ ppm 8.81 (s, 1 H), 8.04 (d, J=5.7 Hz, 1 H), 7.99 (d, J=9.4 Hz, 1 H), 7.50-7.64 (m, 1 H), 7.34 (s, 1 H), 7.17 (t, J=8.1 Hz, 2 H), 7.08 (d, J=5.5 Hz, 1 H), 6.64 (d, J=9.4 Hz, 1 H), 3.65 (dqd, J=9.2, 6.1, 6.1, 6.1, 3.3 Hz, 1 H), 3.27 (dd, J=14.5, 9.4 Hz, 1H), 3.20 (s, 3 H), 2.87-2.94 (m, 4 H), 0.99 (d, J=6.3 Hz, 3 H). $^{19}$F NMR (376 MHz, MeOH-d4) δ ppm −115.06 (s, 2 F).

Example 78

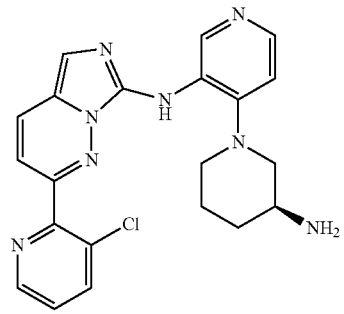 [SMILES: N[C@H]1CCCN(c2ccncc2Nc2ncc3ccc(-c4ncccc4Cl)nn23)C1]

(S)-N-(4-(3-aminopiperidin-1-yl)pyridin-3-yl)-2-(3-chloropyridin-2-yl)imidazo[1,5-b]pyridazin-7-amine The title compound was prepared and isolated as an orange amorphous foam from 3-(azidomethyl)-6-(3-chloropyridin-2-yl)pyridazine (Preparation XXXI) and (S)-tert-butyl (1-(3-isothiocyanatopyridin-4-yl)piperidin-3-yl)carbamate (Preparation XI) following an analogous procedure to Example 2. MS (ESI, pos. ion) m/z: 421.0 (M+1). $^1$H NMR (400 MHz, MeOH-d4) δ ppm 9.25 (1 H, s), 8.69 (1 H, d, J=4.3

Hz), 8.08-8.16 (2 H, m), 8.05 (1 H, d, J=9.4 Hz), 7.58 (1 H, dd, J=8.0, 4.7 Hz), 7.16 (1 H, d, J=5.1 Hz), 6.97 (1 H, d, J=9.4 Hz), 4.61 (1 H, br. s.), 3.16 (1 H, d, J=6.1 Hz), 2.93-3.03 (1 H, m), 2.75-2.86 (1 H, m), 2.54-2.65 (1 H, m), 1.89-1.99 (1 H, m), 1.77-1.88 (1 H, m), 1.62-1.77 (1 H, m), 1.33 (1 H, d, J=10.4 Hz).

Example 79

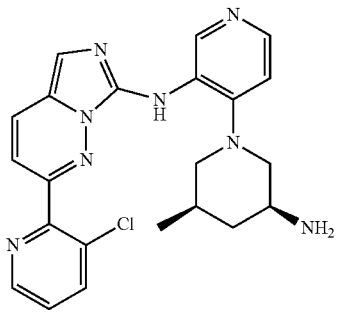 [SMILES: C[C@@H]1C[C@H](N)CN(c2ccncc2Nc2ncc3ccc(-c4ncccc4Cl)nn23)C1]

(S)-N-(4-(3-aminopiperidin-1-yl)pyridin-3-yl)-2-(3-chloropyridin-2-yl)imidazo[1,5-b]pyridazin-7-amine The title compound was prepared and isolated as an orange amorphous foam from 3-(azidomethyl)-6-(3-chloropyridin-2-yl)pyridazine (Preparation XXXI) and tert-butyl ((cis)-1-(3-isothiocyanatopyridin-4-yl)-5-methylpiperidin-3-yl)carbamate (enantiomer 1) (Preparation XXXVIII) following an analogous procedure to Example 2. MS (ESI, pos. ion) m/z: 435.0 (M+1). $^1$H NMR (400 MHz, MeOH-d4) δ ppm 9.28 (1 H, s), 8.68 (1 H, d, J=4.3 Hz), 8.08-8.16 (2 H, m), 8.05 (1 H, d, J=9.6 Hz), 7.58 (1 H, dd, J=8.2, 4.7 Hz), 7.38 (1 H, s), 7.15 (1 H, d, J=5.3 Hz), 6.96 (1 H, d, J=9.6 Hz), 4.61 (1 H, br. s.), 3.40 (1 H, d, J=10.6 Hz), 3.25 (1 H, d, J=11.2 Hz), 2.88-3.01 (1 H, m), 2.38 (1 H, t, J=10.8 Hz), 2.23 (1 H, t, J=11.2 Hz), 1.97 (1 H, d, J=12.9 Hz), 1.89 (1 H, d, J=15.1 Hz), 0.87-0.96 (1 H, m), 0.84 (3 H, d, J=6.7 Hz).

Example 80

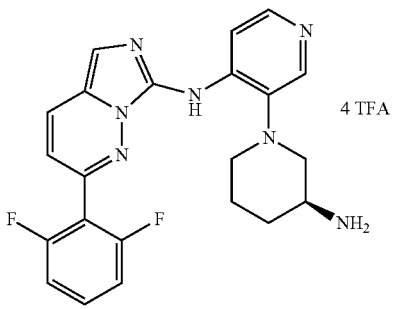 [SMILES: N[C@H]1CCCN(c2cnccc2Nc2ncc3ccc(-c4c(F)cccc4F)nn23)C1]

(S)-N-(3-(3-aminopiperidin-1-yl)pyridin-4-yl)-2-(2,6-difluorophenyl)imidazo[1,5-b]pyridazin-7-amine tetra(2,2,2-trifluoroacetate)

The title compound was prepared and isolated as a yellow tar from 3-(azidomethyl)-6-(2,6-difluorophenyl)pyridazine (Preparation I) and (S)-tert-butyl (1-(4-isothiocyanatopyridin-3-yl)piperidin-3-yl)carbamate (Preparation LI) following an analogous procedure to Example 2. MS (ESI, pos. ion) m/z: 422.0 (M+1). $^1$H NMR (400 MHz, MeOH-d4) δ ppm 8.18 (1 H, d, J=9.8 Hz), 8.09 (1 H, d, J=2.7 Hz), 7.83 (1 H, dd, J=9.2, 2.9 Hz), 7.65-7.72 (1 H, m), 7.64 (1 H, s), 7.48 (1 H, d, J=9.2 Hz), 7.19-7.30 (2H, m), 7.01 (1 H, d, J=9.6 Hz), 3.50-3.61 (2 H, m), 3.30 (1 H, br. s.), 3.12-3.23 (2 H, m), 1.98-2.15 (2 H, m), 1.72-1.92 (2 H, m). $^{19}$F NMR (377 MHz, MeOH-d4) δ ppm −114.95 (2 F, s).

Example 81

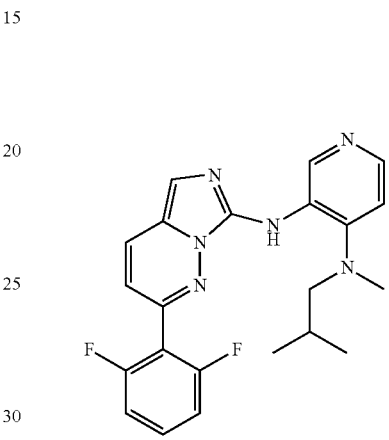

N3-(2-(2,6-Difluorophenyl)imidazo[1,5-b]pyridazin-7-yl)-N4-isobutyl-N4-methylpyridine-3,4-diamine The title compound was prepared and isolated as an orange solid from 3-(azidomethyl)-6-(2,6-difluorophenyl)pyridazine (Preparation I) and N-isobutyl-3-isothiocyanato-N-methylpyridin-4-amine (Preparation LII) following an analogous procedure to Example 2. MS (ESI, pos. ion) m/z: 409.1 (M+1). $^1$H NMR (400 MHz, MeOH-d4) δ ppm 9.14 (s, 1 H), 8.10 (d, J=5.5 Hz, 1 H), 7.98 (d, J=9.4 Hz, 1 H), 7.53-7.64 (m, 1 H), 7.33 (s, 1 H), 7.11-7.22 (m, 3 H), 6.64 (d, J=9.4 Hz, 1 H), 2.87 (d, J=7.4 Hz, 2 H), 2.79 (s, 3 H), 1.91 (dquin, J=13.7, 6.8, 6.8, 6.8, 6.8 Hz, 1 H), 0.87 (d, J=6.7 Hz, 6 H). $^{19}$F NMR (376 MHz, MeOH-d4) δ ppm −115.08 (s, 2F).

Example 82, 83 and 84

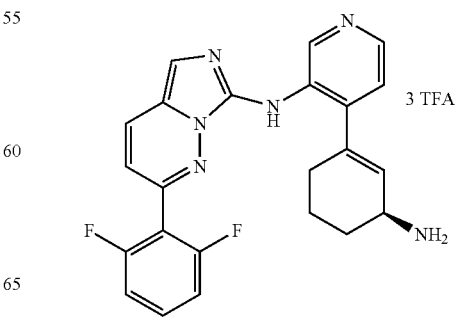

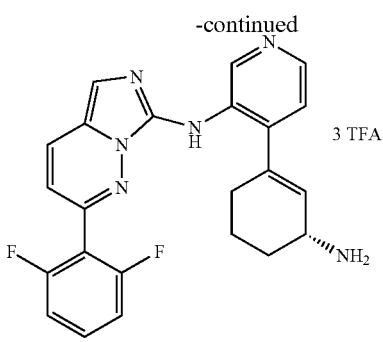

rac-N-(4-(3-aminocyclohex-1-en-1-yl)pyridin-3-yl)-2-(2,6-difluorophenyl)imidazo[1,5-b]pyridazin-7-amine tris(2,2,2-trifluoroacetate), N-(4-(3-aminocyclohex-1-en-1-yl)pyridin-3-yl)-2-(2,6-difluorophenyl)imidazo[1,5-b]pyridazin-7-amine tris(2,2,2-trifluoroacetate) (first eluting enantiomer) and N-(4-(3-aminocyclohex-1-en-1-yl)pyridin-3-yl)-2-(2,6-difluorophenyl)imidazo[1,5-b]pyridazin-7-amine tris(2,2,2-trifluoroacetate) (second eluting enantiomer)

Step 1. rac-2-(3-(3-((2-(2,6-difluorophenyl)imidazo[1,5-b]pyridazin-7-yl)amino)pyridin-4-yl)cyclohex-2-en-1-yl)isoindoline-1,3-dione. A dry, 15 mL, one neck round bottom flask was charged with 3-(azidomethyl)-6-(2,6-difluorophenyl)pyridazine (99 mg, 0.40 mmol, Preparation I), a stirbar, and dry THF (2 mL). The flask was fitted with a septa/Ar inlet, and immersed into an acetone cooling bath maintained by an external chiller set to −5° C. The solution was stirred for 15 min and then PMe$_3$ (0.046 mL, 0.44 mmol) was added via syringe. The solution was stirred for 30 min. A solution of rac-2-(3-(3-isothiocyanatopyridin-4-yl)cyclohex-2-en-1-yl)isoindoline-1,3-dione (146 mg, 0.41 mmol, Preparation LIII) dissolved in dry THF (5 mL) was added, and the reaction was stirred overnight. The THF was removed under a stream of N$_2$, and the residue was partitioned between EtOAc (20 mL) and water (2 mL). The layers were separated, and the organic phase was washed with water (3×2 mL). The EtOAc layer was passed through an unbuffered Varian Chem-Elut CE 1005, and the extraction tube was washed with EtOAc (3×10 mL). The combined elution volume was concentrated in vacuo. The reddish material was dried in a vacuum oven for 30 min (60° C., <1 mm Hg, final pressure: 0.101 mm Hg) to afford 233 mg of material. The crude material was purified by silica gel chromatography (5% EtOH in CHCl$_3$) to afford rac-2-(3-(3-((2-(2,6-difluorophenyl)imidazo[1,5-b]pyridazin-7-yl)amino)pyridin-4-yl)cyclohex-2-en-1-yl)isoindoline-1,3-dione (144 mg, 0.26 mmol, 66% yield). The material was carried on crude with no characterization Step 2. rac-N-(4-(3-aminocyclohex-1-en-1-yl)pyridin-3-yl)-2-(2,6-difluorophenyl)imidazo[1,5-b]pyridazin-7-amine tris(2,2,2-trifluoroacetate), Example 82. A 5 mL, Biotage microwave conical vial was charged with rac-2-(3-(3-((2-(2,6-difluorophenyl)imidazo[1,5-b]pyridazin-7-yl)amino)pyridin-4-yl)cyclohex-2-en-1-yl)isoindoline-1,3-dione (144 mg, 0.26 mmol) and EtOH (2 mL). The vessel was purged with N$_2$ for several min. The solution was then treated with anh. hydrazine (26 mg, 0.81 mmol), and the vessel was crimped with a PTFE-lined seal. The vial was heated to 45° C. for 28 h. The slurry was diluted with EtOH (2 mL), and stirred at RT for 48 h. The slurry was N$_2$-pressure filtered through a glass frit (4 mL Bohdan reaction vessel) fitted with a 0.22 μm PTFE, 25 mm syringe filter unit (Millipore, SLFG025NK). The solids were washed with EtOH (3×2 mL), and discarded. The washes and filtrate were combined, and concentrated in vacuo. The residue was treated with 5% TFA in water (3 mL), and sonicated until a homogenous slurry was observed. The slurry was N$_2$-pressure filtered through a glass frit (4 mL Bohdan reaction vessel) fitted with a 0.22 μm PTFE, 25 mm syringe filter unit (Millipore, SLFG025NK). The solids were washed with 5% TFA in water (3×2 mL) and discarded. The aqueous filtrate and washes were concentrated under a stream of N$_2$ overnight. The reside was reconstituted in water (3 mL) for HPLC purification. The crude was purified by Prep HPLC method 2 to afford rac-N-(4-(3-aminocyclohex-1-en-1-yl)pyridin-3-yl)-2-(2,6-difluorophenyl)imidazo[1,5-b]pyridazin-7-amine tris(2,2,2-trifluoroacetate) (Example 82, 110 mg, 0.15 mmol, 55% yield) as a green solid. MS (ESI, pos. ion) m/z: 419.0 (M+1). $^1$H NMR (400 MHz, D$_2$O)$_6$ ppm 1.55-1.69 (m, 1 H) 1.69-1.80 (m, 1 H) 1.91 (dd, J=12.52, 5.67 Hz, 1 H) 2.01-2.12 (m, 1 H) 2.25-2.38 (m, 1 H) 2.37-2.50 (m, 1 H) 3.89 (br. s., 1 H) 6.03 (br. s., 1 H) 7.15 (d, J=9.59 Hz, 1 H) 7.17 (t, J=8.61 Hz, 2 H) 7.61 (tt, J=8.40, 6.70 Hz, 1 H) 7.73 (s, 1 H) 7.87 (d, J=6.06 Hz, 1 H) 8.21 (d, J=9.78 Hz, 1 H) 8.52 (d, J=5.87 Hz, 1 H) 8.61 (s, 1 H). $^{19}$F NMR (376 MHz, D$_2$O,2,2,2-trifluoroethanol-d3 as internal standard) δ ppm −117.41 (t, J=7.80 Hz, 2F) −78.50 (s, 9F).

Step 3. N-(4-(3-aminocyclohex-1-en-1-yl)pyridin-3-yl)-2-(2,6-difluorophenyl)imidazo[1,5-b]pyridazin-7-amine tris(2,2,2-trifluoroacetate) (first eluting enantiomer) and N-(4-(3-aminocyclohex-1-en-1-yl)pyridin-3-yl)-2-(2,6-difluorophenyl)imidazo[1,5-b]pyridazin-7-amine tris(2,2,2-trifluoroacetate) (second eluting enantiomer). rac-N-(4-(3-Aminocyclohex-1-en-1-yl)pyridin-3-yl)-2-(2,6-difluorophenyl)imidazo[1,5-b]pyridazin-7-amine tris(2,2,2-trifluoroacetate) (80 mg, 0.11 mmol) was purified by supercritical-fluid chromatography (Chiralpak ADH (250× 21 mm, 5 μm), 75% liquid CO$_2$/25% EtOH (20 mM NH$_3$), 65 mL/min). The peaks were repurified using a 21.2×150 mm Phenomenex Luna perfluorophenyl column (100 Å pore diameter, 5 μm particle size, 00F-4448-PO-AX); a 1000-× 0.020 mm id stainless steel tubing was coiled precolumn and immersed, along with the column, into a 45° C. ethylene glycol heat bath; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=0.1% TFA in water; B=0.1% TFA in ACN. The solvent was removed in vacuo to afford N-(4-(3-aminocyclohex-1-en-1-yl)pyridin-3-yl)-2-(2,6-difluorophenyl)imidazo[1,5-b]pyridazin-7-amine tris(2,2,2-trifluoroacetate), first eluting enantiomer (Example 83, 8 mg, 20%) as a white oil. MS (ESI, pos. ion) m/z: 419.0 (M+1). $^{19}$F NMR (376 MHz, D$_2$O) δ ppm −117.46 (t, J=7.80 Hz, 2F) −78.50 (s, 9F); and N-(4-(3-aminocyclohex-1-en-1-yl)pyridin-3-yl)-2-(2,6-difluorophenyl)imidazo[1,5-b]pyridazin-7-amine tris(2,2,2-trifluoroacetate), second eluting enantiomer (Example 84, 8 mg, 20%) as a brown oil. MS (ESI, pos. ion) m/z: 419.9 (M+1). $^{19}$F NMR (377 MHz, D$_2$O) δ ppm −117.42 (s, 2 F) −78.50 (s, 9 F).

Example 85, 86, 87 and 88

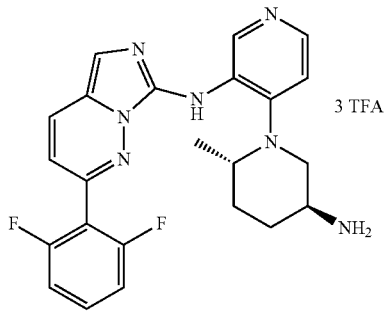

3 TFA

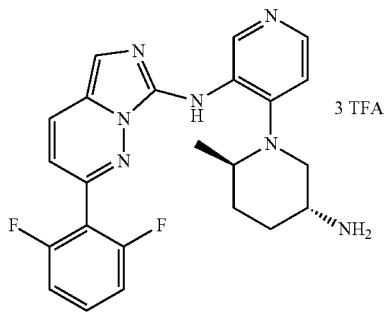

3 TFA

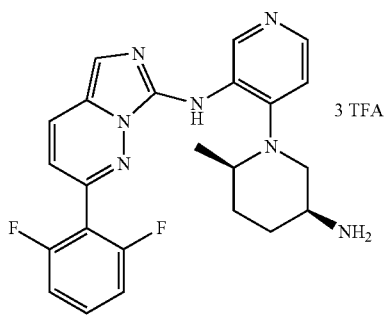

3 TFA

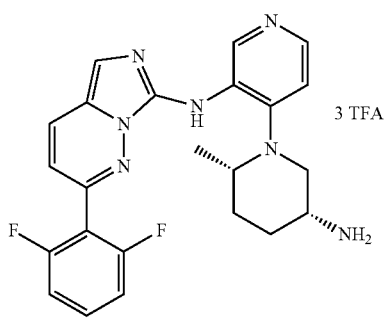

3 TFA

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 1)

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 2)

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 3)

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 4)

Step 1. tert-butyl (1-(3-((2-(2,6-difluorophenyl)imidazo[1,5-b]pyridazin-7-yl)amino)pyridin-4-yl)-6-methylpiperidin-3-yl)carbamate (first eluting diasteromer), tert-butyl (1-(3-((2-(2,6-difluorophenyl)imidazo[1,5-b]pyridazin-7-yl)amino)pyridin-4-yl)-6-methylpiperidin-3-yl)carbamate (second eluting diasteromer), tert-butyl (1-(3-((2-(2,6-difluorophenyl)imidazo[1,5-b]pyridazin-7-yl)amino)pyridin-4-yl)-6-methylpiperidin-3-yl)carbamate (third eluting diasteromer), tert-butyl (1-(3-((2-(2,6-difluorophenyl)imidazo[1,5-b]pyridazin-7-yl)amino)pyridin-4-yl)-6-methylpiperidin-3-yl)carbamate (fourth eluting diasteromer). PMe$_3$ (1.0 M solution in toluene, 2.49 mL, 2.49 mmol) was added dropwise to a solution of 3-(azidomethyl)-6-(2,6-difluorophenyl)pyridazine (587 mg, 2.37 mmol, Preparation I) in THF (10 mL) at RT. The reaction mixture turned purple and an evolution of gas was observed. The reaction mixture was stirred at RT for 1.5 h. A solution of tert-butyl (1-(3-isothiocyanatopyridin-4-yl)-6-methylpiperidin-3-yl)carbamate (869 mg, 2.49 mmol, Preparation LIV) in THF (5 mL) was added, and the bright orange solution was stirred at RT for 50 min. The reaction mixture was concentrated and the crude product was purified by silica gel chromatography (0-10% MeOH in DCM) to give a mixture of stereoisomers (721 mg, 57% yield, ca. 4:1 ratio of cis:trans diastereomers). MS (ESI, pos. ion) m/z: 536.3 (M+1). This material (721 mg) was subjected to two rounds of chiral separation using preparatory SFC (Chiralcel OZ-H column (20×250 mm i.d., 5 μm) 75% liquid CO$_2$/25% MeOH (20 mM NH$_3$) 75 mL/min followed by preparatory SFC (Chiracel OD-H column (20×250 mm i.d., 5 μm) 85% liquid CO$_2$/15% MeOH (20 mM NH$_3$) 70 mL/min) to give tert-butyl (1-(3-((2-(2,6-difluorophenyl)imidazo[1,5-b]pyridazin-7-yl)amino)pyridin-4-yl)-6-methylpiperidin-3-yl)carbamate (first eluting diastereomer) (45 mg, 6% yield) which eluted first from an analytical SFC column (Conditions: 10% MeOH containing 0.2% diethylamine as a cosolvent in supercritical CO$_2$ on a Chiralcel OD-H column (4.6×150 mm, 5 um; with a flow rate of 4 mL/min) MS (ESI, pos. ion) m/z: 536.2 (M+1); tert-butyl (1-(3-((2-(2,6-difluorophenyl)imidazo[1,5-b]pyridazin-7-yl)amino)pyridin-4-yl)-6-methylpiperidin-3-yl)carbamate (second eluting diastereomer) (55 mg, 8% yield) which eluted second from an analytical SFC column (same conditions). MS (ESI, pos. ion) m/z: 536.2 (M+1); tert-butyl (1-(3-((2-(2,6-difluorophenyl)imidazo[1,5-b]pyridazin-7-yl)amino)pyridin-4-yl)-6-methylpiperidin-3-yl)carbamate (third eluting diastereomer) (166 mg, 23% yield) which eluted third from an analytical SFC column (same conditions). MS (ESI, pos. ion) m/z: 536.2 (M+1); tert-butyl (1-(3-((2-(2,6-difluorophenyl)imidazo[1,5-b]pyridazin-7-yl)amino)pyridin-4-yl)-6-methylpiperidin-3-yl)carbamate (fourth eluting diastereomer) (247 mg, 34% yield) which eluted fourth from an analytical SFC column (same conditions). MS (ESI, pos. ion) m/z: 536.2 (M+1).

Step 2. N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 1) (Example 85). To a solution of tert-butyl (1-(3-((2-(2,6-difluorophenyl)imidazo[1,5-b]pyridazin-7-yl)amino)pyridin-4-yl)-6-methylpiperidin-3-yl)carbamate (first eluting diastereomer) (45 mg, 0.084 mmol) in DCM (2 mL) at RT, was added TFA (0.5 mL, 6.73 mmol). The solution was stirred at RT for 30 min. The volatiles were removed under reduced pressure. The residue was treated with DCM (25 mL) and washed thoroughly with 1N NaOH (15 mL). The organic layer was dried over $MgSO_4$, filtered and concentrated. The material was dissolved in DMSO and purified by preparatory HPLC using a Gilson automated platform (Silicycle Silichrome XT $C_{18}$ column; 30×150 mm, 5 μm, 20-95% 0.1% TFA/$CH_3CN$ in 0.1% TFA/water by volume over 12 min.), then dried in a Genevac Series II Evaporator to afford N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 1) (Example 85) (32 mg, 0.04 mmol, 49% yield) as a yellow tar. MS (ESI, pos. ion) m/z: 436.3 (M+1). $^1$H NMR (400 MHz, DMSO-$d_6$) δ ppm 9.10 (s, 1 H), 8.84 (s, 1 H), 8.38 (d, J=6.8 Hz, 1 H), 8.24 (d, J=9.6 Hz, 1 H), 7.99 (br. s., 2 H), 7.66 (quin, J=7.5 Hz, 1 H), 7.53 (s, 1 H), 7.49 (d, J=6.5 Hz, 1 H), 7.32 (t, J=8.3 Hz, 2 H), 6.87 (d, J=9.4 Hz, 1 H), 4.37 (br. s., 1 H), 3.56-3.66 (m, 2 H), 3.09 (d, J=11.3 Hz, 1 H), 1.99-2.21 (m, 2 H), 1.69 (d, J=13.5 Hz, 1 H), 1.36 (d, J=10.2 Hz, 1 H), 0.93 (d, J=6.7 Hz, 3 H). $^{19}$F NMR (376 MHz, DMSO-$d_6$) δ ppm −113.67 (s, 2 F).

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 2) (Example 86). The title compound was prepared and isolated as a yellow tar from tert-butyl (1-(3-((2-(2,6-difluorophenyl)imidazo[1,5-b]pyridazin-7-yl)amino)pyridin-4-yl)-6-methylpiperidin-3-yl)carbamate (second eluting diastereomer) following an analogous procedure to Example 85. MS (ESI, pos. ion) m/z: 436.3 (M+1). $^1$H NMR (400 MHz, DMSO-$d_6$) δ ppm 9.12 (s, 1 H), 8.81 (s, 1 H), 8.37 (d, J=6.3 Hz, 1 H), 8.23 (d, J=9.4 Hz, 1 H), 8.00 (br. s., 2 H), 7.61-7.71 (m, 1H), 7.53 (s, 1 H), 7.48 (d, J=6.3 Hz, 1 H), 7.32 (t, J=8.3 Hz, 2 H), 6.86 (d, J=9.4 Hz, 1 H), 4.31 (br. s., 1 H), 3.53-3.64 (m, 2 H), 3.08 (d, J=11.7 Hz, 1 H), 1.98-2.21 (m, 2 H), 1.61-1.73 (m, 1 H), 1.29-1.42 (m, 1 H), 0.93 (d, J=6.5 Hz, 3 H). $^{19}$F NMR (377 MHz, DMSO-$d_6$) δ ppm −74.24 (s, 6 F), −113.67 (s, 2 F). m/z (ESI, +ve ion) 436.3 (M+H)$^+$.

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 3) (Example 87). The title compound was prepared and isolated as a yellow tar from tert-butyl (1-(3-((2-(2,6-difluorophenyl)imidazo[1,5-b]pyridazin-7-yl)amino)pyridin-4-yl)-6-methylpiperidin-3-yl)carbamate (third eluting diastereomer) following an analogous procedure to Example 85. MS (ESI, pos. ion) m/z: 436.3

(M+1). $^1$H NMR (400 MHz, DMSO-$d_6$) δ ppm 8.84 (s, 1 H), 8.69 (s, 1H), 8.35 (d, J=6.8 Hz, 1H), 8.19 (d, J=9.6 Hz, 1 H), 7.98 (br. s., 2 H), 7.66 (quin, J=7.5 Hz, 1 H), 7.43 (s, 1 H), 7.39 (d, J=6.7 Hz, 1 H), 7.32 (t, J=8.2 Hz, 2 H), 6.80 (d, J=9.6 Hz, 1 H), 4.35 (br. s., 1 H), 3.63 (d, J=10.0 Hz, 1 H), 3.09-3.27 (m, 2 H), 1.66-1.84 (m, 2 H), 1.47-1.64 (m, 2 H), 1.00 (d, J=6.7 Hz, 3 H). $^{19}$F NMR (376 MHz, DMSO-$d_6$) δ ppm −113.62 (s, 2 F).

N-(4-(5-amino-2-methylpiperidin-1-yl)pyridin-3-yl)-2-(2,6-difluorophenyl)imidazo[1,5-b]pyridazin-7-amine tris(2,2,2-trifluoroacetate) (diastereomer 4) (Example 88). The title compound was prepared and isolated as an amorphous yellow solid from tert-butyl (1-(3-((2-(2,6-difluorophenyl)imidazo[1,5-b]pyridazin-7-yl)amino)pyridin-4-yl)-6-methylpiperidin-3-yl)carbamate (fourth eluting diastereomer) following an analogous procedure to Example 85. MS (ESI, pos. ion) m/z: 436.2 (M+1). $^1$H NMR (400 MHz, DMSO-$d_6$) δ ppm 8.85 (s, 1 H), 8.66 (s, 1 H), 8.35 (d, J=6.7 Hz, 1 H), 8.18 (d, J=9.4 Hz, 1 H), 8.02 (br. s., 2 H), 7.61-7.72 (m, 1 H), 7.43 (s, 1H), 7.39 (d, J=6.7 Hz, 1 H), 7.32 (t, J=8.2 Hz, 2 H), 6.79 (d, J=9.4 Hz, 1 H), 4.33 (br. s., 1H), 3.63 (d, J=9.4 Hz, 1 H), 3.10-3.28 (m, 2 H), 1.68-1.85 (m, 2 H), 1.47-1.66 (m, 2H), 1.00 (d, J=6.7 Hz, 3 H). $^{19}$F NMR (377 MHz, DMSO-$d_6$) δ ppm −113.62 (s, 2 F).

Example 89

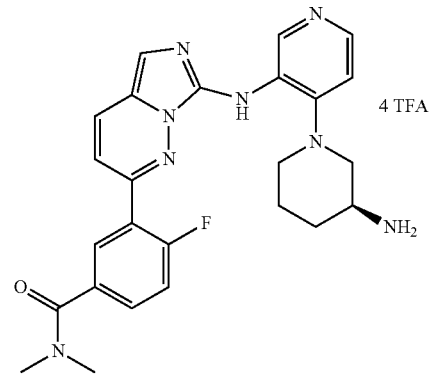 [SMILES: CN(C)C(=O)c1ccc(F)c(-c2ccc3cnc(Nc4cnccc4N4CCC[C@H](N)C4)n3n2)c1]

(S)-3-(7-((4-(3-aminopiperidin-1-yl)pyridin-3-yl)amino)imidazo[1,5-b]pyridazin-2-yl)-4-fluoro-N,N-dimethylbenzamide tetra(2,2,2-trifluoroacetate)

The title compound was prepared and isolated as a green tar from 3-(6-(azidomethyl)pyridazin-3-yl)-4-fluoro-N,N-dimethylbenzamide (Preparation XXXII) and (S)-tert-butyl (1-(3-isothiocyanatopyridin-4-yl)piperidin-3-yl)carbamate (Preparation XI) following an analogous procedure to Example 2 MS (ESI, pos. ion) m/z: 475.3 (M+1). $^1$H NMR (400 MHz, DMSO-$d_6$) δ ppm 9.17 (1 H, s), 8.79 (1 H, s), 8.40 (1 H, d, J=6.5 Hz), 8.20 (1 H, d, J=9.6 Hz), 8.07 (3 H, br. s.), 7.94 (1 H, d, J=5.7 Hz), 7.62-7.73 (1 H, m), 7.44-7.55 (4 H, m), 7.05 (1 H, dd, J=9.5, 2.4 Hz), 3.76 (1 H, d, J=10.6 Hz), 3.45 (1 H, br. s.), 3.19 (1 H, dd, J=12.5, 6.8 Hz), 3.03 (3 H, br.

s.), 2.95 (3 H, br. s.), 1.94 (2 H, br. s.), 1.68 (1 H, d, J=8.2 Hz), 1.59 (2 H, br. s.). $^{19}$F NMR (376 MHz, DMSO-d$_6$) δ ppm −114.03 (1 F, s).

Example 90

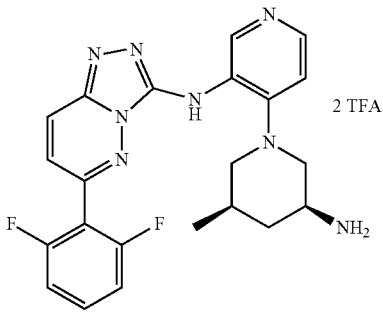 [SMILES: C[C@@H]1C[C@H](N)CN(c2ccncc2Nc2nnc3ccc(-c4c(F)cccc4F)nn23)C1]

N-(4-((3S,5R)-3-amino-5-methylpiperidin-1-yl)pyridin-3-yl)-6-(2,6-difluorophenyl)-[1,2,4]triazolo[4,3-b]pyridazin-3-amine bis(2,2,2-trifluoroacetate)

Step 1. tert-butyl ((cis)-1-(3-((6-chloro-[1,2,4]triazolo[4,3-b]pyridazin-3-yl)amino)pyridin-4-yl)-5-methylpiperidin-3-yl)carbamate. The title compound was prepared and isolated as a yellow solid from tert-butyl ((cis)-1-(3-isothiocyanatopyridin-4-yl)-5-methylpiperidin-3-yl)carbamate (enantiomer 1) (Preparation XXXVIII) and 3-chloro-6-hydrazinopyridazine (Sigma-Aldrich) following an analogous procedure to Example 67 followed by purification by silica gel chromatography (0-5% MeOH in CH$_2$Cl$_2$). MS (ESI, pos. ion) m/z: 459.0 (M+1). $^1$H NMR (400 MHz, CDCl$_3$) δ ppm 9.65 (br. s., 1 H), 8.30 (d, J=5.1 Hz, 1 H), 7.97 (d, J=9.6 Hz, 1 H), 7.61 (br. s., 1 H), 6.99 (d, J=8.2 Hz, 2 H), 4.44 (br. s., 1 H), 3.90 (br. s., 1 H), 3.47 (d, J=8.8 Hz, 1 H), 3.17 (d, J=10.2 Hz, 1 H), 2.45 (t, J=10.6 Hz, 1 H), 2.04-2.29 (m, 3 H), 1.40 (s, 9 H), 0.90-1.04 (m, 4 H).

Step 2. N-(4-((cis)-3-amino-5-methylpiperidin-1-yl)pyridin-3-yl)-6-(2,6-difluorophenyl)-[1,2,4]triazolo[4,3-b]pyridazin-3-amine bis(2,2,2-trifluoroacetate). A 5 mL glass microwave reaction vessel was charged with tert-butyl ((cis)-1-(3-((6-chloro-[1,2,4]triazolo[4,3-b]pyridazin-3-yl)amino)pyridin-4-yl)-5-methylpiperidin-3-yl)carbamate (94 mg, 0.21 mmol) and 2,6-difluorophenylzinc bromide (1.31 mL, 0.66 mmol, Rieke Metals, Inc.) followed by A-Phos (7.3 mg, 10.3 µmol, Sigma-Aldrich). The reaction mixture was stirred and heated at 90° C. for 2 h. The mixture was cooled to RT, quenched with 20 mL of EDTA solution (pH 8.0) and extracted with CHCl$_3$/iPrOH (3/1) (4×20 mL). The combined organic layers were dried over MgSO$_4$, filtered and concentrated. The crude material was dissolved in DMSO and purified using preparative reverse-phase HPLC performed on a Gilson GX-1 equipped with a Phenomenex SiliaChrom XT C$_{18}$ column with UV detection at 254 nm eluting with 20-95% CH$_3$CN in water with 0.1% TFA for 11 min at 45 mL/min to give tert-butyl ((cis)-1-(3-((6-(2,6-difluorophenyl)-[1,2,4]triazolo[4,3-b]pyridazin-3-yl)amino)pyridin-4-yl)-5-methylpiperidin-3-yl)carbamate as a yellow solid. MS (ESI, pos. ion) m/z: 537.2 (M+1). A solution of tert-butyl ((cis)-1-(3-((6-(2,6-difluorophenyl)-[1,2,4]triazolo[4,3-b]pyridazin-3-yl)amino)pyridin-4-yl)-5-methylpiperidin-3-yl)carbamate in DCM (1 mL) was treated with 10 drops of TFA at RT. The solution was stirred at RT for 1 h. The volatiles were removed under reduced pressure. The material was dissolved in DMSO and purified using preparative reverse-phase HPLC performed on a Gilson GX-1 equipped with a Phenomenex SiliaChrom XT C$_{18}$ column with UV detection at 254 nm eluting with 20-95% CH$_3$CN in water with 0.1% TFA for 11 min at 45 mL/min to afford N-(4-((cis)-3-amino-5-methylpiperidin-1-yl)pyridin-3-yl)-6-(2,6-difluorophenyl)-[1,2,4]triazolo[4,3-b]pyridazin-3-amine bis(2,2,2-trifluoroacetate) (34 mg, 0.05 mmol, 24% yield for 2 steps) as a yellow oil. MS (ESI, pos. ion) m/z: 437.0 (M+1). $^1$H NMR (400 MHz, DMSO-d$_6$) δ ppm 9.31 (br. s., 1 H), 8.73 (s, 1 H), 8.42 (d, J=9.6 Hz, 1 H), 8.36 (d, J=6.8 Hz, 1 H), 7.99 (br. s., 2 H), 7.64-7.76 (m, 1 H), 7.50 (d, J=9.8 Hz, 1 H), 7.30-7.40 (m, 3 H), 4.13 (d, J=11.0 Hz, 1 H), 3.95 (d, J=11.7 Hz, 1 H), 3.16 (br. s., 1 H), 2.83 (t, J=11.6 Hz, 1 H), 2.35-2.46 (m, 1 H), 1.97 (d, J=12.3 Hz, 1 H), 1.39 (br. s., 1 H), 1.11 (q, J=12.2 Hz, 1 H), 0.76 (d, J=6.5 Hz, 3 H). $^{19}$F NMR (376 MHz, DMSO-d$_6$) δ ppm −73.98 (s, 6 F), −113.56 (s, 2 F).

Example 91

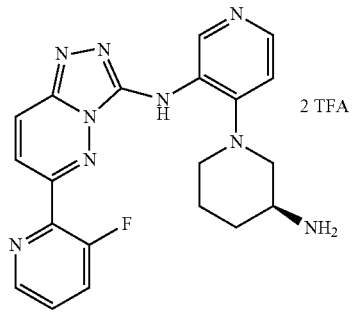 [SMILES: N[C@H]1CCCN(c2ccncc2Nc2nnc3ccc(-c4ncccc4F)nn23)C1]

N-(4-((3S)-3-amino-1-piperidinyl)-3-pyridinyl)-6-(3-fluoro-2-pyridinyl)[1,2,4]triazolo[4,3-b]pyridazin-3-amine bis(2,2,2-trifluoroacetate)

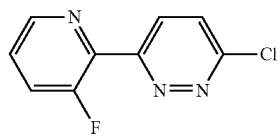 [SMILES: Fc1cccnc1-c1ccc(Cl)nn1]

Step 1. 3-chloro-6-(3-fluoropyridin-2-yl)pyridazine. A mixture of 3-fluoro-2-(tributylstannyl)pyridine (2.35 g, 6.09 mmol, Indofine Chemical Company, #08-1135), 3,6-dichloropyridazine (825 mg, 5.54 mmol, Aldrich, # D73200). CuI (105 mg, 0.55 mmol) and Pd(PPh$_3$)$_4$ (384 mg, 0.33 mmol) in DMF (8 mL) in a sealed glass tube was heated at 100° C. for 90 min. After it cooled to RT, the crude reaction mixture was concentrated and purified by silica gel chromatography (25-75% EtOAc in hexanes) to give 3-chloro-6-(3-fluoropyridin-2-yl)pyridazine (460 mg, 40%) as a brown amorphous solid. MS (ESI, pos. ion) m/z: 209.9 (M+1). $^1$H NMR (400 MHz, DMSO-d$_6$) δ ppm 8.53 (1 H, d, J=4.3 Hz), 8.19 (1 H, d, J=9.0 Hz), 7.99 (1 H, d, J=9.0 Hz), 7.87 (1 H, dd, J=10.4, 9.2 Hz), 7.58 (1 H, dt, J=8.5, 4.3 Hz). $^{19}$F NMR −120.92 ppm.

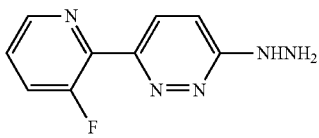 [SMILES: NNc1ccc(-c2ncccc2F)nn1]

Step 2. 3-(3-fluoropyridin-2-yl)-6-hydrazinylpyridazine. To a suspension of 3-chloro-6-(3-fluoropyridin-2-yl)pyridazine (460 mg, 2.19 mmol) in 6 mL of iPrOH was added anh. hydrazine (0.69 mL, 21.95 mmol). The resulting mixture was stirred at RT for 18 h. It was concentrated under reduced pressure to dryness. The residue was stirred in 10 mL of ether and the insoluble yellow solid was filtered and rinsed with 2×2 mL of ether to give 3-(3-fluoropyridin-2-yl)-6-hydrazinylpyridazine (349 mg, 78% yield) as a yellow crystalline solid. MS (ESI, pos. ion) m/z: 206.0 (M+1).

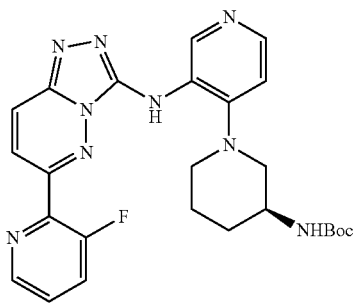 [SMILES: CC(C)(C)OC(=O)N[C@H]1CCCN(c2ccncc2Nc2nnc3ccc(-c4ncccc4F)nn23)C1]

Step 3. N-(4-((3S)-3-amino-1-piperidinyl)-3-pyridinyl)-6-(3-fluoro-2-pyridinyl)[1,2,4]triazolo[4,3-b]pyridazin-3-amine. A mixture of (S)-tert-butyl (1-(3-isothiocyanatopyridin-4-yl)piperidin-3-yl)carbamate (193 mg, 0.58 mmol, Preparation XI) and 3-(3-fluoropyridin-2-yl)-6-hydrazinylpyridazine (113 mg, 0.551 mmol) in ACN (2 mL) was heated at 85° C. for 30 min. After the reaction mixture was cooled to RT, it was treated with DCC (125 mg, 0.60 mmol) and heating was resumed at 90° C. for 2 h. The reaction mixture was concentrated under reduced pressure. The residue was purified by silica gel chromatography (50-100% EtOAc in DCM followed by 1-10% MeOH in EtOAc) to provide (S)-tert-butyl (1-(3-((6-(3-fluoropyridin-2-yl)-[1,2,4]triazolo[4,3-b]pyridazin-3-yl)amino)pyridin-4-yl)piperidin-3-yl)carbamate (250 mg, 90% yield) as a dark green crystalline solid. MS (ESI, pos. ion) m/z: 506.0 (M+1).

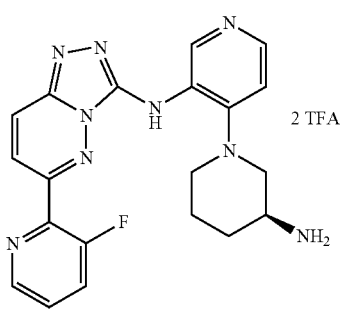 [SMILES: N[C@H]1CCCN(c2ccncc2Nc2nnc3ccc(-c4ncccc4F)nn23)C1]

Step 4. N-(4-((3S)-3-amino-1-piperidinyl)-3-pyridinyl)-6-(3-fluoro-2-pyridinyl)[1,2,4]triazolo[4,3-b]pyridazin-3-amine bis(2,2,2-trifluoroacetate). (S)-tert-Butyl (1-(3-((6-(3-fluoropyridin-2-yl)-[1,2,4]triazolo[4,3-b]pyridazin-3-yl)amino)pyridin-4-yl)piperidin-3-yl)carbamate (248 mg, 0.49 mmol) in 2 mL of DCM was treated with 0.5 ml of TFA. The reaction mixture was stirred at RT for 1 h. The dark green solution was concentrated under reduced pressure. The residue was dissolved in 10 mL of DMSO and purified by Prep HPLC method 3. The desired fractions were collected and lyophilized for 48 h to give N-(4-((3S)-3-amino-1-piperidinyl)-3-pyridinyl)-6-(3-fluoro-2-pyridinyl)[1,2,4]triazolo[4,3-b]pyridazin-3-amine bis(2,2,2-trifluoroacetate) (158 mg, 51% yield) as a brown solid which turned into a sticky brown amorphous solid upon standing on the bench. MS (ESI, pos. ion) m/z: 406.0 (M+1). $^1$H NMR (400 MHz, DMSO-d$_6$) δ ppm 9.19 (1 H, br.), 8.84 (1 H, s), 8.68 (1 H, d, J=4.5 Hz), 8.31-8.50 (2 H, m), 8.04 (3 H, br.), 8.15 (3 H, m), 7.74 (1 H, dt, J=8.4, 4.2 Hz), 7.42 (1 H, d, J=6.3 Hz), 3.81 (1 H, m), 3.26-3.50 (3 H, br.), 3.16 (1 H, m), 1.95 (1 H, m), 1.85 (1 H, m), 1.67 (1H, m), 1.52 (1 H, m). $^{19}$F NMR (376 MHz, DMSO-d$_6$) δ ppm −73.91 (6 F, s), −119.46 (1 F, s).

Example 92

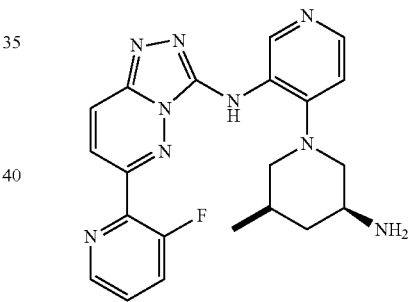

N-(4-((3S,5R)-3-amino-5-methyl-1-piperidinyl)-3-pyridinyl)-6-(3-fluoro-2-pyridinyl)[1,2,4]triazolo[4,3-b]pyridazin-3-amine The title compound was prepared and isolated as a viscous brown amorphous solid from 3-(3-fluoropyridin-2-yl)-6-hydrazinylpyridazine (Preparation XI) and tert-butyl ((cis)-1-(3-isothiocyanatopyridin-4-yl)-5-methylpiperidin-3-yl)carbamate (enantiomer 1) (Preparation XXXVIII) following an analogous procedure to Example 91. MS (ESI, pos. ion) m/z: 420.0 (M+1). $^1$H NMR (400 MHz, DMSO-d$_6$) δ ppm 8.77 (1 H, s), 8.67 (1 H, d, J=4.5 Hz), 8.40 (2 H, m), 8.10 (3 H, br.), 7.98 (1 H, dd, J=10.4, 9.2 Hz), 7.89 (1 H, d, J=9.8 Hz), 7.73 (1 H, dt, J=8.4, 4.2 Hz), 7.43 (1 H, d, J=6.8 Hz), 4.47 (2 H, br.), 4.20 (1 H, m), 3.95 (1 H, m), 3.21 (1 H, m), 2.83 (1 H, t, J=11.7 Hz), 2.46 (1 H, m), 2.03 (1 H, m), 1.57 (1 H, m), 1.16 (1 H, m), 0.82 (3 H, d, J=6.5 Hz). $^{19}$F NMR (376 MHz, DMSO-d$_6$) δ ppm −74.08 (9 F, s), −119.53 (1 F, s).

Example 93

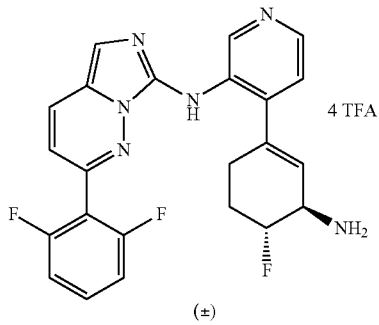 [SMILES: N[C@@H]1C=C(c2ccncc2Nc2ncc3ccc(-c4c(F)cccc4F)nn23)CC[C@H]1F]

(±)

rac-N-(4-((trans)-3-amino-4-fluoropiperidin-1-yl) pyridin-3-yl)-2-(2,6-difluorophenyl)imidazo[1,5-b] pyridazin-7-amine tetra(2,2,2-trifluoroacetate).

Step 1. rac-2-((trans)-3-(3-((2-(2,6-difluorophenyl)imidazo[1,5-b]pyridazin-7-yl)amino)pyridin-4-yl)-6-fluorocyclohex-2-en-1-yl)isoindoline-1,3-dione. A dry, 5 mL, Bohdan vessel was charged with 3-(azidomethyl)-6-(2,6-difluorophenyl)pyridazine (54 mg, 0.22 mmol, Preparation I), dry THF (2 mL) and a spinvane. The vessel was crimped with a PTFE-lined seal, fitted with a Ar inlet, immersed into a ice-water bath, and stirred for 15 min. The solution ws then treated with $PMe_3$ (0.023 mL, 0.22 mmol) and stirred for 45 min. The solution was then treated with rac-2-((trans)-6-fluoro-3-(3-isothiocyanatopyridin-4-yl)cyclohex-2-en-1-yl) isoindoline-1,3-dione (75 mg, 0.10 mmol, Preparation LV) dissolved in dry THF (2 mL). The reaction was stirred at RT for 24 h. The solution was loaded onto a column of Si-Propylsulfonic acid (1.39 g, 0.99 mmol) wet-packed and eluted with dry THF. The silica was washed with dry THF (20 mL), dry EtOH (20 mL), and then 2M $NH_3$ in MeOH (40 mL). The fraction corresponding to the ammonia elution was concentrated in vacuo to afford crude rac-2-((trans)-3-(3-((2-(2, 6-difluorophenyl)imidazo[1,5-b]pyridazin-7-yl)amino)pyridin-4-yl)-6-fluorocyclohex-2-en-1-yl)isoindoline-1,3-dione (112 mg, 0.10 mmol, 100% yield). The material was used without characterization.

Step 2. rac-N-(4-((trans)-3-amino-4-fluoropiperidin-1-yl) pyridin-3-yl)-2-(2,6-difluorophenyl)imidazo[1,5-b]pyridazin-7-amine. A 5 mL, conical Bohdan microwave vessel was charged with 2-((trans)-3-(3-((2-(2,6-difluorophenyl) imidazo[1,5-b]pyridazin-7-yl)amino)pyridin-4-yl)-6-fluorocyclohex-2-en-1-yl)isoindoline-1,3-dione (112 mg, 0.099 mmol), a spin vane and dry EtOH (1.5 mL). The vessel was purged with $N_2$ for several min. The solution was treated with hydrazine, anh. (0.06 mL, 1.98 mmol). The vessel was crimped with a PTFE-line seal and heated at 60° C. for 3 h. The mixture was cooled to RT was $N_2$-pressure filtered through a glass frit (4 mL Bohdan reaction vessel) fitted with a 0.22 μm PTFE, 25 mm syringe filter unit (Millipore, SLFG025NK). The solids were washed with EtOH (3×2 mL), and discarded. The crude was purified using a 21.2×150 mm Phenomenex Luna perfluorophenyl column (100 Å pore diameter, 5 μm particle size, 00F-4448-PO-AX); a 1000-× 0.020 mm id stainless steel tubing was coiled precolumn and immersed, along with the column, into a 45° C. ethylene glycol heat bath; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end; A=0.1% TFA in water; B=0.1% TFA in ACN. The elution volume collected from 15.6-to 20.1 minutes was pooled and the solvent was removed in vacuo to afford 35 mg of material predominantly consisting of 2 peaks. The crude was purified using a 19×150 mm Waters Xterra Prep $C_{18}$ OBD column (100 Å pore diameter, 5 μm particle size, spherical shape, 186002381, a 1 m×0.020 mm id stainless steel tubing was coiled precolumn and immersed, along with the column, into a 45° C. ethylene glycol heat bath; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end; A=0.1% TFA in water; B=0.1% TFA in ACN. The elution volume that eluted from 5.5 to 13.3 min was pooled and the solvent was removed in vacuo to afford 30 mg. The crude was purified using a 21.2×150 mm Phenomenex Luna perfluorophenyl column (100 Å pore diameter, 5 μm particle size, 00F-4448-PO-AX); a 1000-×0.020 mm id stainless steel tubing was coiled precolumn and immersed, along with the column, into a 45° C. ethylene glycol heat bath; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end; A=0.1% TFA in water; B=0.1% TFA-10% 2,2,2-trifluoroethanol—89.9% ACN. The elution volume collected from 17.9- to 19.6 min was pooled and the solvent was removed in vacuo. The material was then dried in a vacuum oven for 1 h (60° C., final pressure: 0.090 mm Hg) to afford rac-N-(4-((trans)-3-amino-4-fluoropiperidin-1-yl)pyridin-3-yl)-2-(2,6-difluorophenyl)imidazo[1,5-b]pyridazin-7-amine (15 mg, 8.4 μmol, 8%) as an orange solid. MS (ESI, pos. ion) m/z: 436.9 (M+1). $^1$H NMR (400 MHz, MeOH-d4) δ ppm 1.98-2.12 (m, 2 H) 2.33 (tq, J=12.94, 4.22 Hz, 2 H) 2.67-2.74 (m, 4 H) 4.07 (ddq, J=13.89, 7.80, 2.50, 2.50, 2.50 Hz, 2 H) 4.90 (dddd, J=50.28, 11.15, 7.80, 3.90 Hz, 2 H) 5.93 (dq, J=4.90, 2.20 Hz, 2 H) 6.88 (dt, J=9.44, 1.44 Hz, 2 H) 7.17 (t, J=8.41 Hz, 4 H) 7.52 (s, 2 H) 7.59 (tt, J=8.51, 6.46 Hz, 2 H) 7.74 (d, J=5.67 Hz, 2 H) 8.12 (d, J=9.59 Hz, 2 H) 8.40 (d, J=5.67 Hz, 2 H) 9.08 (s, 2 H). $^{19}$F NMR (377 MHz, MeOH-d4) δ ppm −183.56 (s, 2 F) −113.53 (s, 4 F) −75.68 (br. s., 24 F).

Example 94, 95, 96 and 97

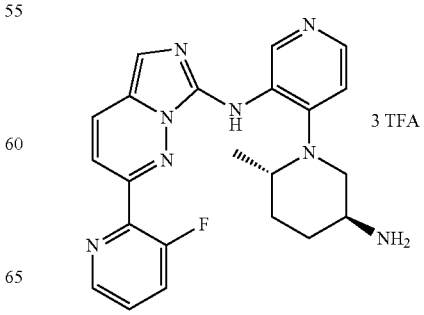

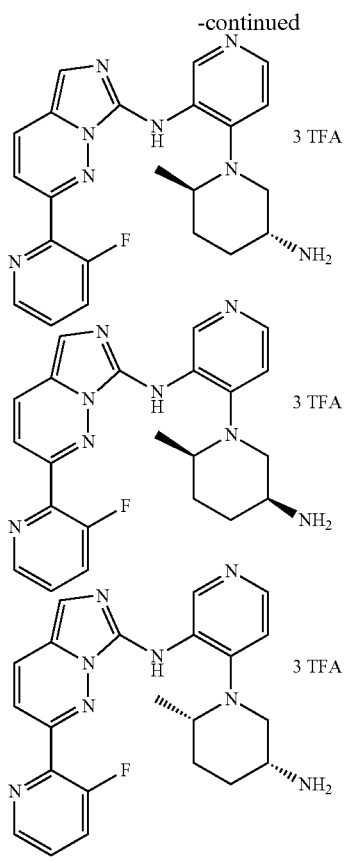

N-(4-((cis)-5-amino-2-methylpiperidin-1-yl)pyridin-3-yl)-2-(3-fluoropyridin-2-yl)imidazo[1,5-b]pyridazin-7-amine tris(2,2,2-trifluoroacetate) (enantiomer 1)

N-(4-((cis)-5-amino-2-methylpiperidin-1-yl)pyridin-3-yl)-2-(3-fluoropyridin-2-yl)imidazo[1,5-b]pyridazin-7-amine tris(2,2,2-trifluoroacetate) (enantiomer 2)

N-(4-((trans)-5-amino-2-methylpiperidin-1-yl)pyridin-3-yl)-2-(3-fluoropyridin-2-yl)imidazo[1,5-b]pyridazin-7-amine (enantiomer 1) tris(2,2,2-trifluoroacetate)

N-(4-((trans)-5-amino-2-methylpiperidin-1-yl)pyridin-3-yl)-2-(3-fluoropyridin-2-yl)imidazo[1,5-b]pyridazin-7-amine (enantiomer 2) tris(2,2,2-trifluoroacetate)

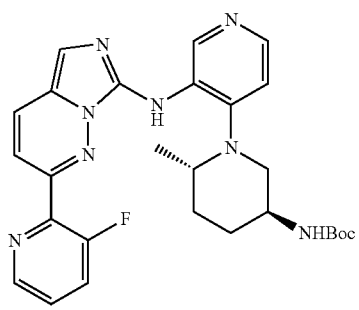

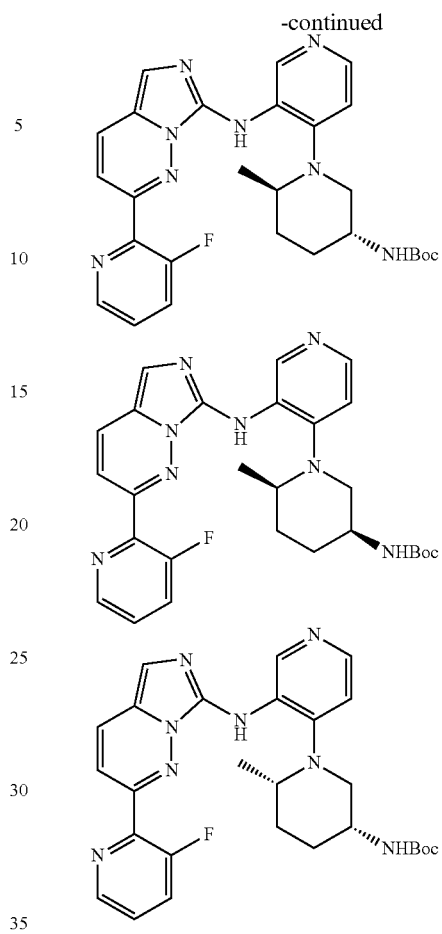

Step 1. tert-butyl ((cis)-1-(3-((2-(3-fluoropyridin-2-yl)imidazo[1,5-b]pyridazin-7-yl)amino)pyridin-4-yl)-6-methylpiperidin-3-yl)carbamate (enantiomer 1), tert-butyl ((cis)-1-(3-((2-(3-fluoropyridin-2-yl)imidazo[1,5-b]pyridazin-7-yl)amino)pyridin-4-yl)-6-methylpiperidin-3-yl)carbamate (enantiomer 2), tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate (enantiomer 1), tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate (enantiomer 2). The title compounds were prepared as a mixture of stereoisomers from tert-butyl (1-(3-isothiocyanatopyridin-4-yl)-6-methylpiperidin-3-yl)carbamate (Preparation LIV) in an analagous manner to Example 85 using 3-(azidomethyl)-6-(3-fluoropyridin-2-yl)pyridazine (Preparation XXVIII) affording 570 mg of the above mixture of stereoisomers (ca. 9:1 ratio of cis:trans diastereomer) after purification by silica gel chromatography (0-15% MeOH in DCM). MS (ESI, pos. ion) m/z: 519.2 (M+1). The mixture of stereoisomers were seperated by three rounds of chiral separation using preparatory SFC (Chiralcel OD-H column (2×20 cm i.d., 5 μm). 80% liquid $CO_2$/20% MeOH (0.1% diisopropyl amine), 70 mL/min). The resulting material was then repurified using preparatory SFC (Chiralpak AS-H column (21×250 mm i.d., 5 μm) 85% liquid $CO_2$/15% MeOH (40 mM $NH_3$), 70 mL/min) and then repurified using preparatory SFC (Chiralpak AS-H column (21×250 mm i.d., 5 μm) 75% liquid $CO_2$/25% 2-propanol (0.2% diisopropyl amine), 70 mL/min. This gave tert-butyl ((cis)-1-(3-((2-(3-fluoropyridin-2-yl)imidazo[1,5-b]pyridazin-7-yl)

amino)pyridin-4-yl)-6-methylpiperidin-3-yl)carbamate, enantiomer 1 (174 mg, 30.5% yield) which eluted first from an analytical SFC column (Conditions: 25% MeOH containing 0.2% diethylamine as a cosolvent in supercritical $CO_2$ on a Chiralcel OD-H column (4.6×150 mm, 5 µm; with a flow rate of 4 mL/min)). MS (ESI, pos. ion) m/z: 519.0 (M+1). $^1$H NMR (400 MHz, $CDCl_3$) δ ppm 9.82 (1 H, s), 8.72 (1 H, br. s.), 8.58 (1 H, d, J=4.5 Hz), 8.25 (1 H, d, J=5.1 Hz), 7.81 (1 H, d, J=9.8 Hz), 7.60-7.70 (1 H, m), 7.47 (1 H, dt, J=8.2, 4.0 Hz), 7.32-7.42 (2 H, m), 7.08 (1 H, d, J=5.1 Hz), 5.65 (1 H, br. s.), 3.96 (1 H, br. s.), 3.13 (1H, br. s.), 2.89-3.03 (2 H, m), 1.75-1.97 (4 H, m), 1.05 (9 H, br. s.), 0.95 (3 H, d, J=6.3 Hz). $^{19}$F NMR (376 MHz, $CDCl_3$) δ ppm −116.76 (1 F, s). This gave tert-butyl ((cis)-1-(3-((2-(3-fluoropyridin-2-yl)imidazo[1,5-b]pyridazin-7-yl)amino)pyridin-4-O-6-methylpiperidin-3-yl)carbamate, enantiomer 2 (217 mg, 38% yield) which eluted second from an analytical SFC column (Conditions: 25% MeOH containing 0.2% DEA as a cosolvent in supercritical $CO_2$ on a Chiralcel OD-H column (4.6×150 mm, 5 µm; with a flow rate of 4 mL/min)) MS (ESI, pos. ion) m/z: 519.0 (M+1). $^1$H NMR (400 MHz, $CDCl_3$) δ ppm 9.82 (1 H, s), 8.71 (1 H, br. s.), 8.58 (1 H, d, J=4.1 Hz), 8.25 (1 H, d, J=4.9 Hz), 7.81 (1 H, d, J=9.8 Hz), 7.58-7.69 (1 H, m), 7.42-7.51 (1 H, m), 7.31-7.41 (2 H, m), 7.07 (1 H, d, J=5.1 Hz), 5.64 (1 H, br. s.), 3.89-4.08 (1 H, m), 3.13 (1 H, br. s.), 2.88-3.03 (2 H, m), 1.74-1.96 (4 H, m), 1.21 (3 H, d, J=6.1 Hz), 1.05 (8 H, br. s.), 0.95 (3 H, d, J=6.1 Hz). $^{19}$F NMR (377 MHz, $CDCl_3$) δ ppm −116.76 (1 F, s). This gave tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate, enantiomer 1 (20 mg, 4% yield) which eluted first from an analytical SFC column (Conditions: 25% 2-propanol containing 0.2% DEA as a cosolvent in supercritical $CO_2$ on a Chiralpak AS-H column (4.6×150 mm, 5 um; with a flow rate of 4 mL/min)) MS (ESI, pos. ion) m/z: 519.0 (M+1). $^1$H NMR (400 MHz, $CDCl_3$) δ ppm 9.81 (1 H, s), 8.57 (1 H, d, J=4.5 Hz), 8.52 (1 H, br. s.), 8.24 (1 H, d, J=5.3 Hz), 7.80 (1 H, d, J=9.6 Hz), 7.59-7.69 (1 H, m), 7.44 (1 H, dt, J=8.3, 4.1 Hz), 7.28-7.36 (2 H, m), 7.04 (1 H, d, J=5.1 Hz), 4.75 (1 H, br. s.), 3.92 (1 H, br. s.), 3.29 (1 H, d, J=8.2 Hz), 3.10 (1 H, br. s.), 2.53 (1 H, br. s.), 2.12 (1 H, br. s.), 2.01 (1 H, dd, J=9.8, 3.9 Hz), 1.69 (1 H, d, J=3.7 Hz), 1.44 (1 H, d, J=7.2 Hz), 1.33 (7 H, br. s.), 1.27 (1 H, d, J=7.4 Hz), 1.21 (4 H, d, J=6.1 Hz), 0.93 (3 H, d, J=6.3 Hz). This gave tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate, enantiomer 2 (21 mg, 4% yield), which eluted as the second peak from an analytical SFC column (Conditions: 25% 2-propanol containing 0.2% DEA as a cosolvent in supercritical $CO_2$ on a Chiralpak AS-H column (4.6×150 mm, 5 um; with a flow rate of 4 mL/min)) MS (ESI, pos. ion) m/z: 519.0 (M+1). $^1$H NMR (400 MHz, $CDCl_3$) δ ppm 9.81 (1 H, s), 8.57 (1 H, d, J=4.5 Hz), 8.52 (1 H, br. s.), 8.24 (1 H, d, J=5.1 Hz), 7.80 (1 H, d, J=9.6 Hz), 7.60-7.69 (1 H, m), 7.44 (1 H, dt, J=8.5, 4.1 Hz), 7.29-7.37 (2 H, m), 7.04 (1 H, d, J=5.1 Hz), 4.75 (1 H, br. s.), 3.92 (1 H, br. s.), 3.29 (1 H, d, J=8.0 Hz), 3.10 (1 H, br. s.), 2.53 (1 H, br. s.), 2.12 (1 H, br. s.), 1.94-2.04 (1 H, m), 1.44 (2 H, d, J=8.0 Hz), 1.33 (7 H, br. s.), 0.93 (3 H, d, J=6.3 Hz).

Step 2. N-(4-((cis)-5-amino-2-methylpiperidin-1-yl)pyridin-3-yl)-2-(3-fluoropyridin-2-yl)imidazo[1,5-t]pyridazin-7-amine tris(2,2,2-trifluoroacetate) (enantiomer 1), Example 94. The title compound was prepared and isolated as a orange foam from tert-butyl ((cis)-1-(3-((2-(3-fluoropyridin-2-yl)imidazo[1,5-b]pyridazin-7-yl)amino)pyridin-4-yl)-6-methylpiperidin-3-yl)carbamate, enantiomer 1 following an analogous procedure to Example 85. The relative stereochemistry was confirmed by NMR studies. MS (ESI, pos. ion) m/z: 419.1 (M+1). $^1$H NMR (400 MHz, MeOH-d4) δ ppm 9.47 (1 H, s), 8.63 (1H, d, J=4.7 Hz), 8.16 (1 H, d, J=5.3 Hz), 8.05 (1 H, d, J=9.6 Hz), 7.82-7.91 (1 H, m), 7.65 (1 H, dt, J=8.4, 4.2 Hz), 7.38 (1 H, s), 7.24-7.33 (2 H, m), 3.39-3.50 (1 H, m), 2.95-3.06 (3 H, m), 1.84-1.99 (2 H, m), 1.67-1.81 (2 H, m), 1.02 (3 H, d, J=6.5 Hz). $^{19}$F NMR (377 MHz, MeOH-d4) δ ppm −120.69 (1 F, s).

N-(4-((cis)-5-amino-2-methylpiperidin-1-yl)pyridin-3-yl)-2-(3-fluoropyridin-2-yl)imidazo[1,5-b]pyridazin-7-amine tris(2,2,2-trifluoroacetate) (enantiomer 2), Example 95. The title compound was prepared and isolated as a brown-orange amorphous solid from tert-butyl ((cis)-1-(3-((2-(3-fluoropyridin-2-yl)imidazo[1,5-b]pyridazin-7-yl)amino)pyridin-4-yl)-6-methylpiperidin-3-yl)carbamate, enantiomer 2 following an analogous procedure to Example 85. The relative stereochemistry was confirmed by NMR studies. MS (ESI, pos. ion) m/z: 419.0 (M+1). $^1$H NMR (400 MHz, MeOH-d4) δ ppm 9.12 (1 H, d, J=1.2 Hz), 8.60-8.67 (1 H, m), 8.33 (1 H, dd, J=6.7, 1.2 Hz), 8.12 (1 H, d, J=9.6 Hz), 7.85 (1 H, ddd, J=11.1, 8.5, 1.2 Hz), 7.67 (1 H, dt, J=8.5, 4.2 Hz), 7.52 (1 H, d, J=6.7 Hz), 7.41-7.46 (1 H, m), 7.29-7.38 (1 H, m), 4.36-4.46 (1H, m), 3.86 (1 H, d, J=9.2 Hz), 3.36-3.44 (2 H, m), 1.98-2.07 (1 H, m), 1.84-1.97 (2H, m), 1.73-1.82 (1 H, m), 1.22 (3 H, d, J=6.7 Hz). $^{19}$F NMR (376 MHz, MeOH-d4) δ ppm −121.31 (1F, s).

N-(4-((trans)-5-amino-2-methylpiperidin-1-yl)pyridin-3-yl)-2-(3-fluoropyridin-2-yl)imidazo[1,5-b]pyridazin-7-amine tris(2,2,2-trifluoroacetate) (enantiomer 1), Example 96. The title compound was prepared and isolated as an orange amorphous solid from tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate, enantiomer 1 following an analogous procedure to Example 85. The relative stereochemistry was confirmed by NMR studies. MS (ESI, pos. ion) m/z: 419.1 (M+1). $^1$H NMR (400 MHz, MeOH-d4) δ ppm 9.55 (1 H, d, J=1.0 Hz), 8.66 (1 H, dt, J=4.5, 1.4 Hz), 8.41 (1 H, dd, J=6.4, 1.1 Hz), 8.16 (1 H, d, J=9.6 Hz), 7.89 (1 H, ddd, J=11.3, 8.5, 1.2 Hz), 7.65-7.76 (2 H, m), 7.50 (1 H, s), 7.43 (1 H, dd, J=9.7, 1.1 Hz), 4.06-4.17 (1 H, m), 3.69-3.82 (2 H, m), 3.11-3.21 (1 H, m), 2.26-2.38 (1 H, m), 2.13-2.24 (1 H, m), 1.84 (1 H, td, J=7.0, 4.1 Hz), 1.62-1.74 (1 H, m), 1.13 (3 H, d, J=6.5 Hz). $^{19}$F NMR (377 MHz, MeOH-d4) δ ppm −121.00 (1F, s).

N-(4-((trans)-5-amino-2-methylpiperidin-1-yl)pyridin-3-yl)-2-(3-fluoropyridin-2-yl)imidazo[1,5-b]pyridazin-7-amine tris(2,2,2-trifluoroacetate) (enantiomer 2), Example 97. The title compound was prepared and isolated as a waxy orange amorphous solid from tert-butyl ((trans)-1-(3-((2-(3-fluoropyridin-2-yl)imidazo[1,5-b]pyridazin-7-yl)amino)pyridin-4-yl)-6-methylpiperidin-3-yl)carbamate, enantiomer 2 following an analogous procedure to Example 85. The relative stereochemistry was confirmed by NMR studies. MS (ESI, pos. ion) m/z: 419.1 (M+1). $^1$H NMR (400 MHz, MeOH-d4) δ ppm 9.62 (1 H, s), 8.60-8.66 (1 H, m), 8.19 (1 H, d, J=5.1 Hz), 8.05 (1 H, d, J=9.6 Hz), 7.87 (1 H, ddd, J=11.2, 8.4, 1.2 Hz), 7.65 (1 H, dt, J=8.6, 4.1 Hz), 7.33-7.41 (3 H, m), 3.09-3.21 (3 H, m), 2.47 (1 H, t, J=11.5 Hz), 2.07-2.16 (1 H, m), 2.01 (1 H, dq, J=13.4, 3.5 Hz), 1.61-1.73 (1 H, m), 1.36-1.49 (1 H, m), 0.97 (3 H, d, J=6.1 Hz). $^{19}$F NMR (377 MHz, MeOH-d4) δ ppm −117.38 (1 F, s).

Example 98, 99, 100 and 101

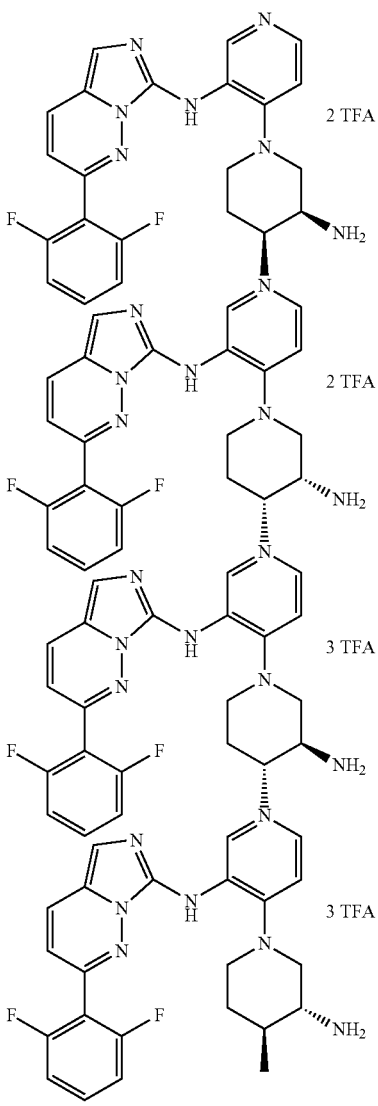

N-(4-((cis)-3-amino-4-methylpiperidin-1-yl)pyridin-3-yl)-2-(2,6-difluorophenyl)imidazo[1,5-b]pyridazin-7-amine bis(2,2,2-trifluoroacetate) (enantiomer 1)

N-(4-((cis)-3-amino-4-methylpiperidin-1-yl)pyridin-3-yl)-2-(2,6-difluorophenyl)imidazo[1,5-b]pyridazin-7-amine bis(2,2,2-trifluoroacetate) (enantiomer 2)

N-(4-((trans)-3-amino-4-methylpiperidin-1-yl)pyridin-3-yl)-2-(2,6-difluorophenyl)imidazo[1,5-b]pyridazin-7-amine tris(2,2,2-trifluoroacetate) (enantiomer 1)

N-(4-((trans)-3-amino-4-methylpiperidin-1-yl)pyridin-3-yl)-2-(2,6-difluorophenyl)imidazo[1,5-b]pyridazin-7-amine tris(2,2,2-trifluoroacetate) (enantiomer 2)

Step 1. tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 1), tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 2), tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 1), tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 2). PMe$_3$ (1.0 M solution in THF, 1.25 mL, 1.25 mmol) was added dropwise to a solution of 3-(azidomethyl)-6-(2,6-difluorophenyl)pyridazine (296 mg, 1.20 mmol, Preparation I) in THF (6.0 mL) at RT. The reaction mixture turned purple and an evolution of gas was observed. The reaction mixture was stirred at RT for 50 min. A solution of tert-butyl (1-(3-isothiocyanatopyridin-4-yl)-4-methylpiperidin-3-yl)carbamate (438 mg, 1.26 mmol, Preparation LVI) in THF (4 mL) was added, and the resulting bright orange solution was stirred at RT for 15 min. The reaction mixture was concentrated and the crude product was purified by silica gel chromatography (0-10% MeOH in DCM) to give tert-butyl (1-(3-((2-(2,6-difluorophenyl)imidazo[1,5-b]pyridazin-7-yl)amino)pyridin-4-yl)-4-methylpiperidin-3-yl)carbamate (613 mg, 1.15 mmol, 96% yield) as a mixture of isomers (ca. 4:1 ratio of cis:trans diastereomers) as an orange solid. MS (ESI, pos. ion) m/z: 536.2 (M+1). The isomers were purified by preparatory SFC (Chiralcel AS-H column (21×250 mm i.d., 5 μm) 80% liquid CO$_2$/20% MeOH (40 mM NH$_3$), 65 mL/min). The resulting material was then repurified using preparatory SFC (Chiralpak AD-H column (21×250 mm i.d., 5 μm) 70% liquid CO$_2$/30% 2-propanol (20 mM NH$_3$) 65 mL/min) to provide tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 1) (167 mg, 27% yield) which eluted first from an analytical SFC column (Chiralpak AD-H column (4.6×150 mm, 5 μm) 70% liquid CO$_2$/30% 2-propanol (0.2% diethylamine), 4 mL/min). MS (ESI, pos. ion) m/z: 536.0 (M+H)$^+$. $^1$H NMR (400 MHz, CDCl$_3$) δ ppm 9.63 (s, 1 H), 8.22 (d, J=5.1 Hz, 1 H), 7.72-7.83 (m, 2H), 7.41-7.53 (m, 1 H), 7.38 (s, 1 H), 7.08 (t, J=8.1 Hz, 2 H), 6.90 (d, J=5.1 Hz, 1 H), 6.57 (d, J=9.6 Hz, 1 H), 5.24 (d, J=9.6 Hz, 1 H), 3.35 (d, J=12.3 Hz, 1 H), 3.09-3.19 (m, 2 H), 2.43 (td, J=11.5, 3.5 Hz, 1 H), 1.79 (br. s., 1 H), 1.59 (br. s., 3 H), 1.32 (s, 9 H), 0.89 (d, J=6.7 Hz, 3 H). $^{19}$F NMR (376 MHz, CDCl$_3$) δ ppm −112.08 (s, 2 F); tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 2) (182 mg, 30% yield) which eluted second from an analytical SFC column (Chiralpak AD-H column (4.6×150 mm, 5 μm) 70% liquid CO$_2$/30% 2-propanol (0.2% diethylamine), 4 mL/min). MS (ESI, pos. ion) m/z: 536.0 (M+1). $^1$H NMR (400 MHz, CDCl$_3$) δ ppm 9.67 (s, 1 H), 8.27 (d, J=5.5 Hz, 1H), 7.80 (d, J=9.4 Hz, 1 H), 7.74 (s, 1 H), 7.43-7.52 (m, 1 H), 7.38 (s, 1 H), 7.08 (t, J=8.2 Hz, 2 H), 6.96 (d, J=5.5 Hz, 1 H), 6.60 (d, J=9.4 Hz, 1 H), 5.23 (d, J=10.0 Hz, 1H), 3.43 (d, J=11.7 Hz, 1 H), 3.14-3.25 (m, 2 H), 2.41-2.54 (m, 1 H), 1.75-1.88 (m, 2H), 1.49-1.55 (m, 2 H), 1.33 (s, 9 H), 0.90 (d, J=6.7 Hz, 3 H). $^{19}$F NMR (376 MHz, CDCl$_3$) δ ppm −112.14 (s, 2 F); tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 1) (40 mg, 7% yield) which eluted first from an analytical SFC column (Chiralpak AS-H column (4.6×150 mm, 5 μm) 85% liquid CO$_2$/15% MeOH (0.2% diethylamine) 4 mL/min). MS (ESI, pos. ion) m/z: 536.0 (M+1). $^1$H NMR (400 MHz, CDCl$_3$) δ ppm 9.78 (s, 1 H), 8.28 (d, J=5.5 Hz, 1 H), 7.78 (d, J=9.4 Hz, 1 H), 7.71 (br. s., 1 H), 7.40-7.49 (m, 1 H), 7.36 (s, 1 H), 6.97-7.11 (m, 3 H), 6.55 (d, J=9.4 Hz, 1H), 4.40-4.48 (m, 1 H), 3.41-3.51 (m, 2 H), 3.32-3.40 (m, 1 H), 2.61-2.77 (m, 1 H), 2.43-2.56 (m, 1 H), 1.79-1.87 (m, 2 H), 1.58-1.70 (m, 3 H), 1.41 (br. s., 9 H), 1.00 (d, J=6.5 Hz, 3 H). $^{19}$F NMR (377 MHz, CDCl$_3$) δ ppm –112.42 (s, 2 F); tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 2) (35 mg, 6% yield) which eluted as the second peak from an analytical SFC column (Chiralpak AS-H column (4.6×150 mm, 5 μm) 85% liquid CO$_2$/15% MeOH (0.2% diethylamine) 4 mL/min). MS (ESI, pos. ion) m/z: 536.0 (M+1). $^1$H NMR (400 MHz, CDCl$_3$) δ ppm 9.70 (s, 1 H), 8.20 (d, J=5.1 Hz, 1H), 7.76 (d, J=9.4 Hz, 2 H), 7.40-7.48 (m, 1 H), 7.35 (s, 1 H), 7.05 (t, J=8.2 Hz, 2 H), 6.92 (d, J=5.1 Hz, 1 H), 6.52 (d, J=9.4 Hz, 1 H), 4.36-4.49 (m, 1 H), 4.00-4.06 (m, 2H), 3.41-3.51 (m, 1 H), 3.33-3.41 (m, 1 H), 3.20-3.29 (m, 1 H), 2.58-2.70 (m, 1 H), 2.40-2.54 (m, 1 H), 1.76-1.85 (m, 1 H), 1.41 (br. s., 9 H), 0.99 (d, J=6.5 Hz, 3 H). $^{19}$F NMR (377 MHz, CDCl$_3$) δ ppm –112.40 (s, 2 F).

Step 2. N-(4-((cis)-3-amino-4-methylpiperidin-1-yl)pyridin-3-yl)-2-(2,6-difluorophenyl)imidazo[1,5-b]pyridazin-7-amine (enantiomer 1), Example 98. The title compound was prepared and isolated as an orange amorphous solid from tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 1) following an analogous procedure to Example 85. The relative stereochemistry was confirmed by NMR studies. MS (ESI, pos. ion) m/z: 436.0 (M+1). $^1$H NMR (400 MHz, DMSO-d$_6$) δ ppm 9.10 (s, 1 H), 8.71 (s, 1 H), 8.37 (d, J=6.3 Hz, 1 H), 8.22 (d, J=9.6 Hz, 1 H), 8.03 (br. s., 2 H), 7.61-7.73 (m, 1H), 7.51 (s, 1 H), 7.46 (d, J=6.7 Hz, 1 H), 7.32 (t, J=8.2 Hz, 2 H), 6.85 (d, J=9.4 Hz, 1 H), 4.01 (d, J=12.9 Hz, 1 H), 3.51-3.67 (m, 2 H), 3.43 (d, J=11.5 Hz, 1 H), 2.73 (t, J=11.2 Hz, 1 H), 1.96-2.11 (m, 1 H), 1.68-1.83 (m, 1 H), 1.43-1.55 (m, 1 H), 0.95 (d, J=7.0 Hz, 3 H). $^{19}$F NMR (376 MHz, DMSO-d$_6$) δ ppm –113.41 (s, 2 F).

N-(4-((cis)-3-amino-4-methylpiperidin-1-yl)pyridin-3-yl)-2-(2,6-difluorophenyl)imidazo[1,5-b]pyridazin-7-amine (enantiomer 2), Example 99. The title compound was prepared and isolated as an orange amorphous solid from tert-butyl ((cis)-1-(3-((2-(2,6-difluorophenyl)imidazo[1,5-b]pyridazin-7-yl)amino)pyridin-4-yl)-4-methylpiperidin-3-yl)carbamate (enantiomer 2) following an analogous procedure to Example 85. The relative stereochemistry was confirmed by NMR studies. MS (ESI, pos. ion) m/z: 436.0 (M+1). $^1$H NMR (400 MHz, DMSO-d$_6$) δ ppm 9.10 (s, 1 H), 8.72 (s, 1 H), 8.37 (d, J=6.5 Hz, 1 H), 8.22 (d, J=9.4 Hz, 1 H), 8.02 (br. s., 2 H), 7.61-7.72 (m, 1 H), 7.51 (s, 1 H), 7.46 (d, J=6.7 Hz, 1 H), 7.32 (t, J=8.2 Hz, 2 H), 6.85 (d, J=9.4 Hz, 1 H), 4.01 (d, J=13.1 Hz, 1 H), 3.52-3.67 (m, 2 H), 3.43 (d, J=11.5 Hz, 1 H), 2.73 (t, J=11.3 Hz, 1 H), 1.97-2.11 (m, 1 H), 1.68-1.83 (m, 1 H), 1.43-1.55 (m, 1 H), 0.95 (d, J=7.0 Hz, 3 H). $^{19}$F NMR (376 MHz, DMSO-d$_6$) δ ppm –113.41 (s, 2 F).

N-(4-((trans)-3-amino-4-methylpiperidin-1-yl)pyridin-3-yl)-2-(2,6-difluorophenyl)imidazo[1,5-b]pyridazin-7-amine tris(2,2,2-trifluoroacetate) (enantiomer 1), Example 100. The title compound was prepared and isolated as an orange amorphous solid from tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 1) following an analogous procedure to Example 85. The relative stereochemistry was confirmed by NMR studies. MS (ESI, pos. ion) m/z: 436.0 (M+1). $^1$H NMR (400 MHz, DMSO-d$_6$) δ ppm 8.92 (s, 1 H), 8.68 (s, 1 H), 8.37 (d, J=6.5 Hz, 1 H), 8.20 (d, J=9.4 Hz, 1 H), 8.07 (br. s., 2 H), 7.62-7.72 (m, 1 H), 7.46 (s, 1 H), 7.40 (d, J=6.7 Hz, 1 H), 7.32 (t, J=8.2 Hz, 2 H), 6.82 (d, J=9.4 Hz, 1 H), 3.87-3.98 (m, 1H), 3.69 (d, J=13.3 Hz, 1 H), 2.90-3.06 (m, 3 H), 1.68-1.84 (m, 2 H), 1.16-1.29 (m, 1H), 0.98 (d, J=6.5 Hz, 3 H). $^{19}$F NMR (376 MHz, DMSO-d$_6$) δ ppm –113.51 (s, 2 F).

N-(4-((trans)-3-amino-4-methylpiperidin-1-yl)pyridin-3-yl)-2-(2,6-difluorophenyl)imidazo[1,5-b]pyridazin-7-amine tris(2,2,2-trifluoroacetate) (enantiomer 2), Example 101. The title compound was prepared and isolated as an orange amorphous solid from tert-butyl ((trans)-1-(3-((2-(2,6-difluorophenyl)imidazo[1,5-b]pyridazin-7-yl)amino)pyridin-4-yl)-4-methylpiperidin-3-yl)carbamate (enantiomer 2) following an analogous procedure to Example 85. The relative stereochemistry was confirmed by NMR studies. MS (ESI, pos. ion) m/z: 436.0 (M+1). $^1$H NMR (400 MHz, DMSO-d$_6$) δ ppm 8.92 (s, 1 H), 8.69 (s, 1 H), 8.37 (d, J=6.5 Hz, 1 H), 8.18-8.24 (m, 1 H), 8.10 (br. s., 2 H), 7.61-7.72 (m, 1 H), 7.47 (s, 1 H), 7.41 (d, J=6.7 Hz, 1 H), 7.32 (t, J=8.2 Hz, 2 H), 6.82 (d, J=9.6 Hz, 1 H), 3.88-3.98 (m, 1 H), 3.65-3.75 (m, 1 H), 2.90-3.06 (m, 3 H), 1.68-1.85 (m, 2 H), 1.14-1.30 (m, 1 H), 0.98 (d, J=6.3 Hz, 3 H). $^{19}$F NMR (376 MHz, DMSO-d$_6$) δ ppm –113.51 (s, 2 F).

Example 102

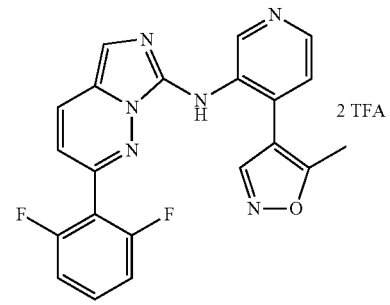 [SMILES: Cc1oncc1-c1ccncc1Nc1ncc2ccc(-c3c(F)cccc3F)nn12]

2-(2,6-Difluorophenyl)-N-(4-(5-methylisoxazol-4-yl)pyridin-3-yl)imidazo[1,5-b]pyridazin-7-amine bis(2,2,2-trifluoroacetate)

A dry, 25 mL, one neck round bottom flask was charged with 3-(azidomethyl)-6-(2,6-difluorophenyl)pyridazine (117 mg, 0.47 mmol, Preparation I), dry THF (3 mL), and a stirbar. The flask was fitted with a septa/Ar inlet and immersed into an ice/water bath. The solution was stirred for 15 min and was then treated with PMe$_3$ (48 μl, 0.46 mmol). The solution was stirred for 1 h, and then placed into a –5° C. refrigerator overnight. The flask was re-immersed into an ice-water bath, and treated with a solution of 4-(3-isothiocyanatopyridin-4-yl)-5-methylisoxazole (91 mg, 0.42 mmol, Preparation LVII) dissolved in dry THF (5 mL). The reaction was stirred for 1 h and then the solvent was removed in vacuo. The residue was treated with 50% aqueous HOAc (2 mL). The flask was placed on a rotovap, evacuated to 500 mm Hg, and immersed into a 40° C. water bath. The flask was rotary agitated for 30 min. The slurry was transferred to a 10 mL Bohdan vessel fitted with a 0.22 μm PTFE, 25 mm syringe filter unit (Millipore, SLFG025NK) with a positive pressure N$_2$ flow introduced from the bottom. The mixture was treated with 5 mL HOAc and the solution became homogenous. The solution was N$_2$-pressure filtered through the device, and the filtrate was concentrated in vacuo. The reddish oil was diluted with HOAc to 2 mL. The crude was purified by prep HPLC method 1 and the solvent was removed in vacuo, and the residue was dried in a vacuum oven for 16 h (60° C., final pressure: 0.080 mm Hg) to afford 2-(2,6-difluorophenyl)-N-(4-(5-methyl-isoxazol-4-yl)pyridin-3-3-yl)imidazo[1,5-b]pyridazin-7-amine bis(2,2,2-trifluoroacetate) (104 mg, 0.16 mmol, 39% yield) as a tan solid. MS (ESI, pos. ion) m/z: 404.9 (M+1). $^1$H NMR (400 MHz, CDCl$_3$) δ ppm 2.54 (s, 3 H) 6.82 (d, J=9.39 Hz, 1 H) 7.17 (t, J=8.31 Hz, 2 H) 7.44 (s, 1 H) 7.58 (tt, J=8.40, 6.50 Hz, 1 H) 7.84 (d, J=5.67 Hz, 1H) 8.07 (d, J=9.39 Hz, 1 H) 8.42 (d, J=5.67 Hz, 1 H) 8.64 (s, 1 H) 9.27 (s, 1 H). $^{19}$F NMR (377 MHz, CDCl$_3$) δ ppm −113.58 (t, J=6.87 Hz, 2 F) −75.59 (s, 6 F).

Example 103

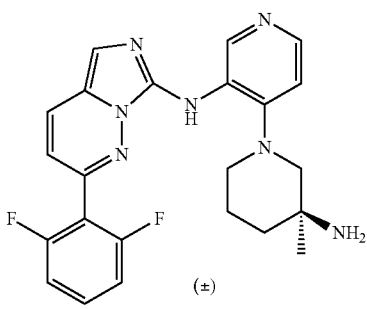 [SMILES: C[C@]1(N)CCCN(c2ccncc2Nc2ncc3ccc(-c4c(F)cccc4F)nn23)C1]

rac-N-(4-(3-Amino-3-methylpiperidin-1-yl)pyridin-3-yl)-2-(2,6-difluorophenyl)imidazo[1,5-b]pyridazin-7-amine The title compound was prepared and isolated as an orange solid from 3-(azidomethyl)-6-(2,6-difluorophenyl)pyridazine (Preparation I) and rac-tert-butyl (1-(3-isothiocyanatopyridin-4-yl)-3-methylpiperidin-3-yl)carbamate (Preparation LVIII) following an analogous procedure to Example 20. MS (ESI, pos. ion) m/z: 436.1 (M+1). $^1$H NMR (400 MHz, CDCl$_3$) δ ppm 9.69 (s, 1 H), 8.20 (d, J=5.28 Hz, 1 H), 7.77 (d, J=9.39 Hz, 1 H), 7.40-7.49 (m, 1 H), 7.37 (s, 1 H), 7.02-7.11 (m, 2 H), 6.94 (d, J=5.28 Hz, 1 H), 6.51 (dt, J=9.44, 1.74 Hz, 1 H), 3.01 (d, J=12.72 Hz, 1 H), 2.72-2.84 (m, 2 H), 2.64-2.71 (m, 1 H), 1.79-1.91 (m, 1 H), 1.69-1.78 (m, 2 H), 1.47-1.53 (m, 1 H), 1.14 (s, 3 H). $^{19}$F-NMR (376 MHz, CDCl$_3$) δ ppm −112.59.

Examples 104 and 105

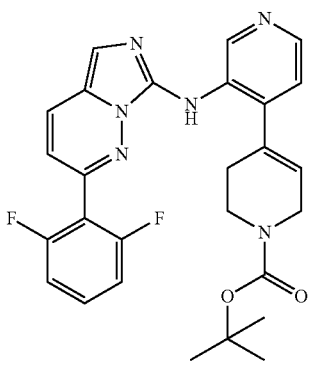

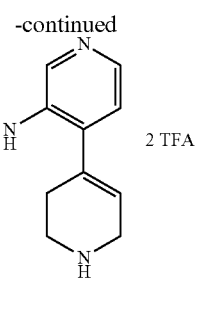

tert-Butyl 3'-((2-(2,6-difluorophenyl)imidazo[1,5-b] pyridazin-7-yl)amino)-5,6-dihydro-[4,4'-bipyridine]-1(2H)-carboxylate 2-(2,6-Difluorophenyl)-N-(1',2',3',6'-tetrahydro-[4,4'-bipyridin]-3-yl)imidazo[1,5-b]pyridazin-7-amine bis(2,2,2-trifluoroacetate).

Step 1. tert-butyl 3'-((2-(2,6-difluorophenyl)imidazo[1,5-b]pyridazin-7-yl)amino)-5,6-dihydro-[4,4'-bipyridine]-1(2H)-carboxylate, Example 104. A dry, 5 mL conical Bohdan vessel was charged with 3-(azidomethyl)-6-(2,6-difluorophenyl)pyridazine (51 mg, 0.21 mmol, Preparation I), a spinvane, and THF (1 mL). The vessel was crimped with a PTFE-lined seal, and pierced with an Ar inlet. The solution was treated with PMe$_3$ (18 μl, 0.17 mmol), and stirred at RT for 1.5 h. The solution was charged to a syringe. A dry, 10 mL Bohdan vessel was charged with tert-butyl 3'-isothiocyanato-5,6-dihydro-[4,4'-bipyridine]-1(2H)-carboxylate (54 mg, 0.17 mmol, Preparation LIX), a stirbar and THF. The solution was stirred for 15 min, and treated with the aza-Wittig solution charged to the syringe. The reaction was stirred for 1 h, and the solvent was removed in vacuo. The residue was loaded onto a 25×100 mL Silicyle diol (PN) column wet-packed and eluted with 10% EtOH in DCE. The initial 125 mL was collected, and the solvent was removed in vacuo. The residue was treated with CHCl$_3$ (1 mL), N$_2$-pressure filtered through a glass frit (4 mL Bohdan reaction vessel) fitted with a 0.22 μm PTFE, 4 mm syringe filter unit (Millipore, SLFGR04NL) and purified using a Phenominex cyano column (250×20 mm, spherical particle, 5 μm particle size, 120 Å pore size, flow =16 mL/min: A=CHCl$_3$; B=EtOH; 1% β isocratic). The solvent was removed in vacuo, and the material was dried in a vacuum oven overnight (80° C., final pressure=0.080 mm Hg) for 2 h to afford tert-butyl 3'-((2-(2, 6-difluorophenyl)imidazo[1,5-b]pyridazin-7-yl)amino)-5,6-dihydro-[4,4'-bipyridine]-1(2 H)-carboxylate (Example 104, 52 mg, 0.10 mmol, 60% yield) as an orange oil. MS (ESI, pos. ion) m/z: 505.0 (M+1). $^1$H NMR (400 MHz, CDCl$_3$) δ ppm 1.42 (s, 9 H) 2.36 (br. s., 2 H) 3.56 (t, J=5.53 Hz, 2 H) 3.97 (br. s., 2H) 5.93 (br. s., 1 H) 6.49 (dt, J=9.39, 1.60 Hz, 1 H) 6.96 (d, J=4.89 Hz, 1 H) 7.01 (t, J=8.22 Hz, 2 H) 7.19 (s, 1 H) 7.37 (br. s, 1 H) 7.38 (tt, J=8.50, 6.20 Hz, 1 H) 7.70 (d, J=9.49 Hz, 1 H) 8.18 (d, J=4.89 Hz, 1 H) 9.71 (s, 1 H). $^{19}$F NMR (376 MHz, CDCl$_3$) δ ppm −113.37 (br. s., 2 F).

Step 2. 2-(2,6-difluorophenyl)-N-(1',2',3',6'-tetrahydro-[4,4'-bipyridin]-3-yl)imidazo[1,5-b]pyridazin-7-amine bis(2,2,2-trifluoroacetate) (Example 105). A dry, 15 mL, one neck round bottom flask was charged with tert-butyl 3'-((2-(2,6-difluorophenyl)imidazo[1,5-b]pyridazin-7-yl)amino)-5,6-dihydro-[4,4'-bipyridine]-1(2H)-carboxylate (46 mg, 0.09 mmol), triethylsilane (5 μL, 0.31 mmol), water (50 μL), and TFA (0.95 mL, 12.79 mmol). The flask was swept with N$_2$ and briefly sonicated. The reaction was stirred for 30 min at RT and was then diluted with water (1 mL). The solution volume was reduced 50% under a stream of N$_2$ and the crude material was purified by prep HPLC method 1. The solvent was removed in vacuo, and the residue was dissolved in water. The solution was N$_2$-pressure filtered through a glass frit (4 mL Bohdan reaction vessel) fitted with a 0.22 μm PTFE, 4 mm syringe filter unit (Millipore, SLFGR04NL). The filtration device was washed with water (1 mL), and the combined filtrate/wash was lyophilized for 24 h. The solid was then dried in a vacuum oven at 60° C. for 24 h (60° C., final pressure=0.080 mm Hg) to afford 2-(2,6-difluorophenyl)-N-(1',2',3',6'-tetrahydro-[4,4'-bipyridin]-3-yl)imidazo[1,5-b]pyridazin-7-amine bis(2,2,2-trifluoroacetate) (52 mg, 0.081 mmol, 89% yield) as an orange solid. MS (ESI, pos. ion) m/z: 404.9 (M+1). $^1$H NMR (400 MHz, D$_2$O) δ ppm 2.63-2.74 (m, 2 H) 3.29 (t, J=6.02 Hz, 2 H) 3.67 (d, J=2.74 Hz, 2 H) 6.10 (br. s., 1 H) 6.92 (d, J=9.49 Hz, 1H) 7.12 (t, J=8.46 Hz, 2 H) 7.49 (s, 1 H) 7.54 (tt, J=8.50, 6.52 Hz, 1 H) 7.73 (d, J=5.87 Hz, 1 H) 8.10 (d, J=9.59 Hz, 1 H) 8.32 (d, J=5.87 Hz, 1 H) 8.51 (s, 1 H). $^{19}$F NMR (376 MHz, D$_2$O) δ ppm −117.58 (t, J=7.48 Hz, 2 F) −78.50 (s, 6 F).

Example 106

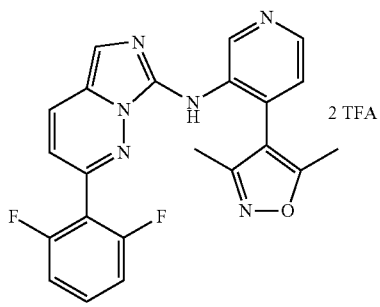 [SMILES: Cc1noc(C)c1-c1ccncc1Nc1ncc2ccc(-c3c(F)cccc3F)nn12]

2-(2,6-Difluorophenyl)-N-(4-(3,5-dimethylisoxazol-4-yl)pyridin-3-yl)imidazo[1,5-b]pyridazin-7-amine bis(2,2,2-trifluoroacetate)

The title compound was prepared and isolated as a yellow solid from 3-(azidomethyl)-6-(2,6-difluorophenyl)pyridazine (Preparation I) and 4-(3-isothiocyanatopyridin-4-yl)-3,5-dimethylisoxazole (Preparation LX) following an analogous procedure to Example 102. The material was purified by prep HPLC method 1. MS (ESI, pos. ion) m/z: 419.0 (M+1). $^1$H NMR (400 MHz, MeOH-d$_4$) δ ppm 2.25 (s, 3 H) 2.41 (s, 3 H) 6.81 (dt, J=9.49, 1.27 Hz, 1 H) 7.16 (t, J=8.36 Hz, 2 H) 7.46 (s, 1 H) 7.58 (tt, J=8.51, 6.36 Hz, 1H) 7.81 (d, J=5.67 Hz, 1 H) 8.07 (d, J=9.49 Hz, 1 H) 8.41 (d, J=5.58 Hz, 1 H) 9.23 (s, 1 H). $^{19}$F NMR (377 MHz, MeOH-d$_4$) δ ppm −113.98-113.42 (m, 2 F) −75.44 (br. s., 6 F).

Biological Activity
Pim-1 and Pim-2
Cloning and Expression:

Full-length human cDNAs encoding Pim-1 (MGC ID 3913552) or Pim-2 (IMAGE ID 5092935) were purchased from Invitrogen, Carlsbad, Calif. These cDNAs were used as templates in PCR reactions to produce full-length DNA clones of the PIMs. Oligonucleotide PCR primers for Pim-1 were 5'-TGGCTGATCAATGCTCTTGTCCAAAATC-3' and 5'-ATTAGAATTCTATTTGCTGGGCCCCGGC-3'. Oligonucleotide PCR primers for Pim-2 were 5'-TGCAGGATCCATGTTGACCAAGCCTCTAC-3' and 5'-ACGTGAATTCTATCCCTGTGACATGGCC-3'. PCR products were digested with BclI and EcoRI for Pim-1 and BamHI and EcoRI for Pim-2 and ligated into a modified baculovirus transfer vector (pFastBac 1) cleaved with BamHI and EcoRI. For bacterial expression, the same cleaved PCR products encoding Pim-1 or Pim-2 were ligated into a modified E. coli expression vector pET28(a) cleaved with BamHI and EcoRI. Amino-terminal hexahistidine tags followed by a thrombin cleavage site were previously added to the vectors using standard methods of molecular biology. Recombinant baculoviruses expressing Pim-1 or Pim-2 were made using standard methods (Fastbac manual, Invitrogen, Carlsbad, Calif.). Infection of Sf9 cells was done at an m.o.i. of greater than 5 for 24-48 h. Cells were harvested by centrifugation and frozen at −80 C. For E. coli expression, cells carrying pET28-His6-Th-Pim-1 or pET28-His6-Th-Pim-2 were picked from a single colony and grown o/n in LB media. The o/n culture was used to inoculate a 2 liter flask with 500 mL media. This was grown o/n and used to inoculate 15-20 liters of Terrific Broth in a New Brunswick Scientific fermentor. The E. coli were grown at 37° C. to and OD600>1.6. The temperature was dropped to 18° C. and o/n expression was induced with 0.5 mM IPTG. Cells were harvested by centrifugation and frozen at −80° C.

Purification

The frozen cell pellets were thawed by stirring in chilled lysis buffer (0.05 M HEPES, pH 8.0, 0.25 M NaCl, 0.01 M 2-mercaptoethanol, 10% (w/v) glycerol, 0.5% (v/v) protease inhibitor cocktail (Sigma P-8340) at a ratio of 1 L/200 g cells until homogeneous. The thawed suspension was applied to a microfluidizer at 10,000 PSI to disrupt the cells and the whole lysates were clarified by centrifugation at 50,000×g for 90 min, 4° C. Imidazole was added to the clarified lysate to a final concentration of 2.5 mM and the lysate was mixed with 10 mL of Talon resin (Clontech) and the slurry rocked gently overnight at 4° C. The slurry was centrifuged at 1,000×g for 5 min, the supernatant decanted, and the resin suspended in 40 mL of lysis wash buffer (lysis buffer at 0.75 M NaCl). This step was repeated 3× and the resin was transferred to a 2.5 cm glass column. Ten column volumes of wash buffer (0.05 M HEPES, pH 8.0, 0.1 M NaCl, 0.01 M 2-mercaptoethanol, 10% (w/v) glycerol) were applied to the resin followed by 10 column volumes of elution buffer (0.05 M HEPES, pH 8.0, 0.25 M NaCl, 0.01 M 2-mercaptoethanol, 10% (w/v) glycerol, 0.1 M imidazole). Fractions were analyzed by SDS-PAGE and those containing the protein of interest were pooled and concentrated. The concentrated protein was applied to an Amersham Superdex 75 (XK 26/60) column equilibrated in 0.025 M Tris-HCl, pH 7.5, 0.1 M NaCl, 0.01 M 2-mercaptoethanol, 10% (w/v) glycerol. The protein eluted at a retention time indicative of it being monomeric and fractions were analyzed by SDS-PAGE. Fractions containing the monomeric protein of interest were pooled, concentrated to ~2 mg/mL, and stored at −80° C.

Pim-3

Pim-3 was purchased from Millipore (UK).

Pim Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 96-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction.

Compounds were prepared in DMSO by conducting 3-fold serial dilutions to give a 10-point dosing curve having a high dose of 1 uM. A reference compound was included on each assay plate in order to validate that plate; on one plate of every assay run, two additional reference compounds were included.

The final buffer conditions were as follows: 60 mM Hepes, pH 7.0, 0.05% BSA, 2 mM DTT. Incubations were carried out at RT (22° C.) for 2 h for Pim-1, 1 h and 30 min for Pim-3, and 45 min for Pim-2. The reaction was stopped by the addition of 3 mM EDTA, and fluorescence was measured by an HTRF® Rubystar microplate reader. For each plate, percent of control (POC) values were calculated for each well. Values for the IC50 IP were estimated using a standard 4-parameter logistic model.

Pim-Mn Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 384-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction.

Compounds were prepared in DMSO by conducting 3-fold serial dilutions to give a 22-point dosing curve having a high dose of 1 µM. A reference compound was included on each assay plate [Costar 3658] in order to validate that plate; on one plate of every assay run, two additional reference compounds were included. The Reaction Buffer consisted of 45 mM Hepes, pH 7.0, 15 mM NaCl, and 1 mM MgCl. The quench/detection buffer consisted of 50 mM Tris, 100 mM NaCl, 0.05% BSA, 0.1% Tween and 3 mM EDTA. Biotinylated BAD peptide (Biopeptide), 10 mM ATP (Sigma), Labeled p-BAD (S112) mAb (Cell Signalling and Perkin Elmer) [with 0.05% BSA and 2 mM DTT added] streptavidin:Allophycocyanin [Perkin Elmer]. Final concentrations—either Pim-1 enzyme [5 pM], or Pim-2 enzyme [0.5 pM], DMSO [1%], BLC BAD (S112) [0.5 µM], ATP [1.5 µM], streptavidin:Allophycocyanin [0.002 mg/mL] and biotinylated-BAD (S112) mAb [100 µM].

Initial incubations were carried out at RT (22° C.) for 30 min for both Pim-1 and for Pim-2. Pim enzyme is added to compound in buffer, and plates are incubated of 30 min. Biotinylated BAD and ATP are added and plates are incubated for 1 h. A mixture of labeled p-BAD (S112) mAb and quench/detection buffer are added and incubated for 2 h. Fluorescence was measured by an HTRF® Envision microplate reader. For each plate, percent of control (POC) values were calculated for each well. Values for the IC50 IP were estimated using a standard 3 or 4-parameter logistic model.

Pim Cell Assay

The KMS-12-BM myeloma cell line was used to determine the in vitro cellular inhibition of Pim kinases. Disruption of Pim signaling by Pim inhibitors was determined by measuring the levels of phospho-BAD (S112) and total BAD. This cellular assay was conducted as follows: The suspension cells were plated out onto 96-well, V-bottom plates at an initial density of 80,000 cells/well in 100 uL of complete growth medium (RPMI Medium 1640—Invitrogen #11875, 20% Heat inactivated FBS—Hyclone #SH 30070.03HI, 1×L-glutamine-Invitrogen #25030). The cells were then incubated overnight at 37° C., 5% $CO_2$. Compounds were initially diluted in DMSO by conducting 3-fold serial dilutions to give a 10-point dosing curve having a high dose of 31.6 uM. In addition to the 10-point dosing curve of the test compound, DMSO alone was run as a control. This dilution in DMSO was then diluted again into cell growth medium. Aliquots (11.1 uL) of the compound diluted in growth medium were then transferred to the appropriate wells of the 96-well plates containing cells to yield a final DMSO concentration of 0.3%. The cell plates were then incubated with compound for 1 hour and 50 minutes at 37° C., 5% $CO_2$. After the 1 hour and 50 min incubation, the cell plates were spun at 1000 RPM for 10 minutes and the compound-containing medium was removed. The cell plates were placed on ice and given 50 uL of ice-cold complete lysis buffer (MSD kit components, Protease Inhibitor Cocktail Tablets—Roche #04 693 116 001) supplemented with 0.5% Membrane Blocking Agent (Amersham Biosciences # RPN2125). The cell plates containing lysis buffer were then immediately stored at −70° C. These prepared lysates were then assayed for phospho-(S112) and total-BAD according to the manufacturer's protocol (Meso Scale Diagnostics, Cat # K15103D-3). The plates were read on the MSD Sector Imager 6000, and results were calculated according to the assay protocol:

((% Phosphoprotein=((2×Phospho signal)/(Phospho signal+Total signal))×100)).

TABLE 2

$IC_{50}$ Activity of compounds of the Invention

| Ex# | Pim_1_IC50 (nM) | Pim2_IC50 (nM) | KMS12_Cell_IC50 (nM) |
| --- | --- | --- | --- |
| 1 | 0.08 | 0.5 | 428 |
| 2 | 14 | 126 | >31000 |
| 3 | 54 | 154 | |
| 4 | 0.9 | 3 | 2670 |
| 5 | 107 | 640 | |
| 6 | 8 | 77 | 6663 |
| 7 | 0.9 | 12 | 6600 |
| 8 | 1 | 3 | 726 |
| 9 | 14 | 99 | 10310 |
| 10 | 409 | >1000 | |
| 11 | 2 | 11 | 5010 |
| 12 | 0.4 | 3 | 1760 |
| 13 | 568 | >1000 | |
| 14 | 35 | 160 | |
| 15 | 0.2 | 2 | 1536 |
| 16 | 44 | 298 | >1000 |
| 17 | 192 | >1000 | |
| 18 | 99 | >1000 | |
| 19 | 3 | 30 | |
| 20 | 0.04 | 0.08 | 40 |
| 21 | 0.3 | 0.6 | 209 |
| 22 | 1.2 | 9.1 | 2390 |

TABLE 2-continued

IC$_{50}$ Activity of compounds of the Invention

| Ex# | | | |
|---|---|---|---|
| 23 | 0.1 | 0.5 | 1402 |
| 24 | 25 | 99 | |
| 25 | 2 | 8 | 777 |
| 26 | 534 | >1000 | |
| 27 | 9 | 121 | >1000 |
| 28 | 38 | 281 | |
| 29 | 206 | >1000 | |
| 30 | 7 | 185 | 21530 |
| 31 | 50 | 136 | |
| 32 | 4 | 27 | |

Values rounded to 4 significant figures

| Ex# | Pim-1 IC50 IP (μM) | Pim-2 IC50 IP (μM) | Pim-1-Mn IC50 IP (μM) | Pim-2-Mn IC50 IP (μM) | KMS-12-BM IC50 IP (μM) |
|---|---|---|---|---|---|
| 33 | 0.0004 | 0.0008 | | | 0.522 |
| 34 | 0.0669 | Undefined | | | |
| 35 | 0.0027 | 0.0088 | | | 0.667 |
| 36 | 0.0192 | 0.11 | | | >31.6 |
| 37 | 0.0001 | 0.0002 | | | 0.095 |
| 40 | 0.0002 | 0.0011 | | | 0.286 |
| 39 | 0.0021 | 0.0078 | | | 1.75 |
| 38 | <0.0001 | 0.0001 | | | 0.0276 |
| 41 | 0.0001 | 0.0005 | | | 0.148 |
| 42 | 0.0086 | 0.0344 | | | 9.86 |
| 43 | 0.0002 | 0.0011 | | | 0.465 |
| 46 | <0.0001 | 0.0001 | | | 0.0521 |
| 47 | 0.0077 | 0.0542 | | | 10.2 |
| 48 | 0.0008 | 0.0032 | | | 0.983 |
| 50 | 0.0073 | 0.162 | | | Undefined |
| 53 | 0.0034 | 0.0109 | | | 1.2 |
| 54 | 0.0001 | 0.0003 | | | 0.221 |
| 55 | 0.0217 | 0.231 | | | |
| 58 | 0.0118 | 0.0659 | | | Undefined |
| 59 | 0.0020 | 0.031 | | | Undefined |
| 56 | 0.0037 | 0.0109 | | | 5.86 |
| 57 | 0.0005 | 0.0054 | | | 2.53 |
| 60 | 0.0001 | 0.0003 | | | 0.116 |
| 61 | 0.0004 | 0.0014 | | | 1.63 |
| 62 | 0.0003 | 0.0004 | | | 0.183 |
| 49 | 0.0182 | 0.113 | | | 12.1 |
| 63 | 0.0003 | 0.0013 | | | 0.235 |
| 64 | 0.0015 | 0.0064 | | | 1.76 |
| 52 | 0.0033 | 0.105 | | | >15.8 |
| 44 | 0.0074 | 0.0488 | | | 6.1 |
| 45 | 0.0001 | 0.0011 | | | 1.07 |
| 51 | 0.0067 | 0.059 | | | Undefined |
| 65 | 0.0001 | 0.0004 | | | 0.0454 |
| 66 | 0.0003 | 0.0013 | | | 0.115 |
| 67 | 0.0045 | 0.0354 | | | Undefined |
| 68 | 0.0383 | 0.0737 | | | |
| 69 | 0.0076 | 0.0352 | | | Undefined |
| 70 | 0.0296 | Undefined | | | |
| 71 | 0.0385 | Undefined | | | |
| 72 | 0.0001 | 0.0001 | | | 0.0864 |
| 73 | 0.0022 | 0.0065 | | | 3.44 |
| 74 | 0.0002 | 0.0005 | | | 0.185 |
| 75 | 0.0036 | 0.0309 | | | 4.63 |
| 77 | 0.15 | >1.0 | | | |
| 76 | 0.0003 | 0.0018 | | | 0.364 |
| 78 | 0.0009 | 0.0026 | | | 0.62 |
| 79 | 0.0002 | 0.0005 | | | 0.132 |
| 80 | >1.0 | >1.0 | | | |
| 81 | 0.0338 | Undefined | | | |
| 82 | 0.0012 | 0.0094 | | | 1.2 |
| 86 | <0.0001 | 0.0010 | | | 0.142 |
| 85 | 0.0027 | 0.0387 | | | Undefined |
| 87 | <0.0001 | 0.0003 | | | 0.0488 |
| 89 | 0.0035 | 0.0053 | | | 1.35 |
| 88 | 0.0066 | 0.029 | | | 9.82 |
| 90 | 0.0010 | 0.0039 | | | 0.509 |
| 91 | 0.0056 | 0.0305 | | | 11.3 |
| 92 | 0.0016 | 0.0106 | | | 2.2 |
| 83 | 0.0011 | 0.0063 | | | 1.09 |
| 84 | 0.0305 | 0.189 | | | Undefined |
| 93 | 0.0024 | 0.0155 | | | 2.6 |
| 95 | 0.0001 | 0.0013 | | | 0.258 |
| 94 | 0.0198 | 0.102 | | | 14.1 |
| 97 | 0.0002 | 0.0028 | | | 0.362 |
| 96 | 0.0153 | 0.136 | | | Undefined |
| 98 | 0.0028 | 0.0157 | | | 12.1 |
| 99 | 0.0003 | 0.0016 | | | 2.7 |
| 102 | Undefined | >1.0 | | | |
| 100 | <0.0001 | 0.0002 | | | 0.0775 |
| 101 | 0.0076 | 0.0324 | | | 6.93 |
| 103 | 0.0022 | 0.0096 | | | Undefined |
| 105 | | | 0.035 | 1.05 | |
| 106 | | | 0.221 | >5 | |

The compounds of the present invention may be administered orally, parentally, by inhalation spray, rectally, or topically in dosage unit formulations containing conventional pharmaceutically acceptable carriers, adjuvants, and vehicles.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment.

The dosage regimen for using these compounds diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)alkyloxy) ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed:
1. A compound of Formula 1'

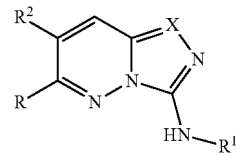

wherein
X is CH;
R is H, halo, alkyl, cycloalkyl, optionally substituted aryl, optionally substituted 5-membered heterocyclyl, or optionally substituted 6-membered heterocyclyl;
$R^1$ is optionally substituted 5-membered nitrogen containing heteroaryl, or optionally substituted 6-membered nitrogen containing heteroaryl; and
$R^2$ is H;
and a pharmaceutically acceptable salt thereof;
provided $R^1$ is not unsubstituted 3-pyridyl when, X is CH and R is 2,6-difluorophenyl; further provided $R^1$ is not 5-methyl-3-phenyl-4-isoxazolyl when, X is CH and R is 2,6-difluorophenyl; further provided R is not H if X is CH; further provided $R^1$ is not 4-(5-methyl-4-isoxazolyl)-3-pyridinyl when X is N and R is 2,6-difluorophenyl; further provided $R^1$ is not substituted 4-pyridinyl; and further provided $R^1$ is not 4-chloro-3-pyridyl when, X is CH and R is 2,6-difluorophenyl.

2. Compound of claim 1 wherein $R^1$ is optionally substituted pyridyl, optionally substituted pyrimidinyl, optionally substituted pyridazinyl, optionally substituted pyrrolyl, optionally substituted isoxazolyl or optionally substituted isothiazolyl; and a pharmaceutically acceptable salt thereof.

3. Compound of claim 1 wherein $R^1$ is substituted 3-pyridyl, substituted 5-pyrimidinyl, substituted 3-pyridazinyl, substituted 3-pyrrolyl, substituted 4-isoxazolyl or substituted isothiazol-4-yl; and a pharmaceutically acceptable salt thereof.

4. Compound of claim 1 wherein $R^1$ is substituted with optionally substituted 4-6-membered heterocyclyl, optionally substituted 4-6-membered heterocyclyloxy, 5-6 membered nitrogen-containing heterocyclylamino, optionally substituted cycloalkyl, optionally substituted cycloalkenyl, optionally substituted aryl, N-alkoxyalkyl-N- alkylamino, N-alkoxyalkylamino, amino, alkylamino or dialkylamino; and a pharmaceutically acceptable salt thereof.

5. Compound of claim 1 wherein R is C1-6alkyl, C3-6 cycloalkyl, optionally substituted 5-membered saturated or partially unsaturated heterocyclyl, or optionally substituted saturated or partially unsaturated 6-membered heterocyclyl; and a pharmaceutically acceptable salt thereof.

6. Compound of claim 1 wherein R is methyl, ethyl, propyl, tert-butyl, cyclopropyl, cyclopentyl, pyran, 5,6-dihydro-2H-pyranyl, 3,6-dihydro-2H-pyranyl, tetrahydropyran, pyrrolidinyl, piperidinyl, morpholinyl, or imidazolidinyl; wherein any ring is optionally substituted with one or more substituents selected from methyl, or oxo; and a pharmaceutically acceptable salt thereof.

7. Compound of claim 1 wherein R is optionally substituted phenyl, optionally substituted 5-membered heteroaryl or optionally substituted 6-membered heteroaryl; and a pharmaceutically acceptable salt thereof.

8. Compound of claim 1 wherein R is optionally substituted phenyl, optionally substituted thiazolyl, optionally substituted pyrazolyl, optionally substituted pyrazinyl, optionally substituted pyridazinyl, optionally substituted pyrimidinyl, or optionally substituted pyridyl; and a pharmaceutically acceptable salt thereof.

9. Compound of claim 1 wherein R is thiazol-2-yl, 2-fluorophenyl, 2,6-difluorophenyl, 2,4-difluorophenyl, 2-chlorophenyl, 2,4-dichlorophenyl, 2-fluoro-3-pyridyl, 2-chloro-3-pyridyl, 2-fluoro-4-methylsulphonylphenyl, or chloro; and a pharmaceutically acceptable salt thereof.

10. Compound of claim 1 wherein $R^1$ is pyrid-3-yl, pyrimidin-3-yl or isothiazol-4-yl, wherein $R^1$ is substituted with amino, C1-4 alkylamino, di(C1-4) alkylamino, N—C1-4 alkoxy-C1-4 alkyl-N—C1-4 alkylamino, N—C1-4alkoxy-C1-4alkylamino, optionally substituted cycloalkyl, optionally substituted cycloalkenyl, optionally substituted aryl, substituted or unsubstituted 5-membered nitrogen-containing heterocyclyl, substituted or unsubstituted 6-membered nitrogen-containing heterocyclyl, 4-6-membered nitrogen-containing heterocyclyloxy, 5-membered nitrogen-containing heterocyclylamino, or 6-membered nitrogen-containing heterocyclylamino, wherein the substituted 5-membered nitrogen -containing heterocyclyl, or substituted 6-membered nitrogen-containing heterocyclyl are substituted with one or more substituents selected from amino, oxo, methyl, and fluoro; and a pharmaceutically acceptable salt thereof.

11. A compound of Formula 2'

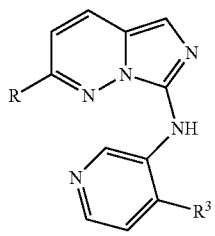

2' wherein

R is halo, optionally substituted phenyl, optionally substituted 5-membered heteroaryl, or optionally substituted 6-membered heteroaryl;

$R^3$ is optionally substituted 4-6-membered heterocyclyl, optionally substituted 4-6-membered heterocyclyloxy, optionally substituted cycloalkyl, optionally substituted aryl, amino, alkylamino or dialkylamino;

and a pharmaceutically acceptable salt thereof.

12. Compound of claim 11 wherein R is phenyl, 2,6-difluorophenyl, 2,3-difluorophenyl, 2-fluorophenyl, 3-fluorophenyl, 2-fluoro-5-nitrophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-hydroxyphenyl, 3-hydroxyphenyl, 3-methoxyphenyl, 3, 5-dimethoxyphenyl, 3-isopropoxyphenyl, 3-trifluoromethoxyphenyl, 2-cyanophenyl, 3-aminophenyl, 3-amino-2-methylphenyl, 2-cyanophenyl, 3-cyanophenyl, 2-chlorophenyl, 2-chloro-6-fluorophenyl, 3-methylsulfonylphenyl, 4-methylsulfonylphenyl, 3-dimethylaminophenyl, 3-amino-4-morpholinophenyl, 3-amino-6-trifluoromethoxyphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3- pyridazinyl, 4-amino-pyridazin-6-yl, 1H-pyrazol-5-yl, 1-methyl-1H-pyrazol-4-yl, thiazol-2-yl, 2-(2-methylpiperidin-1-yl)thiazol-4-yl, or 2-(pyrrolidin-1-yl)thiazol-4-yl; and a pharmaceutically acceptable salt thereof.

13. Compound of claim 11 wherein R is 2,6-difluorophenyl, 2-chloro-6-fluorophenyl, 3-fluoropyridin-2-yl, or 2-(isopropoxy)-pyrazin-6-yl; and a pharmaceutically acceptable salt thereof.

14. Compound of claim 11 wherein $R^3$ is optionally substituted 5-6-membered nitrogen containing heterocyclyl, optionally substituted 4-6-membered nitrogen containing heterocyclyloxy, optionally substituted cycloalkyl, optionally substituted cycloalkenyl, optionally substituted aryl, amino, N-alkoxyalkyl-N-alkylamino, alkylamino or dialkylamino; and a pharmaceutically acceptable salt thereof.

15. Compound of claim 11 wherein $R^3$ is dimethylamino, N-(2-methoxypropyl)-N-methylamino, N-(2-methylpropyl)-N-methylamino, 3,5-dimethylisoxazol-4-yl, 3-aminophenyl, 2-oxo-(1,2-dihydropyrid-5-yl), 1,2,3,6-tetrahydropyridin-4-yl, 2-amino-5-pyridyl, 3-amino-5-pyridyl, 3-aminocyclohexen-1-yl, 3-aminocyclohexyl, 3-azetidinyloxy, 3-piperidinyloxy, 3-amino-pyrrolidinyl, 1-piperidinyl, 3-hydroxypiperidin-1-yl, 3-amino-piperidin-1-yl, 3-methylamino-piperidin-1-yl, 3,4-dihydroxy-piperidin-1-yl, 3-amino-2-methylpiperidin-1-yl, 3-amino-3-methylpiperidin-1-yl, 3-amino-5-methylpiperidin-1-yl, 3-amino-5-trifluoromethylpiperidin-1-yl, 3-amino-6-methylpiperidin-1-yl, 3-amino-4-fluoropiperidin-1-yl, 3-amino-5-fluoropiperidin-1-yl, 3-amino-4-hydroxy-5-methylpiperidin-1-yl, piperazinyl, 3-methylpiperazin-1-yl or 2,5-dimethylpiperazin-1-yl; and a pharmaceutically acceptable salt thereof.

16. A compound of claim 1 selected from
(3R,4R,5S)-3-amino-1-(3-((2-(2,6-difluorophenyl)imidazo[1,5-b]pyridazin-7-yl)amino)pyridin-4-yl)-5-methylpiperidin-4-ol;

(3R,4R,5S)-3-amino-5-methyl-1-(3-((2-(1,3-thiazol-2-yl)imidazo[1,5-b]pyridazin-7-yl)amino)-4-pyridinyl)-4-piperidinol;

(3R,4S,5R)-3-amino-1-(3-((2-(2,6-difluorophenyl)imidazo[1,5-b]pyridazin-7-yl)amino)-4-pyridinyl)-5-methyl-4-piperidinol;

N-(4-((trans-3-amino-2-methyl-1piperidinyl)-3-pyridinyl)-2-(3-fluoro-2-pyridinyl)imidazo[1,5-b]pyridazin-7-amine (enantiomer 1);

rac-N-(4-((cis)-3-amino-5-(trifluoromethyl)piperidin-1yl)pyridin-3-yl)-2-(2,6-difluorophenyl)imidazo[1,5-b]pyridazin-7-amine;

N-(4-((cis)-3-amino-5-methylpiperidin-1yl)pyridin-3-yl)-2-(pyridin-2-yl)imidazo[1,5-b]pyridazin-7-amine;

N-(4-((cis)-3-amino-5-methylpiperidin-1-yl)pyridin-3-yl)-2-(3-fluoropyridin-2-yl)imidazo[1,5-b]pyridazin-7-amine;

(3R,4R,5S)-3-amino-1-(3-((2-(3-fluoropyridin-2-yl)imidazo[1,5-b]pyridazin-7-yl)amino)pyridin-4-yl)-5-methylpiperidin-4-ol;

3-(7-((4-((3S,5R)-3-amino-5-methyl-1-piperidinyl)-3-pyridinyl)amino)imidazo[1,5-b]pyridazin-2-yl)-N-cyclopropyl-4-fluorobenzamide;

3-(7-((4-((3S)-3-amino-1-piperidinyl)-3-pyridinyl)amino)imidazo[1,5-b]pyridazin-2-yl)-N-cyclopropyl-4-fluorobenzamide;

N-(4-(5-amino-2-methylpiperidin-1-yl)pyridin-3-yl)-2-(2,6-difluorophenyl)imidazo[1,5]-pyridazin-7-amine (diastereomer 2);

N-(4-(5-amino-2-methylpiperidin-1-yl)pyridin-3-yl)-2-(2,6-difluorophenyl)imidazo[1,5-b]pyridazin-7-amine (diastereomer 3);

N-(4-((trans)-3-amino-4-methylpiperidin-1yl)pyridin-3-yl)-2-(2,6-difluorophenyl)imidazo[1,5-b]pyridazin-7-amine (enantiomer 1);

N-(4-((cis)-5-amino-2-methylpiperidin-1-yl)pyridin-3-yl)-2-(3-fluoropyridin-2-yl)imidazo[1,5-b]pyridazin-7-amine (enantiomer 2);

N-(4-((cis)-3-amino-5-methylpiperidin-1yl)pyridin-3-yl)-2-(2,6-difluorophenyl)imidazo[1,5-b]pyridazin-7-amine (enantiomer 1);

N-(4-((cis)-3-amino-5-methylpiperidin-1-yl)pyridin-3-yl)-2-(2-fluorophenyl)imidazo[1,5-b]pyridazin-7-amine (enantiomer 1);

(S)-N-(4-(3-aminopiperidin-1-yl)pyridin-3-yl)-2-(3-chloropyridin-2-yl)imidazo[1,5-b]pyridazin-7-amine;

N-(4-((3S,5R)-3-amino-5-methylpiperidin-1-yl)pyridin-3-yl)-2-(thiazol-2-yl)imidazo[1,5-b]pyridazin-7-;

N-(4-((3S)-3-amino-1-piperidinyl)-3-pyridinyl)-2-(3-fluoro-2-pyridinyl)imidazo[1,5-b]pyridazin-7-amine;

N-(4-((trans)-5-amino-2-methylpiperidin-1yl)pyridin-3-yl)-2-(3-fluoropyridin-2-yl)imidazo[1,5-b]pyridazin-7-amine (enantiomer 2);

N-(4-((2R,3S)-3-amino-2-methyl-1piperidinyl)-3-pyridinyl)-2-(3-fluoro-2-pyridinyl)imidazo[1,5-b]pyridazin-7-amine;

N-(4-((3S)-3-amino-1-piperidinyl)-3-pyridinyl)-2-(2,6-difluorophenyl)imidazo[1,5-b]pyridazin-7-amine;

N-(4-((3S,5S)-3-amino-5-methylpiperidin-1yl)pyridin-3-yl)-2-(2,6-difluorophenyl) imidazo[1,5-b]pyridazin-7-amine;

N-(4-((3S)-3-amino-1-piperidinyl)-3-pyridinyl)-2(1,3-thiazol-2-yl)imidazo[1,5-b]pyridazin-7-amine; and N-(4-((cis)-3-amino-5-methylpiperidin-1yl)pyridin-3-yl)-6-(2,6-difluorophenyl)-[1,2,4]triazolo[4,3-b]pyridazin-3-amine;

and a pharmaceutically acceptable salt thereof.

\* \* \* \* \*